US011773443B2

(12) United States Patent
Gromminger et al.

(10) Patent No.: US 11,773,443 B2
(45) Date of Patent: *Oct. 3, 2023

(54) MULTIPLEX DETECTION OF DNA THAT ORIGINATES FROM A SPECIFIC CELL-TYPE

(71) Applicant: Eurofins LifeCodexx GmbH, Constance (DE)

(72) Inventors: Sebastian Gromminger, Constance (DE); Wera Hofmann, Constance (DE); Hamed Said, Constance (DE)

(73) Assignee: EUROFINS LIFECODEXX GMBH, Constance (DE)

( * ) Notice: Subject to any disclaimer, the term of this patent is extended or adjusted under 35 U.S.C. 154(b) by 522 days.

This patent is subject to a terminal disclaimer.

(21) Appl. No.: 16/005,004

(22) Filed: Jun. 11, 2018

(65) Prior Publication Data

US 2018/0334715 A1 Nov. 22, 2018

Related U.S. Application Data

(62) Division of application No. 14/707,363, filed on May 8, 2015, now Pat. No. 10,017,818.

(30) Foreign Application Priority Data

May 9, 2014 (EP) .................................. 14167769

(51) Int. Cl.
  *C12Q 1/6881* (2018.01)
  *C12Q 1/6883* (2018.01)

(52) U.S. Cl.
  CPC ......... *C12Q 1/6881* (2013.01); *C12Q 1/6883* (2013.01); *C12Q 2600/118* (2013.01);
  (Continued)

(58) Field of Classification Search
  CPC ............ C12Q 1/6881; C12Q 2600/154; C12Q 2600/16
  See application file for complete search history.

(56) References Cited

U.S. PATENT DOCUMENTS 5,804,375 A   9/1998   Gelfand et al.
5,994,056 A   11/1999  Higuchi
(Continued)

FOREIGN PATENT DOCUMENTS

CN   101985619 A   3/2011
CN   102216456 A   10/2011
(Continued)

OTHER PUBLICATIONS

Zimmerman et al. Methods in Molecular Biology. 2006. 336:83-100. (Year: 2006).*

(Continued)

*Primary Examiner* — Joseph G. Dauner
(74) *Attorney, Agent, or Firm* — MH2 TECHNOLOGY LAW GROUP, LLP

(57) ABSTRACT

The present invention relates to methods to detect an amount of DNA that originates from cells of a given type, where the sample comprising such DNA in admixture with DNA that does not originate from such cells. Such methods are based on differential methylation, at certain regions, of the DNA that originates from the given type of cells compared to the admixed DNA. Such methods have particular application in the detection, from a biological fluid from a pregnant female, of cell free DNA that originates from a foetus or the placenta of a foetus, or the detection, from a biological fluid from an individual, of cell free DNA that originates from cells of a tumour. Accordingly, such methods have diagnostic, prognostic and/or predictive utility for detecting an increased risk of an individual suffering from or developing a medical condition such as preeclampsia or cancer, and/or (Continued)

to aid subsequent diagnostic, prognostic and/or predictive methods such as the detection of chromosomal trisomy in a foetus, including for twin-pregnancies. The present invention also relates to compositions, kits, computer program products and other aspects that are used in, useful for or related to the practice of such methods.

11 Claims, 3 Drawing Sheets

Specification includes a Sequence Listing.

(52) U.S. Cl.
CPC . *C12Q 2600/154* (2013.01); *C12Q 2600/158* (2013.01); *C12Q 2600/16* (2013.01)

(56) References Cited

U.S. PATENT DOCUMENTS

| | | | |
|---|---|---|---|
| 6,200,756 B1 | 3/2001 | Herman et al. | |
| 6,258,569 B1 | 7/2001 | Livak et al. | |
| 6,331,393 B1 | 12/2001 | Laird et al. | |
| 6,727,356 B1 | 4/2004 | Reed et al. | |
| 6,929,907 B2 | 8/2005 | Agris | |
| 9,822,412 B2 | 11/2017 | Gromminger et al. | |
| 9,822,413 B2 | 11/2017 | Gromminger et al. | |
| 10,017,818 B2 | 7/2018 | Gromminger et al. | |
| 2003/0148278 A1 | 8/2003 | Lauter et al. | |
| 2003/0165859 A1 | 9/2003 | Nazarenko et al. | |
| 2003/0211522 A1 | 11/2003 | Landes et al. | |
| 2004/0229211 A1* | 11/2004 | Yeung | C12Q 1/6883 435/5 |
| 2005/0239101 A1 | 10/2005 | Sukumar et al. | |
| 2006/0019278 A1 | 1/2006 | Lo et al. | |
| 2007/0059753 A1 | 3/2007 | Vener et al. | |
| 2011/0294676 A1* | 12/2011 | Cawthon | C12Q 1/686 506/7 |
| 2012/0040859 A1 | 2/2012 | Sparks et al. | |
| 2012/0065076 A1 | 3/2012 | Peters et al. | |
| 2012/0252015 A1 | 10/2012 | Hindson et al. | |
| 2012/0282613 A1 | 11/2012 | Patsalis et al. | |
| 2012/0302448 A1* | 11/2012 | Hutchison | C12Q 1/686 506/9 |
| 2013/0095496 A1* | 4/2013 | Schwers | C12Q 1/6851 435/6.12 |
| 2013/0288244 A1 | 10/2013 | Deciu et al. | |
| 2013/0337443 A1 | 12/2013 | Lo et al. | |
| 2015/0322511 A1* | 11/2015 | Gromminger | C12Q 1/6886 506/9 |
| 2015/0322513 A1* | 11/2015 | Gromminger | C12Q 1/6883 506/9 |
| 2017/0314073 A1* | 11/2017 | Grömminger | C12Q 1/6827 |
| 2019/0085402 A1 | 3/2019 | Kassis | |
| 2019/0249249 A1* | 8/2019 | Werler | C12Q 1/686 |

FOREIGN PATENT DOCUMENTS

| | | | |
|---|---|---|---|
| CN | 102625854 A | 8/2012 | |
| CN | 102648292 A | 8/2012 | |
| EP | 0 512 334 B1 | 9/1999 | |
| EP | 0 706 649 B1 | 1/2001 | |
| EP | 0 792 374 B1 | 1/2001 | |
| EP | 1524321 A1 | 4/2005 | |
| EP | 0 954 608 B1 | 5/2006 | |
| EP | 1 185 695 B1 | 7/2006 | |
| EP | 0 543 942 B2 | 11/2006 | |
| EP | 1 235 938 B1 | 2/2012 | |
| EP | 2942401 A1 * | 11/2015 | C12Q 1/6881 |
| EP | 3521454 A1 * | 8/2019 | C12Q 1/6827 |
| JP | 2005-261354 A | 9/2005 | |
| JP | 2007-532100 A | 11/2007 | |
| JP | 2013-538565 A | 10/2013 | |
| WO | 00/47764 A2 | 8/2000 | |
| WO | 03/020974 A2 | 3/2003 | |
| WO | 03/062441 A1 | 7/2003 | |
| WO | 2005/035725 A2 | 4/2005 | |
| WO | 2005/098029 A2 | 10/2005 | |
| WO | 2005/118852 A2 | 12/2005 | |
| WO | 2007/132166 A3 | 11/2007 | |
| WO | 2007/132167 A3 | 11/2007 | |
| WO | 2007/140417 A2 | 12/2007 | |
| WO | 2010/033639 A9 | 3/2010 | |
| WO | WO-2010075413 A1 * | 7/2010 | ........... C12Q 1/6851 |
| WO | 2011/018600 A1 | 2/2011 | |
| WO | 2011/034631 A1 | 3/2011 | |
| WO | 2011/092592 A2 | 8/2011 | |
| WO | 2012/007783 A1 | 1/2012 | |
| WO | 2012/092592 A1 | 7/2012 | |
| WO | 2012/149339 A2 | 11/2012 | |
| WO | 2013/057568 A1 | 4/2013 | |
| WO | 2013/132305 A1 | 9/2013 | |
| WO | 2014/011928 A1 | 1/2014 | |
| WO | 2014/043763 A1 | 3/2014 | |
| WO | 2014/055790 A2 | 4/2014 | |
| WO | 2014/168711 A1 | 10/2014 | |
| WO | 2015/013885 A1 | 2/2015 | |
| WO | 2015/138774 A1 | 9/2015 | |
| WO | 2017/220156 A1 | 12/2017 | |

OTHER PUBLICATIONS

Johnson et al. Clinical Chemistry. 2004. 50(3):516-521. (Year: 2004).*
Clausen et al. Fetal Diagn Ther. 2011. 29:155-163. (Year: 2011).*
Xia et al. Genetics and Molecular Biology. 2009. 31(1):20-24. (Year: 2009).*
Zhong et al. Swiss Med Wkly. 2001. 131:70-74. (Year: 2001).*
Deng et al. Prenat Diagn. 2006. 26:362-368. (Year: 2006).*
Kolialexi et al. European Journal of Obstetrics & Gynecology and Reproductive Biology. 2012. 161:34-37. (Year: 2012).*
Tounta et al. In vivo. 2011. 25:411-418. (Year: 2011).*
Macher et al. Clinica Chimica Acta. 2012. 413:490-494. (Year: 2012).*
Hahn et al. Annals of the New York Academy of Sciences. 2000. 906:148-152. (Year: 2000).*
Lo et al. Am J Hum Genet. 1998. 62:768-775. (Year: 1998).*
Ordonez et al. Fetal Diagn Ther. 2013. 34:13-18. (Year: 2013).*
Sperling et al., "Twin pregnancy: the role of ultrasound in management", Acta Obstet Gynecol Scand, 2001, vol. 80, pp. 287-299.
Sorenson et al., "Soluble Normal and Mutated DNA Sequences from Single-Copy Genes in Human Blood", Cancer Epidemiology, Biomarkers & Prevention, Jan./Feb. 1994, vol. 3, pp. 67-71.
Vasioukhin et al., "Point mutations of the N-ras gene in the blood plasma DNA of patients with myelodysplastic syndrome or acute myelogenous leukaemia", British Journal of Haematology, 1994, vol. 86, pp. 774-779.
Lo et al., "Presence of fetal DNA in maternal plasma and serum", The Lancet, Aug. 16, 1997, vol. 350, pp. 485-487.
Muller et al., "Methylated DNA as a possible screening marker for neoplastic disease in several body fluids", Expert Rev. Mol. Diagn., 2003, vol. 3(4), pp. 443-458.
Lo et al., "Quantitative Analysis of the Bidirectional Fetomaternal Transfer of Nucleated Cells and Plasma DNA", Clinical Chemistry, 2000, vol. 46:9, pp. 1301-1309.
Smid et al., "Correlation of fetal DNA levels in maternal plasma with Doppler status in pathological pregnancies", Prenat Diag, 2006, pp. 785-790.
Lo et al., "Rapid Clearance of Fetal DNA from Maternal Plasma", Am. J. Hum. Genet, 1999, vol. 64, pp. 218-224.
Kawai et al., "Methylation profiles of genomic DNA of mouse developmental brain detected by restriction landmark genomic scanning (RLGS) method", Nucleic Acids Research, 1993, vol. 21:24, pp. 5604-5608.
Masuzaki et al., "Detection of cell free placental DNA in maternal plasma: direct evidence from three cases of confined placental mosaicism", J. Med. Genet, 2004, vol. 41, pp. 289-292.

(56) References Cited

OTHER PUBLICATIONS

Flori et al., "Circulating cell-free fetal DNA in maternal serum appears to originate from cyto- and syncytio-trophoblastic cells. Case Report", Human Reproduction, Jan. 29, 2004, vol. 19:3, pp. 723-724.
Chim et al., "Detection of the placental epigenetic signature of the maspin gene in maternal plasma", Proc. Natl. Acad. Sci. USA, Oct. 11, 2005, vol. 102:41, pp. 14753-14758.
Chiu et al., "Hypermethylation of RASSF1A in Human and Rhesus Placentas", The American Journal of Pathology, Mar. 2007, vol. 170:3, pp. 941-950.
Old et al., "Candidate epigenetic biomarkders for non-invasive prenatal diagnosis of Down syndrome", Reproductive BioMedicine Online, Jun. 21, 2007, vol. 15:2, pp. 227-235.
Chim et al., "Systematic Search for Placental DNA-Methylation Markers on Chromosome 21: Toward a Maternal Plasma-Based Epigenetic Test for Fetal Trisomy 21", Clinical Chemistry, 2008, vol. 54:3, pp. 500-511.
Lo et al., "Prenatal Diagnosis of Fetal RhD Status by Molecular Analysis of Maternal Plasma", The New England Journal of Medicine, Dec. 10, 1998, vol. 339, pp. 1734-1738.
Go et al., "Non-invasive aneuploidy detection using free fetal DNA and RNA in maternal plasma: recent progress and future possibilities", Human Reproduction update, 2011, vol. 17:3, pp. 372-382.
Lo et al., "Quantitative Analysis of Fetal DNA in Maternal Plasma and Serum: Implications for Noninvasive Prenatal Diagnosis", Am. J. Hum. Genet., 1998, vol. 62, pp. 768-775.
Lo et al., "Quantitative Abnormalities of Fetal DNA in Maternal Serum in Preeclampsia", Clinical Chemistry, 1999, vol. 45:2, pp. 184-188.
Yu et al., "Quantification of Maternal Serum Cell-Free Fetal DNA in Early-Onset Preeclampsia", Int. J. Mol. Sci, Apr. 8, 2013, vol. 4, pp. 7571-7582.
Hahn et al., "Cell-Free Nucleic Acids as Potential Markers for Preeclampsia", Placenta, 2011, vol. 32, pp. S17-S20.
Li et al., "Hypermethylation of multiple tumor-related genes associated with DMNT3b upregulation served as a biomarker for early diagnosis of esophageal squamous cell carcinoma", Epigenetics, Mar. 2011, vol. 6:3, pp. 307-316.
Ha et al., "Elevated Levels of Cell-Free Circulating DNA in Patients with Acute Dengue Virus Infection", PLOS One, Oct. 7, 2011, vol. 6:10, e25969, pp. 1-7.
Outinen et al., "Plasma Cell-Free DNA Levels Are Elevated in Acute Puumula Hantavirus Infection", PLOS One, Feb. 7, 2012, vol. 7:2, e31455, pp. 1-7.
Forsblom et al., "High Cell-Free DNA Predicts Fatal Outcome among *Staphylococcus aureus* Bacteraemia Patients with Intensive Care Unit Treatment", Plos One, Feb. 10, 2014, vol. 9:2, e87741, pp. 1-9.
Chan et al., "Size Distributions of Maternal and Fetal DNA in Maternal Plasma", Clinical Chemistry, 2004, vol. 50:1, pp. 88-92.
Kimura et al., "Fragment Size Analysis of Free Fetal DNA in Maternal Plasma Using Y-STR Loci and SRY Gene Amplification", Nagoya J. Med. Sci., 2011, vol. 73, pp. 129-135.
Lo et al., "Maternal Plasma DNA Sequencing Reveals the Genome-Wide Genetic and Mutational Profile of the Fetus", Science Translational Medicine, Dec. 8, 2010, vol. 2:61, 61ra91 pp. 1-14.
Elshimali et al., "The Clinical Utilization of Circulating Cell Free DNA (CCFDNA) in Blood of Cancer Patients", International Journal of Molecular Sciences, 2013, vol. 14, pp. 18925-18958.
Sacha Zeerleder, "The struggle to detect circulating DNA", Critical Care, 2006, vol. 10:142, pp. 1-3.
Kirsch et al., "An Improved Method for the Isolation of Free-Circulating Plasma DNA and Cell-Free DNA from Other Body Fluids", Ann. N.Y. Acad. Sci., 2008, vol. 1137, pp. 135-139.
Struble et al., "Fetal Fraction Estimate in Twin Pregnancies Using Directed Cell-Free DNA Analysis", Fetal Diagnosis and Therapy, Dec. 7, 2013, pp. 1-5.

Gauthier et al., "Blood Clearance Kinetics and Liver Uptake of Mononucleosomes in Mice", The Journal of Immunology, 1996, vol. 156, pp. 1151-1156.
Lo et al., "Quantitative Analysis of Aberrant p16 Methylation Using Real-Time Quantitative Methylation-specific Polymerase Chain Reaction", Cancer Research, Aug. 15, 1999, vol. 59, pp. 3899-3903.
Birch et al., "Accurate and Robust Quantification of Circulating Fetal and Total DNA in Maternal Plasma from 5-41 Weeks of Gestation", Clinical Chemistry, 2005, vol. 51:2, pp. 312-320.
Papageorgiou et al., "Fetal-specific DNA methylation ratio permits non-invasive prenatal diagnosis of trisomy 21", Nat. Med., Apr. 7, 2011, vol. 17:4, pp. 1-13.
Tong et al., "Technical concerns about immunoprecipitation of methylated fetal DNA for noninvasive trisomy 21 diagnosis", Nature Medicine, Sep. 2012, vol. 18:9, pp. 1327-1328.
Hindson et al., "High-Throughput Droplet Digital PCR System for Absolute Quantitation of DNA Copy Number", Anal. Chem., 2011, vol. 83, pp. 8604-8610.
White et al., "Evaluation of a Novel Assay for Detection of the Fetal Marker RASSF1A: Facilitating Improved Diagnostic Reliability of Noninvasive Prenatal Diagnosis", PLoS One, Sep. 14, 2012, vol. 7:9, e45073 pp. 1-5.
Qu et al., "Noninvasive Prenatal Determination of Twin Zygosity by Maternal Plasma DNA Analysis", Clinical Chemistry, 2013, vol. 59:2, pp. 427-435.
Lim et al., "Disease specific characteristics of fetal epigenetic markers for non-invasive prenatal testing of trisomy 21", BMC Medical Genomics, 2014, vol. 7:1, pp. 1-11.
Poon et al., "Differential DNA Methylation between Fetus and Mother as a Strategy for Detecting Fetal DNA in Maternal Plasma", Clinical Chemistry, 2002, vol. 48:1, pp. 35-41.
Yegnasubramanian et al., "Combination of methylated-DNA precipitation and methylation-sensitive restriction enzymes (COMPARE-MS) for the rapid, sensitive and quantitative detection of DNA methylation", Nucleic Acids Research, 2006, vol. 34:3, e19 pp. 1-14.
Papantoniou et al., "RASSF1A in maternal plasma as a molecular marker of preeclampsia", Prenatal Diagnosis, 2013, vol. 33, pp. 682-687.
Zeybek et al., "Clinical evaluations of cell-free fetal DNA quantities in pre-eclamptic pregnancies", J. Obstet Gynaecol Res., Mar. 2013, vol. 39:3, pp. 632-640.
Jakobsen et al., "Identifying mild and severe preeclampsia in asymptomatic pregnant women by levels of cell-free fetal DNA", Transfusion, Sep. 2013, vol. 53, pp. 1956-1964.
Chen et al., "Chimerism in Monochorionic Dizygotic Twins: Case Study and Review", Am. J. Med. Genet. Part A, May 22, 2013, vol. 161A, pp. 1817-1824.
Chan et al., "Hypermethylated RASSF1A in Maternal Plasma: A Universal Fetal DNA Marker that Improves the Reliability of Noninvasive Prenatal Diagnosis", Clinical Chemistry, 2006, vol. 52:12, pp. 2211-2218.
Stumm et al., "Diagnostice accuracy of random massively parallel sequencing for non-invasive prenatal detection of common autosomal aneuploidies: a collaborative study in Europe", Prenatal Diagnosis, 2014, vol. 34, pp. 185-191.
Leung et al., "Noninvasive twin zygosity assessment and aneuploidy detection by maternal plasma DNA sequencing", Prenatal Diagnosis, 2013, vol. 33, pp. 675-681.
International Search Report and Written Opinion dated Feb. 3, 2017 from International Application No. PCT/EP2016/077065, 14 pages.
International Search Report and Written Opinion dated Aug. 19, 2015 from International Application No. PCT/EP2015/060188, 16 pages.
Singaporean Search Report and Written Opinion dated Nov. 16, 2017 from Singaporean Application No. 11201608993R, 11 pages.
European Search Report and Written Opinion dated Mar. 18, 2016 from European Application No. 15193966, 9 pages.
Norwitz et al., "Noninvasive Prenatal Testing: The Future is Now", Reviews in Obstetrics & Gynecology, 2013, vol. 6, No. 2, pp. 48-62.
Lim et al., "Non-Invasive Epigenetic Detection of Fetal Trisomy 21 in First Trimester Maternal Plasma", PLoS One, Nov. 2011, vol. 6, No. 11, e27709, 8 pages.

(56) References Cited

OTHER PUBLICATIONS

Tong et al., "Noninvasive Prenatal Detection of Trisomy 21 by an Epigenetic-Genetic Chromosome-Dosage Approach", Clinical Chemistry, 2010, vol. 56, No. 1, pp. 90-98.
Tsaliki et al., "MeDIP real-time qPCR of maternal peripheral blood reliably identifies trisomy 21", Prenatal Diagnosis, 2012, vol. 32, pp. 996-1001.
Lim et al., "Non-invasive detection of fetal trisomy 21 using fetal epigenetic biomarkers with a high CpG density", Clin Chem Lab Med, 2014, vol. 52, No. 5, pp. 641-647.
Chim et al., "Potentail application of fetal epigenetic markers on the non-invasive prenatal detection of chromosomal abnormality", Clin Chem Lab Med, 2014, vol. 52, No. 5, pp. 585-588.
Yin et al., "Placental methylation markers in normal and trisomy 21 tissues", Prenatal Diagnosis, 2014, vol. 34, pp. 63-70.
Tong et al., "Detection of Restriciton Enzyme-Digested Target DNA by PCR Amplification Using a Stem-Loop Primer: Application to the Detection of Hypomethylated Fetal DNA in Maternal Plasma", Clinical Chemistry, 2007, vol. 53, No. 11, pp. 1906-1914.
Ragione et al., "Differential DNA Methylation as a Tool for Non-invasive Prenatal Diagnosis (NIPD) of X Chromosome Aneuploidies", Journal of Molecular Diagnostics, Nov. 2010, vol. 12, No. 6, pp. 797-807.
Tong et al., "Diagnostic developments involving cell-free (circulating) nucleic acids", Clinical Chimica Acta, 2006, vol. 363, pp. 187-196.
Hatt et al., "Microarray-Based Analysis of Methylation Status of CpGs in Placental DNA and Maternal Blood DNA—Potential New Epigenetic for Cell Free Fetal DNA-Based Diagnosis", PLoS One, Jul. 31, 2015, vol. 10, No. 7, e0128918, 12 Pages.
Tong et al., "Noninvasive Prenatal Detection of Fetal Trisomy 18 by Epigenetic Allelic Ratio Analysis in Maternal Plasma: Theoretical and Empirical Considerations", Clinical Chemistry, 2006, vol. 52, No. 12, pp. 2194-2202.
Papageorgiou et al., "Sites of Differential DNA Methylation between Placenta and Peripheral Blood", The American Journal of Pathology, May 2009, vol. 174, No. 5, pp. 1609-1618.
He et al., "Development of a multiplex MethyLight assay for the detection of multigene methylation in human colorectal cancer", Cancer Genetics and Cytogenetics, Oct. 1, 2010, vol. 202:1, pp. 1-10.
Olkhov-Mitsel et al., "Novel Multiplex MethyLight Protocol for Detection of DNA Methylation in Patient Tissues and Bodily Fluids", Scientific Reports, Mar. 21, 2014, vol. 4: 4432, pp. 1-8.
Snellenberg et al., "Development of a multiplex methylation-specific PCR as candidate triage test for women with an HPV-positive cervical scrape", BMC Cancer, Nov. 23, 2012, vol. 12:551, pp. 1-10.
Nygren et al., "Quantification of Fetal DNA by Use of Methylation-Based DNA Discrimination", Clinical Chemistry, Aug. 20, 2010, vol. 56:10, pp. 1627-1635.
Campan et al., "MethyLight", DNA Methylation: methods and Protocols, Second Edition , 2009, vol. 57, pp. 325-337.
Swift-Scanalan et al., "Two-color quantitative multiplex methylation-specific PCR", ' BioTechniques, Feb. 1, 2006, vol. 40:2, pp. 210-219.
Weisenberger et al., "Analysis of repetitive element DNA methylation by MethyLight", Nucleic Acids Research, Dec. 2, 2005, vol. 33:21, pp. 6823-6836.
Weisenberger et al., "DNA methylation analysis by digital bisulfite genomic sequencing and digital MethyLight", Nucleic Acids Research, Aug. 1, 2008, vol. 36:14, pp. 4689-4698.
Indian Office Action dated Jun. 30, 2020 for Indian Patent Application No. 201617040933 (Controller, Dr. Jyoti), 8 pages.
Japanese Office Action dated Mar. 19, 2019 for Japanese Patent Application No. 2016-566621, 13 pages with English translation.
Lee et al., "Non-Invasive Prenatal Testing of Trisomy 18 by an Epigenetic Marker in First Trimester Maternal Plasma", PLOS ONE, Nov. 2013, vol. 8, No. 11, 8 pages.
Papageorgiou et al., "Non-invasive prenatal diagnosis of aneuploidies: new technologies and clinical applications", Genome Medicine, 2012, vol. 4, No. 5, 12 pages.
Russian Office Action dated Dec. 27, 2018 for Russian Patent Application No. 2016147914, 13 pages with English translation.

* cited by examiner

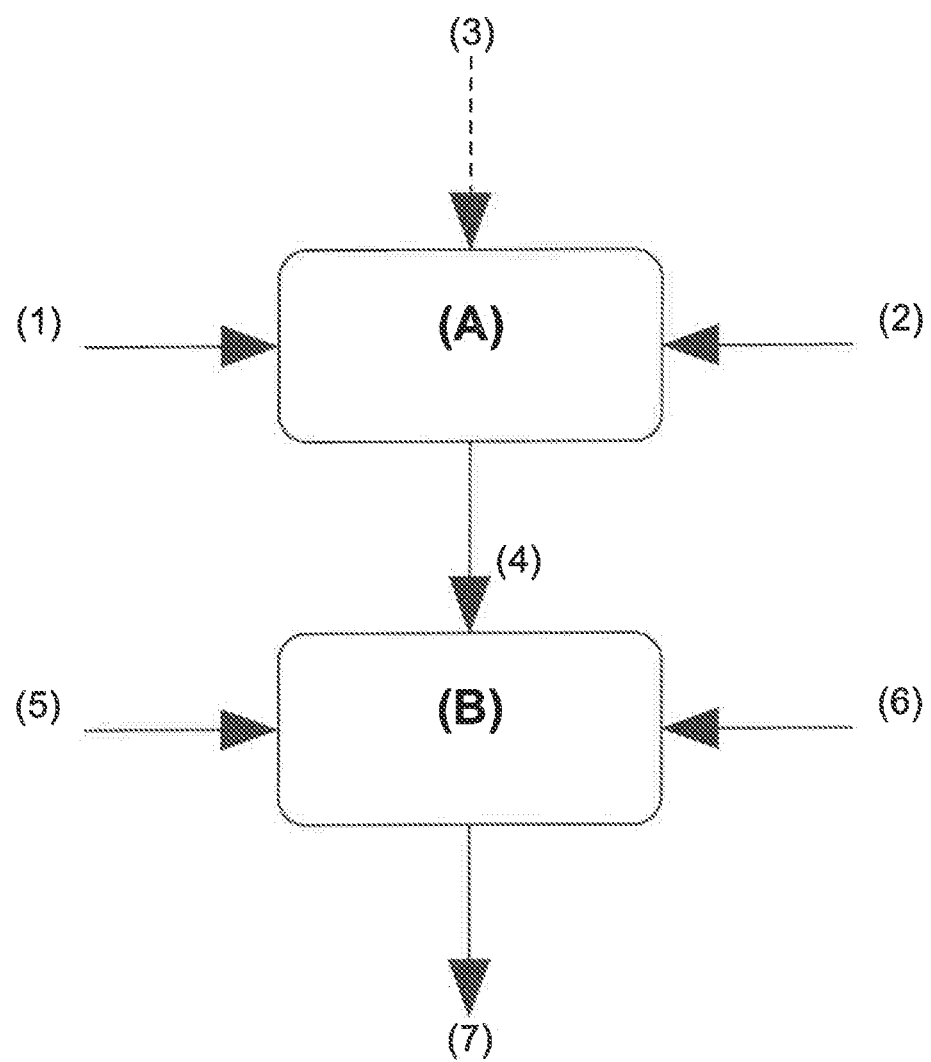

SEQUENCE LISTING

<160> NUMBER OF SEQ ID NOS: 199

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
attgagctgc gggagctggc                                              20

<210> SEQ ID NO 2
<211> LENGTH: 18
<212> TYPE: DNA
<213> ORGANISM: Artificial Sequence
<220> FEATURE:
<223> OTHER INFORMATION: Primer

<400> SEQUENCE: 2
tgccgtgtgg ggttgcac                                                18

<210> SEQ ID NO 3
<211> LENGTH: 15
<212> TYPE: DNA
<213> ORGANISM: Artificial Sequence
<220> FEATURE:
<223> OTHER INFORMATION: Probe

<400> SEQUENCE: 3
acccggctgg agcgt                                                   15

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ggtcatccac caccaagaac                                              20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
tgcccaagga tgctgtcaag                                              20

<210> SEQ ID NO 6
<211> LENGTH: 20
<212> TYPE: DNA
<213> ORGANISM: Artificial Sequence
<220> FEATURE:
<223> OTHER INFORMATION: Probe

<400> SEQUENCE: 6
gggcctcaat gacttcacgt                                              20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ggtgcgaact cctctttgtc                                              20

<210> SEQ ID NO 8
<211> LENGTH: 20
<212> TYPE: DNA
<213> ORGANISM: Artificial Sequence

```
<220> FEATURE:
<223> OTHER INFORMATION: Primer

<400> SEQUENCE: 8
ttaatcaccc agcgcatggc                                                   20

<210> SEQ ID NO 9
<211> LENGTH: 20
<212> TYPE: DNA
<213> ORGANISM: Artificial Sequence
<220> FEATURE:
<223> OTHER INFORMATION: Probe

<400> SEQUENCE: 9
ccctcccggt gggtgataaa                                                   20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tgttcactgg aggactcatc                                                   20

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
cagtccatga gggtgtttg                                                    19

<210> SEQ ID NO 12
<211> LENGTH: 18
<212> TYPE: DNA
<213> ORGANISM: Artificial Sequence
<220> FEATURE:
<223> OTHER INFORMATION: Probe

<400> SEQUENCE: 12
gaggtcccat tctccttt                                                     18

<210> SEQ ID NO 13
<211> LENGTH: 18151
<212> TYPE: DNA
<213> ORGANISM: Homo sapiens
<220> FEATURE:
<221> NAME/KEY: misc_feature
<223> OTHER INFORMATION: RASSF1

<400> SEQUENCE: 13
gacttggcgt ctgaggacag agtccagacc acaaggatct ggagctcagg agagactcgt        60
gggccacagc ccgagaaagc gctgggaatc caaatactat ggcgattggc agtcgcgtag       120
gcgaggcggg ctagagaccc gcccggattt aggcgcgagc cacctccagg ggcggggccc       180
aggccgcact gcgcaggcgc ggctaacccg tttccatggc tgcgagaact gacgctcccc       240
aaccgtcccg caactgtcct gtcccagact ttggcaccgt cggggtccgt cgtcccgaa        300 tgtgacagca tccccacccc ggctgctgcc caggatccgc cggaccccgg cctcgatatg       360
ggagacctgg aactgctgct gcccggggaa gctgaagtgc tggtgcgggg tctgcgcagc       420
```

-continued

```
ttcccgctac gcgagatggg ctccgaaggg tgaggcaccc gggtcaggcg gagtcccgga    480
gtcattgtcc ttgagtcggg gagctggggc ctgactcggg ggaggggctg cccagtgtgg    540
aggggctccc aaatggggga gcagagcgtt ccgagacagg agtattactg ctcctgagcc    600
ccctgtgtcc cctcaggatc aggttaggct tcagtaggat ccagccccca tccccactcc    660
taatgcacac acgtggacgc acatgcactt accctctgag gcaggtggaa ccagcagcat    720
gagaacctgg agaagctgaa catgcaagcc atcctcgatg ccacagtcag ccagggcgag    780
cccattcagg agctgctggt cacccatggg aaggtacccc gaggtcacag gcagggttcc    840
tgccttcccc catacctcac ctactctacc cctccggagt cccctgtgtg cccttcccct    900
ctggcctggt acacctgttc tccctgaagg acaaagagga atgtgttaca tgtttcattt    960
tgtatcccta ttggacagga ctctggcaca ccaggctggg tgcagggcat gagttgatta    1020
gggagaaagc tgtaggtcct agaacagctt aggcttcaag gggaaggccc aaatgctaaa    1080
ggcatctgtg aattgactgt aaggctggtg gtggggaagg ggtggggagg ggttggggag    1140
ggcgggaggg aggggagata acctaactgg aagtggaact tcggcatgga aggaagcagc    1200
cttcccaaca tgaagggggg aagttagaaa ccagggagag gcctggctgg aacatggacc    1260
agggagtgtc accagcagat gacctgagat atcaattgac caaaaaaaaa aaaaaaaag    1320 ccgggcatgg tagctcatgc ctgttatccc agcattttgg gaggccaaga cgggtggatc    1380
atctgaggtc aggagttcaa ggccagcctg gccaacatgg tgaaacccca cctctactaa    1440
aaatacaaaa atttgcagag catggtggtg cacacctgta atcccagcta ctcgggaggc    1500
tgaggcagga gaatcgcttg aacctgggag gcagaggtta cagagagcca agatcatgcc    1560
actgcactcc agcctgggtg acaagagtga aactccgtct caaaaaaaaa aaaaaaaaa    1620 agaaaggtcc tttgcaaaag aaagatggaa ctcatactag gggataggat aggaacaggg    1680
cactgtgaag ggtcctgagt aggagtgagg ccaaggcaca caagagcttt ggaggaccac    1740
agacagggac tagaggagg gcatgaggag aagggctggc ttgaaaggga tgcctgaatg    1800
ggcgggcaga ggataagggt gcaggtgcag gcagggcaag gcagtctggg aactgggcag    1860
gagccagtca cataagcatg agggacatcc acagaggtgt tgggagcagc tggtaatgaa    1920
ggtccaaggt gcaagagaga agtcaggaag gatactcatg ggtctggaat agtttagggg    1980
cccagcagtg tttggggata tcaggttga gctgagccgg ggatggagg gttgccaggc    2040 aaaggtaggc ccatctcatc cctgtccttt accctaccct tcaaaggtcc caacactggt    2100
ggaggagctg atcgcagtgg agatgtggaa gcagaaggtc ttccctgtgt tctgcagggt    2160
ggaggacttc aagccccaga acaccttccc catctacatg gtggtgagct gggcccctgg    2220
ttcatacctc tttctcactcc ttcagagggc tctggaccgg ggaggagagc tggtagcccc    2280
tatcccttcc tcaggccctg tccttctctt tatctgacag gtgcaccacg aggcctccat    2340
catcaacctc ttggagacag tgttcttcca caaggtgagg gactatctct gcccatgggc    2400
cacagttccg ggtcagggcc tggcaggaag ggagattgtg tctgtgtggg gaaggcatca    2460
gacacagaaa gtttcctcc tccttttccc aggaggtgtg tgagtcagca gaagacactg    2520
tcttggactt ggtagactat tgccaccgca aactgaccct gctggtggcc cagagtggct    2580
gtggtggccc ccctgagggg gagggatccc aggacagcaa cccatgcag gtgggttgag    2640 gttacctagg gttgtgaaag cctaggtctg ggttccccaa ggcctgcgca ggtgagggtg    2700
gcccagcgtg aacactgtgt gacctcccag gagctgcaga agcaggcaga gctgatggaa    2760
```

```
tttgagattg cactgaaggc cctctcagta ctacgctaca tcacagactg tgtggacagg    2820
tgagcagtcc gactgggcct gggcctactg tggagggctg gaagaccggg cctgtagcct    2880
gcctctactc acctccttca caacgtccct gccctagcc tctctctcag caccttgagc    2940
cgtatgctta gcacacacaa cctgccctgc ctcctggtgg aactgctgga gcatagtccc    3000
tggagccggc gggaaggagg tagggtcctc ccccaccagc ctaagcccca ggctactgct    3060
tcagggtatc tttttgatag aggggggcag cttgcacaca cgaagacaaa ccctgtcccc    3120
aagcccactg aggataccag gatgcctcag ccaaggttgg cctagacctg agctctgcag    3180
caggccaggc ccatgtgtcc actactgagg ctcaccctgc tctggggtca gcagccctat    3240
agcctgggca agtcctgcag cccaggttct cccattccca ggcagtggtc agtctcccag    3300
cccccacagc tggctcactt gaagagaatt caacgtctgc acccagtgtg ctggttcctc    3360
tccccaggca agctgcagca gttcgagggc agccgttggc atactgtggc cccctcagag    3420
cagcaaaagc tgagcaagtt ggacgggcaa gtgtggatcg ccctgtacaa cctgctgcta    3480
agccctgagg ctcaggcgcg ctactgcctc acaagttttg ccaagggacg gctactcaag    3540
gtcagactcc ctccgcacca gcccccacag ccccagtacc gccctcccca tcctaccccg    3600
actgcgtccc tgctgtttat ctttgcccac ccacctcaac cccagtgctc ttttcagtcc    3660
ttgggcctca ggtgacacac cagctagtgg gacatgggcc cccacaggca ttctcagccc    3720
aacccagccc cttccttttc cttggccccc tggccagcac ctgcatcaca ctggcctcca    3780
ctggacaccc ttgcagcttc gggccttcct cacagacaca ctgctggacc agctgcccaa    3840 cctgcccac ttgcagagtt tcctggccca tctgaccta actgaaaccc agcctcctaa    3900
gaaggacctg gtgttggaac aggtaggcac tggaaagtta gctgctcagg accactgtcc    3960
cactttacca gcaccttcct gccactctcc acttctctct cctagatccc agaaatctgg    4020
gagcggctgg agcgagaaaa cagaggcaag tggcaggcaa ttgccaagca ccagctccag    4080
catgtgttca gcccctcaga gcaggacctg cggctgcagg cgcgaaggta aggcctgtgg    4140
aaatggcagg gagggtggag gggatgcagg aggcatggat gtgggtgggg tgccccacc    4200 ttccagggcc agtcagacct tcctgacttt cccccaggtg ggctgagacc tacaggctgg    4260
atgtgctaga ggcagtggct ccagagcggc cccgctgtgc ttactgcagt gcagaggctt    4320
ctaagcgctg ctcacgatgc cagaatgagt ggtattgctg caggtgaggg tatcctagaa    4380
ccttggacct ctaagcccta ctcccacatc ccccacatgc attgccatcc tcaataccca    4440
cctgcctgca gggagtgcca agtcaagcac tgggaaaagc atggaaagac ttgtgtcctg    4500
gcagcccagg gtgacagagc caaatgaggg ctgcagttgc tgagggccga ccacccatgc    4560
caagggaatc cacccagaat gcaccccctga acctcaagat cacggtccag cctctgccgg    4620
agccccagtc tccgcagtgg agagcagagc gggcggtaaa gctgctgacc gatctccctc    4680
ctcctcaccc caagtgaagg ctcgagactt cctgccccac ccagtgggta ggccaagtgt    4740
gttgcttcag caaaccggac caggagggcc agggccggat gtgggaccc tcttcctcta    4800 gcacagtaaa gctggcctcc agaaacacgg gtatctccgc gtggtgcttt gcggtcgccg    4860
tcgttgtggc cgtccgggt ggggtgtgag gaggggacga aggagggaag gaagggcaag    4920 gcggggggggg ctctgcgaga gcgcgcccag ccccgccttc gggccccaca gtccctgcac    4980 ccaggttttcc attgcgcggc tctcctcagc tccttcccgc cgcccagtct ggatcctggg    5040
ggaggcgctg aagtcgggc ccgccctgtg gcccgcccg gccgcgcttt gctagcgccc    5100
aaagccagcg aagcacgggc ccaaccgggc catgtcgggg gagcctgagc tcattgagct    5160
```

```
gcgggagctg gcacccgctg ggcgcgctgg gaagggccgc acccggctgg agcgtgccaa   5220
cgcgctgcgc atcgcgcggg gcaccgcgtg caacccaca cggcagctgg tccctggccg    5280
tggccaccgc ttccagcccg cggggcccgc cacgcacacg tggtgcgacc tctgtggcga   5340
cttcatctgg ggcgtcgtgc gcaaaggcct gcagtgcgcg cgtgagtagt ggccccgcgc   5400
gcctacgaga gcggaagggg cagccaaggg gcagcgcagt cgccgcgggt caagtcgcgg   5460 cagaggggt cggcggggac agctcccgag gactaggtcc gttactttcg ccccatcgct    5520
gaagagtgcg cgaaaatggt ttatcccttg tcgcactcca ctcgtatctg ggccacagat   5580
gagcagaggt ggctgcttat atgtaaaaat acgctgattt taagtttctt atctttaaaa   5640
tgccttggcc cttcttgaga aagggtttgt gcctactgtc ctcggagtcc atcttcccag   5700
gcttgcctct tctcaaacac tcatgacccc ctccagaacc tttagggtga agggaaatta   5760
ccacctatgg gagggagcct ggaaaaattt agaaccctttg gtgggccccc tgcaagcagg  5820
agttttgttg agtctttatt tagcaaacac ccttttctga cccagtgaat cagatgctaa   5880
aatatgcacg cagccacaca cccagcagtc cttctgcacc cctgggaatc gccagcaagc   5940
aaaggttgct ctcccctggg tagacaccag ctggaatcac caggggtgct tttacagtcc   6000
tccccgctag cctggatccc accgcagacc tgttgaatca actgctggga gtggaccta    6060 ggcatcagta aattttaaaa actcccccaaa ttattgtaac atggagtctg ggttgagcat   6120
cactgctctg gcctatttag gaacttgtgg atggatagtg tcccaggtct gtgtgtgcat   6180
ggagaccctc tcatccggta caagaggaca tcacaaattc agctgggggg agcacaaagt   6240
tgtgacagaa tgcaaagaat gaacaagggg ccgagcgcgg tggctcatgc ctgtaatccc   6300
agcacttcgg aaggcggagg cgggtggatc acctgaggtc aggagttcaa gaccagcctg   6360
gccaacatgg tgaaacctca tgtctactaa aaaataaaaa aaaatgagcc aggcgtagtg   6420
gcgggtgcct gtaatcccag ctactcggga ggctgaggtg ggagaattgc ttgaacacag   6480
gaggcggagg ttgcagtgag ccgagatcgt gccactgccc tccagccttg gcgacagagt   6540
gagactctgt ctcaaaaaaa aaaaaaaaa aaaaagaac aaggctggga cattgcagcg     6600
ttctcaaaga gaaataaagt agccatggag ataagaagca ggatgatttg gcatgtttta   6660
tcagaggtag agacaaggga gaaatcaaag ataagtttgg gcttttgtct ccagtaactg   6720
ggagcctagt ggccattttt gctgcaaaga ggaagctggg caagtgtagc agtgaggctg   6780
aagaaaaggg aattaaattt tggccatgtt cacttgaaac gtcttttaga catcctagtg   6840
aaggtactgg cacggaggat ctagtctgag ggtttaggtc agtgtttcag ccgtggatct   6900
ggggcagatg aatgtagaca gaccaggcca gtgatcagga ctgagcccag acttcatcgt   6960
gagatatgga agttgagtca gaatctgcaa aggagctgag caggagctgc aggggtagg    7020 aggaaaactg ggagagtgta gcccctggga gtcaaaggga gcaagcttca aatgatgctg   7080 aggggtgag aatggagaat ggaacactgg attccatttg gtagtacaca gatcgctgag    7140
gaccctgtcc cggcagtttt cctggaggaa gaggcaagcc tggctggagt gggtagaggg   7200
gagagtgaag gcgaaggatt agagtgtata gagaccagtg tcttggtctg aggggagtag   7260
agacaggtga caaccacagg gcagacgtag gttaaaggtg tttagttttt ccttcaagta   7320
aatgggcaga tgtattccat atacgttccc agtgaagggc cgggtgcggt ggctcaagcc   7380
tgtagtccca gcactttgga aggccgaggc gggtggatca cctgagatca ggagtttgag   7440
accagcctgg ctaacatggt gaaaccccgt ctctactaaa aatacaaaaa ttagctgggc   7500
```

```
atggtggcgg gcgcctgtaa tcctaggtac tcaggaggct gaggcagaag aatcgcttga    7560
acccaggagg cggaggttgc ggtgagccga aatcgcgcca ttgcactcca gcctgggtga    7620
caaaagcaag acgcagtttt ttgttgttgt tttttaatt gccaatgagg aaaggggaag     7680
ttctgtgcta ggcgatagag atccaactgt tgagcaggcc tctctgcctg tggccttccg    7740
gccggtttcc agacgcccag gtggccaaca ttagagtccg cgtagcagtg tgaggtaacc    7800
cactgagata ggtcgggcct gcggagcctg cgagcagcg gccctctccc tggggcttcc     7860
cttcaatctc cgggacattt ccccgacctg gagctcctcc gcctcaccgc caggcctctc    7920
tgcagattgc aagttcacct gccactaccg ctgccgcgcg ctcgtctgcc tggactgttg    7980
cgggccccgg gacctgggct gggaacccgc ggtggagcgg gacacgaacg tggtgagcgc    8040
ggggccgagg gcgtatggga agggcgagga tgggcaggcc acagtgcagg cattctcgag    8100
ggctgcctgg gtgccgcgcg caaggagcgt tctaattgcc gatttcccgg cggcacagag    8160
aggctaattc tgcgcggggg ctgggagggg agcctggatt gccggctccg caagtactcc    8220
acccgctgca agcggacccg ggcccaggct gacccaggct ccgcgcacgc gcacttcccg    8280
caccttcccg ccctcgcctc cggccagagg ccactcttgt gcgcttgccc ggacgctggc    8340
acccgccccc gttccctgtg gtaggtgggg tctgtgagtg gagctccgga gcgatgaggt    8400
cattcctggg ggcgaagcgt gcgtgtcccc gccccggcgt tcctgcccca atgagacaag    8460
agctagatcc cggcgatcta cgtttcagtc ttaacggttg cggcgcggct ctggcccggg    8520
cgcacgcgca cactgacacg cgtacacgca cgcacgcgac cggggcggtg gttggcggct    8580
acggacgcgc aggactgggg gacgggcggg tacggctatg ggcgaggcgg aggcgccttc    8640
tttcgaaatg acctggagca gcacgacgag cagtggctac tgcagccaag aggactcgga    8700
ctcggagctc gagcagtact tcaccgcgcg aacctcgcta gctcgcaggc cgcgccggga    8760
ccaggtggga gccaggggt gccggcgggc gggaggggaa gcggtcgctg gagctccgcc     8820
ctccccggtc cgttgccgcg tcctgggtcg gtgggcagcc ccaccctcct ggctacgtgg    8880
ctccccgcgg gtcctggccg gggacctgcc cgcggaaccg tgcgtaagac cccgattcca    8940
ccgcctagat gctgggtgcc ggggcccect tggtttctgt cacagacagg ttgaacacgg    9000
aaaaagcagc tgtatggctt gtggtagacc tgagccgggc attatccagc tatgactaaa    9060
gccgaccgag cagtttggac tagcacctcg atttccgcgt tcgaatgctc ctgctccctc    9120
cttggggaga ctaggggagg atgtggagag gaagagtcc tcgccaggaa ttgagaagta     9180
tgtttaggaa aacttgagag gcagagagag atcctgctcc tccatctgca ctcctgtatg    9240
gagccagctg agccctcacc tcttccctgt tctggcctgt caccagctgc tggaatgtgg    9300
aagattctgt tcccttcctc tagggtggat ctggagaaag atttgggaat agataggaaa    9360
gaagtcttgt tttggaccat aagcattcag gagcacttta cccacaggaa ggggggaaagc   9420 tagattataa aatgcctaaa gaggtggaaa aagagatcca ggttactaac ccaggactgt    9480
aaggtgtctc ggaacctcct aggtatcccc attatcggag aactgtgtgc cagatgccat    9540
tggtgtgacc accaggctca gagaaccagg cctaggcacc aggaaaaaga acagggact     9600 gtgaagctca gtatgcctgg cagaaatggg gcggaaatcc ttatttaagt aaagaaagtg    9660
gagttgtgag tgatgcttca gataaaattt tacaaaattc cttacaaaat gggtggtgct    9720
cagcacgcca aaatcttagc ccagagcttg ggtgcaaggg ttgagttgag tgtagacccc    9780
tgggcttgtc ttcatgtcag tcagtcctga gccatttcc actgtggaaa ggtgggaaaa     9840
ccacaagaca ctaaccaatt gaaaaggagg gctagccacg gaggtgcaca cctgtaatcc    9900
```

```
cagctacttg ggagggtgag gcagaaggat cacttgaacc tgggaggcag aggttgcagt    9960
gagccaagat cgtgccactg cactccagcc tgagtgacag agtgagactc tgtctcaaaa   10020
atagaaaagg aagccaagta cggtggctca cacctctaat gccaatgctt tgggaggcca   10080
aggcaggtgg atcatttgca atcaggaatt cgaggtcagc ctggccaaca tggtgaaacc   10140
ctatctctac taaacataca aaattagcc gggcatggtg gtgtgtgact gtagtcccag    10200
ctacttggga gactgaatca cttcaaccgg gaggcaaagg ttgcagtgag ccaagatcgt   10260
gccactgcac tccaacctgg gtgacagggt gaggctctgt ctcaaaaaaa agaaagaagg   10320
ctgggcttgg tgactcatgc ctgtaatctc agcattttgg gaggccaagg caggcagatc   10380
acttgaggcc aagagttcga gacctgccag gccaacatag caaaaccccg tctgtactga   10440
aaatacaaaa aaattatctg gccatggtgg tgtgtgcctg taatcccagc tactgggggag   10500 gctgaggcag gagtatcact tgaacccaga agacagaggt tgcagtgagt cgagactggg   10560
ccactgcatt ccagcctgga tgagagca agactctgtc tcaaaaaaaa aaaaaaaaa    10620 aaagaaagaa taggaggctg agaagtccca agttatatgt taaaaaaaaa gaaaaaaaca   10680
tcagttttag gccaggtgca gtggctcaca cctttaatcc cagcactttg gaaagccgag   10740
gtgggtggat catgaggtca ggagttcaag accagcctgg ccaaaatggt gaaacccgt    10800 ctcgactaaa aatacaaaaa attagccagt tgtggtggca ggcacctgta atcccagcta   10860
cttgggaggc tgaagcagag aattgcttga acccaggagg cagagattgc aatgagccaa   10920
gatcgcacca ctgcactcca gcctggaaaa cagagcgaga ctctgtctca aaaaaaaac    10980 catcagtttt tatggacagt ggtagagtgg agggtgggtc cctatggtgc agaagggaaa   11040
ttccatggtc ctgctgtgca tccgactggg atggctgttg aaatcctctt ccagcaggca   11100
gctttggaaa cagaaaaaga aactcttcct cctttagaat cctggaaggg ctgtgcagtg   11160
cctctaatcc aagtctgttt tctgagtgaa gataggagg ttcatcacca gaagggaagg    11220
ggctggaaat gaggtcactg catcccagcc cagggctcct gggtcatcca ggaagggaag   11280
aaggagcaag ctttctcatt gttaggtagg agctcagagc catcacaaga acaagttagc   11340
accatccctg tgccctccct gttctgcaaa caaaatgatc ttccttcttg ccctggcact   11400
agagtctgtc tggcatttct cctgccccta gtactcctcc catctgggta cttcttcccg   11460
ttggtgtact gaacaaacac atccactgct ttattcacag cctccagccc tcattttcca   11520
gggcccacac catttgtttt tactaacccg acaaggttgc ccactgtccc cagtaaggtt   11580
tgtactgggg ttttttactcc agtgctcttc tccatccagg agacctttgg atacttgggg   11640
aagaaaatga gcttaaattc ccaccccctcc cccttaccct ttttcctgta aggccctggc   11700
cttagttctt agcccacat ccttgctggc tgcagaatag cagcgggttc tgggtaagga    11760
gcattctgct aaaacgctcc accctgctcc ctcatctgtc ctctccattt gtccccatca   11820
gatggtttaa gtgcttaagg ggactccagg gcggagtcag ggagaaccct ggctctcctg   11880
ggctaggcac aagatcattc tacaggaaac cttgtgggaa ttcttctggg acaaagtatt   11940
ggtcagcgct gagcttagct gtgtctgtga cactcgcatt ctaactaggg cctatctgac   12000
gtcaacagga agtaaggctg atgcagtggg gccaaggag tctgggagaa gaaagtcggt    12060
tcagagccct ggctgccctg tcccacactc caccccttccg gcaagaatcc agtccctaga  12120
tgaggtgggg agtgagtggt cgagttaaaa atctctgggt cgggtacgat ggttcacgcc   12180
tgtaatccca gcactttggg aggtgaaggc aggcggatca cttgaggtca ggagttcaag   12240
```

```
accaacctgg ccaatgtggt gaaatcccat ctctactaaa aatacaaaaa ttagccgggt   12300
gttgttgtgg cacgcgcctg tagtcccagc tactcgggag tctgaggcag gagaatcgct   12360
tgaacccagg aggcagaact tgcagtgagc caagatccag ccactgcact acagcctggg   12420
cgacagagtg aggcttcgtc tcaaaaaaaa aaaaaatctt tgggccaaat ctccagacag   12480
cacaggcagg tgcagaaacc caccaggaag ctgcctgtgt acctctggca gattggagcc   12540
tggcctaaag ctgccttttta tgcagcttgg gtcaaggtta aacatcatgt cacagtgatt   12600
tttctcacta tgtgtgagac atggagaact ggctccaagt actactctgt ccactggtgg   12660
ctggactact gatgtgcacc actctccact cctctcaccc tgcagtgggt catgccccg    12720 tgccggggca gaggagaaaa atgggctgcc ttctccagga caaaccctca ctccaactca   12780
actagggtgc tgtgatcaga atgtgcaatt gaggtgtgat tttactgatt ttttttttt    12840 ttgagaccga gtttcgctct tgttgcccag gctggagtgc gatggcacga tctcagttca   12900
ctgcaacctc cacctcccga gtttgagcaa ttctcctgcc tcagcctcct aagtagctgg   12960
gattacaggc atgtgccacc acgcctggct aattttgtat ttttagtaga cgggggttt    13020 ctccatgttg gtcaggctgg tctcaaactc ctgacctcag gtgatccacc cgcctcggcc   13080
tcccaaagtg ctagaattac aggcgtgagc caacgtgccc agcctgtttt tgttttttgt   13140
gttttgaagc agggtctcac tcagttcccc aggctggagt gcagtgacac gataatagct   13200
tactgtagct gcaatctccc gggctcaaac gatcctccca cctcagcctc ctgaacagtt   13260
gggactacag gcacaccacc acacctggct aattttttt tttcttttt tagtagagat    13320 gaggtcttgc tatgttgccc aagctggtct caaactcctg aggatcaagt gatcctccta   13380
ccttagcctc ccaaaatgct gggattgcag atgtgagcca ccacccag cctgattta     13440 cttaaatga gagtccctct tcagagtccc tcagctgttc ctggcccctg gccatgtgcc   13500
ttcagttgcc cctgcttctg tggtatcctt aaggctacat tcagtgctga ggccctaggc   13560
aggcagcaga gagaagccaa atgattctgt ctttccctta tccacccaga gcatgcaaaa   13620
ccaggagcag tggtgggttc agggtgggca ccagctatgt atatgtacat cagggacagg   13680 gggcaaagg cagtcagttt ccaaagactg ccccagaggc cattttttcag agaagccctg   13740 ggttcctcaa gggccctgtg tccatgctgg cccatcttgc aggacgagcc tgtggagtgg   13800
gagacacctg acctttctca agctgagatt gagcagaaga tcaaggagta caatgcccag   13860
atcaacagca acctcttcat gagcttggtg agttgactgc tcaggaaggg ggcgtgggga   13920
ggagcaggta cccagctatg tgcctgatac tcagagggtc acaactgagg ttatcttggg   13980
tgggcgcaag cagtaatttg tgcatacca gcctagcccc aagtagactg acatctcacc   14040
tggaacctat tatcaaggtt tggtttctct atttctttag aacaaggacg ttcttacac    14100 aggcttcatc aaggttcagc tgaagctggt gcgccctgtc tctgtgccct ccagcaagaa   14160
gccaccctcc ttgcaggatg cccggcgggg cccaggacgg ggcacaagtg tcaggcgccg   14220
cacttccttt tacctgccca aggatgctgt caagcacctg catgtgctgt cacgcacaag   14280
ggcacgtgaa gtcattgagg ccctgctgcg aaagttcttg gtggtggatg acccccgcaa   14340
gtttgcactc tttgagcgcg ctgagcgtca cggccaaggt gggcttccca ccccaccctg   14400
ccctatgtga gggtatatac gcatgcacct gagcatgcag gggctgagca gctggccctg   14460
tctctgatca ttacttcccc ttcacagtgt acttgcggaa gctgttggat gatgagcagc   14520
ccctgcggct gcggctcctg gcagggccca gtgacaaggc cctgagcttt gtcctgaagg   14580
aaaatgactc tggggaggtg aacgtgagta catagttctt agtttcttgg ttgtcactag   14640
```

```
acaggactga tgggctgtag ctacagtaag gcttggagga ggaattgtgc tggaagacaa    14700
gccctgcaaa acagttccag gagtgtatag gcattgtaac taaagcaaag gcttccagac    14760
cactcatgcc aaagcctagg gttgtcccaa gaagccagga agaattgcct tggtgctttg    14820
atctttcctg gtgtggaaaa tcttctggag atgcaggagt ccatctaatg acatgaggag    14880 gccccttca gacttttac ctggaagctt tctggctcca aggtattagg cctgtggagt    14940
gaaattagac tcagaatatg cctgacctgt ccacaggtaa ttggggaaca tctgacttgg    15000
ttgtctcagt aaggtgaccg ttttgtaggg cccatcttcc atacaaactg ctgtcaggga    15060
tcctaccaga gatcattcag ccaagagcct gacatcagaa agcccagtcc tagcttgtgt    15120
gaacatgagg tgctagtctt ctctggggag ggtctgctgg cttggccatc ccttctgcag    15180
cctgtacact ccccttttgc cccttgcagt gggacgcctt cagcatgcct gaactacata    15240
acttcctacg tatcctgcag cgggaggagg aggagcacct ccgccagatc ctgcagaagt    15300
actcctattg ccgccagaag atccaagagg ccctgcacgc ctgcccctt gggtgacctc    15360 ttgtaccccc aggtggaagg cagacagcag gcagcgccaa gtgcgtgccg tgtgagtgtg    15420
acagggccag tggggcctgt ggaatgagtg tgcatggagg ccctcctgtg ctgggggaat    15480
gagcccagag aacagcgaag tagcttgctc cctgtgtcca cctgtgggtg tagccaggta    15540
tggctctgca cccctctgcc ctcattactg ggccttagtg ggccagggct gccctgagaa    15600
gctgctccag gcctgcagca ggagtggtgc agacagaagt ctcctcaatt tttgtctcag    15660
aagtgaaaat cttggagacc ctgcaaacag aacagggtca tgtttgcagg ggtgacggcc    15720
ctcatctatg aggaaaggtt ttggatcttg aatgtggtct caggatatcc ttatcagagc    15780
taagggtggg tgctcagaat aaggcaggca ttgaggaaga gtcttggttt ctctctacag    15840
tgccaactcc tcacacaccc tgaggtcagg gagtgctggc tcacagtaca gcatgtgcct    15900
taatgcttca tatgaggagg atgtccctgg gccagggtct gtgtgaatgt gggcactggc    15960
ccaggttcat accttatttg ctaatcaaag ccagggtctc tccctcaggt gttttttatg    16020
aagtgcgtga atgtatgtaa tgtgtggtgg cctcagctga atgcctcctg tggggaaagg    16080
ggttggggtg acagtcatca tcagggcctg gggcctgaga gaattggctc aataaagatt    16140
tcaagatcct cctgctgttg gaatctttta tacatataaa gtttttgtag agacatgagt    16200
ctctctgtgt tgcccaggat cctcccaact tggcctccca aagtgttggg attacaggtg    16260
tgagccaccc tgcccagcct ggactcttta ttattatagg cgcagagctg cagttgcccc    16320
tcatggtgcc agaagttgcc aagggtgatg acaggctcc caggtgtctt gcaaagtcac    16380
catggaccaa tttgtgaaga tgtagtatgc atacatactt ggtcatcact cagctccctg    16440
gggctcaggt tgtggtggag acaaaaatgg actgcagtta gaacttaggg aaactggctg    16500
ggcatagtgg ctcacacctg taatcccaac actttggttg gctaggtgg gcagatcact    16560 tgaggccagt agttcgaggc cagcctggcc agcatgcgca aaccccatct ctaccaaaaa    16620
tacaaaaaaa atttagctgg gcgtggtggt gggcgcttgt agtcccagct actcagaagg    16680
ctgaggcagg agaatcgctt gaacccggca ggcagaggtt gcagtgagtg gagatcacac    16740
cactgcactc cgatagagca agactccaac tcaaaaaaaa aaaaaacggc cgggcgcagt    16800
ggctcaggcc tgtaatccca gcactttggg aggccaaggc gggtggatca cctgaggtcc    16860
ggagttcaag actgcctgac caacatggtg aaaccccgtc tctactagaa atacaaaaaa    16920
attagccggc atggtggcag atgcctgtaa tcccaagtac tcgggaggct gaggcaggag    16980
```

| | | | | |
|---|---|---|---|---|
| aatcgcttga | accctggagg | cagaggctgc | agtgagccga | gatcgtgcca ctgcacatta | 17040 |
| tcctgggcga | caagagtgaa | actccatctc | aaaaaaaaaa | aaaaacaaaa ccatcccttc | 17100 |
| aacacacaca | caccacgctc | tgggagaagg | tgtggcataa | ctccttcacc aaatacagag | 17160 |
| ctgccaccgt | ggaccagaca | ctgctcgtga | taccgagggt | atagctgtta acaattcttg | 17220 |
| ctttcattaa | gcatggactc | tgctgggttt | gaaaacactg | aattcgaagt tcttcagaac | 17280 |
| tgaatgtaac | tatgtgaatc | tggccagttc | cttaattttc | tttcaacttg gttagttcac | 17340 |
| ataagcgtgg | caatcgcaaa | aatacagctg | tgaaaataga | agccagatgg gcacccggcg | 17400 |
| gtctggcctt | aggccctgaa | gtgcaggttt | gaggattggt | gcttgcgaag tcctgctagg | 17460 |
| cctgaactca | ggtgttgggg | gacgtcagag | ccgccaaata | cacccaaaag accgggagga | 17520 |
| ctcacggcca | ccactttcct | cggtgggagc | tgtcccagct | ggtcagatcg cgcttgctgg | 17580 |
| gacctgggat | ctcgcaacgc | atgctgggat | gcccagcatc | taagggcgcc cattggtccc | 17640 |
| gcccccacga | cttgagcaac | agccaatcag | aggtggcagc | gtgcggaagc ggaagtgagg | 17700 |
| tttccgtgga | gacagccgag | cctgcggaag | gcggcggcgg | cggcacctgc gatcagcggc | 17760 |
| tggggcaggt | tatggtagtg | cggactgcgg | tgtgagcaga | gcggccacgg ggcccgccat | 17820 |
| gcgccggcgg | ccctgacatg | ggcgccagcg | ggtccaaagc | tcggggcctg tggcccttcg | 17880 |
| cctcggcggc | cggaggcggc | ggctcagagg | cagcaggagc | tgagcaagct tggtgcggc | 17940 |
| ctcggggccg | agctgtgccc | ccttcgtat | tcacgcgccg | cgggtaaggg catgggttcc | 18000 |
| accctggcgg | ggggaacagg | cgggcggcca | ggcgtcccgc | gccacggggg aacttccacc | 18060 |
| gctgtacccc | actacagcca | agccaggacg | accccccatat | tttgagcctc attggagctg | 18120 |
| ggggtggaga | aagccgggca | gtggtctcct | g | | 18151 |

<210> SEQ ID NO 14
<211> LENGTH: 20911
<212> TYPE: DNA
<213> ORGANISM: Homo sapiens
<220> FEATURE:
<221> NAME/KEY: misc_feature
<223> OTHER INFORMATION: TBX3

<400> SEQUENCE: 14

| | | | | |
|---|---|---|---|---|
| agggatctcc | aggctgtcat | ggttgctggg | aaagatgagg | gagggaaagg gggcagagta | 60 |
| cggaggcacc | aggtcagaaa | gacaggagag | aattcagaca | ggaccaaaac agccagaaaa | 120 |
| aataggataa | agaaggtaga | aaaaaaaaaa | aaacaaaaca | aaacatgaga agttaaagcc | 180 |
| tgggaaatag | atacaagaca | agaaagagaa | atagaaacca | agaacaagat tgatgaaagg | 240 |
| aggagaagag | aaagtagaag | gaaaaagaat | aagaaagatt | ccagacacgc attcaaataa | 300 |
| tcctaaatgg | ggatgagcag | aaagacaagg | agaccaaaag | aaaaggggggg ggggggggtgg | 360 |
| tggggaggag | aaagaaagga | atggaaaaag | aaacaaaagg | tgaatgtcct gccctgtctg | 420 |
| tctggtccaa | ccaagaagct | agtgtctgcc | ctggagggag | gaaaggtggg ggagtccagc | 480 |
| ctgtctccaa | gggactgaca | ggcagcttct | ggaccagaga | ggaactaagc tctcaaagca | 540 |
| agctttgggg | aggaggaagg | gatgggggtg | catggtgagt | ggagactcct ggaggaagag | 600 |
| caagcctcca | ctgggttcag | cactgccagg | gggagagtca | gggttcaggg tagcatagca | 660 |
| gtgctaatgt | atgtacccca | gaggggtagg | gggtgctagg | gcaatttgca ggaggaccac | 720 |
| aaacagtaaa | ctagagagct | acttccctgg | gatccgtgat | aagaaaatca cttcctcagg | 780 |
| tgggagaatt | gagcccgaaa | gagaatggga | gcccttgggg | ggcaggcacc tggtcagttt | 840 |

```
caaagctcgt caatatcaaa agaggctggg atcctgagat caaatgggct ggggcactgg      900
gcagaaacga ggagccattg ccaaactgcc aggatgacca gaacgcccct cccccaggaa      960
aagttcatat atgaaccccac ccctgtatga aacttcttaa ttaggtctca tacccccggt    1020
gaatcttgga tgcccttctg tcaacagaat tcccaattta gtgacacctc ggactgaaaa    1080
gagctctgcg gcaaacgggg gtgaaagttt aagagggaat aagcatataa tactcccttg    1140
ccagacctca cacatgctga agggaatatt tacagcaaac tggccaaagc aaacgacccc    1200
gcctacccac catcctttta ccctcctccc cgccctttt gtaaactcca gataaacacc      1260
atttgatcac aaaagggtcg gtttgtcccc tttatagttt gaggcaggca gtgcggcagg    1320
gaaaagtggc gtgggctaag cttccgtctc gggcaaggcc agcttctttg ctggcaccgt    1380
ggcctgggct aaggacagtt gatttggttt tgtttccccc gacccccacc ccgaccccac    1440
ccccacaaag gaacattatt ttcagggtcc tccccccacc cagctttaac actcgcctac    1500
ttgcacccgc actactttaa atgctgcggg cattgcagat agagaggttt ttcagttaat    1560
ttactttttt aattctagag ctacaattaa gtgaaaactc ttttgcgaa aaggtggagg    1620 aatatttcag agacgccaga aattatctgg gtcttttctg acccggaatc tgccctcttt    1680
ctcccttctc ctcccttaa gtcacccttt tctgggactc tgttgaaggg caggctcttt      1740
caacgtctct agtctgtctt ttgttgagtg tgagaccgaa ggaaagagga tcgagggggtc    1800 tgcagagaga aaaagaccgc agatagccgg cagctggcgc ctaatgccgg ggtccgggga    1860
gcgctggcct cgtgggttct cctggaggcc aggcccagca caagccttcg gaacacgctg    1920
gccaatgttt aacccgaatg cagtggccac caggccgctt tgtttgttc gcaaattaat      1980 cacccagcgc atggccggcg ccagagtggg tttatcaccc accgggaggg gggcgcgccg    2040
ggcacgcaga gacaaagagg agttcgcacc ttccgctttt tgatcccaga attacgcgg      2100 cctccctgcc taatacgagc ctcctgggc cgagtctggg aggtcagtca taattggcgg      2160
aagtttgcag accattagca agatgtcgac attttcgatt cgaaccccgc aaactttcct    2220
ctcgttctct gcttcgcgcg ctggaggttg tgtgtgggaga ggagatgggg gtcagaagta    2280
gcgatctggg gtgatcacag ggttaagtta gagctatggg caaaaaatag gcaattgagg    2340
gaggaggaca gtgtgagggg cagaactccc tctcagtcca cccgcggagc caaaaacaaa    2400
tctagacatt tttaagtaaa atccgcaagc tcccctccca tttccaaagc tgacagctgg    2460
ccagaatgca gaggaatgtc tctctgctgt gcgtgggacg cttgggggca ccgagtgggt    2520
gaggaggagg tcggtcacag tgtggttgta gaactacttt gcttccaccc caagtagtgg    2580
ggcagagatt ggcctgcgag ggcaggcagg caaaaccaga tcgctgggat ttggggccgc    2640
tcttgaaaga gcagcgaagg ggccccaggc cccggaggcg agcagtctgg gggagggggt    2700
gcactttttt tttctatttc tttcttttct tttcttttc ttttttttgg ggcgggggtc      2760
cccagagact catgaaaccc tgcagtgact tccgtgttct gtgtaaggcg ggaaatggcc    2820
tggcctttcg caccccttcag gtggggagga gggatgcgg gaggggtgt tatgagccaa      2880 cactctgggg caccaccacc tcgtaatttt ccctctctct cctttctcta ttttaaccac    2940
tggcagagac agagaggacg ccagagaaag acagactgaa agggaaagaa aggggcgaga    3000
tggcgagcca gacggagttc gcagaaccac actattctct ctggtgactt cagggaattc    3060
tcaacgctgg cgccaagctc tcttaaccat gtgcgtcaaa aatgcgaggc tggagaagcc    3120
tgtcgcctca aaagatcctc ccctatctca gcgtggttgg cccacaagag cacttcattt    3180
tcacccttcc cttggtgcca cgttgggggtt tcggggttgc tgggggttgc gcgggtgcac    3240
```

```
aaggcaaaat gcgagagagg cctgtgctgg cctacagaga cacacacatc caaagccctg    3300
agtctcttaa acccctaagc ccccagatca gccctttctc cgttcccttt ccatcgaaga    3360
agctttcatc tcaggaaaga taaaagaaca ttgttttcaa gatttccctc catctaagca    3420
aggatggtcc aagacattgg cccccagaat caagaactgt gggcttaggc gaatcctctg    3480
accccgaccg ggcgctgcgg taacagagtt ggtaattcgg cgattggtaa gatccggtcg    3540
tttcctcccc gtccgcctaa gaggaggccc cacccctacc cgtactaaaa acagtcaact    3600
cgcctctgag gtggggcgt ttcacggttt gttttacaaa ttcaccctcc ctccccgact    3660
tctggccaga ttaagtcccc ggggtggaga aagaactgag gcaccgagag ataagtgcga    3720
tgcctagaga agataccagg ctggcgcgcc tcccccaacc caatcgccca ccccttaccc    3780
tgtgctgtgc acccagccgg gcctcgaggt gagggcagcg gcttggaggg gacaggctca    3840
gaacccagtc tctcgctgtg ctcgctttgt ccagatcctc cattctcttc tctacaccca    3900
cacccacatc caggtggaat atgggggccc gcatgcaaat gaaagacgag atccaaaagg    3960
gctggtaaat gcatttcata aaaatcccaa atccatcttc cccaggagct caggcagggc    4020
cagccgcgca ggctgtgtac gtgttttgtgt gtacgtgttt ttcggtgtgt gtttcagtcc    4080
cagtgtgttg gcgcgtgttc gagtacagat acaccggggg tgtttgggta cccgcacatg    4140
gctgcgggtg gggcgcagtg gagaggaagc ccacacatgc gtgtgctgag atatggccgc    4200
atccttgtgc tcccccagcc cagacgcagg ggagaccagc accgagacac ccgagctcgg    4260
gagcccttca gcggcggccg ggcggagctt ggctccacgt ggggctggag agcacgcaag    4320
cctggagtct cggcgctcgc ttctcggctg ccgccggctt ttgtagaacc gagtggccgg    4380
atggcagctc gcggggaggc tcggccaccc gcccggctcg cccggggcgg ggagaagaag    4440
gagagctgga gagagaaccg gccgcggcgg tcggagaggc gagcggagtg caagagaggc    4500
gagcgcccct gcccggcgcc cgggcgcgct ctccgcccttc cccgcccggc tcgcctgctc    4560
gctggctccc tccctctctc cctccccctt cctccttggc cctgcctcct ccctcgatcc    4620
ccggctggat gactgaggca tttcagacgt gggctgaacc agagcgagcg agcgagctca    4680
ggggctgcag cgatctctcg ataagccacc tagaggcgac tctgtgcgcg cgcgctcccc    4740
agtggctccc gcccgccctc tgatcatgtt gacatattca caggacaggc agtagtaccg    4800
atgcggcgct gcgacgttac agtttccgac accttctttt tataactcag ctctatcccc    4860
cagcactcga cctgtgaaaa ccacgcctat gcagcaacac aattggtccg aaagcgtcaa    4920
agagccaatc aagaggcctc cggctccccg cagcccacag cgcagcccga ccttctagag    4980
ccgccgagca gacgcccggt gaattctaga ggcggcggag ggtggcgagg agctctcgct    5040
ttctctcgct ccctcccctct ccgactccgt ctctctctct ctctctctct ctcccctccc    5100
tctctttccc tctgttccat ttttttccccc tctaaatcct ccctgccctg cgcgcctgga    5160
cacagattta ggaagcgaat tcgctcacgt tttaggacaa ggaagagaga gaggcacggg    5220
agaagagccc agcaagattt ggattgaaac cgagacaccc tccggaggct cggagcagag    5280
gaaggaggag gagggcggcg aacggaagcc agtttgcaat tcaagttttg atagcgctgg    5340
tagaaggggg tttaaatcag atttttttttt ttttaaagga gagagacttt ttccgctctc    5400 tcgctcccctg ttaaagccgg gtctagcaca gctgcagacg ccaccagcga gaaagaggga    5460
gaggaagaca gataggggc gggggaagaa gaaaagaaa ggtaaaaagt cttctaggag    5520
aacctttcac atttgcaaca aaagacctag gggctggaga gagattcctg ggacgcaggg    5580
```

```
ctggagtgtc tatttcgagc tcagcggcag ggctcgggcg cgagtcgaga ccctgctcgc    5640
tcctctcgct tctgaaaccg acgttcagga gcggcttttt aaaaacgcaa ggcacaagga    5700
cggtcacccg cgcgactatg tttgctgatt tttcgccttg ccctctttaa aagcggcctc    5760
ccattctcca aaagacactt ccctcctcc ctttgaagtg cattagttgt gatttctgcc     5820
tccttttctt ttttctttct tttttgtttt gcttttcccc ccttttgaa ttatgtgctg     5880 ctgttaaaca acaacaaaaa aacaacaaaa cacagcagct gcggacttgt ccccggctgg    5940
agcccagcgc cccgcctgga gtggatgagc ctctccatga gagatccggt cattcctggg    6000
acaagcatgg cctaccatcc gttcctacct caccgggcgc cggacttcgc catgagcgcg    6060
gtgctgggtc accagccgcc gttcttcccc gcgctgacgc tgcctcccaa cggcgcggcg    6120
gcgctctcgc tgccgggcgc cctggccaag ccgatcatgg atcaattggt ggggcggcc    6180 gagaccggca tcccgttctc ctccctgggg ccccaggcgc atctgaggcc tttgaagacc    6240
atggagcccg aagaagaggt ggaggacgac cccaaggtgc acctggaggc taaagaactt    6300
tgggatcagt ttcacaagcg gggcaccgag atggtcatta ccaagtcggg aaggtaagca    6360
gtgggggcct cctcccctaa gctgttggag agttttttcc tccctttatt tctctgctcc    6420
cagaacagtc ggttggtcgg ttattacggc ttggacgaaa agttagttcc cctagaaatg    6480
tatgcacaga cttccaggcc ctgccccggt ggcaggaaat ttcagcttac ctgggcatct    6540
gcatgggtct tgcatttggt ctgcatcctg ggttccctcc cgaacagaca gaatttttca    6600
gtggagcaca gacatccctg cagggagcag gaaagaaaaa aaaaaaaggc actctactgc    6660
aagaaactca ctcttcaaac cctcctggaa catccttatt tctttgttga tgttgtgttg    6720
tctgttttat tttgttctca gagagaaaaa cttaaagccc tttcctttg tgtgggtatt     6780 gggaggcctg acaccattcc ccggcccttt ctgccctcca gtctagcctc tgggtctaaa    6840
ggggcctgct gctgccctgg tcagagagaa atcgaagggc attttggttt gtttgcccac    6900
actacttcac gtgtctgtaa cccaagggcg agttcagcag gcaattttgc ataatttaag    6960
attatgtttg cagacttaag gagccagtga ggagacacac acctttttt taatgtgtga    7020 atattatcaa ccatattta cataatgttt aaaggtcctt gcctgaccaa aacctgcctg     7080
gaagagaaga tcctgtaata gtcatttaaa atcactgatt ttttttttgt aatagcattg    7140
aagcctgtaa aggcataaag ttgatacaaa ataaaatcc ccttcatgat atcttaagcg     7200
ttctgtctcc ttccaagcta aatgaggcca agtttggca taaaatcctc ctcaaactca     7260
caagacattt agtcagtttt ccagcaaagt gcttccttgc ttccttttaa gtcaagacta    7320
cagaatgcca acccttctgt gaaattaaca gcaatgtggt ggcacagtct tgcggttttg    7380
gactggccta agaagtgggg gaatgtgtta gcagctccac gggcagatcg gttatcaggc    7440
ccaggagtgc accgaagtct gcaaaattcg ttctgggaac tcactgaagt ccagtttcac    7500
ttcgcccaca gcgggattgc tattctgcag caggaggggg tgcaacttga cgttcatttc    7560
cttgataagt ttaacatttt ctcatcaatg ggtggtggaa aattctagtc ttaactgacc    7620
gcgctttaca aaaatcttac cccaacctgt ttagatctag atacccacag aaaaagacat    7680
gggcaagaat ttgctctcag gagggcaatc tgtaaagtca agcaaggaca aaaaaatat     7740 tgaagaaatt gttagacaat gtagagaatt gcagtgccac aatgcatttg ttttgaacct    7800
tgggacgtct aaatatggcg aaactgagaa tatttaatac gttagttgtg aagaaaacg     7860 attttgcaac cagttgcctc actctgaaac atgtaagctt atcagtcaca atataaagtc    7920
ttagacttgg tttcaatatt atgtgataca taggaaatca aacccaagat tacgggtggt    7980
```

```
ttatctttct ttttcttttc tattctttcg ttttataggc gaatgtttcc tccatttaaa   8040
gtgagatgtt ctgggctgga taaaaaagcc aaatacattt tattgatgga cattatagct   8100
gctgatgact gtcgttataa atttcacaat tctcggtgga tggtggctgg taaggccgac   8160
cccgaaatgc caaagaggat gtacattcac ccggacagcc ccgctactgg ggaacagtgg   8220
atgtccaaag tcgtcacttt ccacaaactg aaactcacca acaacatttc agacaaacat   8280
ggatttgtaa gtttcattgc tctcttcagt aaaattttct cctccttcac tcagtcaaag   8340
gcagtgcttc ccatttcatg agtttcagcc cagacttctc ctttgcttct ccctaagcat   8400
agcaaacttg tcctcgtctg gaaaaaggat tcggggtgtt tctctccaaa taatggaagg   8460
cctggcgttc taaagaaat ggggcaagaa aacttaccgg cttgtgttct atagcaattc   8520
cagctctttg gtagattcct gacctgagag tgaagttaaa aaccattttt taagagctaa   8580
aatcaatttc aaggctatgt attcctaaag gatttgtttt gttttaaaat atcatacttc   8640
tgttttgaaa ccagtgatat tattttctca ggagagttta cgtttcggag ccttgactct   8700
gttggttaaa tggtgtgaat acattttta aaactcgttc ttttactaaa aaagaattg    8760
ggcttaggtg ggagtccggc ttaccctaaa tgaggcttag atcttcagaa aaaaatggtt   8820
tgtgtgttgg gagtgtatat atggattcag tgacagtgct tagaaactta gaaaactttc   8880
attgcttgta gatatcaggc aaaggacctt ttgcgccttt tcctacccct ccccaacatt   8940
tcaataaaat aaacagcgtg ataagcaagg agtaagcaga aagattaggc ccaggaagac   9000
gcgaatggcg cggaaatatc ttcagcgggc aggaattgca tttgaagccc ttgatttgat   9060
taaggcataa atattcctct ctagagttca gcctttcagg gctttaagtg gattgggctc   9120
gtcaattagt gggcgcttaa agtactgaat cattttgtaa attaaaatgc atgttttct    9180
ctatctttta agactttggc cttcccaagt gatcacgcta cgtggcaggg gaattatagt   9240
tttggtactc aggtaggcta gggttcaagg tatgaatgat ccttagatgg tgagggtggg   9300
gggggccctt tggcaactga ggagcaattt ggattctcca gaagataaca tctgtggagc   9360
gaaacgtacc caggggtac tccaaggagg tgggctcgt acaagcgtgg tacctgcgg    9420
tggggaagat ttcagcctgg cagggtcct aagatcccgt ttgttctgct aaatccttgt   9480
tttatgtatg tctcctcttc cctgcccctg cagactatat tgaactccat gcacaaatac   9540
cagccccggt tccacattgt aagagccaat gacatcttga aactccctta tagtacattt   9600
cggacatact tgttccccga aactgaattc atcgctgtga ctgcatacca gaatgataag   9660
gtaaactcaa gggctttcc ttttaatgg tgatattttg ccttccctt aaaagctgct    9720
ttaagtcagg atgagaaagt tacaagagag tggagacgag agtcttgagt tgtcttttgt   9780
gatttgtgga gcatttgggg ggaaaggaca atgacacctc gaggagacag aaaaacacct   9840
tgactaggta ggaacaatgc tgagcaaaaa aacgccatac taattttgcc acagagaaac   9900
tcctagaact gctgtcattg atgccaccca ctcctccccc cctcttgggc tttgtcctgt   9960
ctgttttaag gttcatcttc ttccccttgg ggaagaagga tcaagaagtc acattcaaaa  10020
ggaaccagct aaaaatttaa ggcaaaagcc atttgggatc ctgggaggag aatcctagta  10080
gagaccagct tttctcccct agccagaaat cctgagtagc tggtctggtt tttattacct  10140
tttatgctgc tgtgttatga tgtgtgtgtg tgtgtgcatg tgtgtgcatg catgcgtgtg  10200
gttgaaaaaa cctaccctga tcacagggtc atattaatcg agttgtctga ggcttttgag  10260
ttggggtggc caaagtcacc acttcatttg aattccccc ctcccccagg cctgaatctg   10320
```

```
gaggttagaa ggatccccaa aagggaaagc acctgatatc tagagctatg gtggcctgaa    10380
ggtcatgggc acagaaaaag tgacccttac tgctgattca ccagttccca gattggctgt    10440
tagcagttat ggggtgggag gagggactga agaccctgc tctgcaatcc tggacttcaa     10500
agagagtcca ttttacctga caacacactt cattttgaac tcactgtcat tgtcactgtc    10560
cttgggtcct ctgtggactt catgatgggg atgttccagc taaatttctt tagtgtgaat    10620
accaaaacat gatcttctct ccctgtgaaa cctgaagtct tcaatagagc aatttattcc    10680
aagaacatga atccaaccaa gggtccccct ttccacctct gagtaactct gtgtatataa    10740
cttcttcttc ccaccaaggg gaagggattt gaaagattac acactatagc atttttctca    10800
aagtgcaaaa tgcatgtgcc ctctagaccc agaatcctgt gaaatgaagt tgttaatgta    10860
ataataaaat gtagcatttt tgatcagaca aaaaggccat gggccttctc cacctaatgg    10920
ccatggcaga gcatataaat gaaaacagat gtttccagtg gtcattcagt actgtaactg    10980
tcaatattgt aatttcctca aaccaccccc caggcaaaga aaaaaaaat taaactcact     11040 cccgcactca ctcccgcaca agggtagtga acccccataa atcatttatt ggattcatgg    11100
aaaaggagtg tgtgtgtgtg tgtgtgtgtg tgtgtgtgtg tgtgaaggga gtatgctata    11160
atttatgatt aattgcactg tataaaaatc aaaatgaaag cataatttta agatctacag    11220
gttttccctc ttgatgactt tgacaacact tccatgtcta aacccaaact gttggctgcc    11280
caaagaaaag aatttctttg aataatttca tccccaaatc cctggtttgg cctcatatag    11340
gagatacaag ccctgccaca gtttccttat tatctccttt ccctggcata tctatatgac    11400
ttctgttggc agtcacatct ctagacttgt tgagttggga aaaacaccct caaaacattc    11460
tagaaaatga gaacaatgtc tctgtcttgc ttgtgtctct tccaatagat aacccagtta    11520
aaaatagaca acaaccctt tgcaaaaggt ttccgggaca ctggaaatgg ccgaagagaa     11580
aaaaggtgag ttgaaacaat tatttattag atagtttaga aaaatcccctt tttttaggat   11640 ccaactctga agtgttagaa gtgagatgca ggcacttatc ctaagagcgg gtggaaatca    11700
ttcactttcc ccactgctac atgcttgccg ctatcagtat acccaggaca agtacttttc    11760
ctacctcctt acctttaagg aaattaacta ggctacacca tacttatctc tggaagagaa    11820
gcatcaggga taatagatta tacagggatg cctattaatt cctaattaat ttaagttcat    11880
cctaggcagg tccagaaaag aaccatgcca ttgagaaaat acttgggaat ttttgcaatc    11940
ctgtcttcca ataccatca gacagagctg gggacttcgg aaagatgtat ggctctctcc     12000
ctccttcgtg gggacatgta tcattttgca ttacgtagac agctggagag tatatgaaag    12060
agggtctccc ctcccccacc cccttttcaaa gaatttctaa aatccagaaa atcaccccca   12120 aattttaac ctatcccctt ggggcgggca ttaaaaaata attgctaaca gctaaatata     12180 ttttattcc aattaatttg ttagtaaaac gattacagta aagtgcagca tgaaataacc     12240
acttcctccc aatcttagcc accatccaaa atttgggtat gctggggaca gacagcgttg    12300
tgtttgcagg attggacacc cggttctccc tatataaggc tggcagtcca gctgtctctg    12360
actagatcca gcctcttctc ctgcttttaa ataaaatttc acagcccaag caaatgcctt    12420
ttcctaatga aaccccatct tgaataaatg caactgaagc ctccttcctt tctccctaac    12480
cctctgccac actcttcagc ccagttagag ggtcaaggac aaagcttggg tctatgtggc    12540
tgccctgggg caagcagatt tcagtgaatt agcgttgtcc ctgggcagca ggcagggtgt    12600
gaggtatgtg tgtgccgctt tggaaagggt aaggaaaca aagaggggaa atgtatgtta     12660
cattctgtaa cctgggtgtg ggcttctgcc acagaaaaca gctcaccctg cagtccatga    12720
```

```
gggtgtttga tgaaagacac aaaaaggaga atgggacctc tgatgagtcc tccagtgaac   12780
aagcagcttt caactgcttc gcccaggctt cttctccagc cgcctccact gtagggacat   12840
cgaacctcaa aggtaaacca tgtcacctttt gtgatcactg gactccagtc cctcgtggcc   12900
tggaagagtt gaagggggat ggggcaccaa ccagggcact tgccctttaa aagctagaag   12960
ccttctaaac atccttaaac agaagccaga gttcaaaaag gctatcagg tgtgtctccc     13020 cttccccgct aaggcagtag aaggagagca cagaggcctt tctcccagat ccttatttgg   13080
ctggtgggga gggaggtgg gtgtctgttt gcatactacc tcttggcaag cagctttgaa     13140
aacttgcttg aagcgcttct ctcttttctc tctgtctctg tttctttctc ctcccattct     13200
ctccaaccaa cagaggctcc aactgctgac ttttcactgt ctttgaactc taggttacaa   13260
tgtgttggac tgggtggggg ggaagcaagg gactctgcca cctggaaccg agaaggtggc   13320
ctagaaaaca tccagctata aagcaacaat tgacctggga gaggaggtgg agcactgggg   13380
atctgcggtg ggggtagagc tggggaggt gggtgaggag tggacaagat ggctcaaatc     13440 cccctcagt tacctgtgtt taaagagcaa gcagtattta tttggaaaga cacacacaca    13500
cacacacaca cacacacaca cacacacaca ctctcaacgg gaagaaacct gtttttagt     13560 gaaataaaat gcaagtcctt tatgtcttca atccatttaa gctttaaaca taaaatagga   13620
tccctttttc ttttcttctg gtggaacacc cacagagggt gtggtaaaag cgaaaaaaga   13680
atctatgatc gtccccgggc tgtgagccat ctgtccgaca ctcatctctc tctgcaggga   13740
ctggggcaaa tacaaacggt tcaactgagt actggtgttg aaggacaggt gtccgttctg   13800
ccattatcaa ttcagatgtc agggttcttg ccaaacaaat ccttcagag taattcacaa   13860 atttgtggaa ggtgctgctc tctgtcattc actgattttt tgatagtaat tagaatatgt   13920
tccagctgtg agttttaatg ttacttttta ctttttaaaaa gttaatttgc aatcgaatgg   13980
ggagatgcat gtgaaatctg ccactgtagg aactcaaaaa aagaagtaaa attcattaaa   14040
ataagaagag ctactgatta ggggattgtc catctaaggg aaagtttaaa ctctgggtaa   14100
atactttaaa ttcataatcg cttattgaat tttccagcaa tgttgttggg cacgattatc   14160 cccatttttgc agatgacaac actgaggtgc agagaggcta aggggctttc cccgggatta   14220
cacagccact aagccacgag ctgggattcc aacttgggaa ctggagttcc gttggctcat   14280 actgagata acgcccttct gccttggttt tttccttcgc ctgtggtaga tttatgtccc    14340
agcgagggtg agagcgacgc cgaggccgag agcaaagagg agcatggccc cgaggcctgc   14400
gacgcggcca agatctccac caccacgtcg gaggagccct gccgtgacaa gggcagcccc   14460
gcggtcaagg ctcaccttttt cgctgctgag cggccccggg acagcgggcg gctggacaaa   14520
gcgtcgcccg actcacgcca tagccccgcc accatctcgt ccagcactcg cggcctgggc   14580
gcggaggagc gcaggagccc ggttcgcgag ggcacagcgc cggccaaggt ggaagaggcg   14640
cgcgcgctcc cgggcaagga ggccttcgcg ccgctcacgg tgcagacgga cgcggccgcc   14700
gcgcacctgg cccagggccc cctgcctggc ctcggcttcg ccccgggcct ggcgggccaa   14760
cagttcttca acgggcaccc gctcttcctg caccccagcc agtttgccat gggggcgcc    14820 ttctccagca tggcggccgc tggcatgggt cccctcctgg ccacggtttc tggggcctcc   14880
accggtgtct cgggcctgga ttccacggcc atggcctctg ccgctgcggc gcagggactg   14940 tccgggggcgt ccgcggccac cctgcccttc cacctccagc agcacgtcct ggcctctcag   15000
gtatggatcc ttcttcctgc ctccaccagt cttttccacct ttcgtccagt ttccctgtcc   15060
```

```
tttgccagca gaccctcacc cgatcccttt ggcctagtag ctgtaataat ttttactgag    15120
ccattaccgg gttcaaggct tagctcatgg agttattatg acttcattct ccccattcac    15180
cccaaaaatc tttaaaattt ttccgaagtt aaaggctgtt tccagcagag tagataggta    15240
gtaacaaaga taacagctgg acacagcact tactttcagg cattcttcta agtgcttgct    15300
ctgtattgac tcatttgacc taacccttca ggggtactat tatcacctcc actttacaga    15360
tgaaggcgaa gacgcccaga gatgttgagt gacttgtcca aggtcacaca gcgggtacat    15420
ggtggagctg agactcaacc ccaggctatc tgactccagg gcctctttga gggtttctga    15480
ttttagcttc agagctgaca tgtctcttaa gtgtctcata gccaacccett ccccaggaat    15540 gggactctag gcctggggag gggaagtgac tacttcctga gtaggagttc agtcttgatt    15600
cctccagcct ttcctcccag ttcgaagctc ttctccccac ccccaacccc aagcaggcca    15660
gcctattcct cgaagggtta atggtttgtg cacacgtggg aaatgtcaga ggacagggat    15720
aagcagggac tgggcaggc ctggaggcct gtgtgtggct cagacagctg tgctgggggg    15780
aggtctcagg cggctggaaa caccctgaac tcgatgaaaa ggttctatga ggttttgcat    15840
gctgttgcct tttgttttgt ctgagcacat tcgtctggtc tcccttccct gcgccaagaa    15900
accagattgg cctccccact ccaggggagga gggagctgag gaaaggcttg gcttctggca    15960
tttctcaatt cctcccatct cctctgctgg cttctccggg agaccctgtc ctaggtgggc    16020
aggtggttgg tacaccaagg actacctgaa cagacaaaac cttaagggca cctcaaggca    16080
tgatgcagag aactggccca ggccagggtg cctgcatctt aaatgctgct tctgccaatt    16140
cccagcttag tgcactcctg aactcctgcg gcctacctcg gcttctcacc tggaacacca    16200
gtgaatcatg ctggacgatt tctttgtctc tgtttataac aaatgccctt tttccctccc    16260
ccagccccag tttcctttg cttaagatct tcactgtctg tttttttttgt tttgttttgt    16320 tttgtttgga gaaacttcta ggattgggt gggaggatgg gggttgggga agaagaaaga    16380
tttaaaaaat tattcctact aatttatgtc ctccggcttc cccttggtta cctctgtggg    16440
gtaaactgaa tctgtatccc catttaacag gtgcaaggag atttcctggg ggctgcacac    16500
actgtgtgca gcatattgca ggcttttcact catttaatat ctacaaagtc tcaataagt    16560 atatgaatta cttatgatt ccctgttttt tcttcctata aggaagctga ggcacaagtt    16620
aatcaaagtc tcttggccta gggtgacaca gctaagattt gtacctagag atttctgagt    16680
gttgacttct ctcctgcccc cacctatctc ccccccaaa aaaaaaaaca caacaacaac    16740
aacaacagaa cataccaggg attcatggct tgcccaatgt tggaggggga gaagagagga    16800
gagggatgag ataagctcct cccacccggc tgactcgctg tgtgtctctt ttctcacccc    16860
agggcctggc catgtcccct ttcggaagcc tgttcccttaa cccctacacg tacatggccg    16920
cagcggcggc cgcctcctct gcggcagcct ccagctcggt gcaccgccac cccttcctca    16980
atctgaacac catgcgcccg cggctgcgct acagccccta ctccatcccg gtgccggtcc    17040
cggacggcag cagtctgctc accaccgccc tgccctccat ggcggcggcc gcggggcccc    17100
tggacggcaa agtcgccgcc ctggccgcca gccggcctcc ggtggcagtg gactcgggct    17160
ctgaactcaa cagccgctcc tccacgctct cctccagctc catgtccttg tcgcccaaac    17220
tctgcgcgga gaaagaggcg gccaccagcg aactgcagag catccagcgg ttggttagcg    17280
gcttggaagc caagcggac aggtcccgca gcgcgtcccc gtagaccgct cccagacacg    17340
tcttttcatt ccagtccagt tcaggctgcc gtgcactttg tcggatataa aataaaccac    17400
gggcccgcca tggcgttagc ccttccttt gcagttgcgt ctgggaaggg gccccggact    17460
```

```
ccctcgagag aatgtgctag agacagcccc tgtcttcttg gcgtggttta tatgtccggg   17520
atctggatca gattctgggg gctcagaaac gtcggttgca ttgagctact gggggtagga   17580
gttccaacat ttatgtccag agcaacttcc agcaaggctg gtctgggtct ctgcccacca   17640
ggcggggagg tgttcaaaga catctccctc agtgcggatt tatatatata tttttccttc   17700
actgtgtcaa gtggaaacaa aaacaaaatc tttcaaaaaa aaaatcggga caagtgaaca   17760
cattaacatg attctgtttg tgcagattaa aaactttata gggacttgca ttatcggttc   17820
tcaataaatt actgagcagc tttgtttggg gagggaagtc cctaccatcc ttgtttagtc   17880
tatattaaga aaatctgtgt ctttttaata ttcttgtgat gttttcagag ccgctgtagg   17940
tctcttcttg catgtccaca gtaatgtatt tgtggttttt attttgaacg cttgctttta   18000
gagagaaaac aatatagccc cctacccttt tcccaatcct ttgccctcaa atcagtgacc   18060
caagggaggg ggggatttaa agggaaggag tgggcaaaac acataaaatg aatttattat   18120
atctaagctc tgtagcagga ttcatgtcgt tctttgacag ttctttctct ttcctgtata   18180
tgcaataaca aggtttaaa aaaataataa agaagtgaga ctattagaca aagtatttat   18240
gtaattattt gataactctt gtaaataggt ggaatatgaa tgcttggaaa attaaacttt   18300
aatttattga cattgtacat agctctgtgt aaatagaatt gcaactgtca ggttttgtgt   18360
tcttgttttc ctttagttgg gtttatttcc aggtcacaga attgctgtta acactagaaa   18420
acacacttcc tgcaccaaca ccaataccct ttcaaaagag ttgtctgcaa cattttgtt   18480 ttcttttta atgtccaaaa gtgggggaaa gtgctatttc ctattttcac caaaattggg   18540
gaaggagtgc cactttccag ctccacttca aattccttaa aatataactg agattgctgt   18600
ggggagggag gagggcagag gctgcggttt gactttttaa tttttctttt gttatttgta   18660
tttgctagtc tctgatttcc tcaaaacgaa gtggaattta ctactgttgt cagtatcggt   18720
gttttgaatt ggtgcctgcc tatagagata tattcacagt tcaaaagtca ggtgctgaga   18780
gatggtttaa agacaaattc atgaaggtat attttgtgtt atagttgttg atgagttctt   18840
tggttttctg tattttttccc cctctcttta aaacatcact gaaatttcaa taaattttta   18900
ttgaaatgtc tttgggcctt tgtgttaaatg tttttctttt gggaacctttt cctgaagatg   18960 gacagtcagg ggagggtta gtatcttctt gttctgagtt taccccccttc ccttcgcctt   19020 taaataatta agaccgcccc cagcgaacca aaatgagatg tcactcaagt tacaaagcta   19080
aaaacaaaag tcccttactt gagcgaaggg agccacttca atctgaaatt acttttcctt   19140
taaattaggg agcaaagcag ggagacggaa aggggcctga tgagaataca gaagaaggg   19200 taatttcaga tactttttaag ttttaatgga aaaagactga tgtgctccct aagtcaggtt   19260
ttcccacccg aatccgacca aagtaagct cggcaagtac gaatgttttt cgttttaagc   19320
tcgccctcag ttttgacatc aatctggcga atccaagtcg aaaataccttt cttgcaccag   19380 tgtgtttggc tcggggaaaa ggccagcaga atgccccagc agtccgagcg ggcttggcta   19440
ggcagcaacc ctccaggttg tagaagtgga caagacgcaa cgcctttcca ctcggcaacc   19500
ccccacacag cctgcagtcc ctggtgcctc aaattgaacc cggctggccc aaggcgcccc   19560
tacgaggccc catccatccc gagttgtgcg tgcaaagcgc ggccagctcc gcgaaaactt   19620
agctgtgtca cgcgagggag gagggaaatt atccccgaaa ggggaaaggt aattccaggg   19680
tgcacatttc accccctcca cggcaaaagt cacccaggag gctgacatcc tcccctagtc   19740 tcccccttcaa acccgtctcc aggctgttcg gggagttgcc ttttgaagtt caatttatct   19800
```

```
ttgaaacatt caataaaaaa tgatgaggca ctgtcagtct tttggtctcc cgaccccag      19860 cctcgcctcc gaggtgtgtg tctgttgggg ggcgggggcg gcacgggaag gttcgagggt      19920
tagtccttag ccctttttctt gccctggggg ccatgacgtg aagacccagc tggagcctgc      19980
ctggcggctg cctccctccc cacccccac ccgccacccc ctggagcccg ccagcccggc      20040
cccaagtccc tgtcaccttc aggcctcttg aatgaccgga gaggaggacg cccctccct      20100 tccctcatcc tgtacttgga agggatcgag gtcgagacct tttggagagc ggggcaaagc      20160
cccttccatc tctggccagg cacgtgggga ccctacagc ctcctctgcg atgtctccgg      20220
gggtgggagg gaagacagac aaccagagta tgttggtgcg gagtcgcggg gggggggagg      20280
ggcggggtgc gctgcggggg tggcagggcc tgagctgaga cgggccctgg ggacctttga      20340
ggctggggct cccccgagga ctgggagatt ccaggcgcc gctccttctg cgcagcggct      20400
acagcctgaa gggggcagct ctggatccag cgacaacgcg cggtgtccgc gcctctgaga      20460
aggtggtagt tggctggttg cgctctcccg aattggggaa aaaagaactc agcctccaaa      20520
agggaagaaa tgctttgctt ttctcttctt tctcagtcca aatttgctta cctcctccct      20580
tctctccccc cgcccccgat ttggggaccc tgctcagact tgtgtccagc ctctcttact      20640
ggcgttcctc ttttttttttt tttttttttt ttaatctcct gtgtatctca tttgtatatt      20700
gtgatgttaa tgagtaactc ctgtagcgct gatgggcggg gggtggaggg gatgaacggc      20760
tcgcagtctc tctggatttt gctgcctatt actcacctgg cgccggtcgc aatctcgccg      20820
caggctttat ggtggctgcg ccgcccccag aggccactca gggcaggcgc cttcgccttt      20880
tttctgggct tcgagtgcca cctatctgtc t                                   20911
```

<210> SEQ ID NO 15  
<211> LENGTH: 305  
<212> TYPE: DNA  
<213> ORGANISM: Homo sapiens

<400> SEQUENCE: 15

```
cagcaggcgc gctcccggcg aatctgcctg aatcgccgtg aatgcggtgg ggtgcagggc       60
aggggctggt tttctcagcc ggtcttggct tttctctttc tctcctgctc caccagcagc      120
ccctccgcgg gtcccatggg ctccgcgctc agaacagccc ggaaccaggc gccgctcgcc      180
gctcgctggg ggccaccgc ctctccccgg aacagcctcc cgcgggcctc ttggcctcgc      240
actggcgccc tcacccacac atcgtccctt tatccgctca gacgctgcaa agggccttct      300
gtctc                                                                 305
```

<210> SEQ ID NO 16  
<211> LENGTH: 336  
<212> TYPE: DNA  
<213> ORGANISM: Homo sapiens

<400> SEQUENCE: 16

```
gctttggatt tatcctcatt ggctaaatcc ctcctgaaac atgaaactga acaaagccc        60 tgaaccccct caggctgaaa agacaaaccc cgcctgaggc cgggtcccgc tccccacctg      120
gagggaccca attctgggcg ccttctggcg acggtccctg ctaggacgc tgcgctctcc      180 gagtgcgagt tttcgccaaa ctgataaagc acgcagaacc gcaatcccca aactaacact      240
gaacccggac ccgcgatccc caaactgaca agggacccgg aacagcgacc cccaaaccga      300
cacgggactc gggaaccgct atctccaaag ggcagc                              336
```

<210> SEQ ID NO 17
<211> LENGTH: 139
<212> TYPE: DNA
<213> ORGANISM: Homo sapiens

<400> SEQUENCE: 17
tttccacaac agggagccag cattgaggcg cccagatggc atctgctgga aatcacgggc   60
cgctggtgaa gcaccacgcc ttacccgacg tggggaggtg atcccccacc tcatcccacc  120
cccttctgtc tgtctccctt                                              139

<210> SEQ ID NO 18
<211> LENGTH: 292
<212> TYPE: DNA
<213> ORGANISM: Homo sapiens

<400> SEQUENCE: 18
gctggacaag gagcgctcac tgtagctctg ctgtggattg tgttggggcg aagagatggg   60
taagaggtca aagtcgtagg attctggcga ccgcctacca agggattggg tccacagcac  120
agaggtctga tcgcttcctt ctctgctctg ccacctccag acagcagctc taaccagctg  180
cccagcagca agaggatgcg cacggctttc accagcacgc agctgctaga gctggagcgc  240
gagttcgctt ctaatatgta cctgtcccgc ctacgtcgca tcgagatcgc ga          292

<210> SEQ ID NO 19
<211> LENGTH: 190
<212> TYPE: DNA
<213> ORGANISM: Homo sapiens

<400> SEQUENCE: 19
tgcctgacac tgaccccagg cgcagccagg aggggctttg tgcgggagag ggaggggac    60 cccagcttgc ctggggtcca cgggactctc ttcttcctag ttcactttct tgctaaggcg  120
aaggtcctga ggcaggacga gggctgaact gcgctgcaat cgtccccacc tccagcgaaa  180
cccagttgac                                                         190

<210> SEQ ID NO 20
<211> LENGTH: 706
<212> TYPE: DNA
<213> ORGANISM: Homo sapiens

<400> SEQUENCE: 20
tcggcggaga gacctcgagg agagtatggg gaaaggaatg aatgctgcgg agcgcccctc   60
tgggctccac ccaagcctcg gaggcgggac ggtgggctcc gtcccgaccc cttaggcagc  120
tggaccgata cctcctggat cagaccccac aggaagactc gcgtggggcc cgatatgtgt  180
acttcaaact ctgagcggcc accctcagcc aactggccag tggatgcgaa tcgtgggccc  240
tgaggggcga gggcgctcgg aactgcatgc ctgtgcacgg tgccgggctc tccagagtga  300
gggggccgta aggagatctc caaggaagcc gaaaaaagca gccagttggg cttcgggaaa  360 gactttctg caaaggaagt gatctggtcc cagaactcca gggttgaccc cagtacctga  420
cttctccggg agctgtcagc tctcctctgt tcttcgggct tggcgcgctc ctttcataat  480
ggacagacac cagtggcctt caaaaggtct ggggtgggg aacggaggaa gtggccttgg  540
gtgcagagga agagcagagc tcctgccaaa gctgaacgca gttagcccta cccaagtgcg  600
cgctggctcg gcatatgcgc tccagagccg gcaggacagc ccggccctgc tcaccccgag  660
gagaaatcca acagcgcagc ctcctgcacc tccttgcccc agagac                 706

<210> SEQ ID NO 21
<211> LENGTH: 325
<212> TYPE: DNA
<213> ORGANISM: Homo sapiens

<400> SEQUENCE: 21

| | | | | | |
|---|---|---|---|---|---|
| agatcccggt | gcatttaaag | gccggcgtga | tctgcaccac | gtacctatct | cggattctca | 60 |
| gtttcacttc | gctggtgtct | gccaccatct | ttaccacatc | ccggtagcta | catttgtcta | 120 |
| ccgcttgagc | caccagcgtc | tgaaacctgg | accggatttt | gcgcgccgag | aggtagccgg | 180 |
| aggcggtaat | gaattccacc | cagagggaca | tgctcctctt | gcgcccgtcg | ctcaacttca | 240 |
| gcaccgcgca | gccgggcagt | gagccatcgt | ccacgaagtt | gaacaccccc | atttggttga | 300 |
| gataaagcac | cacttcaaat | tcggt | | | | 325 |

<210> SEQ ID NO 22
<211> LENGTH: 663
<212> TYPE: DNA
<213> ORGANISM: Homo sapiens

<400> SEQUENCE: 22

| | | | | | |
|---|---|---|---|---|---|
| actatgcctt | gagggtcaaa | acgtctggat | ttcctgatcg | atgctgtcgt | cgctgtccac | 60 |
| ggagctactg | tcgccgtcag | agcgggaagg | cacgttcagg | gagtagaagc | gtgggcttgc | 120 |
| agaaagggac | ctgttgctgc | cttacatggg | ggccggcagg | gtagtcttgg | aaatgcccaa | 180 |
| gattgcttcc | gcgcgcgtca | gttcagcgga | cgtgtctgcc | tggcacgagg | accgttctac | 240 |
| aaactcgttc | ctggaagccg | ggctcgctgg | aggcggagct | ttggtttcct | tcgggagctt | 300 |
| gtggggaatg | gtcagcgtct | aggcaccccg | ggcaagggtc | tgtggccttg | gtggccactg | 360 |
| gcttcctcta | gctgggtgtt | ttcctgtggg | tctcgcgcaa | ggcactttt | tgtggcgctg | 420 |
| cttgtgctgt | gtgcggggtc | aggcgtcctc | tctcctcccg | gcgctgggcc | ctctggggca | 480 |
| ggtcccgtt | ggcctccttg | cgtgtttgcc | gcagctagta | cacctggatg | gcctcctcag | 540 |
| tgccgtcgtt | gctgctggag | tctgacgcct | cgggcgcctg | cgccgcactt | gtgacttgct | 600 |
| ttccccttct | cagggcgcca | gcgctcctct | tgaccccgct | tttattctgt | ggtgcttctg | 660 |
| aag | | | | | | 663 |

<210> SEQ ID NO 23
<211> LENGTH: 1985
<212> TYPE: DNA
<213> ORGANISM: Homo sapiens

<400> SEQUENCE: 23

| | | | | | |
|---|---|---|---|---|---|
| gcaagtcggg | tagctaccgg | gtgctggaga | actccgcacc | gcacctgctg | gacgtggacg | 60 |
| cagacagcgg | gctcctctac | accaagcagc | gcatcgaccg | cgagtccctg | tgccgccaca | 120 |
| atgccaagtg | ccagctgtcc | ctcgaggtgt | tcgccaacga | caaggagatc | tgcatgatca | 180 |
| aggtagagat | ccaggacatc | aacgacaacg | cgccctcctt | ctcctcggac | cagatcgaaa | 240 |
| tggacatctc | ggagaacgct | gctccgggca | cccgcttccc | cctcaccagc | gcacatgacc | 300 |
| ccgacgccgg | cgagaatggg | ctccgcacct | acctgctcac | gcgcgacgat | cacggcctct | 360 |
| ttggactgga | cgttaagtcc | cgcggcgacg | gcaccaagtt | cccagaactg | gtcatccaga | 420 |
| aggctctgga | ccgcgagcaa | cagaatcacc | atacgctcgt | gctgactgcc | ctggacggtg | 480 |
| gcgagcctcc | acgttccgcc | accgtacaga | tcaacgtgaa | ggtgattgac | tccaacgaca | 540 |
| acagcccggt | cttcgaggcg | ccatcctact | tggtggaact | gcccgagaac | gctccgctgg | 600 |

```
gtacagtggt catcgatctg aacgccaccg acgccgatga aggtcccaat ggtgaagtgc    660
tctactcttt cagcagctac gtgcctgacc gcgtgcggga gctcttctcc atcgacccca    720
agaccggcct aatccgtgtg aagggcaatc tggactatga ggaaaacggg atgctggaga    780
ttgacgtgca ggcccgagac ctggggccta accctatccc agcccactgc aaagtcacgg    840
tcaagctcat cgaccgcaac gacaatgcgc cgtccatcgg tttcgtctcc gtgcgccagg    900
gggcgctgag cgaggccgcc cctcccggca ccgtcatcgc cctggtgcgg gtcactgacc    960
gggactctgg caagaacgga cagctgcagt gtcgggtcct aggcggagga gggacgggcg   1020
gcggcggggg cctgggcggg cccggggggtt ccgtcccctt caagcttgag gagaactacg   1080
acaacttcta cacggtggtg actgaccgcc cgctggaccg cgagacacaa gacgagtaca   1140
acgtgaccat cgtggcgcgg gacggggcct ctcctcccct caactccacc aagtcgttcg   1200
cgatcaagat tctagacgag aacgacaacc cgcctcggtt caccaaaggg ctctacgtgc   1260
ttcaggtgca cgagaacaac atcccgggag agtacctggg ctctgtgctc gcccaggatc   1320
ccgacctggg ccagaacggc accgtatcct actctatcct gccctcgcac atcggcgacg   1380
tgtctatcta cacctatgtg tctgtgaatc ccacgaacgg ggccatctac gccctgcgct   1440
cctttaactt cgagcagacc aaggcttttg agttcaaggt gcttgctaag gactcggggg   1500
cgcccgcgca cttggagagc aacgccacgg tgagggtgac agtgctagac gtgaatgaca   1560
acgcgccagt gatcgtgctc cccacgctgc agaacgacac cgcggagctg caggtgccgc   1620
gcaacgctgg cctgggctat ctggtgagca ctgtgcgcgc cctagacagc gacttcggcg   1680
agagcgggcg tctcacctac gagatcgtgg acggcaacga cgaccacctg tttgagatcg   1740
acccgtccag cggcgagatc cgcacgctgc acccttttctg ggaggacgtg acgcccgtgg   1800
tggagctggt ggtgaaggtg accgaccacg gcaagcctac cctgtccgca gtggccaagc   1860
tcatcatccg ctcggtgagc ggatcccttc ccgaggggt accacgggtg aatggcgagc   1920
agcaccactg ggacatgtcg ctgccgctca tcgtgactct gagcactatc tccatcatcc   1980
tccta                                                               1985

<210> SEQ ID NO 24
<211> LENGTH: 213
<212> TYPE: DNA
<213> ORGANISM: Homo sapiens

<400> SEQUENCE: 24
atgcgccctc tgcaccccta gagccagaag acgctaggtg ggctgcgcgc tctgccaggc     60
gaaggctgga gcgcagacgg caaagccgcg cgtttcagcc gtggtcgggt ccgcaggacc    120
tgggcgtggg gacaccacca ggcaggagca gaggcaggac tgggacgcca aaagctgaga    180
atcctcgatg cccgcgcgag agccccgtgt tat                                 213

<210> SEQ ID NO 25
<211> LENGTH: 1558
<212> TYPE: DNA
<213> ORGANISM: Homo sapiens

<400> SEQUENCE: 25
ttctggaaac cgggccccac ttgcaggccc ggccaccttg ggttctggtg gccgaagccg     60
gagctgtgtt tctcgcagac tcggggagct acattgtgcg taggcaattg tttagtttga    120
aaggaggcac atttcaccac gcagccagcg ccctgcatgc aggagaagcc cccagggccc    180
```

| | |
|---|---|
| agggtcggct ggctttagag gccacttagg ttgttttaag cacatgtgaa agggcagaca | 240 |
| gcaggggagc aggatatggg taagatcttc gggtctcaga acaggggctg cccttgggct | 300 |
| gtcccggcgc cctgggctct gacactgaag ggtggaatgg aggaaggaat ggagaaagga | 360 |
| cggtggaact ttcgcttccc ctctgggccg ccttccaggg tcatgcctg agctgctttg | 420 |
| atcccagtgt cgcgcatctt ggtccgctac ctcccaggcg atagctactg ggctcctcgc | 480 |
| tggcctcact gggggccatc ccgggcagtg gcctgccctc cgaggcccgc gggacccagc | 540 |
| ccagagctga ggttggagtt ctccgggcca cgttccgggt cgcttaggct cggagatttc | 600 |
| ccggagaccg tcgtcctccc tttctgcttg gcactgcgga gctccctcgg cctctctcct | 660 |
| cctctggtcc ctaaggcccg gagtggttgg cggtactggg gcccgtcgtc atctctgctt | 720 |
| ctaaggcatt cagactgggc tccagctggg accggcagag gaggttctca aggaaactgg | 780 |
| tgggaaatat agttttcttt cgtctggtcg tttaatttaa atgcaacttc ccttggggac | 840 |
| attttcctgg acgttaacca gaccaccttg agatgtcgtt gatgacctag agacccagat | 900 |
| gatgcgtccc aggaaagttc actgctgact attgtcactc ttggcgttat atctatagat | 960 |
| atagacctat gtacatatct ccaccctgat ctctccgtgg acatgaaacc cacctacctt | 1020 |
| gtgaaagccc tacgggtgac acatgactac tacgtctctg tcccaacagg ggctgggcct | 1080 |
| cccctgccta atagttgcca ggagtttcgc agcccaagtg aataatgtct tatggctgaa | 1140 |
| cgtggccaag gactcctgtg atttaggtcc caggaggagc agagacgtcc ccgccccgcc | 1200 |
| tgggccctgc cgcattcaaa gctggaagaa ggcgctgatc agagaagggg cttccaggtc | 1260 |
| ctgggttaga caacaacaa acaaacgaaa ctccacaaca gacacgcctg cccatgaccc | 1320 |
| cacgcaagga cataggaagt tctgtcgcct tcctgctccg cggatagccg cctgccgtct | 1380 |
| gctgccacca gaacgcacgg acgctcgggg tggaggtagt caatgggcag caggggaccc | 1440 |
| ccagccccca caagcgcggc tccgaggacc tggaagcggg tgcctgtcgc tctccgcagg | 1500 |
| ctccgctctg cctccaggag caagatcccc aaaagggtct ggaagctgtg gagaaaac | 1558 |

<210> SEQ ID NO 26
<211> LENGTH: 1264
<212> TYPE: DNA
<213> ORGANISM: Homo sapiens

<400> SEQUENCE: 26

| | |
|---|---|
| tttttttaaac acttcttttc cttctcttcc tcgttttgat tgcaccgttt ccatctgggg | 60 |
| gctagaggag caaggcagca gccttcccag ccagcccttg ttggcttgcc atcgtccatc | 120 |
| tggcttataa aagtttgctg agcgcagtcc agagggctgc gctgctcgtc ccctcggctg | 180 |
| gcagaagggg gtgacgctgg gcagcggcga ggagcgcgcc gctgcctctg gcgggctttc | 240 |
| ggcttgaggg gcaaggtgaa gagcgcaccg gccgtggggt ttaccgagct ggatttgtat | 300 |
| gttgcaccat gccttcttgg atcggggctg tgattcttcc cctcttgggg ctgctgctct | 360 |
| ccctccccgc cggggcggat gtgaaggctc ggagctgcgg agaggtccgc caggcgtacg | 420 |
| gtgccaaggg attcagcctg gcggacatcc cctaccagga gatcgcaggt aagcgcgggc | 480 |
| gcgctgcagg gcaggctgc agccctcggc tgccgcacgt cccactggcc gcccggcgtc | 540 |
| cccttccttc cccctgttgc tgagttggtg ctcactttct gccaccgcta tgggactccg | 600 |
| cgtctccgtg ttgggcggcg gatgctcctg cggcttcttc ggcggggaa ggtgtgcgtc | 660 |
| tccgccgcct cattgtgtgc acacgcggga gcacctggc tccgcctcc cgctgctctc | 720 |
| gcgcccttct acccccttagt tgatggctca ggcccggctg gccagggagc ccgggtcact | 780 |

```
ccggggcggc tgcaaggcgc agacggagag ccgagccggg cgctcactcc gcgttctggt    840
tcgggcaaac ttggaagaac tgcgaccgca gtttgcccag cgccacagtc tgagtggcgc    900
cttctccact cccgcccttg cgccggcagg ggcggtggag agacgcggag ggctccccca    960
gcccctctct ccctatccg tccttcgggc gacagagcgc ccggcgctcg ggccggggc    1020 gggcaaggct gggagggacc ctcgccgggg acctggcctc tggacgccgg cgtttcaagg   1080
ctggtttggg gacttcacgg gctgcctgtt tcagatgtgg ggcgggcttt cccgttaggg   1140
ttcctcagtg cttccccagt tgctgttggc cactcagggc ccggggacac cctgccaccc   1200
ggtctggagc cggcctcgtc tgccagcgaa cagccaactt tagcgggtgg ctcagctggg   1260
gatt                                                                1264
```

```
<210> SEQ ID NO 27
<211> LENGTH: 761
<212> TYPE: DNA
<213> ORGANISM: Homo sapiens

<400> SEQUENCE: 27
cactcagtgt gtgcatatga gagcggagag acagcgacct ggaggccatg ggtgggggcg     60
ggtggtgaag ctgccgaagc ctacacatac acttagcttt gacacttctc gtaggttcca    120
aagacgaaga cacggtggct tcagggagac aagtcgcaag ggcgactttt ccaagcggga    180
gatggtgaag tctttggacg tgtagtgggt aggtgatgat ccccgcagcc gcctgtaggc    240
ccgcagactt cagaaaacaa gggccttctg tgagcgctgt gtcctccccg gaatccgcgg    300
cttaacacat tctttccagc tgcggggcca ggatctccac cccgcgcatc cgtggacaca    360
cttagggtcg cctttgtttt gcgcagtgat tcaagttggg taaccccttgc tcaacacttg    420 ggaaatgggg agaatctccc ccacccgcaa cctcccgcac cccaggttcc caaaatctga    480
atctgtatcc tagagtggag gcagcgtcta gaaagcaaag aaacggtgtc caaagacccc    540
ggagagttga gtgagcgcag atccgtgacg cctgcggtac gctagggcat ccaggctagg    600
gtgtgtgtgt gcgggtcggg gggcgcacag agaccgcgct ggtttaggtg gacccgcagt    660
cccgcccgca tctggaacga gctgcttcgc agttccggct cccggcgccc cagagaagtt    720
cggggagcgg tgagcctagc cgccgcgcgc tcatgtttat t                        761
```

```
<210> SEQ ID NO 28
<211> LENGTH: 1198
<212> TYPE: DNA
<213> ORGANISM: Homo sapiens

<400> SEQUENCE: 28
agtcactcca ggatcagagg ccgcgtcggt tctgcttggg gcatgggcag agggaggctg     60
ctggggccaa gccccggctg gacgcgaggg aagaaactcg tcccaggacc cgcacgccca    120
tacctggctg tcccagagct cttccctagg ccggcacctt cgctcttcct cttcccacc    180 ccctagccct tttgtctctt tttcagacgg atgttttcag tctcaagtgg ttttatttc    240 cgcacaaaac cctgagatca agggcagatc acagactgta ccggaggctc gggtttccct    300
ggactctgtg ctgttctgcg tcccaggtt ggctaggaag gaaggcctgg gccggcgagg     360
tgacgggtct cccgcccagg tcggcaggac ggggggaggt gtgtcccggt aggtccctgg    420
tgagctcacc cgtggcatcg gggacccgcg ggaacccacc gggcgcccac tagagactcg    480
ggtcctaccc tccccacac tactccaccg aaatgatcgg aagggcgcgc taggcctgct    540
```

```
tccaagggct cagtgataaa ggcctcaaaa tcacactcca tcaagacttg gttgaagctt      600
tgggtaggtt tgttgttgtt gttgttgttg tttgtttgtt tgttttagca gacacgtcct      660
ggaaagaggt cctcagaacc caaaggttca ataatgattt gtggatggat tgattatagt      720
ctgatatcgc tctggttcca cagaaacccg gagctccttg gcccactgtt acccagcag       780 acctaaatgg acggtttctg ttttcactg gcagctcaga actggaccgg aagaagttcc       840
cctccacttc cccctcccg acaccagatc attgctgggt ttttatttc ggggaaaaa         900 caacaacaac aacaacaaaa aaaacactag gtccttccag actggatcag gtgatcgggc      960 aaaaacccctc aggctagtcc ggctgggtgc ccgagcatga aaaggcctcc gtggccgttt    1020
gaacagggtg ttgcaaatga aacttttgt aagccataac cagggcatcc tgagggtctg      1080
agttcacggt caaggctgtg ggctactagg tccagcgagt ccaggcctcg ccccgccccc     1140
gagctgccac agccaagatc ttcggcaggg aattcgagac cagggtcctc ccactcct      1198
```

```
<210> SEQ ID NO 29
<211> LENGTH: 377
<212> TYPE: DNA
<213> ORGANISM: Homo sapiens

<400> SEQUENCE: 29
tttcgtgccg ctgttttcaa tgcgctaacg aggcacgtta ttcttagccg cgtccgggag      60
gggatcacat tcctgcgcag ttgcgctgct ggcggaagtg acttgttttc taacgaccct     120
cgtgacagcc agagaatgtc cgtttctcgg agcgcagcac agcctgtccc atcgagaagc     180
ctcgggtgag gggcccggtg ggcgcccgga ggccgctgga gggctgtggg agggacggtg     240 gctcccccact cccgtggcga agggcaggca accagaagc ctctttttgag agccgtttgg    300 gattgagacg agtaagccac agcgagtggt tagaagtagg ttaggaagaa ggggaggtaa     360
gaaagccgag tagggtt                                                    377
```

```
<210> SEQ ID NO 30
<211> LENGTH: 256
<212> TYPE: DNA
<213> ORGANISM: Homo sapiens

<400> SEQUENCE: 30
gttcggtgga caaggggca gcgcccacag caagccggaa agagggaggc gcggggccgc       60
gcttggggcc tgccgctgca cgccagcctg gcaaagagc tgccaccttc tgcgggcgaa     120
gcgggtcggg acgcaggacg gcagcggggc tggaggcagc tacgtgggtc cacacccccca    180 tgccctgcaa ggctccttgg ccctgcttct cctctgtctc ggcgggagag gagcagcctc     240
ggttttacag aatttc                                                     256
```

```
<210> SEQ ID NO 31
<211> LENGTH: 189
<212> TYPE: DNA
<213> ORGANISM: Homo sapiens

<400> SEQUENCE: 31
tgtgccattt agtgagaggt gttttgggca aagaatcaat ttaactgtga ctgaccgacg       60
ggcttgactg tattaattct gctaccgaaa aaaaaaaaa aaaaaagca atgagccgca       120 agccttggac tcgcagagct gccggtgccc gtccgagagc ccaccagcg cggctcacgc      180 ctcagtctc                                                             189
```

<210> SEQ ID NO 32
<211> LENGTH: 707
<212> TYPE: DNA
<213> ORGANISM: Homo sapiens

<400> SEQUENCE: 32

```
agagtcccag ttctgcaggc cgctccaggg ctaggggtag agatggtggc aggtggtgcg    60
tcaactctct agggaagagg aacttgcatt acaaagactt gtctttctga gctgaagtca   120
aaacggggc gtcaagcgcg ctccgtttgg cggcggtgga ggggccgcgc gcccgcgctg    180
tcccagccgg agctgccctg gctggtgatt ggaggtttaa cgtccggaat tcaggcgctt   240
ctgcagctca gatttgccgg ccaaggggcc tcagttgcaa cttttcaaaa tggtgtttct   300
ggaaaataac aaattcagac tcaactggtg acagcttttg ctatagaga atgaaactgc    360
ttcccttttgg cggtggaact cttaaacttc gaagagtgaa agaatacaat gaaataaaat  420
gccataagat cactggattt ttcagaaaaa ggaagacccc aaattactcc caaatgagg    480
ctttgtaaat tcttgttaaa aatctttaaa tctcgaattt ccccctacaa catctgatga   540
gtgctttaag agcaaacgag caaatcccac ctcgagaatc aacaaaccca agctctggcc   600
aaggctctcc ccgcgttttc ttctcgtgac ctggggaatg tcccgcccca tcgctcacct   660
ggctcttgtc atctcgctca tcttgaagtg acccgtggac aatgctg                 707
```

<210> SEQ ID NO 33
<211> LENGTH: 182
<212> TYPE: DNA
<213> ORGANISM: Homo sapiens

<400> SEQUENCE: 33

```
agctgccctc tgtggccatg agcgggtgtc cagccccttc caaggctgca ccggggagac    60
gctggttttc tgctcgctgt gaccgaacaa agcccctaag agtcagtgcg cggaacagaa   120
gagccggacc ccgacgggcc gagtcccaac gtgaggcacc cggcagagaa aacacgttca   180
cg                                                                  182
```

<210> SEQ ID NO 34
<211> LENGTH: 179
<212> TYPE: DNA
<213> ORGANISM: Homo sapiens

<400> SEQUENCE: 34

```
cctcggcagc accggcatgg ctggaggcca gtacggccag gtgtggcggg agggagcgcc    60
gtctggcttg ggtcgtccat cctgacagga cgctgcaagg gcaggagccc cgcgccccgt   120
gtcctgcgcc cccgctcgag gacaagcccc agccgccggt ctccgctggg ttccgacag    179
```

<210> SEQ ID NO 35
<211> LENGTH: 369
<212> TYPE: DNA
<213> ORGANISM: Homo sapiens

<400> SEQUENCE: 35

```
ctttaagagg ctgtgcaggc agacagacct ccaggcccgc tagggatcc gcgccatgga     60
ggccgcccgg gactatgcag gagccctcat caggcgagtg ccccgcgtcc cctgattgc    120
cgtgcgcttc caatcgcctt gcgttcggtg gcctcatatt ccctgtgcg cctctagtac    180
cgtaccccgc tcccttcagc ccctgctcc ccgcattctc ttgcgctccg cgaccccgcg    240
cacacaccca tccgccccac tggtgcccaa gccgtccagc cgcgcccgcg ggcagagccc   300
```

```
aatcccgtcc cgcgcctcct caccctcttg cagctgggca caggtaccag gtgtggctct    360
tgcgaggtg                                                             369

<210> SEQ ID NO 36
<211> LENGTH: 176
<212> TYPE: DNA
<213> ORGANISM: Homo sapiens

<400> SEQUENCE: 36
agacttgcag aactcgggcc ccctggagga gacctaaccg ccacggtctt ggggaggttc     60
cggagggcct cggttgtctg cactcccaac accaagaaac ccctgagacg cgaagctgcc    120
agcgtgctgc cctcagagca gggcgacgca aagccagcgg accccggggt ggcggg        176

<210> SEQ ID NO 37
<211> LENGTH: 167
<212> TYPE: DNA
<213> ORGANISM: Homo sapiens

<400> SEQUENCE: 37
tgctcggctg gggggctcgc tccgcacttt cggtgccaga aaatgcccag aggagcgggg     60
cggccccaga gcctcctttc ggggcgcgag gcccggcgcg tgtgtacgga gtccagtccc    120
cccagggagt ggggtgcccg caccttcccc tccgcgctcg gagccac                  167

<210> SEQ ID NO 38
<211> LENGTH: 1205
<212> TYPE: DNA
<213> ORGANISM: Homo sapiens

<400> SEQUENCE: 38
tcttgcacac ctgcttgtag ttctgcaccg agatctggtc gttgaggaac tgcacgcaga     60
gcttggtgac ctgggggatg tgcaggatct tgctgaccga cagcacctcc tccaccgtgt    120
ccagggacag ggtcacgttg ccgtgtaga ggtactcgag caccaggcgc agcccgatgg     180
acgagcagcc ctgcagcacc aggttgttga tggcccgggg gctggtcagc agcttgtcgt    240
cgggggagga agaaggagtc ccgggctcct cctgcgcgg cggctgctgc tgctgtgacg     300
gctgctgctg cggcggctgc tgctggtcct tgggggcccc caggccgtcc tggccgccga    360
cccctccccc gagagggggg tggctggaga agagcgatcg gaagtactgc gagcaggagg    420
ccagcacggc cttgtggcaa tggaactgct ggccctgggc cgtcagggtc acgtcgcaaa    480
acagctgctt cctccacagc aggttgaggc cgtgcagcag gttgtcgctg tggctggggt    540
cgaaggtgga ggtcctgtcc ccggatctgg acatggcgag ctgactcggt gcacctggct    600
ttaaaccctc ctccaacctg gcagacaggg gtgggggatg ggagggaggg gagcagggtg    660
gtggagcggg tggggtgtgg tcggggtggg aagggtgtg gaggggaggg gagggcgaag    720
aacaagaatc aaggctcagc ttgactccct cctggcgcgc tccggacccc gaccctagga    780
ggaaagtccg aagacgctgg atccgtgagc gccaccagaa gggccctgtc tggggtcccg    840
gcgccggttc tgcgccctgc ggctcctctc gccacctccc acacacttcg tccctcactt    900
tcctaaaacc aaccacctca gctcggctgt tggcagcaac agcagtggca gcagcgacgg    960
caaagtggcg gctgaggccg aggcacctcg tgggctcgtg tccatgccgg ccagatgaa    1020 gggaaaggcc gggaagtggg gagccggggg tgccctgaaa gctcagaggc gaccgacggc    1080
gaaggttcca ggtcaacttg tgcccgaagc tttgctttc gcagttggcc cagtttgggg    1140
gagggggtag gaacaggggc ccgaccagcg tgcggggtgt gcgaatctta gctctccaaa    1200
```

-continued agctg                                                            1205

<210> SEQ ID NO 39
<211> LENGTH: 44
<212> TYPE: DNA
<213> ORGANISM: Homo sapiens

<400> SEQUENCE: 39
cctctgtgtt agtgccctcg ggaatttggt tgatggggtg tttg              44

<210> SEQ ID NO 40
<211> LENGTH: 5002
<212> TYPE: DNA
<213> ORGANISM: Homo sapiens

<400> SEQUENCE: 40
tgatgtcgca cctgaacggc ctgcaccacc cgggccacac tcagtctcac gggccggtgc    60
tggcacccag tcgcgagcgg ccaccctcgt cctcatcggg ctcgcaggtg ccacgtcgg    120 gccagctgga agaaatcaac accaaagagg tggcccagcg catcacagcg agctgaagc    180 gctacagtat cccccaggcg atctttgcgc agagggtgct gtgccggtct caggggactc    240
tctccgacct gctccggaat ccaaaaccgt ggagtaaact caaatctggc agggagacct    300
tccgcaggat gtggaagtgg cttcaggagc ccgagttcca gcgcatgtcc gccttacgcc    360
tggcaggtaa ggccggggct agccaggggc caggctgctg ggaagagggc tccgggtccg    420
gtgcttgtgg cccaagtctg cgcgccgagt cacttctctt gattctttcc ttctctttcc    480
tatacacgtc ctcttcttc tcgtttttat ttcttcttcc attttctctt tctcttccgc    540
tcttccccta ctttccttc tccttttct ttttctttct tactctctcc ttgtccctga    600
gctttcattg accgaccccc cccatttca ttcgccctcc cctcaatgtg ccaacctttg    660
ccctatttcc gatcttccca ggtactggga ggcgggatgg gggtgtgcgt tttcctctag    720
gagccctgtc tttccaagac ccacagaaac caggacctgc ccttattcaa aaccccatgc    780
acttcaagtc tcttttagac aacacatttc aattttccgg gctgactagt ctccctgtgc    840
agaggcagtt gagaggcttt gctctgcaga gggaaaagag ctctctactc tcccacccac    900
catataggca aacttatttg gtcattggct gaaggcacag ccttgccccc gcggggaacc    960 ggcggcagg atacaacagc gctcctggag cccatctctg gccttggcgt tggcgcaggg   1020
actttctgac cgggcttgag gggctcgggc cagctccaat gtcactacct acagcgaggg   1080
cagggtgtaa ggttgagaag gtcacattca ccgctttggg aggacgtggg agaagagact   1140
gaggtggaaa gcgctttgcc ttgctcaccg gccgtccttg ccccggtccc agcgtttgct   1200
gggatttgcc aggatttgcc ggggctccgg gagaccctga gcactcgcag gaagaggtgc   1260
tgagaaatta aaaattcagg ttagttaatg catccctgcc gccggctgca ggctccgcct   1320
ttgcattaag cgggcgctga ttgtgcgcgc ctggcgaccg cggggaggac tggcggcccg   1380
cgggagggga cgggtagagg cgcgggttac attgttctgg agccggctcg gctctttgtg   1440
cctcctctag cggccaagct gcgaggtaca gccctctatt gttctaggag cacagaaacc   1500
tcctgtgtgg gcgcgggtg cgcgagctag agggaaagat gcagtagtta ctgcgactgg   1560
cacgcagttg cgcgcttttg tgcgcacgga ccccgcgcgg tgtgcgtggc gactgcgctg   1620
cccctaggag caagccacgg gcccagaggg gcaaaatgtc caggtccccc gctgggaagg   1680
acacactata ccctatggca agccagggtg ggcgacttcc catggatcgg gtggaggggg   1740

```
gtatctttca ggatcggcgg gcggtctagg ggaacaattc gtggtggcga tgatttgcat   1800
agcgcgggtc ttgggatgcg cgcggttccg agccagcctc gcacagctcg cttccggagc   1860
tgcgagctca ggtttccacc cccgatcccc cgggctttcc tcgcaccgct gagcccagct   1920
tgtggggtgc actcgaccaa cgcccgacag ggctggggaa tgtgacaggc agcaggttca   1980
cccgggcttg ggaggggga gttccgctt tgacagcatt ttcctttgcc gtctgctggt   2040
ggattcctat tcccagtcgg taatcgcccc gcagtgttga tctaagaagg taaagaaaac   2100
taggtttccc tgcaaagagc ctcccccaaa tcggcggact ccggatactt tgagtggatt   2160
tagaaattta tgtaatcttt ctcctttagt ttatttttca tcctctccta cagttttctc   2220
tgatttgctg ttggttcggg gcaagataaa gcagccagta gagagcgata ataatagcgg   2280
cgggaaatga actggagact ggctgacagt tcttaacatt ttgtcataga tcccccccgaa   2340
tgtcccaggc tgtctctggt gggttttagt acccgccggc ttcttgggca ccggggacca   2400
gaaggaactt ggcagctggt cttaggggta cagttaaagg caggatgaca gctattctcc   2460
tgctcatctc agagcgctgc cgcccctca tgccggtcgc gcaaagaaca cagcttttaa   2520
aaaacacgtg ccttctgccc atataggtct gaaagtgatg aggaaagtaa tgcttcgcct   2580
attagcgagt ttcagctttt aaaatgatcc caagcgttgc tgagatgaga aagcgtggca   2640
tcccgggggt cctcagcccc acccgcgccc atggtgcaag tctgcaggga caggcccggg   2700
acagcactgc ccacgctgct agattttccg cagaggatcg ctgaagctgc cttcgtggga   2760
gacagaatgc ctcctccagc gagtggaaaa ggcctgctga ggaccccgct tgctcgagc   2820
attcaaatgt gtgtctgttt tattaccctg ggttgaaaag ggacaagagc tttagccttt   2880
ttatctggcc attttatcag caactacaag tgtgttgagt ggttattatt acataggagg   2940
cttttcagtt tgggtcagt agatcagtct cttcagacac tgatgcagaa gctgggactg   3000
gtaagtaggt attatgtgct cggagcgcta ggggacagga gcaaatggag aagaaaagcg   3060
gaggctttct ccgcccggag tatcgatcgg aatccccgcc ggtacgccgc agagggccct   3120
cgccgttggg ccccgggggt ttaacaagcc cagccgctcc gcaggcggct cggccggact   3180
ctcagaccgg tgcctggaag acaccgtccc tgccccctc ccgccaaacc tgcctcttct   3240
cttctctca taggttatag gttccctttc tctctcattt tggccccgcc ccgggtcct   3300
gccaaacagc caagcaggcc ggggtttagg gggctcagaa tgaagaggtc tgatttggcc   3360
agcgccggca aagctcaccc ttaggcgagg tcacaacaga ggcaggtcct tcctgcccag   3420
cctgccggtg tagtcacagc caagggtggc acttgaaagg aaaagggaga aaacttcgga   3480
gaaatttaga ttgccccaac gttagatttc agagaaattg actccaaatg cacggattcg   3540
ttcggaaagg gcggctaagt ggcaggtggt tgcaaccccg ccggtcggg ccttcgcaga   3600
ggttccccaa gaccagccct tgcagggcgg ttttcagcaa cctgacaaga ggcggccaag   3660
acaaatttct gcgggttcga gcacacactc tcgggcgttg ggcccagag acctctaaac   3720
caagcacaaa caagaaggga gtgagagaac ccaggctaga acttgcacgg gcatcccact   3780
gaggaaaagc gaggcctcgg tggcaggcat gttttcttcc gacgcccgaa aatcgagccg   3840
agcgcccgac tacatttact gcagaggttt ccgcctccag tgagcccgga tcccccagcg   3900
gcctgcccgg agctggtctc cagtcccgc cgtagtccga cgcacggccc tctcctggca   3960
gcaagctccc agcggccagt ctgaagccaa ttctgttcag gcggccgagg gcccttagcc   4020
aacccaccat gatgtcgcct gggccacctg atgcccgcag cggcgggaca cggcccgggc   4080
agtgcgcagt ggctcctgct aggggcaccg cgtgcgtgct tgtctcccgc tgcgccgggg   4140
```

```
acgtccttgg gtgacacggg ccgctgggca cctcccaagc cgaggaaacg gaccccttc      4200 gcagagtctc gcgcccaccc cccaacctcc cacctcgttt ctcgctgcta gggctcccga      4260
ctcagcccac ctctcctggc ggtttagtta gggatcagag ctggagaggc tgaacgcaac      4320
ccgtgccagt acggaacaga cgatatgttt gcctgctagc tgcttggatg aataattgaa      4380
aagttcgctg cagtctgtgc ttcgtcaagt cccgggtgcc gggagaacac cttcccaaca      4440
cgcatcaggg tgggcgggag cgggcagagg aggcgggacc cgagggagga gagtgaaccc      4500
gagcaggaga agcagcccag gcagccaggc gccctcgatg cgagaggctg ggcatttatt      4560
tttattccag gctttccact gtgtggttat gtcactttct caaacaaatg tgtatatgga      4620
gggagatcga tgctgataat gtttagaaga ttaaagagc attaatgctg caacaataa       4680 cgtaaacgtg tggacccaga tttcattgat ctggaacttg atccggcgcg tttccagtaa      4740
gcccgacggc gcgctcttcc cagcagagcg ctcaccagcg ccacggcccc gcggttttcc      4800
agcggtgccg cttcgccagc tctgcgcggg ttctcccgtc tgaccgcagc tcctcccccg      4860
cgaggcccca gcccgcctta cttccccgag gttttctcct cctctcgcgg ggctctctgc      4920
cctctgcacc ccctccccg  acctctgcac cacccgcccc tgtgcgcaca caccgctact      4980
tgcgcttccg gcgatccgcc tg                                               5002

<210> SEQ ID NO 41
<211> LENGTH: 150
<212> TYPE: DNA
<213> ORGANISM: Homo sapiens

<400> SEQUENCE: 41
aaccggagat ctgcttggtg aactgagagg agtccttagg agagcgggga cgccaggggc       60
cgggggacac ttcgctctcg ccctagggaa ggtggtcttg acgctttcta ttgaagtcaa      120
acttgaaaat atcagctgcc gctggactat                                       150

<210> SEQ ID NO 42
<211> LENGTH: 339
<212> TYPE: DNA
<213> ORGANISM: Homo sapiens

<400> SEQUENCE: 42
cgtgagcaga acgcccgccc tggagcagtt aggaccgaag gtctccggag agtcgccggc       60
ggtgccaggt aacgcagagg gctcgggtcg ggccccgctt ctggggcttg ggactccggg      120
cgcgcggagc cagccctctg gggcgaaatc cccgggcggc gtgcgcggtc cctctccgcg      180
ctgtgctctc ccagcaactc cctgccacct cgacgagcct accggccgct ccgagttcga      240
cttcctcgga cttagtggga aaggggttg gaaatgggct gccggactg ggggagctgc        300 tctctggaag cagggaagct ggggcgcacc ggggcaggt                             339

<210> SEQ ID NO 43
<211> LENGTH: 1961
<212> TYPE: DNA
<213> ORGANISM: Homo sapiens

<400> SEQUENCE: 43
tagaagagga agactcctct ggccccacta ggtatcatcc gcgctctccc gctttccacc       60
tgcgccctcg cttgggccaa tctctgccgc acgtgtccat ccctgaactg cacgctatcc      120 tccaccccg  gggggttcct gcgcactgaa agaccgttct ccggcaggtt ttgggatccg      180
```

```
gcgacggctg accgcgcgcc gcccccacgc ccggttccac gatgctgcaa tacagaaagt    240
ttacgtcggc cccgacccgc gcgggactgc agggtccgcc ggagcgcggc gcagaggctt    300
ttcctgcgcg ttcggccccg ggaaagggc gggagggctg gctccgggag cgcacgggcg    360
cggcggggag ggtactcact gtgaagcacg ctgcgcccat ggatcatgtc tgtgcgttac    420
accagaggct ccgggctcca ctaattccat ttagagacgg gaagacttcc agtggcgggg    480
ggaggacagg gtcgagaggt gttaaagacg caaagcaaga aggaaataaa ggggggccga    540
gagggagacc gagaggaagg gggagctccg agcccacgct gcagccagat ccggatgagt    600
ccgtcctccg ccccgggcgg gctctcgctc tcgctggccc tcagcgccgc gcagccagca    660
gcatccccac cgtgacgctc gcatcacacc cgggcgccgg ccgccaccat ccgcgccgcc    720
gccgtcagga ccctcctccc gggcatcgtc gccgccgcgg ggtcgggagg acgcggcgcg    780
cgggaggcgg cggtcgcagg gcgagccccg ggacgccccg agccggggcc ggggccgggg    840
agagggcgca gcgaggtggg ggccagtcca accgacggc agcgacggag cgggcggcgg    900
cggcggcgcc ggcggcggcg gggtggctca gtccccagtc tcagacgcgc cgcgcagcag    960
gtcggagcag cctcccccggg aggatgtcca gcggcagcgc tcctcgctcc agcccttggg   1020
gatcttccgc tgaggcattg aaggcaggaa gaagggtcc gtcatcggct cgccgggctg    1080
cgcgccacct ctgctatctt gcggaaagag gagcgggtgg gtgggcgtct gggaggcggg    1140
ctggagggcg gtgcagggga gcgggcggc cggggggggg gccggggggc ggggaaggga   1200
gggaggagaa aggagccgga agagggcaga gttaccaaat gggctcctta gtcatggctt    1260
ggggctccac gaccctcctg gaagcccgga gcctgggtgg gatagcgagg ctgcgcgcgg   1320
ccggcgcccc ggggctggtg cgcggcagaa tggggccgcg gcggcggcag caaggacatc    1380
ccagccgcgc ggatctgggg gaggggcggg gaggggggtga ggacccggct gggatccgcg   1440
gctcggcccg ccagggcgca gagagaggat gcagccgcaa atcccgagcc ggatcctcgt    1500
gccgacggat aggcgtggaa gcgggagggg ccttcgtgtg aaaatccctt gtggggtttg    1560
gtgtttcact tttttaaggt tagaccttgc gggctctctg cctcccaccc cttctttttcc    1620 atccgcgtaa aggaactggg cgccccctct ccctccctcc ctgggcgca ggtttcgccg    1680 cggactccgc gctcagcttg ggagacacgg caggggcgcg cccccaggga aggcggccgt   1740
aaaagtttcg cggttgagca ctgggcctga tgtccagtcc ccccaccaaa ttactcctgc    1800
aaagacgcgg gcttcttgca attgagcccc ccacctcgag gtatttaaaa ccaccccaag   1860
gcacacacgg accccgttc ccccgcgcca cttcctccta caggctcgcg cggcgcgtta   1920
aagtctggga gacacgagtt gcggggaaac agcaccggaa g                        1961

<210> SEQ ID NO 44
<211> LENGTH: 314
<212> TYPE: DNA
<213> ORGANISM: Homo sapiens

<400> SEQUENCE: 44
aagaaacagc tcatttcgga gctgaggaca aggcgtggga agaagacgcg tttggtttca     60
cccaggcggt tggcggcaaa gctgtgggat gcgcgctgca cactccttcc gtcatcccgt    120
tcccaccttc cacacacacc tgcgggaggt cggacatgtc ctgattgcgt gttcatcacg    180
atggcaaacc gaacatgagg agaacgccac tgacgctggg tgcgccggct ttcccagccc    240
tcgtgcataa cggggaggga gatgcagaag ttttttccaa catcggtgca aaggggaagc    300
tgaggttttc ctat                                                      314
```

<210> SEQ ID NO 45
<211> LENGTH: 584
<212> TYPE: DNA
<213> ORGANISM: Homo sapiens

<400> SEQUENCE: 45

| | | | | | | |
|---|---|---|---|---|---|---|
| tctgtcagct | gctgccatgg | ggcagcggga | aggccctgga | gggtgcctgg | gctgtgtctg | 60 |
| gtcccggcca | cgcgtccctg | cagcgtctga | gaccttgtgg | aacacacttg | acccggcgct | 120 |
| gggacggggt | cggcccacac | gcaccgccag | cccgcaggag | tgaggtgcag | gctgccgctg | 180 |
| gctccttagg | cctcgacagc | tctcttgagg | tcggccctcc | tcccctcccg | agagctcagc | 240 |
| agccgcagac | ccaggcagag | agagcaaagg | aggctgtggt | ggcccccgac | gggaacctgg | 300 |
| gtggccgggg | gacacaccga | ggaactttcc | gcccccgac | gggctctccc | accgaggctc | 360 |
| aggtgctcgt | gggcagcaag | gggaagcccc | atggccatgc | cgcttccctt | tcaccctcag | 420 |
| cgacgcgccc | tcctgtgccc | gcggggaaca | agacggctct | cggcggccat | gcaggcggcc | 480 |
| tgtcccacga | acacgatgga | gacctcagac | gccgtcccca | ccctgtcact | gtcaccatca | 540 |
| cccatcctgt | ccctcacgc | ctccccacat | cccatcatta | ctac | | 584 |

<210> SEQ ID NO 46
<211> LENGTH: 349
<212> TYPE: DNA
<213> ORGANISM: Homo sapiens

<400> SEQUENCE: 46

| | | | | | | |
|---|---|---|---|---|---|---|
| gaagtagaat | cacagtaaat | gaggagttag | ggaatttagg | gtagagatta | aagtaatgaa | 60 |
| cagaggagga | ggcctgagac | agctgcagag | agaccctgtg | ttccctgtga | ggtgaagcgt | 120 |
| ctgctgtcaa | agccggttgg | cgctgagaag | aggtaccggg | ggcagcaccc | gcctcctggg | 180 |
| agagggatgg | gcctgcgggc | acctggggga | accgcacgga | cacagacgac | actataaacg | 240 |
| cgggcgagac | atcagggacc | gggaaacaga | aggacgcgcg | tttcgagcag | ctgcccagtg | 300 |
| ggccacaagc | cccgccacgc | cacagcctct | tcccctcagc | acgcagaga | | 349 |

<210> SEQ ID NO 47
<211> LENGTH: 3510
<212> TYPE: DNA
<213> ORGANISM: Homo sapiens

<400> SEQUENCE: 47

| | | | | | | |
|---|---|---|---|---|---|---|
| tactccggcg | acgggaggat | gttgagggaa | gcctgccagg | tgaagaaggg | gccagcagca | 60 |
| gcacagagct | tccgactttg | ccttccaggc | tctagactcg | cgccatgcca | agacgggccc | 120 |
| ctcgactttc | acccctgact | cccaactcca | gccactggac | cgagcgcgca | agaacctga | 180 |
| gaccgcttgc | tctcaccgcc | gcaagtcggt | cgcaggacag | acaccagtgg | gcagcaacaa | 240 |
| aaaaagaaac | cgggttccgg | gacacgtgcc | ggcggctgga | ctaacctcag | cggctgcaac | 300 |
| caaggagcgc | gcacgttgcg | cctgctggtg | tttattagct | acactggcag | gcgcacaact | 360 |
| ccgcgccccg | actggtggcc | ccacagcgcg | caccacacat | ggcctcgctg | ctgttggcgg | 420 |
| ggtaggcccg | aaggaggcat | ctacaaatgc | ccgagccctt | tctgatcccc | accccccgc | 480 |
| tccctgcgtc | gtccgagtga | cagattctac | taattgaacg | gttatgggtc | atccttgtaa | 540 |
| ccgttggacg | acataacacc | acgcttcagt | tcttcatgtt | ttaaatacat | atttaacgga | 600 |
| tggctgcaga | gccagctggg | aaacacgcgg | attgaaaaat | aatgctccag | aaggcacgag | 660 |

```
actgggcga aggcgagagc gggctgggct tctagcggag accgcagagg gagacatatc    720
tcagaactag gggcaataac gtgggtttct ctttgtattt gtttattttg taactttgct    780
acttgaagac caattattta ctatgctaat ttgtttgctt gttttaaaa ccgtacttgc     840
acagtaaaag ttccccaaca acggaagtaa cccgacgttc ctcacactcc ctaggagact    900
gtgtgcgtgt gtgcccgcgc gtgcgctcac agtgtcaagt gctagcatcc gagatctgca    960
gaaacaaatg tctgaattcg aaatgtatgg gtgtgagaaa ttcagctcgg ggaagagatt   1020
agggactggg ggagacaggt ggctgcctgt actataagga accgccaacg ccagcatctg   1080
tagtccaagc agggctgctc tgtaaaggct tagcaatttt ttctgtaggc ttgctgcaca   1140
cggtctctgg cttttcccat ctgtaaaatg ggtgaatgca tccgtacctc agctacctcc   1200
gtgaggtgct tctccagttc gggcttaatt cctcatcgtc aagagttttc aggtttcaga   1260
gccagcctgc aatcggtaaa acatgtccca acgcggtcgc gagtggttcc atctcgctgt   1320
ctggcccaca gcgtggagaa gccttgccca ggcctgaaac ttctctttgc agttccagaa   1380
agcaggcgac tgggacggaa ggctcttttgc taacctttta cagcggagcc ctgcttggac  1440
tacagatgcc agcgttgccc ctgcccaag gcgtgtggtg atcacaaaga cgacactgaa   1500
aatacttact atcatccggc tcccctgcta ataaatggag gggtgtttaa ctacaggcac   1560
gaccctgccc ttgtgctagc gcggttaccg tgcggaaata actcgtccct gtacccacac   1620
catcctcaac ctaaaggaga gttgtgaatt ctttcaaaac actcttctgg agtccgtccc   1680
ctccctcctt gcccgccctc tacccctcaa gtccctgccc ccagctgggg gcgctaccgg   1740
ctgccgtcgg agctgcagcc acggccatct cctagacgcg cgagtagagc accaagatag   1800
tggggacttt gtgcctgggc atcgtttaca tttgggcgc caaatgccca cgtgttgatg    1860
aaaccagtga gatgggaaca ggcggcggga aaccagacag aggaagagct agggaggaga   1920
ccccagcccc ggatcctggg tcgccagggt tttccgcgcg catcccaaaa ggtgcggctg   1980
cgtggggcat caggttagtt tgttagactc tgcagagtct ccaaaccatc ccatccccca   2040
acctgactct gtggtggccg tatttttttac agaaatttga ccacgttccc tttctcccctt  2100
ggtcccaagc gcgctcagcc ctccctccat ccccccttgag ccgcccttct cctccccctc  2160
gcctcctcgg gtccctcctc cagtccctcc ccaagaatct cccggccacg ggcgcccatt   2220
ggttgtgcgc agggaggagg cgtgtgcccg gcctggcgag tttcattgag cggaattagc   2280
ccggatgaca tcagcttccc agccccccgg cgggcccagc tcattggcga ggcagcccct   2340
ccaggacacg cacattgttc cccgcccccg ccccgccac cgctgccgcc gtcgccgctg    2400
ccaccgggct ataaaaaccg gccgagcccc taaaggtgcg gatgcttatt atagatcgac   2460
gcgacaccag cgcccggtgc caggttctcc cctgaggctt ttcggagcga gctcctcaaa   2520
tcgcatccag agtaagtgtc cccgcccac agcagccgca gcctagatcc cagggacaga    2580
ctctcctcaa ctcggctgtg acccagaatg ctccgataca ggggggtctgg atccctactc  2640
tgcgggccat ttctccagag cgactttgct cttctgtcct cccacactc accgctgcat    2700
ctccctcacc aaaagcgaga agtcggagcg acaacagctc tttctgccca gccccagtc    2760
agctggtgag ctccccgtgg tctccagatg cagcacatgg actctgggcc ccgcgccggc   2820
tctgggtgca tgtgcgtgtg cgtgtgtttg ctgcgtggtg tcgatggaga taaggtggat   2880
ccgtttgagg aaccaaatca ttagttctct atctagatct ccattctccc caaagaaagg   2940
ccctcacttc ccactcgttt attccagccc ggggggctcag ttttcccaca cctaactgaa  3000
agcccgaagc ctctagaatg ccaccccgcac cccgagggtc accaacgctc cctgaaataa   3060
```

```
cctgttgcat gagagcagag gggagataga gagagcttaa ttataggtac ccgcgtgcag    3120
ctaaaaggag ggccagagat agtagcgagg gggacgagga gccacgggcc acctgtgccg    3180
ggaccccgcg ctgtggtact gcggtgcagg cgggagcagc ttttctgtct ctcactgact    3240
cactctctct ctctctccct ctctctctct ctcattctct ctcttttctc ctcctctcct    3300
ggaagttttc gggtccgagg gaaggaggac cctgcgaaag ctgcgacgac tatcttcccc    3360
tggggccatg gactcggacg ccagcctggt gtccagccgc ccgtcgtcgc cagagcccga    3420 tgacttttt ctgccggccc ggagtaaggg cagcagcggc agcgccttca ctgggggcac    3480
cgtgtcctcg tccaccccga gtgactgccc                                     3510

<210> SEQ ID NO 48
<211> LENGTH: 333
<212> TYPE: DNA
<213> ORGANISM: Homo sapiens

<400> SEQUENCE: 48
ttaattcgaa aatggcagac agagctgagc gctgccgttc ttttcaggat tgaaaatgtg    60 ccagtggggcc aggggcgctg ggacccgcgg tgcggaagac tcggaacagg aagaaatagt   120
ggcgcgctgg gtgggctgcc ccgccgccca cgccggttgc cgctggtgac agtggctgcc   180
cggccaggca cctccgagca gcaggtctga gcgttttttgg cgtcccaagc gttccgggcc   240
gcgtcttcca gagcctctgc tcccagcggg gtcgctgcgg cctggcccga aggatttgac   300
tctttgctgg gaggcgcgct gctcagggtt ctg                                 333

<210> SEQ ID NO 49
<211> LENGTH: 385
<212> TYPE: DNA
<213> ORGANISM: Homo sapiens

<400> SEQUENCE: 49
ccggtcccca gtttggaaaa aggcgcaaga agcgggcttt tcagggaccc cggggagaac    60
acgagggctc cgacgcggga gaaggattga agcgtgcaga ggcgccccaa attgcgacaa   120
tttactggga tccttttgtg gggaaaggag gcttagaggc tcaagctata ggctgtccta   180
gagcaactag gcgagaacct ggccccaaac tccctcctta cgccctggca caggttcccg   240
gcgactggtg ttcccaaggg agcccctga gcctaccgcc cttgcagggg gtcgtgctgc    300
ggcttctggg tcataaacgc cgaggtcggg ggtggcggag ctgtagaggc tgcccgcgca   360
gaaagctcca ggatcccaat atgtg                                         385

<210> SEQ ID NO 50
<211> LENGTH: 105
<212> TYPE: DNA
<213> ORGANISM: Homo sapiens

<400> SEQUENCE: 50
gcgcaggtcc ccccagtccc cgagggagtg cgcccgacgg aaacgcccct agcccgcggg    60
cctcgctttc ctctcccggg ttcctgggtc acttcccgct gtctc                   105

<210> SEQ ID NO 51
<211> LENGTH: 147
<212> TYPE: DNA
<213> ORGANISM: Homo sapiens

<400> SEQUENCE: 51
```

```
ttccctcgcg gctttggaaa gggggtgcaa atgcacccct ctgcgggccc gctacccgct      60
gcaacacctg tgtttccttt ctgggcacct tctaggtttc tagatattgc tgtgaatacg     120
gtcctccgct gtacagttga aaacaaa                                         147

<210> SEQ ID NO 52
<211> LENGTH: 365
<212> TYPE: DNA
<213> ORGANISM: Homo sapiens

<400> SEQUENCE: 52
tgggaattta ggtcgggcac tgccgatatg tcgccttcca caaggcgggc ccgggcctct      60
gctgaccgtg caccggtcct ggggctgggt aattctgcag cagcagcgca gcccatgccg     120
gggaatttgc gggcagagga gacagtgagg cccgcgttct gtgcgggaac tcccgagctc     180
acagagccca agaccacacg gctgcatctg cttggctgac tgggccaggc ccacgcgtag     240
taacccggac gtctctctct cacagtcccc ttgcgtctgg ccagggagct gccaggctgc     300
accccgcggt ggggatcggg agaggggcag tgtcgcccat ccccggaagg ctgagcctgg     360
tgcag                                                                365

<210> SEQ ID NO 53
<211> LENGTH: 418
<212> TYPE: DNA
<213> ORGANISM: Homo sapiens

<400> SEQUENCE: 53
cggttttctc ctggaggact gtgttcagac agatactggt ttccttatcc gcaggtgtgc      60
gcggcgctcg caagtggtca gcataacgcc gggcgaattc ggaaagcccg tgcgtccgtg     120
gacgacccac ttggaaggag ttgggagaag tccttgttcc cacgcgcgga cgcttccctc     180
cgtgtgtcct tcgagccaca aaaagcccag accctaaccc gctccttcct cccgccgcgt     240
ccatgcagaa ctccgccgtt cctgggaggg gaagcccgcg aggcgtcggg agaggcacgt     300
cctccgtgag caaagagctc ctccgagcgc gcggcgggga cgctgggccg acaggggacc     360 gcggggggcag ggcggagagg acccgcccctc gagtcggccc agccctaaca ctcaggac     418

<210> SEQ ID NO 54
<211> LENGTH: 906
<212> TYPE: DNA
<213> ORGANISM: Homo sapiens

<400> SEQUENCE: 54
agggaatcgg gctgaccagt cctaaggtcc cacgctcccc tgacctcagg gcccagagcc      60
tcgcattacc ccgagcagtg cgttggttac tctccctgga aagccgcccc cgccggggca     120
agtgggagtt gctgcactgc ggtctttgga ggcctaggtc gcccagagta ggcggagccc     180
tgtatccctc ctggagccgg cctgcggtga ggtcggtacc cagtacttag ggagggagga     240
cgcgcttggt gctcagggta ggctgggccg ctgctagctc ttgatttagt ctcatgtccg     300
cctttgtgcc ggcctctccg atttgtgggt ccttccaaga aagagtcctc tagggcagct     360
agggtcgtct cttgggtctg gcgaggcggc aggccttctt cggacctatc ccagagggtg     420
taacggagac tttctccact gcagggcggc ctggggcggg catctgccag gcgagggagc     480
tgccctgccg ccgagattgt ggggaaacgg cgtggaagac accccatcgg agggcaccca     540
atctgcctct gcactcgatt ccatcctgca acccaggaga aaccatttcc gagttccagc     600
cgcagaggca cccgcggagt tgccaaaaga gactcccgcg aggtcgctcg gaaccttgac     660
```

```
cctgacacct ggacgcgagg tctttcagga ccagtctcgg ctcggtagcc tggtccccga    720
ccaccgcgac caggagttcc ttcttccctt cctgctcacc agccggccgc cggcagcggc    780
tccaggaagg agcaccaacc cgcgctgggg gcggaggttc aggcggcagg aatggagagg    840
ctgatcctcc tctagccccg gcgcattcac ttaggtgcgg gagccctgag gttcagcctg    900
actttc                                                               906
```

<210> SEQ ID NO 55
<211> LENGTH: 860
<212> TYPE: DNA
<213> ORGANISM: Homo sapiens

<400> SEQUENCE: 55

```
cactacggat ctgcctggac tggttcagat gcgtcgttta aagggggggg ctggcactcc     60
agagaggagg gggcgctgca ggttaattga tagccacgga agcacctagg cgccccatgc    120
gcggagccgg agccgccagc tcagtctgac ccctgtcttt tctctcctct tccctctccc    180
acccctcact ccgggaaagc gagggccgag gtaggggcag atagatcacc agacaggcgg    240
agaaggacag gagtacagat ggagggacca ggacacagaa tgcaaaagac tggcaggtga    300
gaagaaggga gaaacagagg gagagagaaa gggagaaaca gagcagaggc ggccgccggc    360
ccggccgccc tgagtccgat ttccctcctt ccctgaccct tcagtttcac tgcaaatcca    420
cagaagcagg tttgcgagct cgaataccct tgctccactg ccacacgcag caccgggact    480
gggcgtctgg agcttaagtc tggggtctg agcctgggac cggcaaatcc gcgcagcgca    540
tcgcgcccag tctcggagac tgcaaccacc gccaaggagt acgcgcggca ggaaacttct    600
gcggcccaat ttcttcccca gctttggcat ctccgaaggc acgtaccgc cctcggcaca    660 agctctctcg tcttccactt cgacctcgag gtggagaaag aggctggcaa gggctgtgcg    720
cgtcgctggt gtggggaggg cagcaggctg cccctcccg cttctgcagc gagttttccc    780
agccaggaaa agggagggag ctgtttcagg aatttcagtg ccttcaccta gcgactgaca    840
caagtcgtgt gtataggaag                                                860
```

<210> SEQ ID NO 56
<211> LENGTH: 452
<212> TYPE: DNA
<213> ORGANISM: Homo sapiens

<400> SEQUENCE: 56

```
ggagcctgaa gtcagaaaag atggggcctc gttactcact ttctagccca gcccctggcc     60
ctgggtcccg cagagccgtc atcgcaggct cctgcccagc ctctgggtc gggtgagcaa    120 ggtgttctct tcggaagcgg gaagggctgc gggtcgggga cgtcccttgg ctgccacccc    180
tgattctgca tccttttcgc tcgaatccct gcgctaggca tcctccccga tcccccaaaa    240
gcccaagcac tgggtctggg ttgaggaagg aacgggtgc ccaggccgga cagaggctga    300
aaggaggcct caaggttcct ctttgctaca aagtggagaa gttgctctac tctggagggc    360
agtggccttt tccaaacttt tccacttagg tccgtaagaa aagcaattca tacacgatca    420
gcgctttcgg tgcgaggatg gaaagaaact tc                                  452
```

<210> SEQ ID NO 57
<211> LENGTH: 1992
<212> TYPE: DNA
<213> ORGANISM: Homo sapiens

<400> SEQUENCE: 57

```
ttttcctgtt acagagctga gcccactcat gtggtgccaa gtagcgacta tctctcggcc    60
acctccaccc agagcaatgt gggcgccccc agcgggtggg agcgattgcc gagcggcgca   120
agggcgttta acgcctaacc ccctcctcct gggttgccaa gccgctaggt cgccgtttcc   180
aacgtggctg cgcgggactg aagtccgacg actcctcgtc ctcagtagga gacacacctc   240
ccactgcccc cagccacgcg agctatgggc agaatcgggg caacggtaat atctggatgg   300
ggcaggctcc cctgaggctg tgcttaagaa aaaaggaatc tggagtagcc tgaggggccc   360
cacgagggggg cctcctttgc gatcgtctcc cagccttagg ccaaggctac ggaggcaggc   420
ggccgagtgt tggcgcccag cccggccgag gactggatgg aggacgagaa gcagcctgcc   480
tctgggcgac agctgcggac gcagcctcgc cgcctcgccg cctcagcctc ggtcccagcg   540
tctctaaagc cgcgcccatt ttacagatgc agggcaggga gacaagaggc atctccgggg   600
gccgagtaga atgatggcgc gggttctccc ggcgccctga tttcgaggct gcgcccgggg   660
ccctacatgc aggcggggag gcctgggccg aaggcgtctg caaggagggg cgagtctgcc   720
cggtccgggc agggagtgag gccacagtca gttctcccta ggaggccgcg cagcgggtag   780
ggtatgggac tggggacgc aacggggacc tggccgaatc agagccctca gcagagaacg   840
ccgaaaactc tggggccggc cgctcgcttc ccgctagtgg aatggtttc cggtcatccg   900
ttcccagtcc agccccgggt agggagctct gatttgcaat gcacagcact tgcgaggttc   960
gaatgccccc gcaatttgca gatggaaata ctaagcctag gccgggcgtg gtggctcaag  1020
cctatcatct cagccctttg ggaggccaag ccgggaggat tgtttgagcc caagaattca  1080
aaaccagcct gagcaacata gcgaccccgt ctctacaaaa taaataaaa taaattatcc  1140
gggcgtggtg gcacgcgcct gtggttccag ctactccgga ggctgaggtg ggaggatcgc  1200
ttgagtccgg gaggtcgagg ctacagtgag ccgtgatcgc accactgcac tccagcctgg  1260
gcgacagagt gagaccttgt ctcaaaaaag gaaaaaaaga aaagaaagt aagcttcaaa  1320
gaagctctga taatagttct gggtcgtgca gcggtggcgg ccccgcgctc tcgcccctaa  1380
agcaagcgct ctttgtactg ggtggaggag ctttgagtag tgagggtgga gatgcagctt  1440
cggggtggcg cagccaccct gacactaggc ccggggtcgc agtgggacag aagagtctgc  1500
cgctctgact tgggctctga gttccaaggg cgccccggcac ttctagcctc ccaggcttgc  1560
gcgctggcgc ctttgccatc cgtgccgaag tggggagacc tagccgcgac caccacgagc  1620
gcagcggtga cacccagagg tcccaccggg ccctgggca gggtaacctt agcctgtccg  1680
cttcggcagc tttgcgaaga gtggcgcgca gctagggctg aggctcttgc ggacctgcgg  1740
tcgaagcagg cggctgagcc agttcgatcg ccaaggcctg gctgccgac agtggtgcgc  1800
gctctgttcc gccgcggccg ggccaggcgc tctggaatag cgatggggggg acacggcctc  1860
caactttctg cagagaccat cgggcagctc cgggcctaag cagcgacctc accgaaggtt  1920
cctgggaacc tttgccaaaa tcccagcctc tgcctcggtc cagctaaacc gtgtgtaaac  1980
aagtgcacca ag                                                      1992
```

<210> SEQ ID NO 58
<211> LENGTH: 448
<212> TYPE: DNA
<213> ORGANISM: Homo sapiens

<400> SEQUENCE: 58

```
ataaaggacc gggtaatttc gcggaatgcg gattttgaga caggcccaga cggcggcgga    60
```

| | |
|---|---:|
| ttccctgtgt cccccaactg gggcgatctc gtgaacacac ctgcgtccca ccccgatcct | 120 |
| aggttgggg gaaagggtat gggaaccctg agcccagagc gcgccccgct ctttcctttg | 180 |
| ctccccggct tccctggcca gcccctccc ggctggtttc ctcgctcact cggcgcctgg | 240 |
| cgtttcgggc gtctggagat caccgcgtgt ctggcaccc aacgtctagt ctccccgcag | 300 |
| gttgaccgcg gcgcctggag ccgggaatag gggtggggag tccggagaac caaacccgag | 360 |
| cctgaagttg ccattcgggt gactcccgag aaagcccggg agcattttgg ccaatgcggg | 420 |
| tttttacctg aacttcagca tcttcacc | 448 |

<210> SEQ ID NO 59
<211> LENGTH: 395
<212> TYPE: DNA
<213> ORGANISM: Homo sapiens

<400> SEQUENCE: 59

| | |
|---|---:|
| aattggaaaa ccctggtatt gtgcctgttt gggggaagaa aacgtcaata aaaattaatt | 60 |
| gatgagttgg cagggcgggc ggtgcgggtt cgcggcgagg cgcagggtgt catggcaaat | 120 |
| gttacggctc agattaagcg attgttaatt aaaaagcgac ggtaattaat actcgctacg | 180 |
| ccatatgggc ccgtgaaaag gcacaaaagg tttctccgca tgtggggttc cccttctctt | 240 |
| ttctccttcc acaaaagcac cccagcccgt gggtccccc tttggcccca aggtaggtgg | 300 |
| aactcgtcac ttccggccag ggaggggatg gggcggtctc cggcgagttc caagggcgtc | 360 |
| cctcgttgcg cactcgcccg cccaggttct tgaa | 395 |

<210> SEQ ID NO 60
<211> LENGTH: 491
<212> TYPE: DNA
<213> ORGANISM: Homo sapiens

<400> SEQUENCE: 60

| | |
|---|---:|
| gggaagcgat cgtctcctct gtcaactcgc gcctgggcac ttagcccctc ccgtttcagg | 60 |
| gcgccgcctc cccggatggc aaacactata agtggcggc gaataaggtt cctcctgctg | 120 |
| ctctcggttt agtccaagat cagcgatatc acgcgtcccc cggagcatcg cgtgcaggag | 180 |
| ccatggcgcg ggagctatac cacgaagagt tcgcccgggc gggcaagcag gcggggctgc | 240 |
| aggtctggag gattgagaag ctggagctgg tgcccgtgcc ccagagcgct cacggcgact | 300 |
| tctacgtcgg ggatgcctac ctggtgctgc acacggccaa gacgagccga ggcttcacct | 360 |
| accacctgca cttctggctc ggtaagggac ggcgggcggc gggaccccga cgcaccaagg | 420 |
| ccggcgaggg gagggcgtag gggtctgaga tttgcaggcg tgggagtaaa ggggaccgca | 480 |
| aactgagcta g | 491 |

<210> SEQ ID NO 61
<211> LENGTH: 1284
<212> TYPE: DNA
<213> ORGANISM: Homo sapiens

<400> SEQUENCE: 61

| | |
|---|---:|
| ctcaggggcg ggaagtggcg ggtgggagtc acccaagcgt gactgcccga ggcccctcct | 60 |
| gccgcggcga ggaagctcca taaaagccct gtcgcgaccc gctctctgca ccccatccgc | 120 |
| tggctctcac ccctcggaga cgctcgcccg acagcatagt acttgccgcc cagccacgcc | 180 |
| cgcgcgccag ccaccgtgag tgctacgacc cgtctgtcta ggggtgggag cgaacgggc | 240 |

| | |
|---|---|
| gcccgcgaac ttgctagaga cgcagcctcc cgctctgtgg agccctgggg ccctgggatg | 300 |
| atcgcgctcc actccccagc ggactatgcc ggctccgcgc cccgacgcgg accagccctc | 360 |
| ttggcggcta aattccactt gttcctctgc tcccctctga ttgtccacgg cccttctccc | 420 |
| gggcccttcc cgctgggcgg ttcttctgag ttaccttta gcagatatgg agggagaacc | 480 |
| cgggaccgct atcccaaggc agctggcggt ctccctgcgg gtcgccgcct tgaggcccag | 540 |
| gaagcggtgc gcgtaggaa ggtttccccg gcagcgccat cgagtgagga atccctggag | 600 |
| ctctagagcc ccgcgccctg ccacctccct ggattcttgg gctccaaatc tctttggagc | 660 |
| aattctggcc cagggagcaa ttctctttcc ccttccccac cgcagtcgtc accccgaggt | 720 |
| gatctctgct gtcagcgttg atcccctgaa gctaggcaga ccagaagtaa cagagaagaa | 780 |
| acttttcttc ccagacaaga gtttgggcaa gaagggagaa aagtgaccca gcaggaagaa | 840 |
| cttccaattc ggttttgaat gctaaactgg cggggccccc accttgcact ctcgccgcgc | 900 |
| gcttcttggt ccctgagact tcgaacgaag ttgcgcgaag ttttcaggtg gagcagaggg | 960 |
| gcaggtcccg accggacggc gcccggagcc cgcaaggtgg tgctagccac tcctgggttc | 1020 |
| tctctgcggg actgggacga gagcggattg ggggtcgcgt gtggtagcag gaggaggagc | 1080 |
| gcgggggca gaggagggag gtgctgcgcg tgggtgctct gaatcccaa gcccgtccgt | 1140 |
| tgagccttct gtgcctgcag atgctaggta acaagcgact ggggctgtcc ggactgaccc | 1200 |
| tcgcccgtgc cctgctcgtg tgcctgggtg cgctggccga ggcgtacccc tccaagccgg | 1260 |
| acaacccggg cgaggacgca ccag | 1284 |

<210> SEQ ID NO 62
<211> LENGTH: 554
<212> TYPE: DNA
<213> ORGANISM: Homo sapiens

<400> SEQUENCE: 62

| | |
|---|---|
| tggagaacct tggggctctgt ggcctcaaag gtaggggtga tttcgagggg ccggcacctc | 60 |
| acagggcagg ttccaccgcg gaaacgcagt catcgcccag cgaccctgct cctggccctc | 120 |
| agcctccccc caggtttctt tttctcttga atcaagccga ggtgcgccaa tggccttcct | 180 |
| tgggtcggat ccgggggggcc agggccagct tacctgcttt caccgagcag tggatatgtg | 240 |
| ccttggactc gtagtacacc cagtcgaagc cggcctccac cgccaggcgg gccagcatgc | 300 |
| cgtacttgct gcggtcgcgg tcagacgtgg tgatgtccac tgcgcggccc tcgtagtgca | 360 |
| gagactcctc tgagtggtgg ccatcttcgt cccagccctc ggtcacccgc agtttcactc | 420 |
| ctggccactg gttcatcacc gagatggcca aagcgttcaa cttgtcctta cacctctgcg | 480 |
| aagacaaggg gaccccccacc gacggacacg ttagcctggg caaccgccac ccctcccggc | 540 |
| ccctccatca gcct | 554 |

<210> SEQ ID NO 63
<211> LENGTH: 772
<212> TYPE: DNA
<213> ORGANISM: Homo sapiens

<400> SEQUENCE: 63

| | |
|---|---|
| tctcacgacc catccgttaa cccaccgttc ccaggagctc cgaggcgcag cggcgacaga | 60 |
| ggttcgcccc ggcctgctag cattggcatt gcggttgact gagcttcgcc taacaggctt | 120 |
| gggggagggtg ggctgggctg ggctgggctg ggctgggtgc tgcccggctg tccgcctttc | 180 |
| gttttcctgg gaccgaggag tcttccgctc cgtatctgcc tagagtctga atccgacttt | 240 |

```
ctttccttttg ggcacgcgct cgccagtgga gcacttcttg ttctggcccc gggctgatct      300
gcacgcggac ttgagcaggt gccaaggtgc cacgcagtcc cctcacggct ttcgggggt       360 cttggagtcg ggtggggagg gagacttagg tgtggtaacc tgcgcaggtg ccaaagggca      420
gaaggagcag ccttggatta tagtcacggt ctctccctct cttccctgcc attttttaggg    480 ctttctctac gtgctgttgt ctcactgggt ttttgtcgga gccccacgcc ctccggcctc      540
tgattcctgg aagaaagggt tggtcccctc agcaccccca gcatcccgga aaatggggag      600
caaggctctg ccagcgccca tcccgctcca cccgtcgctg cagctcacca attactcctt      660
cctgcaggcc gtgaacacct tcccggccac ggtggaccac ctgcagggcc tgtacggtct      720
cagcgcggta cagaccatgc acatgaacca ctggacgctg gggtatccca at             772
```

<210> SEQ ID NO 64
<211> LENGTH: 1362
<212> TYPE: DNA
<213> ORGANISM: Homo sapiens

<400> SEQUENCE: 64

```
tggtttcctt tcgcttctcg cctcccaaac acctccagca agtcggaggg cgcgaacgcg       60
gagccagaaa cccttcccca agtttctcc cgccaggtac ctaattgaat catccatagg      120
atgacaaatc agccagggcc aagatttcca gacacttgag tgacttcccg gtccccgagg     180
tgacttgtca gctccagtga gtaacttgga actgtcgctc ggggcaaggt gtgtgtctag     240
gagagagccg gcggctcact cacgctttcc agagagcgac ccgggccgac ttcaaaatac    300
acacagggtc atttataggg actggagccg cgcgcaggac aacgtctccg agactgagac     360 atttccaaa cagtgctgac atttttgtcgg gccccataaa aaatgtaaac gcgaggtgac    420
gaacccggcg gggagggttc gtgtctggct gtgtctgcgt cctggcggcg tgggaggtta     480
tagttccaga cctggcggct gcggatcgcg gggccggtac ccgcgaggag tgtaggtacc    540
ctcagcccga ccacctcccg caatcatggg gacaccggct tggatgagac acaggcgtgg   600
aaaacagcct tcgtgaaact ccacaaacac gtggaacttg aaaagacaac tacagccccg    660
cgtgtgcgcg agagacctca cgtcaccca tcagttccca cttcgccaaa gtttcccttc       720
agtggggact ccagagtggt gcgccccatg cccgtgcgtc ctgtaacgtg ccctgattgt    780 gtaccctct gcccgctcta cttgaaatga aacacaaaa actgttccga attagcgcaa       840
ctttaaagcc ccgttatctg tcttctacac tgggcgctct taggccactg acagaaacat   900
ggtttgaacc ctaattgttg ctatcagtct cagtcagcgc aggtctctca gtgacctgtg    960
acgccgggag ttgaggtgcg cgtatcctta aacccgcgcg aacgccaccg gctcagcgta   1020
gaaaactatt tgtaatccct agtttgcgtc tctgagcttt aactccccca cactctcaag   1080
cgcccggttt ctcctcgtct ctcgcctgcg agcaaagttc ctatggcatc cacttaccag    1140
gtaaccggga tttccacaac aaagcccggc gtgcgggtcc cttccccgg ccggccagcg    1200 cgagtgacag cgggcggccg gcgctggcga ggagtaactt ggggctccag cccttcagag    1260
cgctccgcgg gctgtgcctc cttcggaaat gaaaacccccc atccaaacgg ggacggag    1320 cgcggaaacc cggcccaagt gccgtgtgtg cgcgcgcgtc tg                        1362
```

<210> SEQ ID NO 65
<211> LENGTH: 476
<212> TYPE: DNA
<213> ORGANISM: Homo sapiens

```
<400> SEQUENCE: 65
gaaagccatc cttaccattc ccctcaccct ccgccctctg atcgcccacc cgccgaaagg      60
gtttctaaaa atagcccagg gcttcaaggc cgcgcttctg tgaagtgtgg agcgagcggg     120
cacgtagcgg tctctgccag gtggctggag ccctggaagc gagaaggcgc ttcctccctg     180
catttccacc tcaccccacc cccggctcat ttttctaaga aaagttttt gcggttccct      240 ttgcctccta ccccgctgc cgcgcggggt ctgggtgcag accctgcca ggttccgcag       300 tgtgcagcgg cggctgctgc gctctcccag cctcggcgag ggttaaaggc gtccggagca     360
ggcagagcgc cgcgcgccag tctattttta cttgcttccc ccgccgctcc gcgctccccc     420
ttctcagcag ttgcacatgc cagctctgct gaaggcatca atgaaaacag cagtag         476

<210> SEQ ID NO 66
<211> LENGTH: 300
<212> TYPE: DNA
<213> ORGANISM: Homo sapiens

<400> SEQUENCE: 66
atcgaaaatg tcgacatctt gctaatggtc tgcaaacttc cgccaattat gactgacctc     60
ccagactcgg ccccaggagg ctcgtattag gcagggaggc cgccgtaatt ctgggatcaa     120
aagcgggaag gtgcgaactc ctctttgtct ctgcgtgccc ggcgcgcccc cctcccggtg     180
ggtgataaac ccactctggc gccggccatg cgctgggtga ttaatttgcg aacaaacaaa     240
agcggcctgg tggccactgc attcgggtta acattggcc agcgtgttcc gaaggcttgt      300

<210> SEQ ID NO 67
<211> LENGTH: 1246
<212> TYPE: DNA
<213> ORGANISM: Homo sapiens

<400> SEQUENCE: 67
atcaacatcg tggctttggt cttttccatc atggtgagtg aatcacggcc agaggcagcc     60
tgggaggaga gacccgggcg gctttgagcc cctgcagggg agtccgcgcg ctctctgcgg     120
ctcccttcct cacggcccgg cccgcgctag gtgttctttg tcctcgcacc tcctcctcac     180 cttttctcggg ctctcagagc tctccccgca atcatcagca cctcctctgc actcctcgtg    240
gtactcagag ccctgatcaa gcttccccca ggctagcttt cctcttcttt ccagctccca    300
gggtgcgttt cctctccaac ccggggaagt tcttccgtgg actttgctga ctcctctgac    360
cttcctaggc acttgcccgg ggcttctcaa ccctcttttc tagagcccca gtgcgcgcca   420
ccctagcgag cgcagtaagc tcatacccg agcatgcagg ctctacgttc cttcctgc     480 cgctccgggg gctcctgctc tccagcgccc aggactgtct ctatctcagc ctgtgctccc    540
ttctctcttt gctgcgccca agggcaccgc ttccgccact ctccgggggg tccccaggcg    600
attcctgatg ccccctcctt gatccgtttt ccgcgctttg gcacggcacg ctctgtccag    660
gcaacagttt cctctcgctt cttcctacac ccaacttcct ctccttgcct ccctccggcg    720
cccccttttt aacgcgcccg aggctggctc acacccacta cctctttagg cctttcttag   780 gctcccccgtg tgccccctc accagcaaag tgggtgcgcc tctcttactc tttctaccca   840
gcgcgtcgta gttcctcccc gtttgctgcg cactggccct aacctctctt ctcttggtgt    900 ccccagagc tccaggcgc ccctccaccg ctctgtcctg cgccggggc tctcccggga     960 atgaactagg ggattccacg caacgtgcgg ctccgcccgc cctctgcgct cagacctccc    1020
gagctgcccg cctctctagg agtggccgct ggggcctcta gtccgcccctt ccggagctca   1080
```

```
gctccctagc cctcttcaac cctggtagga cacccgagc gaaccccacc aggagggcga      1140
cgagcgcctg ctaggccctc gccttattga ctgcagcagc tggcccgggg gtggcggcgg      1200
ggtgaggttc gtaccggcac tgtcccggga caacccttgc agttgc                    1246
```

<210> SEQ ID NO 68
<211> LENGTH: 984
<212> TYPE: DNA
<213> ORGANISM: Homo sapiens

<400> SEQUENCE: 68

```
acaaataaaa caccctctag cttccctag actttgttta actggccggg tctccagaag        60
gaacgctggg gatgggatgg gtggagagag ggagcggctc aaggacttta gtgaggagca      120
ggcgagaagg agcacgttca ggcgtcaaga ccgatttctc cccctgcttc gggagacttt      180
tgaacgctcg gagaggcccg gcatctcacc actttacttg gccgtagggg cctccggcac      240
ggcaggaatg agggaggggg tccgattgga cagtgacggt ttggggccgt tcggctatgt      300
tcagggacca tatggtttgg ggacagcccc agtagttagt aggggacggg tgcgttcgcc      360
cagtccccgg atgcgtaggg aggcccagtg gcaggcagct gtcccaagca gcgggtgcgc      420
gtccctgcgc gctgtgtgtt cattttgcag agccagcctt cggggaggtg aaccagctgg      480
gaggagtgtt cgtgaacggg aggccgctgc ccaacgccat ccggcttcgc atcgtggaac      540
tggcccaact gggcatccga ccgtgtgaca tcagccgcca gctacgggtc tcgcacggct      600
gcgtcagcaa gatcctggcg cgatacaacg agacgggctc gatcttgcca ggagccatcg      660
ggggcagcaa gccccgggtc actaccccca ccgtggtgaa acacatccgg acctacaagc      720
agagagaccc cggcatcttc gcctgggaga tccgggaccg cctgctggcg gacggcgtgt      780
gcgacaagta caatgtgccc tccgtgagct ccatcagccg cattctgcgc aacaagatcg      840
gcaacttggc ccagcagggt cattacgact catacaagca gcaccagccg acgccgcagc      900
cagcgctgcc ctacaaccac atctactcgt accccagccc tatcacggcg gcggccgcca      960
aggtgcccac gccacccggg gtgc                                             984
```

<210> SEQ ID NO 69
<211> LENGTH: 545
<212> TYPE: DNA
<213> ORGANISM: Homo sapiens

<400> SEQUENCE: 69

```
aggaggcgca acgcgctgcc agggcggctt tatcctgccg ccacagggcg gggaccagcc       60
cggcagccgg gtgtccagcg ccgctcacgt gcctcgcctg gagcttagct ctcagactcc      120
gaagagggcg actgagactt gggcctggga gttggcttcg gggtacccaa ggcgacgaca      180
gctgagttgt accacgaagc tcaggccgag gcctcctccc ttgtctggcc ttcgaatcca      240
tactggcagc ctctcctctc aggcactccg cgggccgggc cactaggccc cctgctcctg      300
gagctgcgct atgatccggg tcttgagatg cgcgcgattc tctctgaacc ggtggagagg      360
aggctctgcc ccgcgcggag cgaggacagc ggcgcccgag cttcccgcgc ctctccaggg      420
cccaatggca agaacagcct ccgaagtgcg cggatgacag gaaaagatct tcagttcttc      480
tgccgctaga gaagtgcggg atacaagcct ctattggatc cacaacctgg agtcctgcct      540
tcgga                                                                  545
```

<210> SEQ ID NO 70

```
<211> LENGTH: 1533
<212> TYPE: DNA
<213> ORGANISM: Homo sapiens

<400> SEQUENCE: 70
atctgcgtgc ccttttctgg gcgagccctg ggagatccag ggagaactgg gcgctccaga      60
tggtgtatgt ctgtaccttc acagcaaggc ttcccttgga tttgaggctt cctattttgt    120
ctgggatcgg ggtttctcct tgtcccagtg gcagccccgc gttgcgggtt ccggcgcctg    180
cgcggagccc aaggctgcat ggcagtgtgc agcgcccgcc agtcgggctg gtgggttgtg    240
cactccgtcg gcagctgcag aaaggtggga gtgcaggtct tgcctttcct caccgggcgg    300
ttggcttcca gcaccgaggc tgacctatcg tggcaagttt gcggccccg cagatcccca     360 gtggagaaag agggctcttc cgatgcgatc gagtgtgcgc ctccccgcaa agcaatgcag    420
accctaaatc actcaaggcc tggagctcca gtctcaaagg tggcagaaaa ggccagacct    480
aactcgagca cctactgcct tctgcttgcc ccgcagagcc ttcagggact gactgggacg    540
cccctggtgg cgggcagtcc catccgccat gagaacgccg tgcagggcag cgcagtggag    600
gtgcagacgt accagccgcc gtggaaggcg ctcagcgagt ttgccctcca gagcgacctg    660
gaccaacccg ccttccaaca gctggtgagg ccctgcccta cccgcccga cctcgggact     720 ctgcgggttg gggatttagc cacttagcct ggcagagagg ggaggggtg gccttgggct     780 gaggggctgt gtacagccct aggcggtggg ggagggggaa cagtggcggg ctctgaaacc    840
tcacctcggc ccattacgcg ccctaaacca ggtctccctg gattaaagtg ctcacaagag    900
aggtcgcagg attaaccaac ccgctccccc gccctaatcc ccccctcgtg cgcctgggga   960
cctggcctcc ttctccgcag ggcttgctct cagctggcgg ccggtcccca agggacactt   1020
tccgactcgg agcacgcggc cctggagcac cagctcgcgt gcctcttcac ctgcctcttc   1080
ccggtgtttc cgccgcccca ggtctccttc tccgagtccg gctccctagg caactcctcc   1140
ggcagcgacg tgacctccct gtcctcgcag ctcccggaca cccccaacag tatggtgccg   1200
agtcccgtgg agacgtgagg gggacccctc cctgccagcc cgcggacctc gcatgctccc   1260
tgcatgagac tcacccatgc tcaggccatt ccagttccga aagctctctc gccttcgtaa   1320
ttattctatt gttatttatg agagagtacc gagagacacg gtctggacag cccaaggcgc   1380
caggatgcaa cctgctttca ccagactgca gaccccgct ccgaggactc ttagttttttc    1440 aaaaccagaa tctgggactt accagggtta gctctgccct ctcctctcct ctctacgtgg   1500
ccgccgctct gtctctccac gccccacctg tgt                                 1533

<210> SEQ ID NO 71
<211> LENGTH: 702
<212> TYPE: DNA
<213> ORGANISM: Homo sapiens

<400> SEQUENCE: 71
aggtctcttc agactgccca ttctccgggc ctcgctgaat gcggggctc tatccacagc      60 gcgcggggcc gagctcaggc aggctggggc gaagatctga ttctttcctt cccgccgcca    120
aaccgaatta atcagtttct tcaacctgag ttactaagaa agaaaggtcc ttccaaataa    180
aactgaaaat cactgcgaat gacaatacta tactacaagt tcgttttggg gccggtgggt    240
gggatggagg agaaagggca cggataatcc cggagggccg cggagtgagg aggactatgg    300
tcgcggtgga atctctgttc cgctggcaca tccgcgcagg tgcggctctg agtgctggct    360
cggggttaca gacctcggca tccggctgca ggggcagaca gagacctcct ctgctagggc    420
```

```
gtgcggtagg catcgtatgg agcccagaga ctgccgagag cactgcgcac tcaccaagtg    480
ttaggggtgc ccgtgataga ccgccaggga aggggctggt tcggagggaa ttcccgctac    540
cgggaaggtc ggaactcggg gtgatcaaac aaggaatgca tctcacctcc gtgggtgctt    600
gtgctgcgca aggaattatt accggagcgg ttgcgatggc cttgcccgg cgacccaaga    660 agagtaagca aactaccgtc acccagcgg atcaggtcca at                       702
```

<210> SEQ ID NO 72
<211> LENGTH: 3180
<212> TYPE: DNA
<213> ORGANISM: Homo sapiens

<400> SEQUENCE: 72

```
gatgtcctgt tctagcagc ctccagagcc aagctaggcg agaggcgtag gaggcagaga     60
gagcgggcgc gggaggccag ggtccgcctg ggggcctgag gggacttcgt ggggtcccgg   120
gagtggccta gaaacaggga gctggaggg ccgggaagag cttgaggctg agcggggac     180 gaacgggcag cgcaaagggg agatgaacgg aatggccgag gagccacgca ttcgccttgt   240
gtccgcggac ccttgttccc gacaggcgac caagccaagg ccctccggac tgacgcggcc   300
tgagcagcag cgagtgtgaa gtttggcacc tccggcggcg agacggcgcg ttctggcgcg   360
cggctcctgc gtccggctgg tggagctgct gcgccctatg cggcctgccg agggcgccgc   420
cgagggcccg cgagctccgt ggggtcgggg tgggggacc cgggagcgga cagcgcggcc   480
cgaggggcag gggcagggc gcgcctggcc tggggtgtgt ctgggccccg gctccgggct   540
cttgaaggac cgcgagcagg aggcttgcgc aatcccttgg ctgagcgtcc acggagaaag   600
aaaaagagca aaagcagagc gagagtggag cgagggatgg gggcgggcaa agagccatcc   660
gggtctccac caccgccctg acacgcgacc cggctgtctg ttggggaccg cacggggct   720 cgggcgagca ggggagggag gagcctgcgc ggggctcgtg ttcgcccagg aatcccggag   780
aagctcgaag acggtctggt gttgaacgca cacgtggact ccatttcatt accaccttgc   840
agctcttgcg ccacggaggc tgctgctgcc cggcggctgc tacccaccga acccacgtg   900 gcccctcccc aggggtgtag gggtgacggt tgtcttctgg tgacagcaga ggtgttgggt   960
ttgcgactga tctctaacga gcttgaggcg caaacctagg attccctgag tgttgggtg   1020 cggcgggggg gcaagcaagg tgggacgacg cctgcctggt ttccctgact agttgcgggg   1080 ggtggggcc ggctctcagg ggccaccaga agctgggtgg gtgtacagga aaatattttt   1140
ctcctgccgt gtttggcttt ttcctggcat ttttgcccag ggcgaagaac tgtcgcgcgg   1200
ggcagctcca ccgcggaggg agaggggtcg cgaggctggc gcggaagcg ctgtaggtgg   1260 cagtcatccg tccacgccgc acaggccgtc tgcgccgtcg gaccatcggg aggtctgcag   1320
caactttgtc ccggccagtc cccttgtccg ggaaggggct gagcttcccg acactctacc   1380 ctcccctct tgaaaatccc ctggaaaatc tgtttgcaat gggtgtttcc gcggcgtcca   1440
ggtctgggct gccgggggag gccgagcggc tgctgcagcc tccctgctgc cagggggcgtc   1500 ggactccgct tcgctcacta cgcccaggcc cctcagggc ccacgctcag gacttcgggg   1560
ccacacagca ggacccggtg ccccgacgac gagtttgcgc aggacccggg ctgggccagc   1620
cgcggagctg gggaggaagg ggcgggggtc ggtgcagcgg atcttttctg ttgctgcctg   1680
tgcggcggca ggaagcgtct tgaggctccc caagactacc tgaggggccg cccaagcact   1740
tcagaagccc aaggagcccc cggccacccc cgctcctggc cttttttgcca acgactttga   1800
```

| | |
|---|---:|
| aagtgaaatg cacaagcacc agcaattgac ttcccttccg tggttatttta ttttgtcttt | 1860 |
| gtggatggtg ggcagatggg gagagaggcc cctacctaac ctcggtggct ggtccctaga | 1920 |
| ccacccctgc cagccggtgt ggggaggagc tcaggtccgc gggagagcga atgggcgcca | 1980 |
| ggaggtggga cagaatcctg gaaggtaca gcggacgccc tggaagctcc cctgatgccc | 2040 |
| cagagggccc ttcctgggaa acctcccggg gggtgcccc ataccatccc accggctgt | 2100 |
| cttggcccct cccagggagc cgcaggagaa actagcccta cacctgggat tcccagagcc | 2160 |
| ttctgctggg gctcctgccc ccgacttcgg ataaccagct ccgcacaggt ccccgagaag | 2220 |
| ggccgctggc ctgcttattt gatactgccc cctcccagac aggggctggt cgagcccctg | 2280 |
| gttctgctgc cagactgaag ccttccagac gccacctcgg tttgggcccc cagggccctc | 2340 |
| aggggcccca ggagaggaga gctgctatct agctcagcca caggctcgct cctggtgggg | 2400 |
| gccaggctga aggagtggac cctggagagg tcggaacct tttaacagcc gtgggctgga | 2460 |
| gggtggctac taagtgttcg gtctgggaag aggcatgacc cgcaccatcc cggggaaata | 2520 |
| aacgacttct taagggaatc ttctcgctga gcgggtgctc tgggcagga gattgccacc | 2580 |
| gccagcccac ggaacccaga tttgggctct gccttgagcg ggccgcctgt ggcttcccgg | 2640 |
| gtcgctcccc cgactcagaa agctctcaag ttggtatcgt tttcccggcc ctcggaggtg | 2700 |
| gattgcagat caccgagagg ggatttacca gtaaccacta cagaatctac ccgggcttta | 2760 |
| acaagcgctc atttctctcc cttgtcctta gaaaaacttc gcgctggcgt tgatcatatc | 2820 |
| gtacttgtag cggcagctta ggggcagcgg aactggtggg gttgtgcgtg caggggagg | 2880 |
| ctgtgaggga gccctgcact ccgcccctcc acccttctgg aggagtggct ttgttctaa | 2940 |
| gggtgccccc ccaaccccg ggtccccact tcaatgtttc tgctctttgt cccaccgccc | 3000 |
| gtgaaagctc ggctttcatt tggtcggcga agctccgac gcccccgagt cccaccctag | 3060 |
| cgggccgcgc ggcactgcag ccggggttc ctgcggactg gcccgacagg gtgcgcggac | 3120 |
| ggggacgcgg gccccgagca ccgcgacgcc agggtccttt ggcagggccc aagcacccct | 3180 |

<210> SEQ ID NO 73
<211> LENGTH: 1038
<212> TYPE: DNA
<213> ORGANISM: Homo sapiens

<400> SEQUENCE: 73

| | |
|---|---:|
| tggcggccgg cgggcacagc cggctcattg ttctgcacta caaccactcg ggccggctgg | 60 |
| ccgggcgcgg ggggccggag gatggcggcc tggggggcccт gcgggggctg tcggtggccg | 120 |
| ccagctgcct ggtggtgctg gagaacttgc tggtgctggc ggccatcacc agccacatgc | 180 |
| ggtcgcgacg ctgggtctac tattgcctgg tgaacatcac gctgagtgac ctgctcacgg | 240 |
| gcgcggccta cctggccaac gtgctgctgt cgggggcccg caccttccgt ctggcgcccg | 300 |
| cccagtggtt cctacgggag ggcctgctct tcaccgccct ggccgcctcc accttcagcc | 360 |
| tgctcttcac tgcagggag cgctttgcca ccatggtgcg gccggtggcc gagagcgggg | 420 |
| ccaccaagac cagccgcgtc tacggcttca tcggcctctg ctggctgctg gccgcgctgc | 480 |
| tggggatgct gccttgctg ggctggaact gcctgtgcgc cttgaccgc tgctccagcc | 540 |
| ttctgcccct ctactccaag cgctacatcc tcttctgcct ggtgatcttc gccggcgtcc | 600 |
| tggccaccat catgggcctc tatgggcca tcttccgcct ggtgcaggcc agcgggcaga | 660 |
| aggcccacg cccagcggcc cgccgcaagg cccgccgcct gctgaagacg gtgctgatga | 720 |
| tcctgctggc cttcctggtg tgctgggcc cactcttcgg gctgctgctg gccgacgtct | 780 |

```
ttggctccaa cctctgggcc caggagtacc tgcggggcat ggactggatc ctggccctgg    840
ccgtcctcaa ctcggcggtc aaccccatca tctactcctt ccgcagcagg gaggtgtgca    900
gagccgtgct cagcttcctc tgctgcgggt gtctccggct gggcatgcga gggcccgggg    960
actgcctggc ccgggccgtc gaggctcact ccggagcttc caccaccgac agctctctga   1020
ggccaaggga cagctttc                                                 1038

<210> SEQ ID NO 74
<211> LENGTH: 1200
<212> TYPE: DNA
<213> ORGANISM: Homo sapiens

<400> SEQUENCE: 74
gtcctaacat cccaggtggc ggcgcgctgg ctccctggag cggggcggga cgcggccgcg     60
cggactcacg tgcacaaccg cgcgggacgg ggccacgcgg actcacgtgc acaaccgcgg    120
gaccccagcg ccagcgggac cccagcgcca gcgggacccc agcgccagcg ggaccccagc    180
gccagcggga ccccagcgcc agcgggaccc cagcgccagc gggaccccag cgccagcggg    240
tctgtggccc agtggagcga gtggagcgct ggcgacctga gcggagactg cgccctggac    300
gccccagcct agacgtcaag ttacagcccg cgcagcagca gcaaagggga aggggcagga    360
gccgggcaca gttggatccg gaggtcgtga cccaggggaa agcgtgggcg gtcgacccag    420
ggcagctgcg gcggcgaggc aggtgggctc cttgctccct ggagccgccc ctccccacac    480 ctgcccctcgg cgccccagc agttttcacc ttggccctcc gcggtcactg cgggattcgg    540
cgttgccgcc agcccagtgg ggagtgaatt agcgccctcc ttcgtcctcg gcccttccga    600
cggcacgagg aactcctgtc ctgccccaca gaccttcggc ctccgccgag tgcggtactg    660
gagcctgccc cgccagggcc ctggaatcag agaaagtcgc tctttggcca cctgaagcgt    720
cggatcccta cagtgcctcc cagcctgggc gggagcggcg gctgcgtcgc tgaaggttgg    780
ggtccttggt gcgaaaggga ggcagctgca gcctcagccc caccccagaa gcggccttcg    840
catcgctgcg gtgggcgttc tcgggcttcg acttcgccag cgccgcgggg cagaggcacc    900
tggagctcgc agggcccaga cctgggttgg aaaagcttcg ctgactgcag gcaagcgtcc    960
gggaggggcg gccaggcgaa gccccggcgc tttaccacac acttccgggt cccatgccag   1020
ttgcatccgc ggtattgggc aggaaatggc agggctgagg ccgacccdag gagtataagg   1080
gagccctcca tttcctgccc acatttgtca cctccagttt tgcaacctat cccagacaca   1140
cagaaagcaa gcaggactgg tggggagacg gagcttaaca ggaatatttt ccagcagtga   1200

<210> SEQ ID NO 75
<211> LENGTH: 900
<212> TYPE: DNA
<213> ORGANISM: Homo sapiens

<400> SEQUENCE: 75
caccttcccc gaggtaatta tttctgggg gtagggtg ggggttggga gggtgaagaa     60
aggaagaaaa agaaggccga tcacactggg caccggcgga ggaagcgtgg agtccattga    120
tctaggtact tgtggggagg ggagaacccg agcagcagct gcaaacgaaa gggctgtgag    180
cgagcgggcg ggcgggtggc tggcagcgag gccaccagca gggggggccc gggccgaggc    240
cgcgccacct cggcaccacg cgggcagccg gtgcggcggg gtcgccacgg ccaggggagc    300
gctgggtgcc caccatggca gttatgcaag cggtgacccc ctggtcttgc ctccccgccg    360
```

| | |
|---|---|
| ccctgcactc cttcctcccc gctgccgaca cttggatctc tctagctctt tctctcccct | 420 |
| gtgttttcaa acaggaagtg cacggctgtc tataacgtgc tgccgggtct caggatggag | 480 |
| gagtgaagtc tcctgtcgcc gtggttccag cctccggagc tcgcccaagc cgcgtcccca | 540 |
| gagagcgccc tgagagaaca gggtggccgc ttggtccagg tgcgcggggt cgggtctggg | 600 |
| tccagggagc gggtcgggaa gtctgcggca cggagcactg ctagtgtcgg atctgcatct | 660 |
| ccagctctgt gctgcagctt cacttgcccg ccccccacca ctggcttctc acccggggtc | 720 |
| tctgccaaac tctggctgct gccgccctgg gttcgggccg gcggaaggcc ctgggcgtgc | 780 |
| gctgcggagc cgcctgcgag gactccacta gggcgctttc caggctggac tgccccgggc | 840 |
| tgcgctggag ctgccagtgc tcggggagtc ttcctggagt ccccagctgc cctctccacc | 900 |

<210> SEQ ID NO 76
<211> LENGTH: 200
<212> TYPE: DNA
<213> ORGANISM: Homo sapiens

<400> SEQUENCE: 76

| | |
|---|---|
| ctcttcccaa gttacgccac cggtcgagga cggcaggaga cccccgagtg cagagaaagc | 60 |
| tcaaaccggc agcgaagtcg gtcctagcca agctgaaaaa acgtctcgga tttcgcggac | 120 |
| agcggcctag acacagcccg atcttccagt cctagtgccc tggtcgagac ggttctatcc | 180 |
| ttttgcaaag aagccggaaa | 200 |

<210> SEQ ID NO 77
<211> LENGTH: 400
<212> TYPE: DNA
<213> ORGANISM: Homo sapiens

<400> SEQUENCE: 77

| | |
|---|---|
| tctcggttgc aatccccacc ctcctcaccc agcagggcag gaggcaccca acttggagga | 60 |
| gaaaggggtg ggggaggtga acagagacc ggagagtcac gagggctggg ccgccgagag | 120 |
| caggagaata taccgtgtca cacacctcca ttctctcaca cacgttgcag acacaaatca | 180 |
| ctgacggttt ccacgtgctg cgctcgtgag cggaggtgtt caaagagggg gcagatgagt | 240 |
| tacttcccga gacggaaccg ggggtcccac gtccgccgcc ttcagtagca caaccaatct | 300 |
| ctgaacactc aaaccgcgca tctctggcgc atcaccatcc tatttaaggc cacgggctcc | 360 |
| gcccttttcc tcccctccct tcttttccac tcttttttcca | 400 |

<210> SEQ ID NO 78
<211> LENGTH: 700
<212> TYPE: DNA
<213> ORGANISM: Homo sapiens

<400> SEQUENCE: 78

| | |
|---|---|
| ctgccagaga tgtgtctgtc ttgcgcccccg catgcactgc ctgcggggct gcgctgcact | 60 |
| cccccggcggc gccacgggtc tggccccgc gcttctacgt gttggggga tgcatggacc | 120 |
| ttggagatcc gtagttggcc ctaaccttct cggaatctcc tctgcacgcg ctgcctgttc | 180 |
| ctcctctgca cgctctgtcc gttccttttgc aacttctgtg ggaattgtcc tggcgtggga | 240 |
| aacgcccccg cgctctttgg cacttagggt gtgagtgttg cgccccttgc cgcagcgctc | 300 |
| agggcagcat cccgctcgag gatgcagggt tctcaccaag cagtgagggg gactcacgcg | 360 |
| ccgccgggga gcggagccag gctccgagaa gggagcagga tcgagccgct gggttttcgc | 420 |
| aagccttggg gcctctggcc gcccttccat gcctccgggc gcgggcggct cagcaggtcc | 480 |

```
ccggcttcgg gaagttttgt gcgcggatcg ctggtgggga gggcgcgcgg gccagtggct    540
gagcttgcag cgaagtttcc gtgaaggaaa ctgcatgtgc ctttggaggc gactcgggac    600
tgctgtaggg tggactgggt gtctatggag ttgcgggtca gagcgagtag ggtgggtcct    660
ttcctgggac aggactggga attggggctc gaagtagggg                          700

<210> SEQ ID NO 79
<211> LENGTH: 200
<212> TYPE: DNA
<213> ORGANISM: Homo sapiens

<400> SEQUENCE: 79
aggggtgtcc tccaacatct ctgaaccgcc ttcccttcct cctcactggc gccctcttgc     60
ctcagtcgtc ggagatggag aggcggctga agattggcag gcggcggcca gggtcgaggc    120
tgggagactc agagccgctg aggctgccgg agctcaggga gccgcttagg tagctgtcgc    180
ggtccgacag cgagtccggg                                                200

<210> SEQ ID NO 80
<211> LENGTH: 5000
<212> TYPE: DNA
<213> ORGANISM: Homo sapiens

<400> SEQUENCE: 80
tctgactctc gggctggagc agccgagaca gcgctcccca gcgggactac agaatcccgg     60
gtgtcggcct gggggccctg gattggcagt ggtggagtct tctgagccta acagctacta    120
ggaatgacag agttgcagat ggctttgtcg cccgcggggc ggctcaagcg tcctgggtcc    180
caggcctctg tcctacggcc aggccgccgg ctcaacgggc cgaagggaat cgggctgacc    240
agtcctaagg tcccacgctc ccctgacctc agggcccaga gctcgcatt accccgagca     300 gtgcgttggt tactctccct ggaaagccgc ccccgccggg gcaagtggga gttgctgcac    360 tgcggtctttt ggaggcctag gtcgcccaga gtaggcggag ccctgtatcc ctcctggagc    420
cggcctgcgg tgaggtcggt acccagtact tagggaggga ggacgcgctt ggtgctcagg    480
gtaggctggg ccgctgctag ctcttgattt agtctcatgt ccgcctttgt gccggcctct    540
ccgatttgtg ggtccttcca agaaagagtc ctctagggca gctagggtcg tctcttgggt    600
ctggcgaggc ggcaggcctt cttcggacct atccccagag gtgtaacgga gactttctcc    660
actgcagggc ggcctggggc gggcatctgc caggcgaggg agctgccctg ccgccgagat    720
tgtggggaaa cggcgtggaa gacaccccat cggagggcac ccaatctgcc tctgcactcg    780
attccatcct gcaacccagg agaaaccatt tccgagttcc agccgcagag cacccgcgg     840 agttgccaaa agagactccc gcgaggtcgc tcggaaccctt gaccctgaca cctgacgcg     900 aggtctttca ggaccagtct cggctcggta gcctggtccc cgaccaccgc gaccaggagt    960
tccttcttcc cttcctgctc accagccggc cgccggcagc ggctccagga aggagcacca    1020
acccgcgctg ggggcggagg ttcaggcggc aggaatggag aggctgatcc tcctctagcc   1080
ccggcgcatt cacttaggtg cgggagccct gaggttcagc ctgactttcc cgactccgcc   1140
gggcgcttgg tgggctcctg ggcttctggg ctcacccctta cacctgtgta ctaaagggct   1200
gctaccctcc cgaggtgtac gtccgccgcc tcggcgctca tcgggtgtt ttttcaccct    1260 ctcgcggtgc acgcttttc tctcacgtca gctcacatct ttcagtacac agccactggg   1320
tctccctgcc cctccagcct ttcctaggca gctttgaggg cccagacgac tgaagtctta   1380
```

```
ctgctaggat gggaacacga tgaaaaagga aggggcccag tcaaaagtcc tctcctcttc    1440 ggttttctt caactgtcct tcacaaaaac atttatttct gtcccagcgc cctggcggat     1500
ttcggcagat gggccctagg gggttgtgga ggccaaattc ccaggatgct ggtcctgcct    1560
ttttcattgg ccaaaactgt atttcctaca acgactaaag ataaccaaga actgagtaga    1620
ccctgttctc tcaccagatc tccctggctc tgtttaactt ttcctggtgc aatgcgatgg    1680
caccaccagc tccccaggca ggcaccactc cctcaagata ccatttgggg tagggatttg    1740
agtcctggag agggtcagcg gggcgccggg gtggggtgg aaggagact gacagggaca      1800 caccgcgagc tccgcatact ctcctctgcc cctgtagcc cggggcttta atgaccccaa     1860
gcagatttcc tgtctctggt ctagccagct gcccctaggg ctggatttta tttcttcatg   1920
gggtttcacc ctaaagggcc ccctggtcat gggacctggt tgggaacaaa tgaaagatgt   1980
cttgtagcaa atgctttcag gggagcagaa aagaagattg ggcacttcca gtcacttggt   2040
cactttaggt ggctggaaca aaactggtga cttcacgac tgctacaggg tgaggggtg     2100 aagggtggca gagaggtgac aagccactgg gaatcctatt cagtggggat gccgacaggg   2160
agtggctgta atcaactgag caacatctgt gtgaatgtta ttcacaggtc aggacagcag   2220
cttggtcttc ccaggtgagg aactgaggac tggcctgcat agatttgtgc agtaggtgag   2280
tagcttccaa atttatttc agaacttcca tgtagtacct gcctctccat ttaaatattt    2340
tttaaaattt tattattta aatatttct tggttagctt tccaagaggg aggaaaagag     2400
gggagttgca acaagtagtg cccctatgct gggattcatt ttccagagta aagcctggga   2460
ctggcaccct gaccctacc ggcaggtgaa aactccaggc aaactgctga gatcccacct    2520
gggctggctg agatagtgcc tggggtgcat ccctcagcag ctgccacctg gccctgggg    2580 ccatctcttt ctctggcatc aagcagccag gtgtcaaggc cttcccagca atccatgctg   2640
catggctggg tcttgttcta gcaggtcgat gggcagggac tggtagctta gccagggcac   2700
cagtgcgtgg ctgtgggttt gtgtgcttct gtggagaagc atgatgtgta tgtgtgtgtg   2760
tgggcacagg catgaggaag ggttcatttg tgcaggtatc tcccatgtat atcagtgtgg   2820
gagagtgcct gaggatgtgt ttgtgtgtct gaaaatgggc ggagggtctg ttgtgctaat   2880
gtgtgcaggg gtgaacatgt gtgtgacagt ctgtgtgttt ccctgagtgg tggctgcgtg   2940
agagggtgag gggatttggt gttgtctacc atgcccggca catgcaggc tcttaataat    3000 cttgaattta attaatgtta aatgtgtatg ttcccatcct tgtggaagtt ggtatagagc   3060
ctgttttcct gtgattgtga gactggaaaa tgggggacgg gcaggggcga gacaggatac   3120
agaggctact gttttcttcc tccctagaag taagtacata gaagagtggg ctctggcacc   3180
tcacgggaca tcaccaagtc ctgtgtggct ggctaggctg tcccaaggtg gcttcaggca   3240
tcacttgaat cttttgagac cttcaggcag tagcctgcca ttcaccctgt cagtcagcag   3300
aagttgggcc cacacaggcc atagaaacac agagcagttc ccgggaggac ctgagctgtc   3360
cctgagagca gagcttccag gagaggccgc aggaactgcc ttgaccggaa ttcctcttgg   3420
ggtgcaaagg tggagggaca catggtgcga ccccaggcag aggactgcag ccactccgtg   3480
cagtcccagc ctctgggta gcccttgac ctccaggcct gcacagatcc aaggccgagg     3540
tccaggctcc agcgccaaat tagctggcct agcagcctgc agccgctcta atctcaacta   3600
ggaaggaatc cttgcgctta gaaagtccaa gcgaaagggt attctgattt tatcccggtt   3660
ttaccagaaa atgctgaaag gaaaagcccc gagaggacac agtgctctag gaactcgggg   3720
cgccacgagc gcctcatccc ctcccttccg cccggccgcg gtgccctggt cgctgaggga   3780
```

```
cgcggtcagt acctaccgcc actgcgaccc gagaagggaa agcctcaact tcttcctctc    3840
ggagtcctgc ccactacgga tctgcctgga ctggttcaga tgcgtcgttt aaagggggg     3900
gctggcactc cagagaggag ggggcgctgc aggttaattg atagccacgg aagcacctag    3960
gcgccccatg cgcggagccg gagccgccag ctcagtctga cccctgtctt ttctctcctc    4020
ttccctctcc caccctcac tccgggaaag cgagggccga ggtaggggca gatagatcac     4080
cagacaggcg gagaaggaca ggagtacaga tggagggacc aggacacaga atgcaaaaga    4140
ctggcaggtg agaagaaggg agaaacagag ggagagagaa agggagaaac agagcagagg    4200
cggccgccgg cccggccgcc ctgagtccga tttccctcct tccctgaccc ttcagtttca    4260
ctgcaaatcc acagaagcag gtttgcgagc tcgaatacct tgctccact gccacacgca     4320
gcaccgggac tgggcgtctg agcttaagt ctggggtct gagcctggga ccggcaaatc       4380
cgcgcagcgc atcgcgccca gtctcggaga ctgcaaccac cgccaaggag tacgcgcggc    4440
aggaaacttc tgcggcccaa tttcttcccc agctttggca tctccgaagg cacgtacccg    4500
ccctcggcac aagctctctc gtcttccact tcgacctcga ggtggagaaa gaggctggca    4560
agggctgtgc gcgtcgctgg tgtggggagg cagcaggct gccctccccc gcttctgcag     4620
cgagttttcc cagccaggaa aagggaggga gctgtttcag gaatttcagt gccttcacct    4680
agcgactgac acaagtcgtg tgtataggaa ggcgtctggc tgtttcggga ctcaccagag    4740
agcatcgcca accagaacgg cccacccggg gtgtcgagtc ttggtaggga aatcagacac    4800
agctgcactc ccggcccgcg ggccttgtgg catataacca tttatatatt tatgatttct    4860
aattttatta taaaataaaa gcagaaatat ttcccgaaga acattcacat gagggcatta    4920
cggggagacg gcaagtcggc ggctcggggg gcgcgctcag ccgggagcgc tgtagtcaca    4980
gtcccgggag aagagcgcg                                                 5000
```

<210> SEQ ID NO 81
<211> LENGTH: 1500
<212> TYPE: DNA
<213> ORGANISM: Homo sapiens

<400> SEQUENCE: 81

```
tggaacaagt gtcagagagt aagcaaacga ctttctgagc tgtgactctg ctcctcgact     60
gcccacgtgc tctccgctgt ctgcactcct gcctcacctg ggctgactcg gactctccac    120
ctcctttgct gcttccggca tgagctaccc aggagcctaa ggcgctcctt cccgcaactc    180
cggtccccgc gccccgggac tgcaaatcct ttaaacagag gccccagagc tagggggtttt   240
cccaggctct ggtgggcgtg ggctgacagt cgctgggagc cccgcaacag gggggatgtc    300
caggcaggta tgcacccagc tccccggcgtt tcccggagtc accacaatgt ttccctttct   360
ctctccccca cgtatgctgc taggggtact ccccagatag gattttcttt gtcttttctc    420
ctagtaacac cgaagccctc tcgtgcccgg ggactgcaga ggaacgccag accatccgga    480
ccttgcggga tggctcggtg tgtgtgtttt actgtgtgtc ggagtgtcgc gcatgtgtgc    540
gtgttgggc gcgttatcaa caggggccta gggcaccccc actctttctt gctctcttcc    600
cccatcactt catggacctc cgaggcgcaa agcgctcgac cctctcctgg gctcagtggc    660
ttgggtactc cgggctgagc tcagctgggg agtcccctta cccagcccgc accggcaccc    720
cgaagcttca aagttgcggc aaacagttgc ggggagcaga ggaactgagg tccaggccag    780
cgcgcccgcg gtcgctcgcc ttggggagca ggctgagccg agggtcgtgc gggtgcgcgg    840
```

| | |
|---|---:|
| cagaggcggt aggaggcgga ggagaggggg gagaaagagg gggcggtggg gaacagctgc | 900 |
| cggggtaggc gaggcgcaag gtggctcccc gcggccccgc gccccgcggc tctcggacgc | 960 |
| accaggcagc caatggctgc gcagaggtgt acagcagatg gcgtctgact gcgccgttcc | 1020 |
| ttcctcctcc tcctcctcct ccttctcttc ctcctcctcc ttctcttcct cctcctcctc | 1080 |
| cttcagtgct gaggagccag agtcgccgcc gggttgccag acgctggaat gggtggtctt | 1140 |
| ccgacacaca ccaccatctt tcttgcgctc gggaagctcg gggctcagcg gctcccagag | 1200 |
| gttacggcgg cggctctggc gagacgggtg agtgcaagca cgcggagccc cgagtcgggg | 1260 |
| atgccgggcc ccctggccgg ccgactgggg cgcggggtgg cagcgccggg aaggggggcg | 1320 |
| cgctgccggc gcagactttg ctcttttcctc gccggacagc catcgtcgcc ccttctccca | 1380 |
| gccagacgcg ggaacttgga agcggatctt ctcggacgcc tctggcttgg ggctgcggga | 1440 |
| agcgtgggct gcccggggcg cagtgtgcgg agaccctcta ggcgggcggg gacgccccac | 1500 |

<210> SEQ ID NO 82
<211> LENGTH: 800
<212> TYPE: DNA
<213> ORGANISM: Homo sapiens

<400> SEQUENCE: 82

| | |
|---|---:|
| gttattatcc acggggtcct aattaaagct tgattaaaat gcccttcttt ctctaaaaaa | 60 |
| ttacgaacta ggcaacttca tacattttga atggcgcagt gtttcctctt ccaactgttt | 120 |
| agtttgtagt atactatgta agcaacatca attatcaacc cttgcaagat gacaacatga | 180 |
| gcctgtgggg gaagcacttg aggggaggga ggagaaactt ctctttttta ataatcagcc | 240 |
| ggaaacaatg tttaacaaga atctgatgag gtcactgcag taaatatttt tcctcttaca | 300 |
| gagccaatca tcacggaggg atcccctgaa tttaaagtcc tggaggatgc atggactgtg | 360 |
| gtctccctag acaatcaaag gtgtttgctt tctgctctgt tgcttttaaa ttgtatggga | 420 |
| aaggaagatt ggtccgacgg cgcgcttgtg gcccggccgg agcttgcgtg cgcgttctga | 480 |
| cggctgggtg ctgtgttaca ggtcggcgca gttcgagcac acggttctga tcacgtcgag | 540 |
| gggcgcgcag atcctgacca aactacccca tgaggcctga ggagccgccc gaaggtcgcg | 600 |
| gtgacctggt gccttttttaa ataaattgct gaaatttggc tggagaactt ttagaagaaa | 660 |
| cagggaaatg accggtggtg cggtaacctg cgtggctcct gatagcgttt ggaagaacgc | 720 |
| ggggagact gaagagcaac tgggaactcg gatctgaagc cctgctgggg tcgcgcggct | 780 |
| ttggaaaaac aaatcctggc | 800 |

<210> SEQ ID NO 83
<211> LENGTH: 40
<212> TYPE: DNA
<213> ORGANISM: Homo sapiens

<400> SEQUENCE: 83

| | |
|---|---:|
| tccctgctgt gggacccgag gagaggagaa ctggttcgct | 40 |

<210> SEQ ID NO 84
<211> LENGTH: 500
<212> TYPE: DNA
<213> ORGANISM: Homo sapiens

<400> SEQUENCE: 84

| | |
|---|---:|
| tctctctctc tctcttgctt ggtttctgta atgaggaagt tctccgcagc tcagtttcct | 60 |
| ttccctcact gagcgcctga aacaggaagt cagtcagtta agctggtggc agcagccgag | 120 |

```
gccaccaaga ggcaacgggc ggcaggttgc agtggagggg cctccgctcc cctcggtggt    180
gtgtgggtcc tgggggtgcc tgccggcccg gccgaggagg cccacgccca ccatggtccc    240
ctgctggaac catggcaaca tcacccgctc caaggcggag gagctgcttt ccaggacagg    300
caaggacggg agcttcctcg tgcgtgccag cgagtccatc tcccgggcat acgcgctctg    360
cgtgctgtga gtacaacctg ctccctcccc gggcacagat atgacagagg ggcttagagg    420
gggcccagct ttgagatggg ttgttcttat gtcacaggac agagtgatct gacatgcaca    480
cttccccgcc accctgtcat                                                500
```

<210> SEQ ID NO 85
<211> LENGTH: 500
<212> TYPE: DNA
<213> ORGANISM: Homo sapiens

<400> SEQUENCE: 85

```
tgtcctcgaa gaagggcctg agcagcagca gaggacccca ggcgaccgtg cctgagccgg     60
gcgccgacga cgactgagca cctgatatgt ccccggcact cgcagccccg cggccggagt    120
cgctgtgggt gagcggtcgt cgagcttcac agaggccggg ctctgtgcca gggccccgac    180
agggcaggaa gcagatagag tcccacaagc acaagcccag tgcgcagaaa gggttactta    240
aaaaataagt tctgtgataa aatcaaacag ggtgaagggc tggaaacagg tcatgagggc    300
gcaaacaggt cgtgagggcg caaacaggtc gtgagggcgc aaacaggtcg tgagggcgca    360
aacaggtcgt gagggcgcaa acaggtcgtg agggcgcaaa cagatcgtga gggcgcaaac    420
aggtcgtgag ggcgcaaaca ggtcgtgagg gtgcaaacag gtcgtgaggg cgcaaacagg    480
tcgtgagggt gcaaacaggt                                                500
```

<210> SEQ ID NO 86
<211> LENGTH: 300
<212> TYPE: DNA
<213> ORGANISM: Homo sapiens

<400> SEQUENCE: 86

```
aaatgagacc tctggggaga ctgtcaaccc caggggtaaa acaaaaattc tgatcagaaa     60 ctgagttttcc caagaaggg gctaaatgtt ttccaacact ttcggggctc agggaagatg    120
actctgtaag gacactgaga atcttcctcg cgtgccacgg ggaggaggac tggggggcgtt    180 tgagggctc agcgcaccag aggagtgagg tggaggaggg cgttcccgcg tcctcctctt    240
caatccagag cagctcaacg acgtggctcc ctttctatgt atccctcaaa gccttcgcgt    300
```

<210> SEQ ID NO 87
<211> LENGTH: 600
<212> TYPE: DNA
<213> ORGANISM: Homo sapiens

<400> SEQUENCE: 87

```
taggctctag tggacctagc agtgggagag ctacttgggc tggtttcttt cctgacgctg     60
cagggatggg catcggcctg gaaccagaag cgcaggagct gggccacggc agagtaatta    120
agaaaataat gaaattgatg gcggatgggg gcgctagaaa tcctgggggcg tctacttaaa    180 accagagatt cgcggtcggc cccacggaat cccggctctg tgtgcgccca ggttccgggg    240
cttgggcgtt gccggttctc acactaggaa ggagcctgaa gtcagaaaag atggggcctc    300
gttactcact ttctagccca gccctggccc ctgggtcccg cagagccgtc atcgcaggct    360
```

| | | |
|---|---|---|
| cctgcccagc ctctggggtc gggtgagcaa ggtgttctct tcggaagcgg gaagggctgc | 420 | |
| gggtcggga cgtcccttgg ctgccacccc tgattctgca tccttttcgc tcgaatccct | 480 | |
| gcgctaggca tcctcccga tcccccaaaa gcccaagcac tgggtctggg ttgaggaagg | 540 | |
| gaacgggtgc ccaggccgga cagaggctga aggaggcct caaggttcct ctttgctaca | 600 | |

<210> SEQ ID NO 88
<211> LENGTH: 800
<212> TYPE: DNA
<213> ORGANISM: Homo sapiens

<400> SEQUENCE: 88

| | | |
|---|---|---|
| gaggttgctg actcaggagc caggagctga gaaactccta ggctagcagc cgttgagcct | 60 | |
| aattttattt tctggctttc tccgaaatgt ctcgtttccc tcatctttct ggtccttttc | 120 | |
| gtctctctta ttttcccaa aacgtctacc tcacttcgtc ttcctttctc ctcccctccc | 180 | |
| cctctctttc ctctatactc tcttcccatt tagcccttgca ggcccctcct ccccggtgtt | 240 | |
| ggagagctca aagacgcgcg aaactcaagg atctggccct gaccagggac gggattaggc | 300 | |
| gggaagtggt gacggcctga aaaggctggg ctcgaacccg tgccttcctg aaaggactct | 360 | |
| ccccgccaca agtcacaccc acccgcaggc ctgctggcca aagaaacaaa ggagtcgggc | 420 | |
| gtggatccag gagaaacagg ttttcgctct cggatctccc tgggcaaatc agggatcctg | 480 | |
| agcgctatac cccgcagtcg tacggagcct ctgggaaagg ggatttaagg gtgacttcca | 540 | |
| ctttcagctt cggctacttg ttgcctgcgg tccaagcctt ctctgcttcc tcctacctcg | 600 | |
| tcttaggcct ctgtagaaag tgcacgccgc gtttccccctt ccaggctctg agagggcctg | 660 | |
| caggcccgtg gccgcctccg acaagatgcc ttccagtgct agggggggcca ctttggcggg | 720 | |
| atggggtcg gttggttaaa aaaaacttaa gttctggctc agtcgagtgt ggcaaaagcc | 780 | |
| gagggtcggg ggttgggggg | 800 | |

<210> SEQ ID NO 89
<211> LENGTH: 2000
<212> TYPE: DNA
<213> ORGANISM: Homo sapiens

<400> SEQUENCE: 89

| | | |
|---|---|---|
| tactgacctg gtctccgcct caccggcctc ttgcggccgc tgcagaagcg cactttgctg | 60 | |
| aacaccccga ggacgtgcct ctcgcacagg gagcgcccgt cttttgctggg gctggagcgg | 120 | |
| cgcttggagg ccgacactcg gtcgctgttg gactccctcg cctgccgctt ctgccggatc | 180 | |
| aaggagctgg ctatcgccgc agccatagct gctcagcgag ggcctcaggc cccagcctct | 240 | |
| actgcgccct ccggcttgcg ctccgccggg gcgagggcag gacctgggcg gccagggaaa | 300 | |
| gggcagtcgc ggggaggcag tgctaaaatt tgaggaggct gcagtatcga aaacccggcg | 360 | |
| ctcacaaggt tagtcaaagt ctgggcagtg gcgacaaaat gtgtgaaaat ccagatgtaa | 420 | |
| acttccccaa cctctggcgg ccggggggcg gggcggggcg gtcccaggcc tcttgcgaa | 480 | |
| gtagacgttt gcaccccaaa cttgcacccc aaggcgatcg gcgtccaagg ggcagtgggg | 540 | |
| agtttagtca cactgcgttc ggggtaccaa gtggaagggg aagaacgatg cccaaaataa | 600 | |
| caagacgtgc ctctgttgga gaggcgcaag cgttgtaagg tgtccaaagt atacctacac | 660 | |
| atacatacat agaaaacccg tttacaaagc agagtctgga cccaggcggg tagcgcgccc | 720 | |
| ccggtagaaa atactaaaaa gtgaataaaa cgttcctttta gaaaacaagc caccaaccgc | 780 | |
| acgagagaag gagaggaagg cagcaattta actccctgcg gcccgcggtt ctgaagatta | 840 | |

```
ggaggtccgt cccagcaggg tgaggtctac agaatgcatc gcgccggctg cggcttttcca      900 ggggccggcc acccgagttc tggaattccg agaggcgcga agtgggagcg gttaccggga      960
gtctgggtag gggcgcgggg cggggcagc tgtttccagc tgcggtgaga gcaactcccg      1020
gccagcagca ctgcaaagag agcgggaggc gaggagggg ggaggcgcg agggagggag      1080 ggagatcctc gagggccaag caccctcgg ggagaaacca gcgagaggcg atctgcgggg      1140
tcccaagagt gggcgctctt tctctttccg cttgctttcc ggcacgagac gggcacagtt      1200
ggtgattatt tagggaatcc taaatctgga atgactcagt agtttaaata agcccctca      1260 aaaggcagcg atgccgaagg tgtcctctcc agctcggcgc ccacacgcct ttaactggag      1320
ctccccgcca tggtccaccc ggggccgccg caccgagctg gtctccgcac aggctcagag      1380
ggagcgaggg aagggaggga aggaagggggc gccctggcgg gctcgggatc aggtcatcgc      1440
cgcgctgctg cccgtgcccc ctaggctcgc gcgccccggc agtcagcagc tcacaggcag      1500
cagatcagat ggggattacc cgccggacgc aaggccgatc actcagtccc cgcgccgccca      1560 tcccggccga ggaaggaagt gacccgcgcg ctgcgaatac ccgcgcgtcc gctcgggtgg      1620 ggcggggct ggctgcaggc gatgttggct cgcggcggct gaggctcctg gccggagctg      1680
cccaccatgg tctggcgcca ggggcgcagg cggggcccct aggcctcctg gggctacctc      1740
gcgaggcagc cgagggcgca acccgggcgc ttggggccgg aggcggaatc aggggccggg      1800
gccaggaggc aggtgcaggc ggctgccaac tcgcccaact tgctgcgcgg gtggccgctc      1860
agagccgcgg gcttgcgggg cgccccccgc cgccgcgccg ccgcctcccc aggcccggga      1920 ggggggcgctc agggtggagt cccattcatg ggctgaggct ctgggcgcgc ggagccgccg      1980
ccgcccctcc ggctggctca                                                  2000

<210> SEQ ID NO 90
<211> LENGTH: 800
<212> TYPE: DNA
<213> ORGANISM: Homo sapiens

<400> SEQUENCE: 90
gggggacaca gagaggaggg gttgcgggcc tgtgagaatg aagagcacag agcggagagg       60
gggaggagga gggaaaggaa ggcgtggcag tgagagagaa gaggaagaag agaggaggag      120
tggggagggg agggagagca agacagcagc gggtctggat tcccctccga gccacatctg      180
gtcaggttct aagtaattag aagatttttc cattggttta cccaagggct ctctctctga      240 ttaatttcg aaagagttgg ccaattttaa tcatagcaaa cacgatgatc acggtgatca      300
tggcctgaac agctaaaagc agaaaataaa accccagaa cggactatga tcttgaccct      360
tgcccgtggt caccggctgg gcccacaccc agggttctga gctgttggga gccaaggctg      420
ggtggacagg ggcttccgag gagctgtccg cagcggggcg gggaggcggg ccccggggc      480 ccgggcactc cgcgtcaccc cccggcaggg cccagagcgg caggcggcg tgcgcccag      540 ggcctgcgca ccgtggggc tcttcccgc ccacgaggcc taggtgctgc cgcagccacc      600
ccaggaaggg ccccaggcca cagtcgcagc gccaggagtt gtgccccaac aggacctccg      660
tcagccgggg cagagcccca aacacgtcgc caggcagggt ctccagctgg ttgtggtcga      720
gctggacgct ctccaggctg ctgagattgc ggaagagggc acggggcagg gcgcgcagcc      780
tgttgcggcg cagggacacc                                                  800

<210> SEQ ID NO 91
```

<211> LENGTH: 550
<212> TYPE: DNA
<213> ORGANISM: Homo sapiens

<400> SEQUENCE: 91

| | | | | | | |
|---|---|---|---|---|---|---|
| gccccggtgc | accgcgcgtc | cagccggccc | aactcgagct | agaagcccca | accactgccc | 60 |
| agtgcctgag | ttgcagtctt | gggtccttta | gaaacctgga | gatgtgcgta | aaattcagat | 120 |
| gccggtattc | ccgaacttcc | ccaggcctca | gcatatctcg | gcggcctgtg | gacagatggg | 180 |
| aggctaccaa | tcgctccggc | gtccgcagcc | cgacccctgc | cgccagaccc | cggacgtctt | 240 |
| ccggataata | aagttcccgc | tctaattcat | tttccctaat | ctggacgccc | ctaatctaca | 300 |
| gcttttattg | cgcccagtta | aaagtcgagg | gaattcgctg | tccctccgcg | ctcggataat | 360 |
| taccccctaaa | tggccacggc | agcccttgt | gtttcctgga | gattagaacc | ccgcagtcat | 420 |
| caatggcagg | gccgagtgag | ccgccaatca | cctccgctca | ctccctgaga | gccgctggcc | 480 |
| tgggccgcag | gaggagaggc | cataaagcga | caggcgcaga | aaatggccaa | gccccgaccc | 540 |
| cgcttcaggc | | | | | | 550 |

<210> SEQ ID NO 92
<211> LENGTH: 2000
<212> TYPE: DNA
<213> ORGANISM: Homo sapiens

<400> SEQUENCE: 92

| | | | | | | |
|---|---|---|---|---|---|---|
| agggtgcctc | tgttcaaatt | agaaaaggc | gccccctcag | ggcagactca | gcccagctgc | 60 |
| caggggacaa | gtcctggcta | cgggagctg | gagctgggtt | tcacctccag | gtgcctcctt | 120 |
| ggcggggcgc | cccgtgcagg | ctacagccta | cagctgtcag | cgccggtccg | gagccggagc | 180 |
| gcgggaatca | ctcgctgcct | cagcccaagc | gggttcactg | ggtgcctgcg | gcagctgcgc | 240 |
| aggtggagag | cgcccagcct | gggaggcagt | agtacgggta | atagtaggag | ggctgcagtg | 300 |
| gcagaagcga | gggtggccgc | agcacttcgc | cgggcaggta | ttgtctctgg | tcgtcgcgca | 360 |
| ccagcacctt | tacggccacc | ttcttggcgg | cgggcgccga | ggccagcagg | tcggctgcca | 420 |
| tctgccggcg | ctttgtcttg | tagcgacggt | tctggaacca | gattttcacc | tgcgtctcgg | 480 |
| tgagcttcag | cgacgcggcc | aggtctgcgc | gctcgggccc | ggacaggtag | cgctggtggt | 540 |
| taaagcggcg | ctccagctcg | aagacctgcg | cgtgggagaa | agcggcccgc | gagcgcttct | 600 |
| tgcgtggctt | gggcgccgcc | ggctcctcct | cctcctccgc | gacgcctgcc | ggcccgctgc | 660 |
| cgcccccgcc | gccggccccg | ctgcacagcg | cggacacgtg | tgcacctctg | ggccaacac | 720 |
| cgtcgtcctc | ggtccttggg | ctgcggtcgc | ctgcggaccc | cggtgggaac | agaaacaaga | 780 |
| gactgtcagc | gccacagacg | aggtgaggcc | gggcctcaac | tgcagggtc | acggagtgg | 840 |
| ggcggaaata | cactttgatc | ccactcaagc | ggagcggagg | tctgggaggc | cctgggcccg | 900 |
| ggagaccagt | cttagactct | tgccccactg | ggtatcccat | ctaggcctct | tctggggagg | 960 |
| gcggcagact | cagccgctgt | gtcaacgctg | tgttgtcgag | accagctccc | caccctctct | 1020 |
| gggccccagg | ctcccctcag | taacttgggg | cactcgaccc | gagcatccgc | gaaagccctc | 1080 |
| ccggctctca | gcgttgagca | ttgggattct | agactgcatt | tccgtctctc | tgcttgggtt | 1140 |
| cacgcgcctc | tccacactta | gttcacacgc | acacgcgc | gcgtcctcgc | agcacacact | 1200 |
| tgtctggtgc | aggtaaggga | aggtggaggc | ggatcctggg | gccaaaggta | tttagaatct | 1260 |
| ttcacccctca | gccgctggg | attgctgtga | gagacatgga | aacaggctga | gccgaggcct | 1320 |
| tagatgagag | gatggactgg | agagtaaaga | gggagggttg | ccctgcatc | gagtttttgg | 1380 |

-continued

| | |
|---|---|
| accctgatcc cacaccagct tctcggtctc gtacccgccc ttccgaagaa ctccagcaga | 1440 |
| aaggtccagc ggtcccctgt gcttgaggcc tacagaagct tgtacccaac tagggcaggc | 1500 |
| acccgggtct tccagaccac aggacaggac aggccacggc tgaggaggcc tctctcctgc | 1560 |
| ctccaggatg aactaaagac ccaatccggg atcttcggcc tagggctgct ctcccagacc | 1620 |
| tggggtctga gaaagccaaa ccagcccttt ccccaaagct ctagttctgc agattctcag | 1680 |
| ctctggccca ctcggaggtg ttcttcacca cctatccacc tactgtgggg cccggccctg | 1740 |
| ggaccttgaa ctggcaggtc tctggtccag agctaggtca ctggctacct gaggtctctg | 1800 |
| aaccctcac ttttccgctt ccctgatttt ggggatttgg ggacagacac ggcagaaagc | 1860 |
| actggcgacg aactcaaaaa ctcccgaacg caaggggcag cggttctccc aacccagtct | 1920 |
| aatgcacatt ggcccaggat gtctcaggcc tcaccccagg acgtagggct ctgaggagct | 1980 |
| actccggtct ctcgcgggct | 2000 |

<210> SEQ ID NO 93
<211> LENGTH: 1000
<212> TYPE: DNA
<213> ORGANISM: Homo sapiens

<400> SEQUENCE: 93

| | |
|---|---|
| gagaagggat gtggcggggg gctcctccgg ccctggactc cctgggtgga ctagaaaagg | 60 |
| gcaaagaagt ggtcacatct gtgggccaga ctggtgcgcg atctttggag gcgcagcagc | 120 |
| aaggccgcgc cagggctgag cccagaccgc ccacgaggag gccgccagg cccggagcag | 180 |
| cggcgcgtgc gggggcgtgc cgagcgcagg ctctagggcc cctgcttcgc cccagctgga | 240 |
| ccccgcggc ggtcggtgca gctcgagcgt gtgggctgcg atgccctgcc tgagacttcg | 300 |
| ggctagggat gcggcggga agtggggtg cggcggcagc tgcagattag attcctttt | 360 |
| tttttggccg gagggacgtg caaacttcta gtgcccgggc caagagggcg accccggagg | 420 |
| tgcgtaggtg gccctccggg ttcccgcttc tcctagtgcc tctgaaaata ccgtcagggt | 480 |
| aaagggagac aggcagtaag tcttaccacc accgcccttt ccccatgtca ttggccaaaa | 540 |
| actgaacatt aagataaagc agctgtttca gtcaatggaa agcggtaggg cgaggttgta | 600 |
| cccaaaaccc ggtttagacg gccaatgaag tcctaggaaa agccgccccg ggggcacgtt | 660 |
| caggtggagc ggctgcacct cgggtcgttc taagggatgg gctgcgtggt acccacggaa | 720 |
| ttcatgggtc caaaaggtcc tggtcacctg tccaaacatc catcccctgg cgcatggcgg | 780 |
| ttgacaagat ggcccggcca cccagaggaa ggaggatccg ggacggggaa cttcgcgccg | 840 |
| ggaagctgta gcccagagct gcagctcagc attcgcaaga gattcatctt tttttctct | 900 |
| cgtgttcgga gaaacagata aacaagacac cgcctcatca gataagaacg tctccttcga | 960 |
| tgtcacggat ttcaagaggt agctggagaa actgacgtca | 1000 |

<210> SEQ ID NO 94
<211> LENGTH: 1300
<212> TYPE: DNA
<213> ORGANISM: Homo sapiens

<400> SEQUENCE: 94

| | |
|---|---|
| caggtcaggc agaacttctg cccttcccgc tactggcacc ccaagcaggg atgcactggg | 60 |
| atgcgtggca ggggcgggat ctcctggag cgtctcagcc cagcagggag tggggaagca | 120 |
| agagggaagg cttaccttcc tcggtggctg gcaggaggtg gtcgctgcta gcgaggggga | 180 |

| | |
|---|---|
| tgcaaaggtc gttgtcctgg gggaaacggt cgcactcaag catgtcgggc caggggaagc | 240 |
| cgaaggcgga catgacccgg gcgcagcggt ccttcacctg cacgcagagc gagtggcatg | 300 |
| gctggatggt ctcgtctagg tcatcgaggc agacggggc gaagagcgag cacaggaact | 360 |
| tcttggtgtc cgggtggcac tgcttcatga ccagcgggat ccaagcgccg gcctgctcca | 420 |
| gcacctcctt catggtctcg tgcccagca ggttgggcag ccgcatgttc tggtattcga | 480 |
| tgccgtggca cagctgcagg ttggcaggga tgggcttgca attgctgcgc ttgtaggaga | 540 |
| agtcgggctg gccaaagagg aagagcccgc gcgccgagcc caggcagcag tgcgaggcga | 600 |
| ggaagagcag cagcagcgag ccagggccct gcagcatcgt gggcgcgcga ccccgagggg | 660 |
| gcagagggag cggagccggg aagggcgag gcggccggag ttcgagcttg tcccgggccc | 720 |
| gctctcttcg ctgggtgcga ctcggggccc cgaaaagctg gcagccggcg gctggggcgc | 780 |
| ggagaagcgg gacaccggga ggacagcgcg gcgaggcgc tgcaagcccg cgcgcagctc | 840 |
| cgggggggctc cgaccgggg gagcagaatg agccgttgct ggggcacagc cagagttttc | 900 |
| ttggcctttt ttatgcaaat ctggaggtg ggggagcaa gggaggagcc aatgaagggt | 960 |
| aatccgagga gggctggtca ctactttctg ggtctggttt tgcgttgaga atgcccctca | 1020 |
| cgcgcttgct ggaagggaat tctggctgcg ccccctcccc tagatgccgc cgctcgcccg | 1080 |
| ccctaggatt tctttaaaca acaaacagag aagcctggcc gctgcgcccc cacagtgagc | 1140 |
| gagcagggcg cgggctgcgg gagtgggggg cacgcagggc accccgcgag cggcctcgcg | 1200 |
| accaggtact ggcgggaacg cgcctagccc cgcgtgccgc cggggcccgg gcttgttttg | 1260 |
| ccccagtccg aagtttctgc tgggttgcca ggcatgagtg | 1300 |

<210> SEQ ID NO 95
<211> LENGTH: 500
<212> TYPE: DNA
<213> ORGANISM: Homo sapiens

<400> SEQUENCE: 95

| | |
|---|---|
| tgcgatcatt aaaatcagtt ccttccctcc tgtcctgagg gtaggggcgg gcagatttta | 60 |
| ttacttctct tttcctgata gcagaactga ggcggggttg tggaggagcg acggaggacc | 120 |
| acctctaact tcccttcact tcctggattt gaagcctcag ggccaccggc ctcagtcctg | 180 |
| ttacggtggc ggactcgcga ggttttccag cagctcattc cggacggcg gtgtctagtc | 240 |
| cagtccaggg taactgggct ctctgagagt ccgacctcca tcggtctggg agcgagtggt | 300 |
| tcgagttcag atgctgggaa ccgtcgcttc tccccggccg ggctcgctgt tttctcctcc | 360 |
| gctcgccgtc atcaagcccg gctatgagca gggctttaaa tcctccctcc ctcacccgca | 420 |
| ggtttaccga gcagcccgg agctctcaga catgctgcgc tgcggcggcc agaggagggg | 480 |
| tgggggcatt gccctctgca | 500 |

<210> SEQ ID NO 96
<211> LENGTH: 500
<212> TYPE: DNA
<213> ORGANISM: Homo sapiens

<400> SEQUENCE: 96

| | |
|---|---|
| gggcttgggc cgcaggcttc cctggacttc cgcagtcccc cttctcccca ttccagaacc | 60 |
| tgccgagccc ctgctgcatc tgggaccccg cttcaccgtt tcccaatccc agcggttagc | 120 |
| ccctgcgccc ccttttggt ctccactttg ccgttcgaaa atgcctaggt tggtggatcg | 180 |
| accctccgcg gagcaaagac ggatggctgg caggagcagg ttcaggagct gggccaaggt | 240 |

```
attctctgct tccgcctttg tgtccgcccc ccgcccccct gctccccgct tcccgccagc    300
atctctcctt ttctgctcag gagtgtttgg cccggcggtc cacccggct tcccgagata    360 cgctagagtt gccccacgt cctgtccgcc gcgcccctac ccaccgggtt gccttcgggg    420
cccttcggtg ctgtgtagtc ggcgtggcgc tgtgagctag gcgaacagga accccaggc    480 ccgccacgtc tacgctatta                                              500
```

<210> SEQ ID NO 97
<211> LENGTH: 600
<212> TYPE: DNA
<213> ORGANISM: Homo sapiens

<400> SEQUENCE: 97

```
ttctggggcc tggatgggtg cgagcgggac ccggggagt gggagtcgcc aggctctgag     60
caagcaaggg ctgcacctgc acctctgccg ggcatgaaga aaggtaagga aggaaggagc    120
tcacccgggt gggagacaga gccggggcgc gcgagcttgg tgtgggggcg ccactccggg    180
gcggagggga ggggctacca gtgacttctc cgagtcggga gctagaaaga ggcttccggc    240
caggttccct tggaacaggt gtcggagttg ttgggagagg gggctgcaag aaagaggggt    300
gcagaaactg gttcattaga tggaggctct gggcggaacc gcgaggacac cctggcagcg    360
cgctgtgcct gcgttaggcc gggaggggag aggcctccgg acggcgaagt gtccctaggg    420
acccagacgc ctcgggagcg atccgggccg ctgcgaagcc ctgcccacca ggagtggatc    480
cccaggattc acctcccggc tgcctgctct gagctgagaa ggggatctgg ttcttcacaa    540
taccgtggat ggcggggaag gggagggagc ctggggtaaa atcccatctt ggtttcctcg    600
```

<210> SEQ ID NO 98
<211> LENGTH: 1300
<212> TYPE: DNA
<213> ORGANISM: Homo sapiens

<400> SEQUENCE: 98

```
tgtcacagaa accccagcag cgcagccacc ggactgggtt ctggaggccg agccgcagtc     60
cgtgcggcgg cgctgggaag agaaggcgcc ccggcagctc ccctgccacc ggccccgagg    120
agcggctggc tcccccagcc cagcgccgcc gccgccggt aactccaggc gcaactgggc    180
gcaactgggg cagctgcgac accgaatccc tcacatctgc aacctgggtg ctgcggccac    240
tgagaaaatg gaggcgcaga ccaacgagcg gtgccgcgac cgagagacct cggctggcga    300
aatggtggtg ccgggagcct gcgagtgacg ccagccggcg gggttgtcaa ggacaacatt    360
cgttttgacg cagccaatgg cgccgtcacc aagaaaccat cgactctgag aaaaaagaga    420
ggttcggcca ccgagaaact ccgtacgaca agtgctgtgg cagaaaaacc gcctactccg    480
cgccacaggc aaaacagcca atggaaaccc caggtgctgc gaccgtgaca ccggcactag    540
agggtctcgg atggagaaag cggcgcacgg agaccaggaa actatgtgta gcacaactag    600
cagaaaaccg tctggtcggc catccgggag aaagcgcgga tcagaaacaa gcgacttcga    660
tgcagggaac cgcgcagcca ctgaagaaag tgacccacgt ggcagtggtg ccagcgaaac    720
actgcagttt ggacggcagc tgtggggatg ccacagaaa acatgcactg ccactgaagt    780
acatccagct ccgcggagct agtgttcata tgatcaagaa accgccagtt gggctctgct    840
agaaactttt agtcctccct taacggctat cctaccccaca acagacaatg cctttaccca    900
gcacctagcg gtgctgagac ccgcctgggc cagcacagag cgcagagcag tacgggtacg    960
```

| | |
|---|---|
| gagaaacgcc ggactcagtg aaaccagcct tgcctccagc ggattccccg gcttcgccgg | 1020 |
| acgccacagg cagagtgccg cggggaaacc tctggctccc taaaccgatt agattgtggg | 1080 |
| agtggggggg acactcacaa gttgtgtgga agggaaccag cggcaatggg acccggcgag | 1140 |
| cacttgcccg cagcaaatgc ctgcgctgct gcaaaaaaaa caacttttgg cgcaaagaat | 1200 |
| gttgcggcca gagagcatcc gctgtcgctg acaaaggagt agcaatggca atgagaaacc | 1260 |
| gccggcgcca cggccgaccg cggcggctca cgcctatgat | 1300 |

<210> SEQ ID NO 99
<211> LENGTH: 2100
<212> TYPE: DNA
<213> ORGANISM: Homo sapiens

<400> SEQUENCE: 99

| | |
|---|---|
| caaacgctga gagacaaaaa gacaccaaca cccaccagga ctgcgtcctg ccagctcttc | 60 |
| actccgctga cctgaccttc cacgcccta gtcctcgagc ggacttgacc tgtgggggag | 120 |
| taccgaaccg tcccatgag gccctccaag cggccaggtg gcctccgcca ctctctccac | 180 |
| ccccacctcc tccaccccc agcccatcgg tccatcttcg atctgcaaaa cacgccgggt | 240 |
| cagcgacgca tcggtcccag gcttgtgacc acctctttct ctgttacttg gggagccagg | 300 |
| cccaccgctc aggatcacag tgaggagaaa aaagacacaa acgccaggac agggcggctg | 360 |
| gggaaggaaa ctgctaggga ccgctcattg tcagcctggc gtgtcccacg atcgcagga | 420 |
| cccgtcgagg ctttgctctc tgcgacccga atactcctgg gcctctcgac ctcctcctcg | 480 |
| gactcaggcg tccgcgtctc cggtcatcac gggagaccaa ttggtttaca aatagtgatg | 540 |
| ataaacctgg gaccgacctt ggggctgtgt aaaagtctac tgacagatgt aatggagggt | 600 |
| tgttagcagt cacaaagcct gtcggacccg tagcattagt tcaagagact attttcgtgt | 660 |
| cgcaccaaaa ttactgcgcg tgtaaaccaa tttccccgac ggaagaataa acagagattc | 720 |
| gtttgaagcg cgagatgaaa acagatgggg tatcgcaaac agttccccaa aatacaacag | 780 |
| acttctgggc caattacacg tggttagctc tgaatggcag aggaaatagt tttctttgct | 840 |
| gctaaatgtc acaaaagtca cctaaaggca cagaggaggc cgctctgttt ttgcgaaact | 900 |
| tgctaaaatt aatctgcgct gggccacttg cagaaagcag aaccacctcc cgcccccacc | 960 |
| tcgcctccag ccgccggggt tcaggcgttt gtgaaagaca gaacctttgg gctagggacc | 1020 |
| cgggcactgg tgcttcgaag tccgaatccg ccggccgaga aaacgacaag agaaagaaaa | 1080 |
| tccagcgggc gctctctcca gcgccaggcc ggtgtaggag ggcgctgggg ctcggcctgc | 1140 |
| caccccctacc cgacattggg aagcagcccc tgcgctcccg cggcgcctca gcctccggtc | 1200 |
| cccgccccga ggtgcgcgtt cctcctcccg catgcccgtc tcgggcccca cggagcaaga | 1260 |
| agatagacga tgacgaggcg cgcccatcca tccgggccga cgaggtcagg cccgcgccac | 1320 |
| aggcaaaaat tgcgcaagcc cggccgcagg gatttcgcgg gcgcctgggt cccaggtgcg | 1380 |
| cggccgaaat cctcagggaa aatcccgagg ggccaacggt ctaggccaca gggctgctgg | 1440 |
| gcccgggcct ggctcagagc gcattcgggc ggggaggccg cacgccgcac ccgggcctct | 1500 |
| cctccgagcc cgaggcaggc actgagctcc gggccagcca ggtgcctccc ggctggtgcg | 1560 |
| agaccccggg cctgctggga ggcgtgggca gggcagggca gggctgaacc ccagcgactg | 1620 |
| aatctcgaag gcaggaggcc tcggaggtca tcggcccagc tcgcctgaaa ctgtccctgc | 1680 |
| tcgtgccagg gcgcgggcag aggagaaagg acagggcgga gcaagccac tgcagaactg | 1740 |
| cggtcggtgg ctgcgaaggg tccgggtcac cgcgctcccg gacgccggaa gccgcgctgg | 1800 | cggggccgcg gggagggagg ctgggtaccg gggccgtccg gccggaggaa gcggctccgg    1860 ccgcgctgtc cgcgcttggg agccgcgtgc agggttcagc cgtgtttcag ttgccctctg    1920 acctgacccc gggcgcacaa aggcctcccg ggtgcgccgc catggcccag tcttccagtc    1980 gctgccaaat taatgagccc acgtcaggtt gggtttacag ctcggccggg aagcagccga    2040 gtggaaaatg agctcggggc cgctccagag gctcccgcac aactgcagag gctgcccgcg    2100

<210> SEQ ID NO 100
<211> LENGTH: 250
<212> TYPE: DNA
<213> ORGANISM: Homo sapiens

<400> SEQUENCE: 100
tttccaagac agaaggaggg aactaggcgc ctttttttcca ctccgctgac cccaacgtct     60
gggctgtgcg ttgtaacgca gttggcgggg ccttcagctt gggatgaggg cgaaggggct    120
cgggatgggt gggaaagcaa ggaccgggca acaggtgggg aggtggcgga cttttgtctc    180
ggggaaggaa atcggctgtg ctgaaagggc ggaaagcagt agcgcacaga actagtgtct    240
gcggggtccc                                                           250

<210> SEQ ID NO 101
<211> LENGTH: 250
<212> TYPE: DNA
<213> ORGANISM: Homo sapiens

<400> SEQUENCE: 101
ccctcctgtg gctgcttggg cagacgcctg tggcctgtcg gatgcggccc acatcgagag     60
cctgcaggag aagtcgcagt gcgcactgga ggagtacgtg aggagccagt accccaacca    120
gcccagccgt tttggcaaac tgctgctgcg actgccctcg ctgcgcaccg tgtcctcctc    180
cgtcatcgag cagctcttct tcgtccgttt ggtaggtaaa accccatcg aaactctcat     240 ccgcgatatg                                                           250

<210> SEQ ID NO 102
<211> LENGTH: 2000
<212> TYPE: DNA
<213> ORGANISM: Homo sapiens

<400> SEQUENCE: 102
tcctcctttg tgtatgtcaa cccagaggat ggacggatct ttgcccagcg tacctttgac     60
tatgaattgc tgcagatgct gcagattgtg gtggggttc gagactccgg ctctccccca    120
ttgcatgcca acacatctct gcatgtgttt gtcctagacg agaatgataa tgccccagct    180
gtgctgcacc cacggccaga ctgggaacac tcagccccc agcgtctccc tcgctctgct    240
cctcctggct ccttggtcac caaggtgaca gccgtggatg ctgatgcagg ccacaatgcg    300
tggctctcct actcactgtt gccacagtcc acagccccag gactgttcct cgtgtctaca    360
cacactggtg aggtgcgcac agcccgggcc ttactggagg atgactctga cacccagcag    420
gtggtggtcc tggtgaggga caatggtgac ccttcactct cctccacagc cacagtgctg    480
ctggttctgg aggatgagga ccctgaggaa atgcccaaat ccagtgactt cctcatacac    540
cctcctgagc gttcagacct taccctttac ctcattgtgg ctctagcgac cgtcagtctc    600
ttatccctag tcaccttcac cttttctgtca gcgaagtgcc ttcagggaaa cgcagacggg    660 gacggggtg gagggcagtg ctgcaggcgc caggactcac cctccccgga cttctataag    720

```
cagtccagcc ccaacctgca ggtgagctcg gacggcacgc tcaagtacat ggaggtgacg      780
ctgcggccca cagactcgca gagccactgc tacaggacgt gcttttcacc ggcctcggac      840
ggcagtgact tcactttct aagacccctc agcgttcagc agcccacagc tctggcgctg      900
gagcctgacg ccatccggtc ccgctctaat acgctgcggg agcggagcca ggtgaggggc      960
tcggcgccgc cccgggcgac ccctgggggc ggcactggag aagccgcccg tcctcataag     1020
ggattgaact tgcatccact cctctccggc cggcttggtc gctggctgcg ctccacccga     1080
ttctcgggat cattggaccg tttgcgcgaa accagagtgg ccgattaagg gatgggctc     1140 cgagcaccgg gggtggtggc gactgtgggc gaggggaggt gggaccgacc cccacccta      1200 cactcaaaaa aggccggggc ctccttcgag cttccggtga atttcgggcg atttccgcgg     1260
gtgtcggggg tcccgggagg aggcagtcac agatccaccc ctgcagccag cctcctaggc     1320
gccggctccg gcacgcttcg ccggtctgta gatttcctct tcgatttctc cccagctccc     1380
agcatctgtg acttcactgt taccctccct atccccgcat cacccaaccg cacctgtctg     1440
cgggacttag gtgtgcgcgc ggggctcatg cgtgtcctcc ctgctggcca cccccacggc     1500
ccacacaagt tgcacgggct cgccacgccc cgccaacacg tgcgcggacg cacgcacgca     1560
ctcctcgcac gtgggcttac gcgaatacca gctttcactg ccactcgctc gcggccagat     1620
tcacaggcct gttccggtcc actcgcagct cccctctgcc gctccctccg ccgggctcag     1680
gagtactcgt agctgattgt gcgcgcctga gggtcccaga tcgcggccgc ccaggaccag     1740
gcgaggactc cggagcctcc tctcacctct cccacctgcg ccccgggctg gccgggtcg      1800 cctgggggc ggcctgagcg aggcgcgggg ccaggagcgc tggagcgact gccgctctaa     1860
gtgccgggcg gcaggactc tacgatcctt gggccagagg tccggatggt cccgggactc     1920
cgtctcaagg gtcggcgacc cctcaaccca gaagcctcga gcaggcggac aggcagagct     1980
gcccagtggc cgaggcgcgg                                                  2000

<210> SEQ ID NO 103
<211> LENGTH: 1100
<212> TYPE: DNA
<213> ORGANISM: Homo sapiens

<400> SEQUENCE: 103
atttgtcgtt gtgccattgc tgccactgtt gttcttgtcc agggaaacac cggtggccaa       60
cccagatcgg atacaatggt gcggctctgg actgagcctc caaccacatt agccatgggc      120
agcattgttg ctgccgctgc tgttatttta attatgattg tacgttaacc accaccttcc      180
ttcctctgcc tcccttcagc tgcaatgatg tatgttactt tttggtaact ggatttcatt      240
aacatttatg aactctcata agtagtagaa aaaagcaatt tgtgtggaag aattttccac      300
ctcattaaac agtgttcttt tggggggtcaa gctgatattt ttttgttgt tagatttttt      360 ttataggtcc tttgtccttc cctaagccct gggggatgaa aggagagccg tccacccagc      420
gaggggcttg tgtgccctag agggcgctgg gccccgcgcg ctttcctggc tgtccccgcc      480
ggctttccac cctcccaaaa gcccaggtgc ccaccgtggg tcgctgcggc ctttcccctt      540
cttggccaaa tccgattact tcgcagcctg cagatggcat cgccggctaa gggcagcctg      600
cggcaggtcc ccgagcctga gcactcctcc tatctggggc ctgagaggac gctctgggct      660
ttttcccagg cccagggtgc gcggcctgct agcgcctttc gaggcacagt cccaagatag      720
gctcttgtcc ttcgacgccc ccttggcaca agcgcactgg cgcctccgc tcaacccacc       780 ttgcctttgg ggcgggcttc aaccctggga agacaggcct gggggaagcg agaggagagg      840
```

```
cccgaataga ggttccggct caatctttcc cagacggagg cctggtgttt ccagctcagt      900
tgcatcttcc agccgcgggc tcctggccca aacagaatgt gtttgctttc acaccgggac      960
ggcaagcgga gtccgcctca gtgagcagcg agctgcgcag tccggacggg tgtcgccccc     1020
agagactcgc cagccgcccc cagacactcg ccagccgtcc ccatctctaa tccaccgtcc     1080
aggcccgggc cctgggaaga                                                 1100
```

<210> SEQ ID NO 104
<211> LENGTH: 800
<212> TYPE: DNA
<213> ORGANISM: Homo sapiens

<400> SEQUENCE: 104

```
ccgtgtctcc cttaagaact ggggcctcat ctccactcca gctgcgcgtg cacgtgtgct       60
cccggcagga cgcgcgccca ggagcgcgct ggggctgcc ccgcccctct ctccctcccc      120
cgcgggtaaa ctccgggcat ccatcagtct gttaattgca ctaattagag atcgcagagg      180
tgttaattgg aaaaccctgg tattgtgcct gtttggggga agaaacgtc aataaaaatt       240 aattgatgag ttggcagggc gggcggtgcg ggttcgcggc gaggcgcagg gtgtcatggc      300
aaatgttacg gctcagatta agcgattgtt aattaaaaag cgacggtaat taatactcgc      360
tacgccatat gggcccgtga aaaggcacaa aaggtttctc cgcatgtggg gttcccttc      420 tcttttctcc ttccacaaaa gcaccccagc ccgtgggtcc ccccttggc cccaaggtag      480 gtggaactcg tcacttccgg ccagggaggg gatgggggcgg tctccggcga gttccaaggg    540
cgtccctcgt tgcgcactcg cccgcccagg ttctttgaag agccaggagc ctccggggaa     600
gtgggagccc ccagcggccc gcagactgcc tcagagcgga agaggcagcc gcggctttga     660
cccagcttcc ttccgacggc atctgcagga gcctctaggc ctgacatagg ctccgaggtg     720
ccctggctcc cccacgggga atgctgaggg ttgggccact aggtcctgcc taagtgcagg     780
acctgagcct cagacaaatc                                                  800
```

<210> SEQ ID NO 105
<211> LENGTH: 300
<212> TYPE: DNA
<213> ORGANISM: Homo sapiens

<400> SEQUENCE: 105

```
gggattgccg gctttgagaa aatatgaaga aaccgatttc tccttccact ttgccagtgc       60
actttccttc cactttcact ggtgctgggg gcggcgcact ctttacgaca tataagcgga      120
aaattctgca aaagtggccc ccggggatcc ccgcccgacc cctgtctgtc gctaatgtgg      180
gcctgtctcc ggaaattcga ggttgggcct ttgcctgaat ctgttgctat tgctcccctt      240
gctaccgctg acacttggca ccgccgcctc ctagcagcgg ccagacgcgg ggctggggc      300
```

<210> SEQ ID NO 106
<211> LENGTH: 400
<212> TYPE: DNA
<213> ORGANISM: Homo sapiens

<400> SEQUENCE: 106

```
gttgcgagcg cggcacaggt tgctggtagc ttctggactc tggaggcttg gccttccttc       60
taagccgatg gcggggaaag aacctcgttt ccacagcttc cccgacccc gccgcttgcc      120 atttggggac gggaagcgcg cccgggtcgc ttcacgtccc tctgggccgg agccctttcc     180
```

| | |
|---|---|
| atggctggct cctctggggg cccttgggcc tgtgagcagc gtctccttcc ctcagagaag | 240 |
| aatcctttcc ttcccccatc gaagtgtccc tttctgtatc ctgaaataac ccctcctggg | 300 |
| tgaggccagt tcccctctgt cgccctcctc ccgcaggcgt ccgggagcct cgtgaggacc | 360 |
| ccgtgcagtt gagtccaggc gacaggtgcc tccccaggtg | 400 |

<210> SEQ ID NO 107
<211> LENGTH: 800
<212> TYPE: DNA
<213> ORGANISM: Homo sapiens

<400> SEQUENCE: 107

| | |
|---|---|
| cagtgcgccc cttaccggag cacccatggc ctcccgcgtt accccaaatt ttgtaggcag | 60 |
| actgtcagag ttcgaagcca gctgtgtcct ctgcgggccg tgtgacccta ggctatctgg | 120 |
| gctgctcgga gccttagttt ccctagttgt gaagagggag ggtgtgacca tggcccggag | 180 |
| ctctccgaaa ggctgtgcgg attgctcggt ggcgggatgt ggagcgcgtc ttctatgatg | 240 |
| ccaggtgctg gccaagcgct cgatgcaggc tgctccagtt aggtcgatgc gatggcggga | 300 |
| agcactttcc tctgcaatgg agagacgccg acaccccgag cccgaaggct tgcaaggcgc | 360 |
| gctctcgcca ctggggtcgg ggatccgtgg gttctctatc ccgcttaccc actccatcct | 420 |
| tagcagctgt cgtcggtccc agacctctac cttggagaga ccaaggcggc ccagagccca | 480 |
| ggagactact cgcgcggtacg ccaggatcca gaagtggatt ctgacttcta aagacccctc | 540 |
| ccaagccaac gctatcaggg tccctgcaag cggttgactg tggcggaggc agaaccaaaa | 600 |
| cctttgctct gcccgcggcg ctccagcctc tcacccagga cagtgctctg ggctccagcc | 660 |
| gctgcagtgg ggtcgggaca cagacgccga gttagaagcc ccgccgctgc aggtccctgc | 720 |
| ttggtcggcg cggtgacggt gtcgctggcg gcggcggggg ccttcctttg gctgcccggc | 780 |
| catttaatca gagctattat | 800 |

<210> SEQ ID NO 108
<211> LENGTH: 1000
<212> TYPE: DNA
<213> ORGANISM: Homo sapiens

<400> SEQUENCE: 108

| | |
|---|---|
| tttagtattt aaggagaaaa gcctcatttt ccagaatcga ataagcgaat taatcgcaca | 60 |
| attgtgtaga atggaactca gtctgtaaaa aatcaagacc aacgtacttt ttaatattct | 120 |
| aacatctcca agtagtagtt acaagtattg tacccatgaa gtccaggtaa ttaatttgtt | 180 |
| caatgtcaca ctgttaaaag tcaggtgggc tccaaagcac agtcctaacc agcatgctct | 240 |
| actgcctcct ctgaggcaac agccgaagtg cagaccactg ggaataaata gctgcccggt | 300 |
| cttccccact cctaaattct cccgacagac cccaaagcct ctctgagagc ctctctgacc | 360 |
| gccctgcggc ccaccccgag ttccggcat cctctgggat ccctcttcct ggagccaaaa | 420 |
| cctacgcagg ctccttttcct ccgagctggt tgctaggtga tctccgaagg ctgtccgaag | 480 |
| tctcgcgagg gcggacccgt tgcctgatga cgagagttgg gagtgtggct ggggctgcgg | 540 |
| atctccagca gtggcgttac ttctagcggc tggataccgg gttctccgcg agatcgcgag | 600 |
| atcccgagat attctccccg cacggaagcg acgactggcc tggccagagg actcgcgtgg | 660 |
| gagcgaggtg ccggccccga caggacggtg aggtatgcag aagtaaggcg gggcgccccc | 720 |
| tgcgggaagc gagcgcgccc cggaaaatga gcgcctcccc acaccaaggt gtccaggagt | 780 |
| gagtgcggga aggaactcgg ccgccggag ttgtggcctc atcgtgcttc ccgccaaaaa | 840 | cgccttggta ctgtcgggac gcggctaagc gtggacgcgc ccgcatctgc ccctcctccg    900 cagtggtgga agacacccgc ggagcgccgg tggataaggg ccgttcctg agaccagagc    960 tgtatccgca gcaggtcagc acttcgtgcg ccctgtgtgc    1000

<210> SEQ ID NO 109
<211> LENGTH: 300
<212> TYPE: DNA
<213> ORGANISM: Homo sapiens

<400> SEQUENCE: 109
agcggcgctg ttcccgggct gggtgcagct gctaaggaca aggcccctgc tccgaagaac    60
gcggtggctc ggggataccc tgaaagggac ggccatggcg cacatgggat gccctagggt   120
tcgtgggagg gcatgcaggc gcagcccccg caggggttgg cctgccagag aaggcagggg   180
agagcactcg gggctgcaca atggtgtgg ccggagggaa ggtgcagcct tgtgtgtgtc    240
tggatgaggg ctgggcatag gagcttggta tttgatcctg aaagctctgc gtttccaaag   300

<210> SEQ ID NO 110
<211> LENGTH: 600
<212> TYPE: DNA
<213> ORGANISM: Homo sapiens

<400> SEQUENCE: 110
gagtcatact tgtagtcaca tccttttcct ttctccaacc cactggttaa tcatgaaagg    60
ctcttctgat tggctgcctc ctggcagtag tgcctcagcg cgacggttcg ggagcaaata   120
aataattccc gctgggaagc tgtttctcag acaggagcag cgacacccct gccacgcctg   180
ccgcctggag ttgagtgggg taagcacgcc ggcctccagg aatcgacggt gccacgtggt   240
tcttcttgca cttctcttct tctccagttt caggggacac cgtggggtgt gcgagcccgg   300
gggagcgcag ggaagggcgg gttgggctgc aggtgggaat gtgcggtcct tctgcgccct   360
caacagagct tccttccttt tgccaaggt ccccgtgccg ccttcagcgc gcctccttat    420
gcacctctac ctctgctgca gcgtacctct tccgcagccc tagcggcctc cccgagggc    480 gccgcggcct cggctgtccc tcccctgcct ggcacgacca cctgacccc agcgacccaa    540 gaagcaagtt gtgtttgcag acgcaaaggg gctgtcgttg gtatcggtgc actggtttga    600

<210> SEQ ID NO 111
<211> LENGTH: 1700
<212> TYPE: DNA
<213> ORGANISM: Homo sapiens

<400> SEQUENCE: 111
acactttctg tgtgggaggg cacaagacat gggctatgac atggccagag accccacctt    60
ctttacacat gtaaaaacca accaaatcaa gatgcgtcaa cggtgattct tcctcccaca   120
ttgtttccct ttttaaactg ttatttttc aatccatgga gcagttgaga acgggtatg    180 catctctcct cccctcccct tctatcaaag cctgtaagac acataaggaa atccaaagcc   240
acagtaatag agagagagag agagagagag agagagagag agagaaaaca   300
gaacaaaaga atcctccttt ggcttgtttt tccagggtgg ccaggcaagg tgtgaaaatc   360
catatttccc tctgggctgg caggtagaag ttactgggaa ggctgcgctc ccttctctcc   420
caccggctct cacatccagg ctgttccctc accctcagcc tccccagcg ccagcttcct    480 cctccgcctc tctgcagcca ggcctcccct gcaaggcgga ccttggccca ccttggttcc   540

```
gggccaaggc ggcgggaaag gcaccgctac ctgcagccgc acgactccac caccatgtcc    600
tcgtactgct tgtagaccac attattgccc gcgtcgatgt atagaatgct gatgggagtc    660
aatttggtgg gcacgcagca gctgggcggg gtggagccgg ggtccatgga gttcatcagc    720
gtctggatga tggcgtggtt ggtgggctcc aggtgcgagc gcagcgggaa gtcgcataca    780
ccctcgcagt gataggcctc gtactccagg ggcgcgataa tccagtcgtc ccagcccagc    840
tccttgaagt tcacgtgcag gggcttcttg ctgcagcgta gcctggactt cttgccgtgc    900
cgcttgccat ggcgactggc gaaggccgtg cgccgccgcc ggcggccggg cgagggcagc    960
caaggcctgg catccggggc gcccgacggg ggcggccacg accccctcgg ccccgcgccc   1020
gggcccgcag cctcggccga gcccagctgc tcgcgcatct ctgcgaacag gttcttgcgc   1080
tgggatctgg tgaataccac cagcagggcc cgctcctggg gaggccgcac cctccggccg   1140
aagcccagac tccgcaggtc cggggcggc ggttgctggg gtccccgcgc gcgcgcctcg   1200
gcctccccgg cgtccagctc gccccatgcg gcccgcagct ccaagcacag ctgcttccag   1260
ggctggtggc gcaggccctg ccacacgtcg aagacttccc agccggccgg cggcgccccc   1320
tgcgggtcca gggtccgcgc gtccagcagt aggggcgaaa ggcaagggaa gagctgcacg   1380
tggagcggcc cggctggtgg cccccagggc gctgagggcg cctggcgaaa gagccgcagc   1440
tccgcgccca ccagctcttc tttgtctgag agcatggaca catcaaacaa atacttctgt   1500
ctccggagag gagtgtgcga gagatcgtct gcgagataaa aataattac agtcagtttc   1560 acttaagggg gagatcagcc cggtgctctt cggccgcccc gggaggaaaa gggcggggag   1620
tgggggcagg tcggccgggc agtccagctt gcccggccca gggcctgacc accccggctc   1680
cccatctggc tggtgcatgg                                               1700

<210> SEQ ID NO 112
<211> LENGTH: 2000
<212> TYPE: DNA
<213> ORGANISM: Homo sapiens

<400> SEQUENCE: 112
gcccgctgtg aatgtaggtg aggtgatccc gggaacctgg gtctgaaatc agacctgtgt     60
tgccattggg agcacggaga gaggggaagc gccctgctta ggcccaggcc gggcgtcctg    120
gtggtgggac cgcagccgca ctcacctcca ggccaacgga caaggttcct gcaagccagc    180
agggccactc tgtgcttggc ctactgcagc tcccctgcag ctcctttcct ctccctcccc    240
ggagcgctct cctctctcct ctcccctctc ttctctctcc tctctcgtct cctggggcat    300
cccgggtgga gggatgtagg ggtcgctcct cggtgccagg ccgggaagca gctcaggcct    360
cccaagagct tggcgctcag tctgggaaaa ggggttcctc tggcctcagg acgttctcc    420 gccccacccc caccccctgg gagcctgaac catctggaag ggatcttagt cggggggttgg    480 gaggagagcc cgtggatagg aggagggggc gattctaggc cgaatccagc ccctgaggtg    540
tcactttcct ttcctgcggc ccgtcaccgc tgatagatgg ggctgagggc agaggaagga    600 aaagaaaac ctccgaggtc agtgcggggc gaggtgagcc cctcccaggg ccctctggcc    660
caggaggatg aagcgcgccg gcttcgctct tgcacgccgg cttgccatcc gggtaagcgc    720
gggaaaggcg gccacagggc gcggcggcag cgcagcgcgt gggatctcac gacccatccg    780
ttaacccacc gttccaggga gctccgaggc gcagcggcga cagaggttcg ccccggcctg    840
ctagcattgg cattgcggtt gactgagctt cgcctaacag gcttgggag ggtgggctgg    900 gctgggctgg gctgggctgg gtgctgcccg gctgtccgcc tttcgttttc ctgggaccga    960
```

```
ggagtcttcc gctccgtatc tgcctagagt ctgaatccga ctttcttcc tttgggcacg      1020 cgctcgccag tggagcactt cttgttctgg ccccgggctg atctgcacgc ggacttgagc      1080
aggtgccaag gtgccacgca gtcccctcac ggctttcggg gggtcttgga gtcgggtggg      1140
gagggagact taggtgtggt aacctgcgca ggtgccaaag gcagaagga gcagccttgg       1200 attatagtca cggtctctcc ctctcttccc tgccattttt agggctttct ctacgtgctg      1260
ttgtctcact gggttttgt cggagcccca cgccctccgg cctctgattc ctggaagaaa       1320
gggttggtcc cctcagcacc cccagcatcc cggaaaatgg ggagcaaggc tctgccagcg      1380
cccatcccgc tccacccgtc gctgcagctc accaattact ccttcctgca ggccgtgaac      1440
accttcccgg ccacggtgga ccacctgcag ggcctgtacg gtctcagcgc ggtacagacc      1500
atgcacatga accactggac gctggggtat cccaatgtgc acgagatcac ccgctccacc      1560
atcacggaga tggcggcggc gcagggcctc gtggacgcgc gcttcccctt ccggccctg       1620 cctttacca cccacctatt ccaccccaag caggggggcca ttgcccacgt cctcccagcc      1680
ctgcacaagg accggccccg ttttgacttt gccaatttgg cggtggctgc cacgcaagag      1740
gatccgccta agatgggaga cctgagcaag ctgagcccag gactgggtag ccccatctcg      1800
ggcctcagta aattgactcc ggacagaaag ccctctcgag gaaggttgcc ctccaaaacg      1860 aaaaagagt ttatctgcaa gttttgcggc agacacttta ccaaatccta caatttgctc       1920
atccatgaga ggacccacac ggacgagagg ccgtacacgt gtgacatctg ccacaaggcc      1980
ttccggaggc aagatcacct                                                  2000

<210> SEQ ID NO 113
<211> LENGTH: 2000
<212> TYPE: DNA
<213> ORGANISM: Homo sapiens

<400> SEQUENCE: 113
cactcccccg ccgcctccgc ccctaaccct cggccccgtg cgcgagcgag cgagggagcg        60
aacgcagcgc aacaaaacaa actagtgccg gcttcctgtt gtgcaactcg ctcctgagtg       120 agtcggggc cgaaagggtg ctgcggctgg gaagcccggg cgccggggac ctgcgcgcgc       180
tgcccggcct ggccggagcc tgtagcccgg gggcgccacg gccgggctcg cagtccccc       240 acgccggccc cccggtcccc gccgagccag tgtcctcacc ctgtggtttc cttcgcttc       300 tcgcctccca aacacctcca gcaagtcgga gggcgcgaac gcggagccag aaacccttcc      360
ccaaagtttc tcccgccagg tacctaattg aatcatccat aggatgacaa atcagccagg      420
gccaagattt ccagacactt gagtgacttc ccggtccccg aggtgacttg tcagctccag      480
tgagtaactt ggaactgtcg ctcggggcaa ggtgtgtgtc taggagagag ccggcggctc      540
actcacgctt tccagagagc gacccggggcc gacttcaaaa tacacacagg gtcatttata      600
gggactggag ccgcgcgcag acaacgtctc ccgagactga acattttccc aaacagtgct      660
gacattttgt cgggccccat aaaaaatgta aacgcgaggt gacgaacccg gcggggaggg     720
ttcgtgtctg gctgtgtctg cgtcctggcg gcgtgggagg ttatagttcc agacctggcg      780
gctgcggatc gccgggccgg tacccgcgag gagtgtaggg accctcagcc cgaccacctc      840
ccgcaatcat ggggacaccg gcttggatga gacacaggcg tggaaaacag ccttcgtgaa      900
actccacaaa cacgtggaac ttgaaaagac aactacagcc ccgcgtgtgc gcgagagacc      960
tcacgtcacc ccatcagttc ccacttcgcc aaagtttccc ttcagtgggg actccagagt     1020
```

```
ggtgcgcccc atgcccgtgc gtcctgtaac gtgccctgat tgtgtacccc tctgcccgct    1080
ctacttgaaa tgaaaacaca aaaactgttc cgaattagcg caactttaaa gccccgttat    1140
ctgtcttcta cactgggcgc tcttaggcca ctgacagaaa catggtttga accctaattg    1200
ttgctatcag tctcagtcag cgcaggtctc tcagtgacct gtgacgccgg gagttgaggt    1260
gcgcgtatcc ttaaacccgc gcgaacgcca ccggctcagc gtagaaaact atttgtaatc    1320
cctagtttgc gtctctgagc tttaactccc ccacactctc aagcgcccgg tttctcctcg    1380
tctctcgcct gcgagcaaag ttcctatggc atccacttac caggtaaccg ggatttccac    1440
aacaaagccc ggcgtgcggg tcccttcccc cggccggcca gcgcgagtga cagcgggcgg    1500
ccggcgctgg cgaggagtaa cttggggctc cagcccttca gagcgctccg cgggctgtgc    1560
ctccttcgga aatgaaaacc cccatccaaa cgggggacg gagcgcggaa acccggccca    1620
agtgccgtgt gtgcgcgcgc gtctgcgagg gcagcggcgg caggggagg aggaggcaga    1680 ggcggggtgg ctggaccctc ggcatcagct cattctcccc tgctacacac atacacacac    1740
aaataatgtt tctaaaaagt tcagttgcga ctttgtgcct cgcctgtcct gttcatcctc    1800
gtcctgggcc ggggaatgct tctgggggcc gaccccggga tgctggctaa ttgctgccgg    1860
cgggttccgt cgccggtgtg accctggacg gcgcggacgc cgtacagggg gtcccgggag    1920
gggcagtggc cgcggcactc gccgccggtg cccgtgcgcg ccgcgctctg ggctgcccgg    1980
gcggcgcagt gtggacgcgg                                                2000

<210> SEQ ID NO 114
<211> LENGTH: 800
<212> TYPE: DNA
<213> ORGANISM: Homo sapiens

<400> SEQUENCE: 114
ctgaaaagcc gtcagggaaa ccacacatgt tcaaccctg gcggctcccc caaacctctc      60
atttccagta actgtgtgtt tccgctcgtc aacagctgaa accgagcgga acttgggggg    120
ccccaccacg cggccctgct gtgcggcacg gggctcatct gtccccggc tgcggggagt     180 cagctctcac cgcccacctc cttcccagat agtctctgtg cccactcgac ggcccggcaa    240
gcccagcccc tgcctgccac ggccacagca gcctcagaga gctgccctct ctggccaggg    300
tcagggcctg agctgctgcc tcccgcaggg tcgagggcag gacacttgtc tgaggcttgg    360
gtggggcaat ggcacctcct cagggcctca gccccgggc aggctcggtg accatgggcc     420
tacagcaggg aaaattctgg gccaaaagct ccagcctcct actagggcat ctgtctgcaa    480
atgcacctta acctgaccgc ttgggctgtg ggggagcctg tttcagggaa agtgagggac    540
gcgccagttt cctcctttgg acttgatgag gcacgaacgc atctctaata aagccaggtc    600
tccccgccgt ggctccctgg gcgggtgcct gtggctcggg ccatgagtca cgctgggtaa    660
ccccactacg gggaagaggg caggaagctg ggagccaccg cctctgtgcc cggttgtcat    720
ctcggcacga gggcgaccgt cggcttcgtc ctgccctcat ggctgagggc ttttgggatg    780
tggcgggaga cgggggagtc                                                 800

<210> SEQ ID NO 115
<211> LENGTH: 500
<212> TYPE: DNA
<213> ORGANISM: Homo sapiens

<400> SEQUENCE: 115
aaatcatcag aatggctaaa atgaaaaaga cagacaacag caagtgctga caagggtgtg     60
```

```
gggcggccaa atgctcctgc actgctggca ggggacctga gaactgcagg gcattccctg    120
gcttcctgcc cctcctggga ctggggaccc cccagggaca gcctaaggga actgcattta    180
tcttcacgtc tgccaaaaga taacacgaag atgttcaaag ctaagccccc aggctggtaa    240
gagctccaag gcaccagcag tgtgtgcaga actgggggga gtctgttctc ccagggatgc    300
tcccatcacc tgctgccagc agtggggcat gccggtcccc tggggtgtgg ccaagggct    360 gtgtctcctg cccgggctgc cggcccctct caggttcact ttcccatctc taagcccacg    420
tctcgctgca gttcaagttt gccaggccac caacgggtga cacgcccggc gcagtggggg    480
actccgcact ttctgcgcac                                                500
```

<210> SEQ ID NO 116
<211> LENGTH: 1200
<212> TYPE: DNA
<213> ORGANISM: Homo sapiens

<400> SEQUENCE: 116

```
acccttgtg cctgggtccc ataaacaatg tgctttttaa aggggagccc cctcccagct     60
ccggcctttt tctccagcgt gggcagccaa tcagctgcgc agagctgcat agctggaccg    120
ctttccattc tgagtagcaa caacgtacta atttgatgca cacatggatg cctcgcgcac    180
tctgcaaatt catcacccgc atcttgcatt agtcatctga cggactgcca agtgtttcat    240
tttctttcca tgtgacttta ttattaccac ctctctcctc tcttccaaaa acctcccaaa    300
aagggcggtg gggcggggg cggggcaggg agagggagag aaatccagca gacatctagc    360
tctgcctttc tttcccagcc acagccaggg tagggctgat aaggcgctga tgcgttgatg    420
gcagccttgc agagctagac ctgcacttaa cttgcagctg cctcccgagc ctccaagatg    480
tccacgccct gggtgacagg cggcagggcg ctgcccgtg ctccccggc tctgctcgac    540 agcagcacgc agtgagagcc tcgcgccgc cgaggagcaa ctcatggtgc ctccgctttg    600
ttttagttca tcaaatttct acgactcatt aggcactttg ccactgctct tcttcctcct    660
ccttccgcct cccgctccc ccaccccac tatttttct tcctgtccct catcgtgccg    720
ccctaactct ggctcccggt tccgttttg acagtaacgg cacagccaac aagatgaacg    780
gagctttgga tcactcagac caaccagacc cagatgccat taagatgttt gtcggacaga    840
tcccccggtc atggtcggaa aaggagctga agaactttt tgagccttac ggagccgtct    900
accagatcaa cgtcctccgg gaccggagtc agaaccctcc gcagagtaaa ggtacagagc    960
gcggggcggg ggtcgccagg cgtccaggtg ggcgtcgcgg ggcactgggg ctgtccgagc   1020
ccccagcctg caggaggaag ggcgggtagg caggagggct ggaagcagcc ggtgctggcg   1080
gcccctgtgc tccaggggct gctcccgact cctccccgca ccccgcccg cctgcccgcc   1140 gggacaggtt ggaggcggga gagagggacc gaggcagggc gggagcgcag aggctcggtc   1200
```

<210> SEQ ID NO 117
<211> LENGTH: 800
<212> TYPE: DNA
<213> ORGANISM: Homo sapiens

<400> SEQUENCE: 117

```
taacaaataa gccgcccgtg gtccgcgctg tgggtgaccc ttggcgcctt cgaggtctgg     60
agccctaggg taaataagga aacgggggcgc ctctagagtt ttaaatgaac tctgttattg    120
gaagcttcag tagggaccct gaaaacaatt aacgtcttaa ttagcatttt aatgtctcca    180
```

| | |
|---|---|
| ttattacggc gcgggctcta gctcagccct ttaccttacc ttctcaccgt taacagggga | 240 |
| gggggattgt attttagtt catcttttta tgttttgag ttgttatcct gtctgtctga | 300 |
| ttccagcctc gagggtttga tgatgcggcc cgagcctggc tgtggtcgcc tgtcggggct | 360 |
| ggagcgggac cctcagccgg gccgggcctg ggggctaacg ttttcacagt gcgccctgag | 420 |
| tttccttggg ttactgctgg gaccgcgcag gaggaagcaa agagtttttc gagctagacc | 480 |
| aacaggaaac acattgacgg aaatgttgcc atagcccatg gggtggcttt aactggccgc | 540 |
| ccccgcgggc tgggtgtgaa atcagaggag gccgcggctc ccccggccag gattggaggc | 600 |
| tcctcgcgca acctaatgcg ggtgtccggg cccgagcgct tcccgcgcag ccaggccttg | 660 |
| tcggtgcagc agccccgctc ctccccaaca cgcacacacc cggtgttcgc aagtgcggct | 720 |
| caccaaggga gatccaaggg ggcaaaaagt tatgtataaa tccgagagcc actggggaaa | 780 |
| gagggtcgtg gtattgtaag | 800 |

<210> SEQ ID NO 118
<211> LENGTH: 500
<212> TYPE: DNA
<213> ORGANISM: Homo sapiens

<400> SEQUENCE: 118

| | |
|---|---|
| ctaccctgtg ctatcctgag ctgtagtctt ctgaaatgat cgtttggctt cccagccaag | 60 |
| gcagggctcc cccaaagttc attcccactc ttgcagtttc acctcgggat gcttccgcag | 120 |
| aatttcagcg cctaagcaga caaggtcaaa gtaaaccgct tcaccgctgc ttctggcgca | 180 |
| ggggcccaga gcgcgtgcag ctccccagca cagaccaaca gcaggagagg ggtccgggcg | 240 |
| ggagccctgg gctgtagata agcaaaacgc acccattttc tctcctattt actccagagg | 300 |
| cacctctcct cccccactcc tggcatctct ttatcactgg ctccctctcc ctgtggcata | 360 |
| tttttgggta gtagaatgct gaggtcacag ggagcggctc tttatccaag cagtggggac | 420 |
| atcagcctgg agcctgagc atgaaccagc aagatgcaga ctctcgctct tgactttggg | 480 |
| ctccaggagc tgccccgacc | 500 |

<210> SEQ ID NO 119
<211> LENGTH: 1100
<212> TYPE: DNA
<213> ORGANISM: Homo sapiens

<400> SEQUENCE: 119

| | |
|---|---|
| cagtgctccg ctccgggaaa ttgcatcgtc acgacaaacg ggaccgtgat aaaacgaccc | 60 |
| tttccgtcct tatttgtaga tcactcagac gagattgaac tgcacttgtt tccccttcga | 120 |
| ggggagccgc gttttcaggg tagccgaagg cttggggctg agggggggcc ctcaccaagg | 180 |
| cgcgggtggg ggccggagcc tcaactcgat gagaagtgac aggcgtttgg gggatctggg | 240 |
| ctccggccgg gaccagcgca agcagggact ttgcggggac accgcttctc caacagagca | 300 |
| aggcctggcc cacgtttccg gtttctccta acttccttt attgccttcc tttgcttcgc | 360 |
| aagttccatc taccctcca gctacagagc cccacctcta ggcacaggaa gcttcccgga | 420 |
| aaaagaaagg ctgtcccaga aagagaccga gagagacttt ccaaacttcg ggcatagcca | 480 |
| cggcaattcc cagtctgcta atgccaaggc gggcgcgtaa ggccgcctaa atctagacct | 540 |
| ccctcctcac tcatttcaaa aaataacaac gtgccagcca cctccgcaga taccgccggc | 600 |
| tggtgcttgc ccaggagacg ccagggccag agcgccactc ccagcatcga aatgcagag | 660 |
| agaaagcgca gctccaaatt ccccttcaga ggttaagcct caatcattgt gtcccttccc | 720 |

```
tagggactgc tggcgctctc gcccactggc gatgattatg cgcctagaac tcgaccgcga    780
agcaactaat aggaaaacat atggtgtcaa tttggatgct ccgcgcctcg cgcacacccg    840
ggaacgagcg gcacaaagcc ctgccggccg gcccgcgacc ccgcgcccct cggggcctgc    900
cagccgggcc gcagcgacaa acgctcaggg ctgcgcgccc tggctggggc cgcccgaga     960 gacagcctgc ggctggggag tctgagctcc aaggggagag cccagccgcc gaaggcgagc   1020
ctaccggcca agccctgggg tccggcaggt tctgcacaac tactcccgca aagctcgcca   1080
cctttgtgcc ctttcctcag                                                1100
```

<210> SEQ ID NO 120
<211> LENGTH: 500
<212> TYPE: DNA
<213> ORGANISM: Homo sapiens

<400> SEQUENCE: 120

```
gggccctcgc ggctcaagcg ccagcgctgg agagagagtc tgagggtacc acgggcgtgc     60
tggcctgggt gctcactccc gccctccttc atgagcggct ttcctctggg tgtgtccagg    120
gcatcacaga gctcttctgc ccaaacccgg aggcctacca gggcctgccc accttgcctc    180
cttccacact ctctgtagca gcagccgcag ccatggcggg gatgaagaca gcctccgggg    240
actacatcga ctcgtcatgg gagctgcggg tgtttgtggg agaggaggac ccagaggccg    300
agtcggtcac cctgcgggtc actggggagt cgcacatcgg cggggtgctc ctgaagattg    360
tggagcagat cagtgagtgt ccgctgcccg cttgctgaac tcggcaccat gggcggccgc    420
cacgggtgtc tctgggcact tccgggccat ccctgctgct cagctcccga taatggtgtc    480
acggtgactc aggcattagc                                                500
```

<210> SEQ ID NO 121
<211> LENGTH: 600
<212> TYPE: DNA
<213> ORGANISM: Homo sapiens

<400> SEQUENCE: 121

```
tgtttacgga atcgggatcg aggggccgat aagtagttta cacgccggcc agagcagagg     60
gctggaggtc ggagttgggg gctggaggaa cgggtggcgt ttttaggatt cagtaacagg    120
atcacagctt tttcttgtgg tggaagctat tggaatttgg ggagggtagc acgagggtc     180 ctgcagctcc gcgtgtgaaa aagcgtttag gtaggcgatg aaagtagttg atctgagcca    240
tggcaggcga gccccgaatt tttgctgctt cccctgaaa gtgtttcttt aggaggagag     300
gacttgggcc acacaggacc cggtcctaag agagcgattc cgggaagcgg acagatcgaa    360
gagaccttct gggcgaagcg gcagggcagc ctcgcggggc tgggagtgga tctgaggtcc    420
cgacccaggc ggctcggagt gctccaggag ccacctgggt ctgcgggcgc agcgcggcgg    480
ggcgggagcg gtggcccgca ggggccgcgg cctgcgatga aggccggggg gcagcgctag    540
cagcgaggtg ccacagtggg ccgaggagtc tgggctgtgg cccagggtag gaccggctca    600
```

<210> SEQ ID NO 122
<211> LENGTH: 150
<212> TYPE: DNA
<213> ORGANISM: Homo sapiens

<400> SEQUENCE: 122

```
acctaaacca agctctccct ccctgccgtc tccttccctg gcctgggtct gaaggagagg     60
```

| aggtgcccag aagttcagag cggcataacc acagagatac tacctaatta acataccaga | 120 |
| agcataaaga actcatttgc attggagagt | 150 |

<210> SEQ ID NO 123
<211> LENGTH: 900
<212> TYPE: DNA
<213> ORGANISM: Homo sapiens

<400> SEQUENCE: 123

| ataactacgg gggtgggggt ggggaaggaa gagatccaag gaggcagaag gctgcggtca | 60 |
| aaatattttg gggtggcaga gtcacgtagg atgtggctgt gggttctggc agcccagaga | 120 |
| ttcagctccc gcctcctccc tcagagcgag tccatagcta ccctcacgtc ccccgtggcg | 180 |
| gtcctcgcca cgctccggag cgggttaccc atgagggtgc tagacctggg cagcgggaac | 240 |
| ctcgaagagg tggagattgc aggctgggac tccagatttc gggcagggat gcggggaagg | 300 |
| gaagacgcct cgctggaggc ggaatggagg gcaaggcgaa ggaggatggt gcaggaaacg | 360 |
| gcgacaaggc gcccggccag gcccgcgagc taccgagacc cgggttccaa tcctcccccc | 420 |
| ttccgcaaac gcccgggttc gaggtacctg gcgggcaagg gccgcagcgg agcgaagcgg | 480 |
| gctggccatg gggaggctgc ggggacgcgg ggctgcagag agcggcagtg gcacggagcg | 540 |
| cgcggctgga agcgaaagca ggcggtgtgg ccaagccccg gcgcacggcc catagggcgc | 600 |
| tgggtaccac gacctgggc cgcgcgccag ggccaggcgc agggtacgac gcaacccctc | 660 |
| cagcatccct tggggaggag cctccaaccg tctcgtccca gtctgtctgc agtcgctaaa | 720 |
| accgaagcgg ttgtccctgt caccggggtc gcttgcggag gcccgagaat gcgcgccacg | 780 |
| aacgagcgcc tttccaagcg cagatatttc gcgagcatcc ttgtttatta acaacctct | 840 |
| aggtgaatgg ccgggaagcg cccctcggtc aaggctaagg aaacctcgga gaaactacat | 900 |

<210> SEQ ID NO 124
<211> LENGTH: 600
<212> TYPE: DNA
<213> ORGANISM: Homo sapiens

<400> SEQUENCE: 124

| cagtccagcc gcttgcctca cttcttcccg cttgccttat ctccccgcag acgtggttcc | 60 |
| cctgcagccc gaggtgagca gctaccggcg cgggcgcaag aaacgcgtgc cctacactaa | 120 |
| ggtgcagctg aaggagctag agaaggaata cgcggctagc aagttcatca ccaaagagaa | 180 |
| gcgccggcgc atcccgcca ccacgaacct ctctgagcgc caggtaacca tctggttcca | 240 |
| gaaccggcgg gtcaaagaga agaaggtggt cagcaaatcg aaagcgcctc atctccactc | 300 |
| cacctgacca cccacccgct gcttgcccca tctatttatg tctccgcttt gtaccataac | 360 |
| cgaacccacg gaaagacgct gcgcgggtgc agaagagtat ttaatgttaa ggaaagagaa | 420 |
| gaaccgcgcc gccggaggc agagaggctc catggccgtg ctgctgggcc atccccaact | 480 |
| ccctatccca tccccagcct ccaccccat ccagatggga ctcacgtggc ttcaacagct | 540 |
| ttggaaatgg gtcccgagtg ggccgtgcga ggaaggctgt cgacctctac tcctccttgc | 600 |

<210> SEQ ID NO 125
<211> LENGTH: 1500
<212> TYPE: DNA
<213> ORGANISM: Homo sapiens

<400> SEQUENCE: 125

| caagatcgac tttcttagga agggggagag gagggaactc ttcacgaagg gaggtgggag | 60 |

```
tccacctcag acctctattg gaaggaaatc gagttgttcc ggggactga ggtctcttgc    120 ataaggcatg ggatccttat tattattatt attatttta atcccccgc ggaggagctc    180 tgggcaaatg aataccgagg cgccgctcta gctggttagg cttgggatgc gataactcag    240
tgccctcttg cagacttgca tagaaataat tactgggttg tcgtggaggg gacacgagac    300
agagggagtt ctccgtaatg tgccttgcgg agagaaaggt ccaagaatgc aattcgtccc    360
agagtggccc ggcaggggcg gggtgcgagt ggtggtgga gtaggggtgg gagtggagag    420
aggtggtttc tgtagagaat aattattgta ccagggcccg ccgaggcacg aggcactcta    480 tttttgttttg taatcacgac gactattatt tttagtctga tcaatgggca caatttctaa    540
gcagcgcagt ggtggatgct cgcaaacttt tgcgcaccgc tggaaaccca ctaggttgag    600
ttgcaaaacg taccgcgtag acgccctgg tggcgccgag agaagagcta ggcctgccca    660
gcacagagcc ggagagcgtc gggccttccg gaagggtaag ttctccgcca aggggtcccg    720
agggagctgg acgtctgaat ctggacttgc ccccagcttc ggggttcgat tctgggtttt    780
gcgcgtcccc aaccccagg gctttccgaa gcatggcctg gctccaggcc cggtcctgta    840
aggactggaa cggcagcaaa atgtgcaggg aggcagtcgg ccggcagagc tgcggcggga    900
gccaaggtca ggcccgcggg gagagcgggc agcttccagc gccggccaca agctcccagg    960
ccagctgggc cgcagacccc tttgcttcca gagagcacaa cccgcgtcct ttctctcagc   1020
caggctgcag tggctgcccc gagcttcgct ttcgtttccc aagctgttaa taacgatatg   1080
tccccaaatc cgaggctcgt gtttgctccc agatgccaag aacgcaaccc gaaatccttc   1140
tcccaaaccc taggtcgacg agatgagttc ctacttgacc tctgagccga ggtgggccgg   1200
aaaccgaggc ctaggcccg ccggggctgc aaggaaaagg ggaaactccg agcgtagcgt   1260
cttttccttg tggttccttt ctccggcatc ccggactgcg ggccctgcag ccacctggac   1320
cggcattcaa aggattctgc aagtccagct tcacagactg gctttcccag acgctccgaa   1380
gcccgcacca cgaacagaat aaaggagaga cgagagatcg caactagatt tgagaatcct   1440 cgttctttc cccaatcgtt cgggcagtaa actccggagc cggctacagc gcgcatcctc   1500
```

<210> SEQ ID NO 126
<211> LENGTH: 500
<212> TYPE: DNA
<213> ORGANISM: Homo sapiens

<400> SEQUENCE: 126

```
actgtcctcc tccctcaatt gcctattttt tgcccatagc tctaacttaa ccctgtgatc     60
accccagatc gctacttctg accccatct cctctcccac accaacctcc agcgcgcgaa    120
gcagagaacg agaggaaagt ttgcgggtt cgaatcgaaa atgtcgacat cttgctaatg    180
gtctgcaaac ttccgccaat tatgactgac ctcccagact cggccccagg aggctcgtat    240
taggcaggga ggccgccgta attctgggat caaaagcggg aaggtgcgaa ctcctctttg    300
tctctgcgtg cccggcgcgc cccctcccg gtgggtgata aacccactct ggcgccggcc    360
atgcgctggg tgattaattt gcgaacaaac aaaagcggcc tggtggccac tgcattcggg    420
ttaaacattg gccagcgtgt tccgaaggct tgtgctgggc ctggcctcca ggagaaccca    480
cgaggccagc gctccccgga                                                500
```

<210> SEQ ID NO 127
<211> LENGTH: 900
<212> TYPE: DNA

<213> ORGANISM: Homo sapiens

<400> SEQUENCE: 127

| | | | | | |
|---|---|---|---|---|---|
| ctcagggaat | cacatgtccg | cctggcctgg | cctggtacca | aatgtttata | gacaggacga | 60 |
| gggtcgctgg | aatcgcctcg | ctcctttcag | cttggcgcta | aggcgcgaat | ctcgatcctc | 120 |
| ctagtatttc | tctggcgtct | gtctctatct | cagtctctgc | ttttgtctct | ttctccctcc | 180 |
| ctccgcccca | gtctttccgt | ctcttttttcc | tcgaatgcac | gtggaattcg | gaattgaaaa | 240 |
| ttgaggtcag | aatctccctt | tttcttccag | ttatccgcgc | cgctgcccca | cgcctagcgg | 300 |
| cttggatctg | catagacatc | tatctacccg | caacaagatc | cgagctgcag | aagcaaacct | 360 |
| aatctgtctc | cgcaccatcc | cctgctctgt | agacccactg | ccccatccca | cgccacatcc | 420 |
| ttgaggttca | gtagcgact | ccagcggatg | attcggagaa | tgccctgctt | ccaaaggcc | 480 |
| ccaacccgtg | ttttattttt | cttttccttt | tgcccgcttg | accaactttg | gtttctttca | 540 |
| gggcccggag | gtgcctgcgc | cgcgcttggc | tttgctttcc | gccgcccag | gagacccggg | 600 |
| actgtggttt | ccgctcgcca | catcccagcc | tggtgcgcac | acaagagcct | ggcgagcttc | 660 |
| cctcgcgcgc | ttacagtcaa | ctactttggg | cctcggtttc | cctgctcctt | gtagatcaga | 720 |
| gaagggacgg | gcgaaatgcc | tgcgaggag | ggttggcgaa | tgggttggtt | ggtggcaaga | 780 |
| ctgcagttct | tgtacatgga | cggggttgg | ggggtcaaca | ctggaagaac | tcctgcctga | 840 |
| cgccaagagc | cacccgcttt | ccagctcgtc | ccactccgcg | gatgtttacc | caccttcatg | 900 |

<210> SEQ ID NO 128
<211> LENGTH: 500
<212> TYPE: DNA
<213> ORGANISM: Homo sapiens

<400> SEQUENCE: 128

| | | | | | |
|---|---|---|---|---|---|
| tttggggcac | ccaacccttc | ccaagcctcg | gttttcccga | tcttgtggga | tccttgcggc | 60 |
| gcgaatgggg | ttgaagcac | cttggaagct | acagagtacc | gggtcgggac | aatttccggc | 120 |
| actgccccag | ttcagtggtt | tatagaaaat | ttctttctct | ctctcaggtc | cactaagacc | 180 |
| gagagagaga | gagaagtcga | ctctggcaca | cccgggcgag | gggctgccgg | gattcggag | 240 |
| ctggcgcggt | tgattttttc | cgagaatcct | ccacttgggg | tgacgtcggg | cagcgcgcgc | 300 |
| gggccgtgag | gttaatgccc | aggcttttct | ctaaagcgtc | cgggaatgat | ccggcgaata | 360 |
| aaacgggtgt | ctgcaaagtt | aatgaattgt | acaaggaggc | tgagggtggg | gacttcgacc | 420 |
| cggggagcca | gaggcggttc | tggtggacgc | ttccccgtgc | gcctagggt | gcgctgggct | 480 |
| ttcccagccg | aggtctgcag | | | | | 500 |

<210> SEQ ID NO 129
<211> LENGTH: 2000
<212> TYPE: DNA
<213> ORGANISM: Homo sapiens

<400> SEQUENCE: 129

| | | | | | |
|---|---|---|---|---|---|
| ccagacagtt | aaggtaaaac | gttgaagtca | agaggaagta | gtgagtctgt | tgccaactgg | 60 |
| atagggttgg | tcctgtccca | tctaaatgta | ttagaattaa | gtggctttta | aaaatgagct | 120 |
| ggtcatcttc | agcccacggg | ctggccaatt | tggaacttaa | tgggcctttg | cgtcctcctt | 180 |
| ccctgagcct | cctttttattc | cagacttctc | agtgtgagtc | tgtgcgtccc | tccgacgatc | 240 |
| tcagggagtg | gggtgccttc | atctgcctgt | tccctgttcc | tcaggctgac | gctcccgctg | 300 |
| tcctcccgc | ctcccctcac | tccttttctc | cctcccttcc | tccttgtggg | gaggctcttg | 360 |

| | |
|---|---:|
| gccagggtcc ctgagcccgg gcgggtgctg gcagaggacg cagaagggt gaggtcacgt | 420 |
| ctcccttgag ccccgagccg ctggcttttc agagcctcgc cacaagccgg cggccagagc | 480 |
| cccagaccac acagaccgtg cgctcctccg ccctcccggc gccgccggcc tcgcccatgt | 540 |
| ctcagtacgc ccctagcccg gacttcaaga gggctttgga cagcagtccc gaggccaaca | 600 |
| ctgaagatga caagaccgag gaggacgtgc ccatgcccaa gaactacctg tggctcacca | 660 |
| tcgtctcgtg tttttgccct gcgtacccca tcaacatcgt ggctttggtc ttttccatca | 720 |
| tggtgagtga atcacggcca gaggcagcct gggaggagag acccgggcgg ctttgagccc | 780 |
| ctgcagggga gtccgcgcgc tctctgcggc tcccttcctc acggcccggc ccgcgctagg | 840 |
| tgttctttgt cctcgcacct cctcctcacc tttctcgggc tctcagagct ctccccgcaa | 900 |
| tcatcagcac ctcctctgca ctcctcgtgg tactcagagc cctgatcaag cttccccag | 960 |
| gctagctttc ctcttctttc cagctcccag ggtgcgtttc ctctccaacc cggggaagtt | 1020 |
| cttccgtgga ctttgctgac tcctctgacc ttcctaggca cttgcccggg gcttctcaac | 1080 |
| cctctttct agagccccag tgcgcgccac cctagcgagc gcagtaagct catacccga | 1140 |
| gcatgcaggc tctacgttcc tttccctgcc gctccggggg ctcctgctct ccagcgccca | 1200 |
| ggactgtctc tatctcagcc tgtgctccct tctctctttg ctgcgcccaa gggcaccgct | 1260 |
| tccgccactc tccgggggt ccccaggcga ttcctgatgc cccctccttg atcccgtttc | 1320 |
| cgcgctttgg cacggcacgc tctgtccagg caacagtttc ctctcgcttc ttcctacacc | 1380 |
| caacttcctc tccttgcctc cctccggcgc cccctttta acgcgcccga ggctggctca | 1440 |
| cacccactac ctctttaggc ctttcttagg ctccccgtgt gcccccctca ccagcaaagt | 1500 |
| gggtgcgcct ctcttactct ttctacccag cgcgtcgtag ttcctccccg tttgctgcgc | 1560 |
| actggcccta acctctcttc tcttggtgtc ccccagagct cccaggcgcc cctccaccgc | 1620 |
| tctgtcctgc gcccggggct ctcccggaa tgaactaggg gattccacgc aacgtgcggc | 1680 |
| tccgcccgcc ctctgcgctc agacctcccg agctgcccgc ctctctagga gtggccgctg | 1740 |
| gggcctctag tccgcccttc cggagctcag ctccctagcc ctcttcaacc ctggtaggaa | 1800 |
| cacccgagcg aaccccacca ggagggcgac gagcgcctgc taggccctcg ccttattgac | 1860 |
| tgcagcagct ggcccggggg tggcggcggg gtgaggttcg taccggcact gtcccgggac | 1920 |
| aacccttgca gttgcgctcc ctcccccacc ggctcacctc gcctgcagct gggccacgga | 1980 |
| actccccggc cacagacgca | 2000 |

<210> SEQ ID NO 130
<211> LENGTH: 600
<212> TYPE: DNA
<213> ORGANISM: Homo sapiens

<400> SEQUENCE: 130

| | |
|---|---:|
| ctctctgggc cttaggaaaa tggaaatgac acctgtacct gcccttccag gactgacagg | 60 |
| aggggctgct ccatgaaacc tcactgctgc ggtcataatg tcattatctt ttgccttaaa | 120 |
| gggatttctt ctgcaccagc acctaaagtg gcagcccctt acccttggcc atcagctgga | 180 |
| ccctggtgct ctcctggagc ccaaaacctc tgttttgtgt tgcatcctgc tgaccagcca | 240 |
| cagtccacac ccatctgagt gtctgagcag aacagcccag aggccacacc aggatggctt | 300 |
| tccaccggtc accttccccc acccactcat aaaccctgcg tctctggggg agagggtggc | 360 |
| gaggtcccct ccccacatag atggaaacac tgaggcctga ttcatggtgc ccctgtgaa | 420 |

| | |
|---|---|
| gcgcctcatg gccagcaccg gggggcagca ggccagggcg gggacacata cccggttctc | 480 |
| gtcgtagatg atctgcacca ggctgcggtg cttcgactcg atgggcggcg gtgacacggg | 540 |
| cttctcaggc tcgggcggct tggcagcctc ctcctccagc tgttgctgtg gggagaggca | 600 |

```
<210> SEQ ID NO 131
<211> LENGTH: 400
<212> TYPE: DNA
<213> ORGANISM: Homo sapiens

<400> SEQUENCE: 131
```

| | |
|---|---|
| cttgaaaact cccagccccc tttgtccaga tggggatgga ggtggccagg ctgccccgtt | 60 |
| gattgtgtgc cgaggagccc tccccgggaa ggctgtgatt tatacgcgca ggcttgtcac | 120 |
| ggggtgaaag gaagggccac ttttcattt tgatccaatg ttaggtttga aagccaccca | 180 |
| ctgctgtaaa ctcagctgga tccgcgggcc gtgattaaac acattgcccg ctttgttgcc | 240 |
| gagatggtgt ttcggaaggc gctgtgaatg cacttccctt tgcggggctc acacagacaa | 300 |
| gatgtgtgtt gcaaggatga ggcgcctgct cggcctccag cccagggccg ggaagggaga | 360 |
| aggtgctgtg cgtcgctgcc tgtgtcgccc gcggctctcc | 400 |

```
<210> SEQ ID NO 132
<211> LENGTH: 1200
<212> TYPE: DNA
<213> ORGANISM: Homo sapiens

<400> SEQUENCE: 132
```

| | |
|---|---|
| cgcgtcaggg ccgagctctt cactggcctg ctccgcgctc ttcaatgcca gcgccaggcg | 60 |
| ctcaccctgc agagcgtccc gcctctcaaa gaggggtgtg acccgcgagt ttagatagga | 120 |
| ggttcctgcc gtggggaaca ccccgccgcc ctcggagctt tttctgtggc gcagcttctc | 180 |
| cgcccgagcc gcgcgcggag ctgccggggg ctccttagca cccgggcgcc ggggccctcg | 240 |
| cccttccgca gccttcactc cagccctctg ctcccgcacg ccatgaagtc gccgttctac | 300 |
| cgctgccaga acaccacctc tgtggaaaaa ggcaactcgg cggtgatggg cggggtgctc | 360 |
| ttcagcaccg gcctcctggg caacctgctg gcctggggc tgctggcgcg ctcggggctg | 420 |
| gggtggtgct cgcggcgtcc actgcgcccg ctgccctcgg tcttctacat gctggtgtgt | 480 |
| ggcctgacgg tcaccgactt gctgggcaag tgcctcctaa gcccggtggt gctggctgcc | 540 |
| tacgctcaga accggagtct gcgggtgctt gcgcccgcat tggacaactc gttgtgccaa | 600 |
| gccttcgcct tcttcatgtc cttctttggg ctctcctcga cactgcaact cctgccatg | 660 |
| gcactggagt gctggctctc cctagggcac cctttcttct accgacggca catcaccctg | 720 |
| cgcctgggcg cactggtggc cccggtggtg agcgccttct ccctggcttt ctgcgcgcta | 780 |
| cctttcatgg gcttcgggaa gttcgtgcag tactgccccg gcacctggtg ctttatccag | 840 |
| atggtccacg aggagggctc gctgtcggtg ctggggtact ctgtgctcta ctccagcctc | 900 |
| atggcgctgc tggtcctcgc caccgtgctg tgcaacctcg cgccatgcg caacctctat | 960 |
| gcgatgcacc ggcggctgca gcggcacccg cgctcctgca ccagggactg tgccgagccg | 1020 |
| cgcgcggacg ggagggaagc gtcccctcag cccctggagg agctggatca cctcctgctg | 1080 |
| ctggcgctga tgaccgtgct cttcactatg tgttctctgc ccgtaattgt gagtccccgg | 1140 |
| gccccgaggc agcagggcac tgagactgtc cggccgcgga tgcggggcgg gaagggtgga | 1200 |

```
<210> SEQ ID NO 133
<211> LENGTH: 2000
```

<212> TYPE: DNA
<213> ORGANISM: Homo sapiens

<400> SEQUENCE: 133

```
cttccgccgc ggtatctgcg tgcccttttc tgggcgagcc ctgggagatc cagggagaac     60
tgggcgctcc agatggtgta tgtctgtacc ttcacagcaa ggcttccctt ggatttgagg    120
cttcctattt tgtctgggat cggggtttct ccttgtccca gtggcagccc cgcgttgcgg    180
gttccgggcg ctgcgcggag cccaaggctg catggcagtg tgcagcgccc gccagtcggg    240
ctggtgggtt gtgcactccg tcggcagctg cagaaaggtg ggagtgcagg tcttgccttt    300
cctcaccggg cggttggctt ccagcaccga ggctgaccta tcgtggcaag tttgcggccc    360
ccgcagatcc ccagtggaga agagggctc ttccgatgcg atcgagtgtg cgcctccccg    420
caaagcaatg cagaccctaa atcactcaag gcctggagct ccagtctcaa aggtggcaga    480
aaaggccaga cctaactcga gcacctactg ccttctgctt gccccgcaga gccttcaggg    540
actgactggg acgccctgg tgcgggcag tcccatccgc catgagaacg ccgtgcaggg    600
cagcgcagtg gaggtgcaga cgtaccagcc gccgtggaag gcgctcagcg agtttgccct    660
ccagagcgac ctggaccaac ccgccttcca acagctggtg aggccctgcc ctacccgccc    720
cgacctcggg actctgcggg ttggggattt agccacttag cctggcagag aggggagggg    780
gtggccttgg gctgagggc tgggtacagc cctaggcggt ggggggaggg gaacagtggc    840
gggctctgaa acctcacctc ggcccattac gcgccctaaa ccaggtctcc ctggattaaa    900
gtgctcacaa gagaggtcgc aggattaacc aacccgctcc cccgccctaa tcccccccct    960
gtgcgcctgg ggacctggcc tccttctccg cagggcttgc tctcagctgg cggccggtcc   1020
ccaagggaca ctttccgact cggagcacgc ggccctggag caccagctcg cgtgcctctt   1080
cacctgcctc ttcccggtgt ttccgccgcc ccaggtctcc ttctccgagt ccggctccct   1140
aggcaactcc tccggcagcg acgtgacctc cctgtcctcg cagctcccgg acacccccaa   1200
cagtatggtg ccgagtcccg tggagacgtg agggggaccc ctccctgcca gcccgcggac   1260
ctcgcatgct ccctgcatga gactcaccca tgctcaggcc attccagttc cgaaagctct   1320
ctcgccttcg taattattct attgttattt atgagagagt accgagagac acggtctgga   1380
cagcccaagg cgccaggatg caacctgctt tcaccagact gcagaccct gctccgagga   1440
ctcttagttt ttcaaaacca gaatctggga cttaccaggg ttagctctgc cctcctct    1500
cctctctacg tggccgccgc tctgtctctc cacgccccac ctgtgtcccc atctcggccg   1560
gcccggagct cgcccacgcg gacccccgcc ctgcccagc tcagcgctcc ctggcggctt    1620
cgccgggct cctagcgggg aaaggaagg ggataactca gaggaacaga cactcaaact   1680
cccaaagcgc atgattgctg ggaaacagta gaaaccagac ttgccttgaa agtgtttaag   1740
ttattcgacg gaggacagag tatgtgagcc tttgccgaac aaacaaacgt aagttattgt   1800
tatttattgt gagaacagcc agttcatagt gggacttgta ttttgatctt aataaaaaat   1860
aataacccgg ggcgacgcca ctcctctgtg ctgttggcgc ggcgggaggg ccggcggagg   1920
ccagttcagg ggtcaggctg gcgtcggctg ccggggctcc gcgtgctgcg ggcggggcgg   1980
gcccggtggg gattgggcgc                                               2000
```

<210> SEQ ID NO 134
<211> LENGTH: 1000
<212> TYPE: DNA
<213> ORGANISM: Homo sapiens

<400> SEQUENCE: 134

```
agtttgggga gccttttctc catttgagaa aaaacaaact tacagcgagg ggtgaggggt      60
tagggtttgg gattggggaa aatgtgggtg gggagccccc ccaaggaagt gaggaggggg     120
ctgcaaggat tacacctggg catacgtttc cctagaaatc acattcattg tattttttata   180
atttattcta aatctttcat gcgaagaaag tcagtagtga gtgttagtac tggtggccct    240
cctgatcaca cttgcatctc ttgagtgtgc cttaaaggtc ttgggaatgg aaaatataaa    300
aactgcttcg tgatgcgtca tctttatccc ccactccccc acccattcca atatattttc    360
tacttccagc ctaaattcgg ggcccctac cgaggccggc catgatcttg agggcggcat     420
aggggaggcc gcgctctgtc caccccagcc tggtgatgcc gttcgcttct tgtgcccggt    480
attgtgggct acatgccttt ccggcgtacg gagctgagcg tccaggccag tgcccctcaa    540
cctctcagta atgtttaccc gaggccgtcg tgcaatgaga ctattcgcat ggcattgtca    600
acgcggcggc gcgcgcgtct cggccctccg cggcttgcca gactgtcctg caaaccacct    660
caccegtctc tttggcgcag gagactcagg ctgtaaccgg agaaaacact tcaccctgga    720
accctaactc aggtcctggc aaaagatgcg agaggaagac ttgctctctt aataaatctc    780
ggccgcccgc acatctggcc cctagacctg ctcggtagag gactggctgg tggatgcgcg    840
gtccaggccg tgggcactcg acccacctct attttccttc ccgaggcgcc cctggattac    900
cactttcggt ttgcgcttac atccgggatg tcgaatttcc cagggaatca taattattttt   960
atctataatt tattctaacc ccaaggttcc aagaaaatct                         1000
```

<210> SEQ ID NO 135
<211> LENGTH: 1100
<212> TYPE: DNA
<213> ORGANISM: Homo sapiens

<400> SEQUENCE: 135

```
acattccttc taaaatgtgg gcttttctgtg tacatgggcg cgcattccca ggactcggtt    60
ccctgggtgg aattcaccca ggaatacaat cgattttctg aacctgcgta aggccacagg   120
cagctctgaa aatgaaagcg tttgctaagt gggggagatc tcaccgatcg aacgtttaaa   180
aatggctttg tcttcattca gctctcccga tttattctgt gttttacaaa tagaagctca   240
gagcttctgt cgcccagtcc ttgcatgact catggcggtg ccacacggg tttcagggat    300
aacgggatgt ttagaaaatc gctgcatatc ggagtttcct agcacgttcc atttatactg   360
aacgcaggcg ccgctgaaa atccagcctc gactcttgct aatgactggg taggaccctc    420
ggggtcctgc gacggtgctg gagggtgttc ccggctccga tgtggggagg cctgcgcggg   480
gactaggttc tcgagaggcg agcgggcgcg ccagagaacc cgagactgct gcggggccgg   540
atgcgggatc cctgggctgc ggttctacgc agaaacgcca atggccatgc ctccccagct   600
cctcccagcc ccagtcacta ggccggcgcc tggcccggag atcctcccag agccctggcg   660
gtgccatcat gccggagaag acaagctcgg ccccgctgga attcgctcca aacacagatg   720
ctcatttttg gaatattcta gaaaaataac aagatcttgt ttgtcgttat gattcacggg   780
aggtaactga tgggagggcc atttacatga gggcagacac tgtggggcga aggtgacttc    840
tggacgtagg cttttaaagta ggaacggctc caaattccca atatctccgg ccttaccggt    900
tgcaaatcgg accetgcggg gaaaaccaga cacttctgtt tcgtggcttt cgggctgcct   960
ccagcccacg caggctcgtt tagtccccgt ggagtcagcc ccgagccttc ctagtcctgg  1020
aacaagggct ccaggtcgcg gccgcgggaa gccgccaaga gggcggggag tagggattcc  1080
```
ctccagctcc gcagggcatc                                          1100

<210> SEQ ID NO 136
<211> LENGTH: 1500
<212> TYPE: DNA
<213> ORGANISM: Homo sapiens

<400> SEQUENCE: 136
tcctcctcgg cctcagatgt cgtcccacct gcccacgagc agggaacctg gaacccactc    60
tcccggcagt ccccagcggg ttccgccacc cggcggccgc ccctgacacc gagtgggtgg   120
gaggaagagg cagctggcgg ggatgggcca ttgagaccte ttgaaaaata ttaaaagaca   180
ggatgggtag agatttctcc gggagaaagt tcgagggtgc atcgggtcgc ggctgggagg   240
agtacccgaa atgccagcag gagaaatgca acctgtttag gccacacctt caatccccga   300
ggctgtctgg agagactgcg tgcggggac ttgccggcgt tcccacaccg cgcctgcaat   360
ccactcccgc ggctgcctgg cctctgccac tcgcggcttg aagccagtgg ctctcaagcc   420
ctcggccccg cggcggcccg cgcagccttc accggcgcc ggcaccacga agcctggccg    480
cagtggactc cccgcagctc gctgcgccct ggcgtctccc gtcgaggagg gagggacgga   540
ggcctgagcc gggagctccc tggcggtggt cgggccgccc ccttgaggc ctgctccccc    600 ctctcggcct cgccaaatcc ctgaaagccc agtccccctt cgtcacccg gggcttcta     660 atcactcggt atcgatttcc ctaactcttt tcatcctgtt gaagacacat cttaaaacac   720
tccagcccgg agtgtgctct gggctttatc cacactaata aaatgattta cccttctctc   780
cgcgctctcc tcacagagga aaatcgttcg agccccggct atttgtgtgt gatcagtaaa   840
tatttagtgc gctgacatcc ttagctgggc ttcggatcga ttcggggccc accgggaggt   900
gcgcacggtc cgggcggggc cgcgccgagc tcgccgaggg ggctcctccc gccctcgccg   960
ccggccgctg atttacggcc cctgcaacca gctaagggg gcgaaagcgc gcctggaaaa   1020
ttggcttttc aacctttac ttttgacatt cagccacttc cccaggctct aattctcgcc    1080
cgcactcctc cctcccgccc tactaagggt tgccctgtgc gccctgcgag cccttccagc   1140
agcaacgcgc ggcgctcgcg ccccctcggc ccggggacca cctatcacag ccctgagccg   1200
cgacgcgggg aggccccggc ccctgctatg ggggtcgcct ccttcgagga gagatgctct   1260
ccgcccgccc acacctctga gggaggagag ggggtggaga agcccagagc tgcatctgct   1320
ggatgacgag ccgctctccc tgctaccctt tctccgaccc gtcggccttt tcctactct    1380 ggagactgat cctcgacgtc catcgggccg gatggcgtcg ggtggaagcg ttactttcct   1440
cgcagaaaaa ctcctcctct ttcctaagat cagaaaaagc gcttagcttg gaattgttag   1500

<210> SEQ ID NO 137
<211> LENGTH: 600
<212> TYPE: DNA
<213> ORGANISM: Homo sapiens

<400> SEQUENCE: 137
cctaggcatt tcagcccgt tttgctggag ggggcatttg aggcctggcc agcttagcca     60
gcctacaagg agtgttactg gggtgaaaac agccagcggg gaccagtctg cttgtggccc   120
gccaggtgcc tgggatgggg aagcagcaaa tgcccacctt cctgcccaac cccctcctcc   180
ctcttcatgg ggggaactgg gggtggcagc ggctgccggg tgcagcggg ctcaggcctg    240 tggccctgcc tgacgttggt ccccatcaag ccatgtgacg agaccaggcc acaagaaaga   300

```
ggtttcaaca agcgttatcg tttcctggaa ctccaactcg gcgacttccc cgaagaccgg    360
ctgtgcctgg cgggcgggct gcgcacagcg gggacaaggc tgcccccttc ctcctccgct    420
gcctccgcgg ccgcgtctat ctcagtctga ctacctggaa gcagcactcc accctccagc    480
ccagcggccc tcggctcagc tgccaggtca ccggcaaccc cggagcggt ggggcagggg     540 ctgctccgcc agcctctgtg atgttcaggc cgggctgcac cagcccggga ccctaggtg     600
```

<210> SEQ ID NO 138
<211> LENGTH: 700
<212> TYPE: DNA
<213> ORGANISM: Homo sapiens

<400> SEQUENCE: 138

```
gcactggttc ccctttacct gagccaacaa cctaccagga agtttccatc aagatgtcat     60
cagtgcccca ggaaacccct catgcaacca gtcatcctgc tgttcccata acagcaaact    120
ctctaggatc ccacaccgtg acaggtggaa ccataacaac gaactctcca gaaacctcca    180
gtaggaccag tggagcccct gttaccacgg cagctagctc tctggagacc tccagaggca    240
cctctggacc ccctcttacc atggcaactg tctctctgga gcttccaaa ggcacctctg      300 gaccccctgt taccatggca actgactctc tggagacctc cactgggacc actggacccc    360
ctgttaccat gacaactggc tctctggagc cctccagcgg ggccagtgga ccccaggtct    420
ctagcgtaaa actatctaca atgatgtctc caacgacctc caccaacgca agcactgtgc    480
ccttccggaa cccagatgag aactcacgag gcatgctgcc agtggctgtg cttgtggccc    540
tgctggcggt catagtcctc gtggctctgc tcctgctgtg gcgccggcgg cagaagcggc    600
ggactggggc cctcgtgctg agcagaggcg gcaagcgtaa cggggtggtg gacgcctggg    660
ctgggccagc ccaggtccct gaggaggggg ccgtgacagt                          700
```

<210> SEQ ID NO 139
<211> LENGTH: 300
<212> TYPE: DNA
<213> ORGANISM: Homo sapiens

<400> SEQUENCE: 139

```
tgtccgacag gcacacagag cgccgccagg cacggccctc attcttcacc ccgagctccc     60
gcaaggtcgg cgaggaggct ggagcagcgg gtaggaagcg ggccgaggct ccccgacgc     120 tgggccgcaa ctgtcatcgc agatccctga aaaacgagct ctgtaatcgt tgccgtcagc    180
gggtgtacaa ttgcagcctt atgtttcctg ccgctgttta ccttcctgag cggcgcccag    240
agatgcacac acgctgccct gaagcgggac gtgacctctg ggcacctgtg aggtcctggg    300
```

<210> SEQ ID NO 140
<211> LENGTH: 500
<212> TYPE: DNA
<213> ORGANISM: Homo sapiens

<400> SEQUENCE: 140

```
gtcggctcct gcgctcccaa cggggtggcc gtttccttcc tcgcaccctc ttctctcccg     60
gtgcctgcgg tcccaccttc cagataccccc tcggagagtc cagctgagct ctcgccagag   120 ctttccccctt ccaacccgct cgacttgccc agatcccaag ctgggcttct ctctccatcg    180
ccccagaaag tgggtcttgg agaccgaggc aagaatttgg gcctccgctt ctgttccaga    240
ccccggaccc cttgccaaaa tgcggcagat gtgcagattg ggccgcgctt ggttcctggc    300
tgggtttatg gagcctgcgg ctgaggcagg ctccgcagac cccgagccag agtgggattt    360
```

```
aacggcggcc ggtgcgctgt gcttggtcaa ccccggtaac cgtcacgctg ctagtgatat      420
gaaaaaaacc tgccagcgtt ctgcttttct gccccgctgc agtctttagc acccgccagg      480
attctgtccg agtgtttgga                                                 500
```

<210> SEQ ID NO 141
<211> LENGTH: 1000
<212> TYPE: DNA
<213> ORGANISM: Homo sapiens

<400> SEQUENCE: 141

```
tttagtgtgt gcataaaaca tcccagctaa tctcaaatag acttttcctg agcagaggct       60
gaaatttgca agtaatgcaa agaagactcc gggagagcgt cgccgatggt ggagcgggag      120
acgggcgtgg ggagcccac tgcagtgctg ggatcgaagt ggtgctgacc ccaagacctc      180
tcccctcctc ctcccccggg agcttctcca gggttatttg ggaaatgagg gggaactcca      240
atccctgaga aagcgctcag gggcttgctg aggtgagcgc aaatggaagc acaaggccgg      300
gctggccgtg ggctcagtaa ccagtcggct gcccggcttg cgccagcact aaatgctcga      360
tcagaaagag aaaagaggc gcataattc caaatttcag gaaagtcaa atcggagagg       420 ggggacgcag gtctcttcag actgcccatt ctccgggcct cgctgaatgc ggggctcta      480 tccacagcgc gcggggccga gctcaggcag gctgggcga agatctgatt ctttccttcc      540
cgccgccaaa ccgaattaat cagtttcttc aacctgagtt actaagaaag aaaggtcctt      600
ccaaataaaa ctgaaaatca ctgcgaatga caatactata ctacaagttc gttttgggc      660 cggtgggtgg gatggaggag aaagggcacg gataatcccg gagggccgcg gagtgaggag      720
gactatggtc gcggtggaat ctctgttccg ctggcacatc cgcgcaggtg cggctctgag      780
tgctggctcg gggttacaga cctcggcatc cggctgcagg ggcagacaga gacctcctct      840
gctagggcgt gcggtaggca tcgtatggag cccagagact gccgagagca ctgcgcactc      900
accaagtgtt aggggtgccc gtgatagacc gccagggaag gggctggttc ggagggaatt      960
cccgctaccg ggaaggtcgg aactcggggt gatcaaacaa                           1000
```

<210> SEQ ID NO 142
<211> LENGTH: 500
<212> TYPE: DNA
<213> ORGANISM: Homo sapiens

<400> SEQUENCE: 142

```
catggtgctt caggaaggga ggggacgaga gccctgggct tgtggtgtcc acgtggacag       60
ctaatgagga gccttgccga tgaggagcat gcgttcccga cggggcggcc gaatgcggaa      120
ggagccgcca ttctctccgc cctgaccgcg ggattctctg cagcagatga gaaacggcgc      180
tgactcagca gggtccctcc caggccccga gcggtcatct ggtgaccccc gcgcttcccc      240 cacgcccag ccggagaagg gcaaagggaa gtcccggctc caaggcgcac ccagagatgc      300
ggtgcatgtg gcaggatggc ccagccccgt cggcagcccc agcttcctgc ccctggtttc      360
cttcctccca cgggctacag gcctctgatg agctttggaa agcaggaaac acacaggcta      420
gtaactatga atgggtccaa aaaacactcc ttattacttt aaactactta ggaagaagca      480
cagcgttgcc aaacgccaga                                                 500
```

<210> SEQ ID NO 143
<211> LENGTH: 1200
<212> TYPE: DNA

<213> ORGANISM: Homo sapiens

<400> SEQUENCE: 143

| | | | | | |
|---|---|---|---|---|---|
| gcgcgggggg | ccggaggatg | gcggcctggg | ggccctgcgg | gggctgtcgg | tggccgccag | 60 |
| ctgcctggtg | gtgctggaga | acttgctggt | gctggcggcc | atcaccagcc | acatgcggtc | 120 |
| gcgacgctgg | gtctactatt | gcctggtgaa | catcacgctg | agtgacctgc | tcacgggcgc | 180 |
| ggcctacctg | gccaacgtgc | tgctgtcggg | ggcccgcacc | ttccgtctgg | cgccgcca | 240 |
| gtggttccta | cgggagggcc | tgctcttcac | cgccctggcc | gcctccacct | tcagcctgct | 300 |
| cttcactgca | ggggagcgct | tgccaccat | ggtgcggccg | gtggccgaga | gcggggccac | 360 |
| caagaccagc | cgcgtctacg | gcttcatcgg | cctctgctgg | ctgctggccg | cgctgctggg | 420 |
| gatgctgcct | ttgctgggct | ggaactgcct | gtgcgccttt | gaccgctgct | ccagccttct | 480 |
| gcccctctac | tccaagcgct | acatcctctt | ctgcctggtg | atcttcgccg | gcgtcctggc | 540 |
| caccatcatg | ggcctctatg | gggccatctt | ccgcctggtg | caggccagcg | ggcagaaggc | 600 |
| cccacgccca | gcggcccgcc | gcaaggcccg | ccgcctgctg | aagacggtgc | tgatgatcct | 660 |
| gctggccttc | ctggtgtgct | ggggcccact | cttcgggctg | ctgctggccg | acgtctttgg | 720 |
| ctccaacctc | tgggccagg | agtacctgcg | ggcatggac | tggatcctgg | ccctggccgt | 780 |
| cctcaactcg | gcggtcaacc | ccatcatcta | ctccttccgc | agcagggagg | tgtgcagagc | 840 |
| cgtgctcagc | ttcctctgct | gcgggtgtct | ccggctgggc | atgcgagggc | ccggggactg | 900 |
| cctggcccgg | gccgtcgagg | ctcactccgg | agcttccacc | accgacagct | ctctgaggcc | 960 |
| aagggacagc | tttcgcggct | cccgctcgct | cagctttcgg | atgcgggagc | ccctgtccag | 1020 |
| catctccagc | gtgcggagca | tctgaagttg | cagtcttgcg | tgtggatggt | gcagccaccg | 1080 |
| ggtgcgtgcc | aggcaggccc | tcctgggta | caggaagctg | tgtgcacgca | gcctcgcctg | 1140 |
| tatggggagc | agggaacggg | acaggccccc | atggtcttcc | cggtggcctc | tcggggcttc | 1200 |

<210> SEQ ID NO 144
<211> LENGTH: 600
<212> TYPE: DNA
<213> ORGANISM: Homo sapiens

<400> SEQUENCE: 144

| | | | | | |
|---|---|---|---|---|---|
| gggcgggttg | ccacactgtc | ccctttctgc | atgggaggaa | gggggctcga | gaactgagtc | 60 |
| agccacacaa | aacgaggatg | gacagaactc | ctgagtagcg | agggtgcctg | ccgggcgcga | 120 |
| ggaggagggg | gaaagacgagg | aagacgagga | ggaggaatag | ggagcaccac | atgcagagg | 180 |
| ggctgcctca | gaccacaaag | cgcttcctca | tcctttcctc | gcccttgat | gccgccggca | 240 |
| acgtgactct | gcgagcagcg | gggcagacgc | caggtctccc | tcgcaggcgg | gaaagggct | 300 |
| ccaaggcggg | tgctgccttg | ctcgggtcac | atggctacgt | gggggccttg | ctcaaattca | 360 |
| cttcctgcct | tcattacaaa | actgtcaaag | gggatcgcac | gtttgcaggg | tgtcacccaa | 420 |
| gcattctggt | tttgcaaacg | acgctgtgcg | gcaggcggtc | tgatacctga | tgagctcggt | 480 |
| gtggcgggt | cggcagcatt | tcctccgggg | ttttgagctc | tggccacttc | tccttttgtt | 540 |
| ccacccaatc | tcacccactt | ctgggcttcg | aggccagagt | gtcttaacaa | gggggcacgt | 600 |

<210> SEQ ID NO 145
<211> LENGTH: 500
<212> TYPE: DNA
<213> ORGANISM: Homo sapiens

<400> SEQUENCE: 145

```
gagcgagact ttgtctcaaa aaaaaaaaaa accaaataaa ttgaaagctg agaaattcag      60
agcacaagaa gacaagcgcg ccccctcttt tagctgtcaa catggcggag ccgtccctgg     120
tgacgcagcc tccaaaggcc tccctgtgcc ctcctgagac cgcaagaggg aaagtggcag     180
cgacagtgat cgtggtgtct ttgtggcggt tgtgttgacc tcactgaccc ccgaagtgcc     240
gctctagggt ctgtcctcag cggtgacccg gccgggtcga agggcagagt tccgctgtca     300
ctagccctcc acccgtcctg tgtgctggga tgccctcgcg gcgccgtcca cgccaccgcc     360 gcccctctt gtgggttctg tctcctccgt gtctaggatc ctcctgcatc cgttttcct      420 tcctcccttc tctccctccg tctgtcttgc ccgcacctga ggttgtcgca gaggcgctga     480
gacgggccag caggagctgt                                                 500

<210> SEQ ID NO 146
<211> LENGTH: 600
<212> TYPE: DNA
<213> ORGANISM: Homo sapiens

<400> SEQUENCE: 146
tgctgtcccg gtcctgtcgc agtcctcaaa gatgctagag tgacagtcct ctaggggtag     60
agatggtcgt cctcccagga aaggtggcc cggagacttg gaggtgggat caatcctgcc     120
agtcctggat caggaggcct ctgtcggcg ccgccccct tcctcctcca tcagcaacag      180
gcggcgccgg ccagcctcat agtcagcctc atccacactg accagcaggc gaacagcctc    240
ccggcccaca gcctctcgca gggcctcagt caggaacacg ccccgcaggg cctgcagcag    300
ggcgccactc aggtagtcgc cccagaaggc gtccagatag gagagctctg agaacttgat    360
gtcacaaacc acagagccca ggtcccttga gcgcagcact gcggtggcct gcccaaacac    420
gtccagctgc cgcgccagcg cctggggccg ccgggatgcc acgccctgct ccaaggctgg    480
cccatgctcg cagtactctg ctcgaacccg gagccggatg tctgcagggg aaggagggat    540
ttgtcaggga gggggccaac actagacaca cttatgggga acgccaccct tcctccctcc    600

<210> SEQ ID NO 147
<211> LENGTH: 500
<212> TYPE: DNA
<213> ORGANISM: Homo sapiens

<400> SEQUENCE: 147
tgatgcccgg cccccagggg ggcagaggcg ccgccaccat gagcctgggc aagctctcgc     60
ctgtgggctg ggtgtccagt tcacagggaa agaggcggct gactgcagac atgatcagcc    120
acccactcgg ggacttccgc cacaccatgc atgtgggccg tggcggggat gtcttcgggg    180
acacgtcctt cctcagcaac cacggtgcga gctccgggag cacccatcgc tcaccccgca    240
gcttcctggc caagaagctg cagctggtgc ggagggtggg ggcgcccccc cggaggatgg    300
catctccccc tgcaccctcc ccggctccac cggccatctc cccatcatc aagaacgcca    360 tctccctgcc ccagctcaac caggccgcct acgacagcct cgtggttggc aagctcagct    420
tcgacagcag ccccaccagc tccacggacg gccactccag ctacggtgag ggcctgggcc    480
atcttggccc acttttcaga                                                500

<210> SEQ ID NO 148
<211> LENGTH: 110
<212> TYPE: DNA
<213> ORGANISM: Homo sapiens
```

```
<400> SEQUENCE: 148
tttgggccac gaggcaagtt caaagcggga gacttttgtt ttataaaatg atggtgagca        60
gctccggttt tatgtcaaac atcagggttt cgtgcaggat ataaacattt                  110

<210> SEQ ID NO 149
<211> LENGTH: 800
<212> TYPE: DNA
<213> ORGANISM: Homo sapiens

<400> SEQUENCE: 149
tgcctgagcg cagagcggct gctgctgctg tgatccagga ccagggcgca ccggctcagc        60
ctctcacttg tcagaggccg gggaagagaa gcaaagcgca acggtgtggt ccaagccggg       120
gcttctgctt cgcctctagg acatacacgg accccctaa cttcagtccc ccaaacgcgc       180
accctcgaag tcttgaactc cagccccgca catccacgcg cggcacaggc gcggcaggcg       240
gcaggtcccg gccgaaggcg atgcgcgcag ggggtcgggc agctgggctc gggcggcggg       300
agtagggccc ggcagggagg cagggaggct gcagagtcag agtcgcgggc tgcgccctgg       360
gcagaggccg ccctcgctcc acgcaacacc tgctgctgcc accgcgccgc gatgagccgc       420
gtggtctcgc tgctgctggg cgccgcgctg ctctgcggcc acgagccctt ctgccgccgc       480
gtggtcagcg gtgagtcagg ggccgtctcc ccgaagaacg agcggggaga ggggaccacg       540
gggcgcggcg ggcagcctgt tctcgggcgg aggctctccg gggcgttgga aacctgcatg       600
gtgtaaggac ccgggaggag gcggggagaa attgattgtg ctgttctcct ccctctcttc       660
tctaacacac acgcagaaaa gtttaaattt ttgtgaagcg cttgcttacg tagctgcgga       720
gcgagcctct gcttcattac gagcggcata gccttttca ggagtgattt ccactttctt       780
tgtgagagag ttgaccacac                                                   800

<210> SEQ ID NO 150
<211> LENGTH: 600
<212> TYPE: DNA
<213> ORGANISM: Homo sapiens

<400> SEQUENCE: 150
ttcaatttac actcgcacac gcgggtacgt gggtgttcgg ggtagggcac tgatctgggg        60
aaggtctccc ccccgcgacc caactcatct ttgcacattt gcagtcctcc ctcggtgcac       120
tcctggcggg gatctggcca gtgcagcgca ctgggaccga gggcagagcc cgcggagtga       180
ggccaggaga gacttcaggc ctctaaggac acagctgagg ctaaggctga gttgaacgca       240
gcccctcccg cggctcgtcc cctctccagt gtctctcccg taaggtgccg ctcccaacag       300
caatgggtcg agatgtagag gaaacactct gtacgttatt tttccgccca cccttttagcg      360 cctgaggaga cagacagtgt agactttagg gtacaattgc ttcccctctg tcgcggcggg       420
gtggggagcg tgggaagggg acagccgcgc aaggggccag cctgctccag gtttgagcga       480
gagagggaga aggaggtcca cggagagaca agaatctccc tcctcccacg cccaaaagga       540
ataagctgcg gggcacaccg cccgcctcca gatcccccat tcacgttgag ccggggcgcg       600

<210> SEQ ID NO 151
<211> LENGTH: 1400
<212> TYPE: DNA
<213> ORGANISM: Homo sapiens

<400> SEQUENCE: 151
gcctgaagac catttcttcc tctcttaggg acctgctggt ctccagctga ttcggtccag        60
```

```
gaggaaaaac ctcccacttg ctcctctcgg gctccctgca aggagagagt agagacactc    120
ctgccaccca gttgcaagaa gtcgccactt cccctccag ccgactgaaa gttcgggcga    180
cgtctgggcc gtcatttgaa ggcgtttcct tttctttaag aacaaaggtt ggagcccaag    240
ccttgcggcg cggtgcagga agtacacgg cgtgtgttga gagaaaaaa atacacacac     300 gcaatgaccc acgagaaagg gaaagggaa aacaccaact acccgggcgc tgggctttt     360 cgacttttcc tttaaaaaga aaaagttttt tcaagctgta ggttccaaga acaggcagga   420 gggggagaa gggggggggg gttgcagaaa aggcgcctgg tcggttatga gtcacaagtg    480
agttataaaa gggtcgcacg ttcgcaggcg cgggcttcct gtgcgcggcc gagcccgggc   540
ccagcgccgc ctgcagcctc gggaagggag cggatagcgg agccccgagc cgcccgcaga   600
gcaagcgcgg ggaaccaagg agacgctcct ggcactgcag gtacgccgac ttcagtctcg   660
cgctcccgcc cgccttcct ctcttgaacg tggcagggac gccggggac ttcggtgcga    720 gggtcaccgc cggttaact ggcgaggcaa ggcggggca gcgcgcacgt ggccgtggag    780
cccggcctgg tcccgcgcgc gcctgcgggt gccccctggg gactcagtgg tgtcgcctcg   840
cccgggacca gagattgcgc tggatggatt cccgcgggca gaggcagggg gaaggagggg   900
tgttcgaaac ctaatacttg agcttctttg caaagtttcc ttggatggtt ggggacgtac   960
ctgtataatg gccctggacc agcttccctg ttggagtggc cagagaagtg tgtaaaacac   1020
actagagggg cagggtggaa aaagagactg ccttcaaaac ttgtatcttt tcgatttcat   1080
tttgaaaaat aactacaaat ctattttaat tttacaaagt tagactcata gcattttaga   1140
tatcaatgtc ttcatttaac agaagtgaag atggagcaaa cgctcaatca gcgtctgtat   1200
ttattcgctc ctgttgtgcc agggtgcgtt tttgccgagc ggttgccttt ctttactcac   1260 aaaacccct tgatgtctgt cctccacgtt ttacgaggga gagccggatc ttttgaagtt   1320
tgtatcatct aaagcaggta tattgggatg actatggata gaatttaacc tgaaaacact   1380
gaagttgaca gctgacaaag                                              1400

<210> SEQ ID NO 152
<211> LENGTH: 250
<212> TYPE: DNA
<213> ORGANISM: Homo sapiens

<400> SEQUENCE: 152
tgcttcaacc ggaaatgtgg ttgaattacc cttacagtga acctgatcag tggtaacagg    60
agatgctaga acaggaaaag acaagtttcc ccttttcctcc ctatcccatc aattactttg   120
aggtgtattt tttctttgca acccctccag agaagtcggc aatgtttaac gagcatgcct   180
gccaagtggc ttgccttata cctcattatg aagtgatact cagggccact aacacatcgc   240
acagcattgc                                                         250

<210> SEQ ID NO 153
<211> LENGTH: 500
<212> TYPE: DNA
<213> ORGANISM: Homo sapiens

<400> SEQUENCE: 153
tatgattccc tcgatttccc tcaatcttaa ccattgtgga tcacagcagg agggccagaa    60
agtgagcttc agcctggcac cgggacctca gcctctccct taaactttcc ctaatcctcg   120
gagctagtgt tactcaagtg actccacagt gttgcccgat cccttcagac atggccttga   180
```

```
tgatctccaa aactcatgct acctttgcca gcctaaagca tccactctgt gccccaaaac    240
gtgaatgtca ataccctc aaggcagaag gctatttcta tttttgtttg tttctgttta    300
aggcaacaat caccaacatt tggtacacat gagccatcct gtgaaacatc aaggcgcttc    360
gttggcagca agtcaacttc ggtttcagaa gaaagctgca ctatttcctg aggttagagg    420
tttaaaccaa aacaagacaa ccacatttta accccaaatc tgccgactga gggtaaccat    480
gatccttcct tcacagcacc                                                500

<210> SEQ ID NO 154
<211> LENGTH: 150
<212> TYPE: DNA
<213> ORGANISM: Homo sapiens

<400> SEQUENCE: 154
tactaaatca acccaaaccc gagaacccgg tcatggagaa ataaatgata gtaatctatg     60
ctgttcatct gttccatcac tcactcactc tcttgctgaa caagaaaggg ccacccatgt    120
agcaaaccac atgtaaagag ccgggaagac                                    150

<210> SEQ ID NO 155
<211> LENGTH: 300
<212> TYPE: DNA
<213> ORGANISM: Homo sapiens

<400> SEQUENCE: 155
tattattttg ttcaaagtag acgggtatac taacatctgt gggcaagttt accacacgcc     60
acttaaaaca ggctaacagg gtcatatgcc aaaacgttca ggtttgcatt tttgaaaagc    120
tcagagatct gacagatgtg ttccggccgc gatttaacat gcggctccag tgagaaggaa    180
gcagatatga caaatggttc acttatttca gaactaaaac cccagaggag cagcctgagc    240
caaaaaggga agtgatcaat ggaaaagacg gtcgaatctg ctcacaggca aggcaagggg    300

<210> SEQ ID NO 156
<211> LENGTH: 400
<212> TYPE: DNA
<213> ORGANISM: Homo sapiens

<400> SEQUENCE: 156 gcagggtga ctggtcctct ctctctgcac ctcgcaggat ttctctggaa gatctgagcc      60
cgagcgtcgt gctgcacatg accgagaagc tgggttacaa gaacagcgac gtgatcaaca    120
ctgtgctctc caaccgcgcc tgccacatcc tggccatcta cttcctctta aacaagaaac    180
tggagcgcta tttgtcaggg gtaagtgcga ccctagaggc gatcgtctct gctgtctgtg    240
gaaaaaagag ctcctacacc caaagtgctt ctcagttgct gacacttgat ccaagctgct    300
aatttaatct aatgtgaggc tgagttttct gaatgtggga taaagtcgta gctaaacctg    360
cttctcaggg agtgcctttt atctgcaatg ttttttcaaat                          400

<210> SEQ ID NO 157
<211> LENGTH: 10000
<212> TYPE: DNA
<213> ORGANISM: Homo sapiens

<400> SEQUENCE: 157
gtctttcccg cccccttgtc taaactcaaa accgagtccg ggcgcgcctt gcagggcgcc     60
cgagctctgc agcggcgttg cgggctgaac ccatccggca caaactgcgg gccactggcc    120
cctcacacct gggagtttgc ggcgctggcc tgcagcccgg ggcccacgtg gcggaagctt    180
```

-continued

```
tcccgggcgc gcgctgcgca gccccgcggg gccggggaga caccgctcgg gagtcctccg    240
ctcggctgca gaatctttat cagctgcact ttaccgcagc cctggctagg acgctaggcg    300
gtggagcgcc ctatccaggt gcgccgccgc accatggatc accgcgcccg gtcccgcagt    360
cccgccatgg cctggggagg cccgaagccc ggggacagtg gccggcccat ctccggctcc    420
gcggaccccc ggctcaggcg ggagggcagg cgggtccctg caggcccca gggagcccgg    480 gagcctctct ctggcgtcat tcagtcccgg ggcaacctga agcgcggtag atattggaga    540
gggggcgtct gttgggggga cctggcgtca ttactgatgg ctagcaggga ggagggaacg    600
ggttgtcacc tcggcctcat aaggccgtga gtgagtagtc cagggcctct tcaggcattt    660
ttgaaactgg attaactagg ggggaaattg tagcactgaa gccaccgtga ctgtcttttg    720
cgctgtgtgg aaactccggt aaaactcttt gggcaacagt cttatcacca gctcttcaac    780
gtgtgcagcc cttctggtcc tgtccctgtt ctgggcccca ggaatgcaaa gcaggtccag    840
gcactgtgaa gaccctggcg gtggaggaag aggcttcccg gctgtggagg aagccagacc    900
cttacaacac aagacgagaa ccagacctgc gtgggggagc tctggatgct acaggggctc    960
aaggaggggt ggagggggcct tcccaggcca acccctgaac ggcttggaca agatgctcag   1020
atggacggga ggaacggcgt gtgggatggg ggagctggag gcgggtgggt gggggggga   1080 ggatggggaa agcgctggcc cacccagtgt gggaggggta gaggaaaagc ccgcaggggc   1140
caggttggga ccccgtaggc cgggttagag ggcttggact tgatcctgac aggcgacagg   1200
gagacatatt gctacttatt atgtgcacag tggccagatc tctaaagaaa acaccatccc   1260 ccaccccac ccccatata gtaaaccagg tggtccgccc agtgctccca gggaggtgat    1320
gggaaatccc actccatacc ctgcggtgag gggttccatg ccctccacgt gtgcaactac   1380
tccgggccca gggaaacact gggccccatc cggtaacccc cggcccagtc gggtttccca   1440
gttcacatta taaccaaacg gtcttgccag ctagacagac agacacccct gacctgttta   1500
ccctgatcct ctgctctcag gattaatcac aacttgtcga aggggggtggc ttccagtggg   1560 gtggaccgct ctgtcaatgc cagcgtgtgt ctagcatctc ctggggtggg ggtgtgggga   1620
agggaggtgt aggatgaagc cctagaagcc tcaggcaatt gtgatccggt gggctggata   1680
ctgaagccca cccctgcctt gacctcaatt ttcagtatct tcatctgtaa aatgggaaca   1740
acctgccttc ctcctagccc taagggggct gctgtcaaga ttggctgaga tagctgtttg   1800
caagctgagc tcaatgaaag ttcattgtgt cccctcagt cctatcccaa tatcgtctca   1860
ctgcaaaggt gggggggcagc ttaacttcaa gggcacttca aggatagcca ggtggctgtc   1920
agcccagctt tccaggatgg gagcaggatc ttgacagaag ggttgactgg gaggggcagt   1980
tgctggtttg ggcttcgtta ggttgcattt ttgtttgttg tcctttcatt tccctggggc   2040 agcaccccctt cctgcaagct ccaggccttc ctctggaatg ctcctagagc ccaacctctg   2100
ctggtgcctg agcttaagcc aggccagcta agggatcct ggattcacac ggcctcacag    2160
tcactcagat tgttagcaga agacaaaaat tacaagggga gggcgtcatg tgattcttac   2220
acaccctcca aatccagcag acaccttgga agccacaggt agcttcaaga aacccatttt   2280
acggatgaga acctgagatg gagaaaggac aactggagat ctctgagtct ctgagccac    2340 actccctacc tccctgcacc tccaggcact ctgctggcag gatcttgggc aaatgcccac   2400
agctctctga gagtcagttt tcctgtctgt aaaatgggag tcataccttc ctcctatggc   2460
cggtgagaga ctaaattaaa ctatgtctgt caagacacct gaaactcctg gcacaattta   2520
```

-continued

| | | | | |
|---|---|---|---|---|
| ggttgccttc | aagtggtcac | agttgtcatt | aggtggaagt | caacacccca atcattgtaa | 2580 |
| aggtgcccat | ataccccaag | atccagatta | cagctctcac | agtttattat atacagcgaa | 2640 |
| aaaacacata | acacacccttt | gcccacatttt | acatgtattt | tacggaccat gtttcacatc | 2700 |
| agtccgcatg | cacatctgca | cgtgtgtgca | ttcggcagta | tttaccaagc acctgccaag | 2760 |
| tgccagggcc | tgtcctccgc | acccggcgtg | aactgtcctg | gaccagtccc gggagccgcg | 2820 |
| gttctgacca | gccgtgctga | ccctggacga | ctccatgagc | tgttttgtga aaagacacg | 2880 |
| ccatttgttt | gcagagttct | gacttctgag | gggtcatgta | gcacatgttt ggtagccaaa | 2940 |
| cgctgtcatt | cacgaccagg | agcgatggct | gcaatgcctt | tttctttgct ttgctttccg | 3000 |
| gtgccgggag | ccttgcctcc | cgccgccacc | cctggtcagc | tctgcgcaag aacgtcgttc | 3060 |
| tgtttggcag | ccaggccgag | acgcagcctg | aatgtgagca | ggaactcgga aagggaagg | 3120 |
| gagagaatca | gaaagaaggc | ccgggaggga | cccgggaagc | agtgggaggt ctgcgccctg | 3180 |
| gagcccccgcg | agagcccgcc | ggtttggcac | gggctcctcc | cgggccgccc ggcggtccaa | 3240 |
| caaaggccgg | ccccgacacg | cacccggtct | tttgtgggag | agaaacacaa agaagaggga | 3300 |
| aaaacacgga | ggaggccaac | agcaccagga | cgcgggggcc | aaccaggaac tcccggagcc | 3360 |
| ggggcccatt | agcctctgca | aatgagcact | ccattcccca | ggaaggggcc ccagctgcgc | 3420 |
| gcgctggtgg | gaaccgcagt | gcctgggacc | cgcccaggtc | gcccacccccg ggcgccgggc | 3480 |
| gcaggacccg | gacaagtcct | ggggacgcct | ccaggacgca | ccaggcaag cttgggcacc | 3540 |
| gggatctaat | ttctagttat | tcctgggacg | gggtggggag | gcataggaga cacaccgaga | 3600 |
| ggtactcagc | atccgattgg | caccagggcc | aagggagccc | aggggcgaca cagacctccc | 3660 |
| cgacctccca | agctactccg | gcgacgggag | gatgttgagg | gaagcctgcc aggtgaagaa | 3720 |
| ggggccagca | gcagcacaga | gcttccgact | ttgccttcca | ggctctagac tcgcgccatg | 3780 |
| ccaagacggg | cccctcgact | ttcaccctg | actcccaact | ccagccactg gaccgagcgc | 3840 |
| gcaaagaacc | tgagaccgct | tgctctcacc | gccgcaagtc | ggtcgcagga cagacaccag | 3900 |
| tgggcagcaa | caaaaaaga | aaccgggttc | cgggacacgt | gccggcggct ggactaacct | 3960 |
| cagcggctgc | aaccaaggag | cgcgcacgtt | gcgcctgctg | gtgtttatta gctacactgg | 4020 |
| caggcgcaca | actccgcgcc | ccgactggtg | gccccacagc | gcgcaccaca catggcctcg | 4080 |
| ctgctgttgg | cggggtaggc | ccgaaggagg | catctacaaa | tgcccgagcc ctttctgatc | 4140 |
| cccacccccc | cgctccctgc | gtcgtccgag | tgacagattc | tactaattga acggttatgg | 4200 |
| gtcatccttg | taaccgttgg | acgacataac | accacgcttc | agttcttcat gttttaaata | 4260 |
| catatttaac | ggatggctgc | agagccagct | gggaaacacg | cggattgaaa aataatgctc | 4320 |
| cagaaggcac | gagactgggg | cgaaggcgag | agcgggctgg | gcttctagcg gagaccgcag | 4380 |
| agggagacat | atctcagaac | tagggggcaat | aacgtgggtt | tctctttgta tttgtttatt | 4440 |
| ttgtaacttt | gctacttgaa | gaccaattat | ttactatgct | aatttgtttg cttgttttta | 4500 |
| aaaccgtact | tgcacagtaa | aagttccccca | acaacggaag | taacccgacg ttcctcacac | 4560 |
| tccctaggag | actgtgtgcg | tgtgtgcccg | cgcgtgcgct | cacagtgtca agtgctagca | 4620 |
| tccgagatct | gcagaaacaa | atgtctgaat | tcgaaatgta | tgggtgtgag aaattcagct | 4680 |
| cggggaagag | attagggact | gggggagaca | ggtggctgcc | tgtactataa ggaaccgcca | 4740 |
| acgccagcat | ctgtagtcca | agcagggctg | ctctgtaaag | gcttagcaat tttttctgta | 4800 |
| ggcttgctgc | acacgtctc | tggcttttcc | catctgtaaa | atgggtgaat gcatccgtac | 4860 |
| ctcagctacc | tccgtgaggt | gcttctccag | ttcgggctta | attcctcatc gtcaagagtt | 4920 |

```
ttcaggtttc agagccagcc tgcaatcggt aaaacatgtc ccaacgcggt cgcgagtggt    4980
tccatctcgc tgtctggccc acagcgtgga gaagccttgc ccaggcctga aacttctctt    5040
tgcagttcca gaaagcaggc gactgggacg gaaggctctt tgctaacctt ttacagcgga    5100
gccctgcttg gactacagat gccagcgttg cccctgcccc aaggcgtgtg gtgatcacaa    5160
agacgacact gaaatacttt actatcatcc ggctcccctg ctaataaatg gaggggtgtt    5220
taactacagg cacgaccctg cccttgtgct agcgcggtta ccgtgcggaa ataactcgtc    5280
cctgtaccca caccatcctc aacctaaagg agagttgtga attctttcaa aacactcttc    5340
tggagtccgt cccctccctc cttgcccgcc ctctacccct caagtccctg cccccagctg    5400
ggggcgctac cggctgccgt cggagctgca gccacggcca tctcctagac gcgcgagtag    5460
agcaccaaga tagtggggac tttgtgcctg ggcatcgttt acatttgggg cgccaaatgc    5520
ccacgtgttg atgaaaccag tgagatggga acaggcggcg ggaaaccaga cagaggaaga    5580
gctagggagg agaccccagc cccggatcct gggtcgccag ggttttccgc gcgcatccca    5640
aaaggtgcgg ctgcgtgggg catcaggtta gtttgttaga ctctgcagag tctccaaacc    5700
atcccatccc ccaacctgac tctgtggtgg ccgtattttt tacagaaatt tgaccacgtt    5760
ccctttctcc cttggtccca agcgcgctca gccctccctc catccccctt gagccgccct    5820
tctcctcccc ctcgcctcct cgggtccctc ctccagtccc tccccaagaa tctcccggcc    5880
acgggcgccc attggttgtg cgcagggagg aggcgtgtgc ccggcctggc gagtttcatt    5940
gagcggaatt agcccggatg acatcagctt cccagccccc cggcgggccc agctcattgg    6000
cgaggcagcc cctccaggac acgcacattg ttccccgccc ccgcccccgc caccgctgcc    6060
gccgtcgccg ctgccaccgg gctataaaaa ccggccgagc ccctaaaggt gcggatgctt    6120
attatagatc gacgcgacac cagcgcccgg tgccaggttc tcccctgagg cttttcggag    6180
cgagctcctc aaatcgcatc cagagtaagt gtccccgccc cacagcagcc gcagcctaga    6240
tcccagggac agactctcct caactcggct gtgacccaga atgctccgat acaggggtc    6300 tggatcccta ctctgcgggc catttctcca gagcgacttt gctcttctgt cctccccaca    6360
ctcaccgctg catctcccct accaaaagcg agaagtcgga gcgacaacag ctcttttctgc    6420 ccaagcccca gtcagctggt gagctccccg tggtctccag atgcagcaca tggactctgg    6480
gccccgcgcc ggctctgggt gcatgtgcgt gtgcgtgtgt ttgctgcgtg tgtcgatgg    6540 agataaggtg gatccgtttg aggaaccaaa tcattagttc tctatctaga tctccattct    6600
ccccaaagaa aggccctcac ttcccactcg tttattccag cccgggggct cagttttccc    6660
acacctaact gaaagcccga agcctctaga atgccacccg caccccgagg gtcaccaacg    6720
ctccctgaaa taacctgttg catgagagca gaggggagat agagagagct taattatagg    6780
tacccgcgtg cagctaaaag gagggccaga gatagtagcg aggggacga ggagccacgg    6840 gccacctgtg ccgggacccc gcgctgtggt actgcggtgc aggcgggagc agcttttctg    6900
tctctcactg actcactctc tctctctctc cctctctctc tctctcattc tctctctttt    6960
ctcctcctct cctggaagtt ttcgggtccg agggaaggag gacccctgcga aagctgcgac    7020 gactatcttc ccctgggggcc atggactcgg acgccagcct ggtgtccagc cgcccgtcgt    7080
cgccagagcc cgatgacctt tttctgccgg cccggagtaa gggcagcagc ggcagcgcct    7140
tcactggggg caccgtgtcc tcgtccaccc cgagtgactg cccgccggag ctgagcgccg    7200
agctgcgcgg cgctatgggc tctgcgggcg cgcatcctgg ggacaagcta ggaggcagtg    7260
```

```
gcttcaagtc atcctcgtcc agcacctcgt cgtctacgtc gtcggcggct gcgtcgtcca    7320
ccaagaagga caagaagcaa atgacagagc cggagctgca gcagctgcgt ctcaagatca    7380
acagccgcga gcgcaagcgc atgcacgacc tcaacatcgc catggatggc ctccgcgagg    7440
tcatgccgta cgcacacggc ccttcggtgc gcaagctttc caagatcgcc acgctgctgc    7500
tggcgcgcaa ctacatcctc atgctcacca actcgctgga ggagatgaag cgactggtga    7560
gcgagatcta cggggccac cacgctggct tccacccgtc ggcctgcggc ggcctggcgc    7620
actccgcgcc cctgcccgcc gccaccgcgc acccggcagc agcagcgcac gccgcacatc    7680
accccgcggt gcaccacccc atcctgccgc ccgccgccgc agcggctgct gccgccgctg    7740
cagccgcggc tgtgtccagc gcctctctgc ccggatccgg gctgccgtcg gtcggctcca    7800
tccgtccacc gcacggccta ctcaagtctc cgtctgctgc gcggccgcc ccgctggggg    7860
gcgggggcgg cggcagtggg gcgagcgggg gcttccagca ctgggcggc atgccctgcc    7920
cctgcagcat gtgccaggtg ccgccgccgc accaccacgt gtcggctatg ggcgccggca    7980
gcctgccgcg cctcacctcc gacgccaagt gagccgactg gcgccggcgc gttctggcga    8040
caggggagcc aggggccgcg gggaagcgag gactggcctg cgctgggctc gggagctctg    8100
tcgcgaggag gggcgcagga ccatggactg ggggtgggga atggtgggga ttccagcatc    8160
tgcgaaccca agcaatgggg gcgcccacag agcagtgggg agtgagggga tgttctctcc    8220
gggacctgat cgacgctgt ctggcttaa cctgagctgg tccagtagac atcgttttat    8280
gaaaaggtac cgctgtgtgc attcctcact agaactcatc cgaccccga cccccacctc    8340
cgggaaaaga ttctaaaaac ttctttccct gagagcgtgg cctgacttgc agactcggct    8400
tgggcagcac ttcgggggg gaggggtgt tatgggaggg ggacacattg gggccttgct    8460
cctcttcctc ctttcttggc gggtgggaga ctccgggtag ccgcactgca gaagcaacag    8520
cccgaccgcg ccctccaggg tcgtccctgg cccaaggcca ggggccacaa gttagttgga    8580
agccggcgtt cggtatcaga agcgctgatg gtcatatcca atctcaatat ctgggtcaat    8640
ccacaccctc ttagaactgt ggccgttcct ccctgtctct cgttgatttg ggagaatatg    8700
gttttctaat aaatcgtgg atgttccttc ttcaacagta tgagcaagtt tatagacatt    8760
cagagtagaa ccacttgtgg attggaataa cccaaaactg ccgatttcag gggcgggtgc    8820
attgtagtta ttattttaaa atagaaacta ccccaccgac tcatctttcc ttctctaagc    8880
acaaagtgat ttggttattt tggtacctga gaacgtaaca gaattaaaag gcagttgctg    8940
tggaaacagt ttgggttatt tgggggttct gttggctttt taaaattttc ttttttggat    9000
gtgtaaattt atcaatgatg aggtaagtgc gcaatgctaa gctgtttgct cacgtgactg    9060
ccagccccat cggagtctaa gccggctttc ctctatttg gtttattttt gccacgttta    9120
acacaaatgg taaactcctc cacgtgcttc ctgcgttccg tgcaagccgc ctcggcgctg    9180
cctgcgttgc aaactgggct tgtagcgtc tgccgtgtaa cacccttcct ctgatcgcac    9240
cgcccctcgc agagagtgta tcatctgttt tattttgta aaacaaagt gctaaataat    9300
atttattact tgtttggttg caaaaacgga ataaatgact gagtgttgag atttaaata    9360
aaatttaaag taaagtcggg ggatttccat ccgtgtgcca ccccgaaaag gggttcagga    9420
cgcgatacct tgggaccgga tttggggatc gttcccccag tttggcacta gagacacaca    9480
tgcattatct ttcaaacatg ttccgggcaa atcctccggg tcttttttcac aacttgcttg    9540
tccttatttt tattttctga cgcctaaccc ggaactgcct ttctcttcag ttgagtattg    9600
agctccttta taagcagaca tttccttccc ggagcatcgg actttgggac ttgcagggtg    9660
```

| | | | | |
|---|---|---|---|---|
| agggctgcgc | ctttggctgg | gggtctgggc | tctcaggagt | cctctactgc | tcgattttta | 9720 |
| gatttttatt | tcctttctgc | tcagaggcgg | tctcccgtca | ccaccttccc | cctgcgggtt | 9780 |
| tccttggctt | cagctgcgga | cctggattct | gcggagccgt | agcgttccca | gcaaagcgct | 9840 |
| tggggagtgc | ttggtgcaga | atctactaac | ccttccattc | cttttcagcc | atctccacta | 9900 |
| ccctccccca | gcggccaccc | ccgccttgag | ctgcaaagga | tcaggtgctc | cgcacctctg | 9960 |
| gaggagcact | ggcagcgctt | tggcctctgt | gctctttcct | | | 10000 |

<210> SEQ ID NO 158
<211> LENGTH: 100
<212> TYPE: DNA
<213> ORGANISM: Homo sapiens

<400> SEQUENCE: 158

| | | | | | | |
|---|---|---|---|---|---|---|
| tttttaatgc | tcagagaagt | tcgtattact | gattcgggaa | cactgagttt | ttcagctcct | 60 |
| gtaaaactat | tttcaggttt | attttcaagt | acattcttta | | | 100 |

<210> SEQ ID NO 159
<211> LENGTH: 400
<212> TYPE: DNA
<213> ORGANISM: Homo sapiens

<400> SEQUENCE: 159

| | | | | | | |
|---|---|---|---|---|---|---|
| caccctagag | gcaaggacgg | ggtctgtgtc | aagaggcttc | ccagagaagt | gaaaactctg | 60 |
| caggtgcagc | cgctgggaga | gcatcaagaa | gggcagggtg | gaggggcagg | gggcgaaggg | 120 |
| aggggtgaa | gcccgcaccc | tacccccaca | tgaaactgat | tccactaccc | catctctgca | 180 |
| agcgtccaga | ggcagagagg | ccaacatttc | ggggacagct | tggaggcggg | agatttaggc | 240 |
| agggctcctt | aaacttttat | gtgcatgaaa | atcaggccaa | tcacgggct | cttgagcaaa | 300 |
| tggggacgat | gattcagcag | gtctgggctg | aggcctcaga | ttctgcactt | ctaacaagtt | 360 |
| cccaggtggt | agtgatgctg | ccagtccaaa | gaccacactg | | | 400 |

<210> SEQ ID NO 160
<211> LENGTH: 5000
<212> TYPE: DNA
<213> ORGANISM: Homo sapiens

<400> SEQUENCE: 160

| | | | | | | |
|---|---|---|---|---|---|---|
| tgcttcagtg | gggtaaactt | gaaccgctga | gaagacaagc | agggagtcgg | tctcgctgag | 60 |
| attttacct | gtggttctag | gaacgcagag | gcatgtgagt | gttcaggctt | tgcatagacc | 120 |
| actaagccac | ttctaagaac | aaggctacct | gagccatttt | gcaaaaatat | gtacgtgccg | 180 |
| aggcttttcc | tccccacacc | tacctcaact | ctttctgccg | acacactgca | cttttcaagg | 240 |
| gaacccaagt | ttgggttcgg | caagaattgt | acgttgcaca | ccgtgtgtga | taattccagg | 300 |
| gaatttcaat | cgcatcttgt | cttccttcct | aagcaaattc | ggtgggaacc | tggtgtggtg | 360 |
| tgatagaaaa | agccccgagt | tctctgtggt | agaccacatc | aatttcatgt | gccagtctct | 420 |
| cagactccgg | cttgcctctc | tcaaggaagg | gaacaatggt | ttgcttggct | tcactcctct | 480 |
| cttcccccc | aatttccaca | tgggtatctg | gctaaaaatg | agttacaggt | ttccttctgt | 540 |
| gagaattgca | tggactgata | aagtaccatc | ccaggaagaa | aacaaagatg | ctgtcttccc | 600 |
| tttcggctca | cagttgccgt | tggggaggga | acacacgctg | taaattatag | gcagccagaa | 660 |
| gtgaccgcat | tgaccactgc | gagtggccca | gctatggcaa | caggctgaga | actctggggg | 720 |

```
agagccattt gttggcaggg atggtgattc ttctagcatc aagctctaag atgatgacca    780
aacggtatca aaagaaatga tattttgcta cctctccggc ttgggtgaat gatgtggaca    840
gttaacctgg acaatttaaa cctttatgtt gatggatcac ttggatgaaa ttaaccagga    900
aattgccaag atttcacttg gccctctgac atcaaatctc aatattatat taccaaatta    960
gagattctaa agaaccctga gttcctttca ctgaaaggaa ggagtggaaa aacctttcca   1020
gatgatccct tttgagtctt ggtgcgagct caggccctcc ctacactgcc tccgtgaaag   1080
ctaaccgacc cttgttccta acctagcgca ggtcagctga gtgtccatcg ggcacaggag   1140
ccctgggctt gtccgggaga tagccagact cctgctattt cctgatgtct gcatagctca   1200
gcgtgtccct caccatcttt gccgttggcc agtaaggaga gccccagggg ccagcactgc   1260
acactgaaac ccaacctatt gctcaatgga atgcttaaaa atttcctgaa tctgccttcc   1320
tgagttgata aaataggaaa caatacacgt tctgaggggg tactgaaagc agagtaaagc   1380
caggaagatc ttttttttct gttattctat acaaatattg cttcctctgc ttgttagcag   1440
cccagaggaa atgcagccag ggagccgttt gcagcttttc accagtggcc ggtgtctctg   1500
tgttaccaac caaacgacgc tgcaagacta gtgactaacg cacgtctgca tgattcaact   1560
tcactaaaat tccctctgct gccagtaaag aagcacttga aaactcttta atttgaaact   1620
tgagcttggt taatgacttg ttttcttctc tttctcttta acttctctct tgccatctcc   1680
aacacacaca cacacacaca cacacacaca cacacacaca cacacacact ctctctctct   1740
ctctctctct ctctctctct ctctcatcaa gttttttaat ttcagggacc cggaaacata   1800
cagccccgtg cattcacaat agcatttgct gtgataaagt ggccggcaag ccctctgcat   1860
tcccctgctc acttagctgt atgaataaat aatgagtcac agatacaatt tgggtgctca   1920
agagagtttg tagccagaaa attaattatt ctcccatccc agcccactcc atctcagctt   1980
tgccaaacca tcaagataca ctttgcaggc actggtcaga gtgcgtgccc cgacgcacac   2040
ggcaatgcct ttgagacatt ttatgttatt attttttgttt gtttaagcac agccctcttt   2100
taccacgaaa gatacacaag acgcacatgc acacacatac tcacacactc acagctcaac   2160
cacagctttg tccatttcaa gaggctggtt tcaaaaatgg agacaggttt tccaccctgg   2220
ctgttcctat tcataagcct gtaatctaac gacttaagct gcgagaatgc ttaactcggg   2280
aaacttctct attgcccttt tccagagaga cctcggtatg ccacaatttg cttcctttct   2340
ctcttgaaag atgctggttg tctctttgca ttgaggctac aaggaaaaac acagcacagc   2400
cccatgctga tgattttaac ctaaccaagt ctgtcagtct cctgtactct ctgccttata   2460
gagacagctg ccttgccact ttggccctga agtccccagg ctggtgcaag gctatctgag   2520
agcctccgcc tcctgcccca cactggcacc agccctcctg gctggctctg tgcatgtgcc   2580
tgctaagccc cagggcaggc tgcattctgg gccacacagc atgccgagtt aaggataact   2640
cagacacagg cattccgggc aagggacagc aaaataaaac ccaggagct tcgtgcaagc    2700
ttcataatct ctaagccttt aaacaagacc agcacaactt actcgcactt gacaaagttc   2760
tcacgcaccg actgaacact ccaacagcat aactaagtat ttattaaaac atttctgaag   2820
agcttccatc tgattagtaa gtaatccaat agacttgtaa tcatatgcct cagtttgaat   2880
tcctctcaca aacaagacag ggaactggca ggcaccgagg catctctgca ccgaggtgaa   2940
acaagctgcc atttcattac aggcaaagct gagcaaagt agatattaca agaccagcat    3000
gtactccacct ctcatgaagc actgtgggta cgaaggaaat gactcaaata tgctgtctga   3060
agccatcgct tcctcctgaa aatgcaccct cttctgaagg cggggactc aatgatttct    3120
```

| tttaccttcg gagcgaaaac caagacaggt cactgtttca gcctcacccc tctagccta | 3180 |
| catctctctt tcttctcccc tctgctggat acctctggga ctcccaagc cctattaaaa | 3240 |
| aatgcacctt tgtaaaaaca aatattcaaa ttgttaaaga ttaaaaaaaa aaaaaaagcc | 3300 |
| agcgccgcct tggctgtggg ttggtgatgc tcaccacgct gcgaaaccct gtggtttgca | 3360 |
| ttcagtgtga ttcgtcctgc ctgctgacca ctatgctggg ttcagacttc tgacactgcc | 3420 |
| aggctaccca acttgtggtt ctgtggttgt ttatgaggcc caagaagtt ttcacacaac | 3480 |
| ccaaattaca aatttaactg ttcccctttc cacagcccat ctcaattggt tcttgccaat | 3540 |
| catgtgactt aagtgatgtc aattttttt tttcttttct gagcaatgcc cttccttccc | 3600 |
| tccacctgcc ctcccccagg ctgtgcaaga aaatagccga gtagactttg caagaggggg | 3660 |
| ggatgtagaa aaagtgact cagtcactta ttatatctca atggtctttg ctgatttagt | 3720 |
| acaactcggc tcctgttgtt atttgtggtt tttggaacta ctgattattt tgataaagat | 3780 |
| ttcattgctg cttattcaat agtaattcaa cgctggcatc aagccgctgc tccgacagga | 3840 |
| tgtggatccc atcatttaaa atgctaggca tcagctccgg gagagttaag tccttggtaa | 3900 |
| cgtctatcat ggcataagtg aaactataaa agggaaaaat aaataaaaag aatgttttg | 3960 |
| gtgagagtct gacccctaca acgggctggc aactcacagg tattttaaag cctgggaaag | 4020 |
| ggaaagaatt ttacttttga aataaaagga ctgttttaat gaaaccaaaa ttatgtggtt | 4080 |
| ttattccccc taaatggaca actttagtat gtatctcttt cagtaaagag ataaaatcat | 4140 |
| agtacagtct taacacacac acacacacac acacacacac acacacacac acaaattagg | 4200 |
| aagctaaagg aaaacaaagc agagagaatt tctgtatttg ggacaaagca gtggttactc | 4260 |
| tgcagatgtt tatttgtatt gtcacttggg aaagctccct gtattgcctt tctctagttc | 4320 |
| aattcaaatc aataggctaa tttacacctg taggtaaaac tacactttga gcacatgagg | 4380 |
| atgccacaat agaaggggaa ccaggaggag acacttctcc tggggctgac taatgaatat | 4440 |
| tatatagcgc gtcctctacc ttagaaagac atgcctgttt gaagatgcta aaaacaggat | 4500 |
| aattttgtaa gtgggcaaac cactgtggtc acacgtattt cattttccgg ccccactggc | 4560 |
| tttacctgct gacaactaaa acgtcatttt gttttgtagt tccaagatga agaaaggctt | 4620 |
| attttcctga tttactacct tattcatttg gctctgctct gcctacatcc gccatagcac | 4680 |
| tctgcgcacg tgaaatttcg acacataggg tcaagagaac ctgtgtgatg atgggttgta | 4740 |
| aatgccagtc ctggattcta agctgcagta gccagcacag gcacttcaga aaggctgaac | 4800 |
| tcccacaaca ctccctcggt tttccctcat ccacttaatt tcacacacac aaagacccac | 4860 |
| aacgatagta gcttccatgg cacaagtctt tcaaaggaa cagacacaat ttttacttac | 4920 |
| tcctgttttg actaaagcag gaattgaaac tcaacagacc gctttctctt acacttgtga | 4980 |
| gaagttagct ggccacatgt | 5000 |

```
<210> SEQ ID NO 161
<211> LENGTH: 500
<212> TYPE: DNA
<213> ORGANISM: Homo sapiens

<400> SEQUENCE: 161
```

| agggaaaaga gataacgaaa gaaagaaaga aaaaaaaag ggccggcaat tcatgtaca | 60 |
| tttgttttgg cattcgctga attctagaga tgaaaacaat ctcctgcttt taattcagtc | 120 |
| cacgtgcaac aaagttgtac gttgggagat ctggctttta ataagaacga ttaacaagcg | 180 |

```
tttttgatca caggaagttg agaagagtcg ctgcttctaa gaatacaata aacattgact        240
agcagttaga cggtccatct ttctctatca gccgtttagc agcctctact ttgatttggg        300
gcaaatgcga gatgggacca ggagagagct ccccacaccc ccaccaccac gtgggcagtg        360
gttctgttcc agagcgcctt ccttcctgtc cagggaggca ggctgctgag gccgtttctg        420
ggcaagaggc cattgtcggg atatttgctt tagatagctt gcagctgggc tgagtgggtg        480
tttcattcag actcaacaca                                                   500

<210> SEQ ID NO 162
<211> LENGTH: 700
<212> TYPE: DNA
<213> ORGANISM: Homo sapiens

<400> SEQUENCE: 162
agcctggcgc acccgcccta atttgagtca gggaccctag gcgcctgcag ctccggttcg         60
ggttgagtgc ctcctgtcag gatgtgaagc tgctgtcccc ccggggggcc tccagcactg        120
ctgaggactc agcagtcagc ctctcctccc acttgggctc atttacagag agcatctcca        180
ggaatcagtc atggggaaag gggaaacgcg gagtgacaac acaacacgta gaaagttctc        240
tgccgccttg gtcaggcttg tcagcctcac agcccatcct gctcctgcgg gaggaaaagt        300
gagcagaact cagcccggag atgagccgca ggccggcagc ccctgcctct gccctgcttg        360
ttgtgactgc aatgcaaggc tctctgtagg tgcggggat tcgggttaaa tgggtctcca        420
gtggtccagc gctcccagca aaggccgacc acaagaatta gcgggctagt tatttaccat        480
aaccatatac aaaaccacaa gcatcagcgt tccctcaaat acatccgaga cgctgtatat        540
ctctttatta aagcctgtca gggtttgtta ttgcacagct tggccttgaa ccccaactaa        600
accaggctgc ttgagcaaag aaccaagcaa tgcaagcatt caggcaggac cattataacc        660
ctgaggccaa aggcagaagc agggagagga gacgtcttcc                             700

<210> SEQ ID NO 163
<211> LENGTH: 500
<212> TYPE: DNA
<213> ORGANISM: Homo sapiens

<400> SEQUENCE: 163
agaccagcct cggtcttcgg cctgcgggtt ctgcaaagtc aggctagctg gctctccgcc         60
tgctccgcac cccggcgagg ttccggtggg aggggtagg gatggttcag ccccgccccg        120
ctagggcggg gcctgcgcct gcgcgctcag cggccgggcg tgtaacccac gggtgcgcgc        180
ccacgaccgc cagactcgag cagtctctgg aacacgctgc ggggctcccg ggcctgagcc        240
aggtctgttc tccacgcagg tgttccgcgc gccccgttca gccatgtcgt ccggcatcca        300
tgtagcgctg gtgactggag gcaacaaggg catcggcttg gccatcgtgc gcgacctgtg        360
ccggctgttc tcgggggacg tggtgctcac ggcgcgggac gtgacgcggg gccaggcggc        420
cgtacagcag ctgcaggcgg agggcctgag cccgcgcttc caccagctgg acatcgacga        480
tctgcagagc atccgcgccc                                                   500

<210> SEQ ID NO 164
<211> LENGTH: 17000
<212> TYPE: DNA
<213> ORGANISM: Homo sapiens

<400> SEQUENCE: 164
cacgcgcccc ggcctggctg gaggggccaa cccagcgggg cccgcctgcc cgccggcctt         60
```

```
tctgtaactt tctctcttta aacttccaat gaatgaacgt gcctcttctt acggatttgt    120
ttagattagg gaatagattc ctcgctgata gcgttgcttt gcaaataaga cctcctatat    180
tattcaaacc aaacgagttt gtgtctttaa aggactatag cagccccatt ctatgttaag    240
ggttggctat tacaattatt atatgcttag ggaaaaaatg taagcccgt agtttgtgct    300 tttcttgatg tacagaaagg tttatcttag gtggataggt tttgttttgt ttcttaaatg    360 ggatttttt ggttcgtgtc tttgaagggc tgtttcgcga cgtcattaat gaactaatcg     420
gttttcagat ttcaagacgg tgtgtaattg atgtaaccac tgaggaattt cagtgcacac    480
cagactaaga ctcttccagc gcaggggatt ccagatgctt cttgggccct ctggaagcca    540 tgggatgtt tccagaccga aggagggct tgctgggga cagatgtgc tgcctctccc       600 cgacccagga ttttgaggcc atgtttccgt taatctggac cgagagccct ctgggagagg    660
gaggcaggtc gtaggggcg ggggtgaggg ggagcgagat gaggtcgtcg ctggacgctg     720
ggctcccttg tcgttgtcct tttccccaga atccatggtc aggcctaggg agccacccct    780
gggtgctcga gatgagtccc cacctcact gaaggtcggt cactggatgt ttgtgtgcat     840 cgtaagggc ccaccgaagt cccgaagcct tctcagggac cagcgagaaa gaggagcagg    900
cttgggagac agggaaggaa aatgcagggg aaagggctca cccctcgacc ccaggtaaaa    960
ttagaaggaa cgtgtggcaa cccaggtgca gctttggtcg ctcgctcaag gactttgcta    1020
gtcactacca ttaattaatt aatcactatc attaactacc aaggacaccg tttttattcc    1080
cctaaaagcg tcaccttgag gggaatggag aattgggcag cagctatgca aatcctggga    1140
caggagacac tgcctgagga ccctctctca ctcccaatcc cagaacccga agttatcccc    1200
gacaaccaag tccaagcaca tgaaccaaga cgatcagctt caggcagctc cttacccca    1260 caagcggccc aggaggtggg cattatcccc caccctggg atttctccat ccctccctct     1320
tctctcctgc gggagagaga gctgtggtca cccagttggg cgcgatggct ctggactaat    1380
ggggtctcta gacccagggc acaaaggcca atctgccagg ggttactgca tgtaatgaga    1440
taatcagaca tgttgaccaa cctaaaagaa aagactctcc cagggagtaa ctcccagtga    1500
aataatttat taaaaaagc aaaaaagaga cataaatttc tctctactac ttgaggaaac     1560
agcaaacaga acgaattagg gtcttggcct ctgcaggaat aaattatttc cgacttggtc    1620
tggatacctg taattatttg taagctgtgg gtagtaaatac tgtaattgtc ccccggtcct    1680
ttctggaagt agcaatgacc ccaaggacaa ttggtgacgt ctccacaggg tttacacatg    1740 gaaggagtg aaaaatcgag gaattctttc agatagccca gaccaaaaat cctctcagcc     1800
atgaaaaggt catatatgtg atgctgggcc aagcggactt ttctggagta accatatcat    1860
aactgattgc ggatgtagac aagagcgtat aaaccaaata ggcttgaatc aacgcagtcc    1920
tggattttct gttgcctctg cttgctgggg cagtggaagt tcttaaactc cacttcagag    1980
gttgaaaatt cttccccctc ccccacctcc ttagtgacaa ggtctctgat ctcctgctgc    2040
cactgcaata gcctctccca tcccgcgggg aacggccgga gttcttccct tgatctctcc    2100
cgagtcggct tccgctgggg atggatcgca ggtaggcgcc ggcgcggcct ggggaagaac    2160
agttgcggag catctgaagc ggaaaatcca agcagatgtg aggcgatccg ggcccgcctc    2220
gttcctcttg gggcctgaat tcttccaga taagtttcct aatggaacat ttctaagagg     2280
tggggtacga ggcggcttgc tcgcacgcgc agtgggacag actgcgggtg gggacgtact    2340
gagaggtccg gacctcaatg cgtccgaccc gtctccacac cgcccttttc cagcccccag    2400
```

```
tctcctttca ttccctactc ttcaggctcc tttggggcca gtgggtgaac cgccatttag   2460
aacggtgcct cggactcggg ggtcgtgcgc tccatctctg cctcccccct ggggcccgcg   2520
aggctggtcc gggctttctg agctgggcgt tcggctttag gcccaatacc tggaccagga   2580
atttcttctc cccgcgccag aagggaaaga cataggaggt gtcccaatct gcggtcaccg   2640
ccgatgctcc tgaccactct agtgagcacc tgcccggtac ttttccattc aacagagct   2700 tccagcttca tactaactat cccacatacg gcctgtgggt attagctcta agtgtccttt   2760
tccgagggcc cgaggctccc cctccagcag ggagagctcc gggacggccc ccaccaaggg   2820
ttgggtttct tccttcacaa ttccacagag gcatccctgt ccttcctacc tgggaaacct   2880
cgaggtgcgg tgcccgtgta cttctggtac tttgcgtggt gccatcaggg accccagagc   2940
cacagctgcg tgtgtgtgtg gatgtgtgtg tgtgtgtgcg cgcgcgcgcg tgtacggcga   3000
aaggatgtgc ttgggggagc cgagtacaca acgtctgctt gggcagctgc tgggcaggcg   3060
ttgggcctgg aggtatctca cacccacgta tcttccagtc ttcaaacacg gcattgctct   3120
gcctcccgta gcgcgcttcg aacctgcctc gcggacacgt gaacagaggc tgtccctggg   3180
aagataagtg cgctttcccg taaaatccgg gaaatttgcc ttgaggaaag tttccgttct   3240
tgttacttgt cgggtttctc ccacttccac ttagccatgt ttctgcgatc tgggtaatcc   3300
ctttcaagcc caggaggaat tctcccgggt ccataattga gggtcggaag ccgtgggggt   3360
gagaaacgca ttaaatcctc ccgaagccca ggaggtgcca gagcgggctc aggggggccgc   3420 ctgcggaagc tgcggcaggg gctgggtccg tagcctctaa ccccttggag ctccttctcc   3480
cagaggcccg gagccggcag ctgtcagcgc agccaggagc gggatcctgg gcgcggaggt   3540
gggtccgact cgccaggctt gggcattgga gacccgcgcc gctagcccat ggccctctgc   3600
tcaagccgct gcaacaggaa agcgctcctg gatccgaaac cccaaaggaa agcgctgtta   3660
ctctgtgcgt ccggctcgcg tggcgtcgcg gtttcggagc accaagcctg cgagccctgg   3720
ccacgatgtg gactccgcaa ggggctaggg acaggcaggg ggagagcccg ggtttgcgca   3780
caccttccag cccctggagg gagcctgctc ggcttcgaac gccttcgaac ttttgacctt   3840
caaaggagtc cctggaaaag gtcaggacg cctgctgcag gcacggttgc cgaaggccag   3900
gccttcctgg cgcaggggag ggccaggga gggaagcgga tactcagtcg ctgtccgacg   3960
gcgagttttc ggagcagcag gctcatgatc ccgggccagt ggcagagca gtgacaccga   4020 gaacccaaat ctccgcgccc ccatccgcgg cccggtgtcc tccggcccc tgctgacctc   4080 caggtcacgc acccccactgc tccacggctc tgcagcctgt ggcacacggc cgagagtccc   4140
cacatgatct cgacgccaag gtaaggaatt gccctgcgtc ctctgagcct gtctctggcc   4200
tggggggccg ggaaagctgc actcctggaa gaggtgggt tatgtgaccg ccgctgcagg   4260
ggtgcgcgga ggactcctgg gccgcacacc catttccagg ctgcgggagc cggacagggg   4320
agggcagagg ggggacaaaa ggactcttta ggtccaaaat gaccctgaag gagagtccag   4380
aatgcccagt ggccgcgtct gcaacggagt cttctttctc caattgcctt ctgccccatc   4440
accatgggcc ccacctgcgc cacctgcgcc caccctgtga ccctggctca gcgaccttgg   4500
cccttaatcg cccaacgccg attcctcaaa attccggctg cgctgaatcg ggctgctttt   4560
gccgccgccc cggcagttgg gccctgtttc cgccggcgcc ctgggagagg cctcaccact   4620
cggctgggct ccctggcccc tcccttcccc tggcctgagc gccctgcgg cctcccgctc   4680 ctcctgagaa ggcgacaatc tctttgcacc ttagtgtttc gaggacagaa agggcagaag   4740
ggtcacttcg gagccactcg cgccgttttc acgtgtgtgt gtaatggggg gagggggct   4800
```

```
cccggctttc cccttttcag ctcttggacc tgcaacaccg ggagggcgag gacgcgggac    4860
cagcgcaccc tcggaaggct cgatcctccc cggcagggcg cctggccaac gagtcgcgcc    4920
gcctcctctc ggccgcgcct gctggtgacc ttcccgagag ccacaggggc ggcctcggca    4980
cccctccttc cctcgccctc cctgccgccc atcctagctc cggggtccgg cgaccggcgc    5040
tcaggagcgg gtccccgcgg cgcgccgtgt gcactcaccg cgacttcccc gaacccggga    5100
gcgcgcgggt ctctcccggg agagtccctg gaggcagcga cgcggaggcg cgcctgtgac    5160
tccagggccg cggcggggtc ggaggcaaga ttcgccgccc ccgcccccgc cgcggtccct    5220
cccccctccc gctccccct cgggaccca ggcggccagt gctccgcccg aaggcgggtc    5280
tgccataaac aaacgcggct cggccgcacg tggacagcgg aggtgctgcg cctagccaca    5340
catcgcgggc tccggcgctg cgtctccagg cacaggggagc cgccaggaag ggcaggagag    5400
cgcgcccggg ccagggcccg gccccagccg cctgcgactc gctcccctcc gctgggctcc    5460
cgctccatgg ctccgcggcc accgccgccc ctgtcgccct ccggtccgga ggggccttgc    5520
cgcagccggt tcgagcactc gacgaaggag taagcagcgc ctccgcctcc gcgccggccg    5580
cccccacccc ccaggaaggc cgaggcagga gaggcaggag ggaggaaaca ggagcgagca    5640
ggaacggggc tccggttgct gcaggacggt ccagcccgga ggaggctgcg ctccgggcag    5700
cggcgggcgg cgccgccggg ttgctcggag ctcaggcccg gcggctgcgg ggaggcgtct    5760
cggaaccccg ggaggccccc cgcacctgcc cgcggcccac tccgcggact cacctggctc    5820
ccggctcccc cttccccatc cccgccgccg cagcccgagc ggggctccgc gggcctggag    5880
cacggccggg tctaatatgc ccggagccga ggcgcgatga aggagaagtc caagaatgcg    5940
gccaagacca ggagggagaa ggaaaatggc gagttttacg agcttgccaa gctgctcccg    6000
ctgccgtcgg ccatcacttc gcagctggac aaagcgtcca tcatccgcct caccacgagc    6060
tacctgaaga tgcgcgccgt cttccccgaa ggtgaggcct caggtgggcg gccggggacg    6120
ctggggagcc cggcggcccc ggcccaggcg ggaagcgcaa gccagcccgc ccagaggggt    6180
tgccgcggcc tggcgtccag agctggggcg tctgagggag gttgcgtgag ggtcttcggc    6240 ttcgcgctg gcttggggcg aggggccagg gccttggcgg cccaggcgac caaaccctct    6300
cctggtccag ggctgggtga gggcgaatta cgaattgttc caggggcagg cagtccccca    6360 gccgcacgg ccagcgagtt ctttctggtt ttgttctttc tcccttttcct ccttccttcc    6420 ttcgccagtg cattctggtt tggtttggat tttttctct ctttctttcc tttctttctt    6480
tctttctctt tcttttcttt tctttcttcc tctttctttc attctcccct tccttccttc    6540
cttggccccc tctctccctc cctccttcct tccttccttt gccaatgcat tggtttgttt    6600
tctttccttt tctgctttcc ttcctttctt tggaagttca tctctggtttt gctttctttc    6660 tttccccatc ccttcctttc tttatccctc cttcccttcc tcctttcctt tctacgattc    6720
cctttatttt tccttcattc ctccctcttt ttgtctcttc tggaggaggt gaaggagggt    6780
cagcttcagg cgctgcgagt cagcggggat cacggtgagg cccaagcact gcaggctgag    6840
gccacagagc gaacacttgt gctgagccgg gccctctcgt gaggctgggg tgcgggaagt    6900
ccgggcagga gagacccgcc cccgccgttg ctgagctgag acccggctga aagagagggg    6960
tccgattaat tcgaaaatgg cagacagagc tgagcgctgc cgttcttttc aggattgaaa    7020
atgtgccagt gggccagggg cgctgggacc cgcggtgcgg aagactcgga acaggaagaa    7080
atagtggcgc gctgggtggg ctgccccgcc gcccacgccg gttgccgctg gtgacagtgg    7140
```

```
ctgcccggcc aggcacctcc gagcagcagg tctgagcgtt tttggcgtcc caagcgttcc   7200
gggccgcgtc ttccagagcc tctgctccca gcggggtcgc tgcggcctgg cccgaaggat   7260
ttgactcttt gctgggaggc gcgctgctca gggttctggt gggtcctctg ggcccaggag   7320
ctgggagggc tgcgccggcc tctggagccc cgggagccag tgccgaggta gggagacaac   7380
ttccgccgca gggcgccgga cggtcggggc agagcaggcg acaggtgtcc ctaggccgca   7440
gggcgcttcc atagcgccat ccccaccagg cactctactc gaaatcggaa agctcgacct   7500
tttgcgttcg cctctgccaa gcctgttatt tgtgctggcc gctgggtctg gagctgcgct   7560
tctcggcccc tccccggtgg agcgcagagg gctggtctgc aagcgcggcc tccagccccg   7620
cggctccccg gcccaggagc caggcgcggg ctgacccggg agcacccggc agcggagggg   7680
gctggaagcg gaccctaggc ctctcctgtg ccaccggcc ctaccgcgcg gccgcggggc    7740
gctctcctct cgggcgcagc ggtccttcag cccagggcag gttcctccct ttcctactcg   7800
gaacgtggca aagataccc agtcccagcc cctccagctg agagctgttg cccaaggtcg    7860
tcgctacttg tccgctcaat ggtgacccct tggcagagaa ctaggdatga ttccactccg   7920
gttgatgttt taggggaaat taaaagaaca ttcggttttc tgagtctcct tccggggagg   7980
cgtggtggta actggtttgc tgggaagagc cgttccttaa ccgcatgcaa caaagcaggt   8040
gtggaatccg gacgagaggg cactcactgc cttctgcccc ctttggaaat agaaaaagcc   8100
ttcgaagcag caatccaaag atcaaatgat ttgcggtcaa tgatttcaat taaaccagaa   8160
attagtaagg gagggccgag aagacacggc tgctcagaag ctgttcgctg tttgagggat   8220
ttcccggaga gcctgttaaa agatgcgaag tggtgggtgt accgctcagc caccttttaaa  8280
ccggctctgt gcgttctggc tctggaaagc aagtctccag gcatttgggc tcagaattgc   8340
tgggccccga gtttgggcgg gggtggtcct tctgggggtc aggccttgag cagcttgcac   8400
tggtggcagg tttgggagca gttgaggggc ttcctgtgtg tcttttggag ggggtgaccc   8460
tggaagttgg cactctggaa gggagctgtt tggccctaga gttttggaaa gggccctgaa   8520
cctgttcggt cccccctcgga aagggaaggg agcagtggct tagtccctcc ctcctccatt   8580
cgtgcaatgc ctggggtagg ggtagacctg gagccggtgg actcatatcc ttggaattcg   8640
tcaggacagc tgctccgggg ccttggccct cagtcagtct ggggctgagg agtagggaag   8700
ctgggaactt ggggcagagg aagaagatgc gtttagaaag acctccatta tgcaaactgg   8760
agtccattta tgcaaactgg tcaccctccc agtagctcca aagagtggca gtggagtggc   8820
atcttgattg atttaacctc ttctcagggg acctgggtct gcgagggagg atatggctgc   8880
ggggttggaa taggatctgt ctgagctgcc agggtcaggg tggtggccct agggaggttt   8940
tagggccagg gtggtcccgg gctgtggcag gggctctcag atcgcctcgg gctctcagct   9000
gcaaggtgaa aaataccatg aggaattgat ctgccaaggg cggtcttgtc tcaaagcaag   9060
tggattgctg gggtaaagaa tctagagacc agcttaggac tctggagga agaaaaaaaa    9120
aaaaagaata gcatagtcct aaggaactgc aaggatcacc agattaaccc ttcatacctg   9180
gggaaattaa ggccagacat gacacaggcc tttcccaagg ctctgtagca agggcaatag   9240
caggccagtt gctgccactg cggtcctgtg gggcatgttc tcactccact gcacccagga   9300
ggctgccagc ctctgttcct tttaacatag atctcctcag ttgttaagac agaaagagga   9360
actcagaggg gtccctgtgt gcaaggcaga gggagaccac cagaaccagg gtaagcaccc   9420
cacttggtag ccagttcaag gacttgggga tgttttcaac atttacagcg aggtttgagg   9480
ccccattgtc atgcagcgct actcggcctt ggtctcctta tctgtaaaat gggcccatta   9540
```

```
gcaatgcaca gggttgctgt gatgaagggt gaggtcccac aagcaaaagc tgtgcagtga    9600 gggggggaatc ctaagcattg ttcctatgcc attcacccct tcctgtgagc tccccatatt   9660
ccctggctca aaggagtctt gaatggcagg gatggaggac tcactgcctg gactttgaag   9720 accccctgctt tctgggtgac cacctttttct tcccctttgac agtgaactaa tacattggag  9780
gtagatagtg ctgggaagag gacaggagac cacggctgac tttggacatg ggctcgaaat   9840
tgataacttg atgagtcttg gagggtggtt aagataagct cggggctggg gcagcgctga   9900
ggtctgatgg tcagccagcc ctccccaaag tgtggccctc cgttctggag atagggcttt   9960
tggaaactgc aaaagcgtcc tggcaggcca gctctggttg ctccctggcc atagctgctc  10020
tgactacagg cagcaggacg caggtcggcc tctgcccatc ggaggtcaga ggcagggcct  10080
ccagcaccag actcagcagt gccactgcaa acctggcaca acaggctggt cccaggactc  10140
agctcagcag tgaagttgga accaaggtt gagtctcccc atctcccttt ccccaacccg   10200
aaagacccaa gatgggtgtg ggtgaaagag ggagaaagaa ttgctactcc agaaactgtc  10260
atttgcccac acgaaacgag gtggggttca aggtctgaac tcttccagtg cctgggtgcc  10320
tttgggttta aattcagctg caggtgcccc catcaccact tccacctgag cacaccacga  10380
gaagccaggt tatcttagaa actgtttccc ggaatcaaag cgacttgatt tggagagttg  10440
ggtgaggaga aactcacccc tatcccctc agggcgtcag agatgtgagg caattctcta  10500
cctccgctgg aaaaaatgca gatttattaa aggtcgactg tttagcagaa caacgtagat  10560
tttttacaac gctttccccg tctctgcttt gaagcctgcc aggctgcagc tgggatcca   10620 ggagggaaag cccgcaggcg cagaggggac aatccgggaa gtggtaaagg ggacacccgg  10680
gcacagggcc tgtgctttcg ttgcaggcga ggaagtggag cgcgcgctgc agattcagcg  10740
cggggctaga ggaggggacc tggatccctg aaccccgggg cggaaaggga gcctccgggc  10800
ggctgtgggt gccgcgctcc tcggagccag cagctgctgg ggcggcgtcc gaactcccca  10860
ggtctgcgca cggcaatggg ggcaccgggc cttctgtctg tcctcagaat acgtaggata  10920
cccgcgggcg acaagccggg ccaggctagg agcctccttc cctgcccctc cccatcggcc  10980
gcgggaggct ttcttggggc gtccccacga ccaccccctt ctcacccggt ccccagtttg  11040
gaaaaaggcg caagaagcgg gcttttcagg gaccccgggg agaacacgag ggctccgacg  11100
cgggagaagg attgaagcgt gcagaggcgc cccaaattgc gacaatttac tgggatcctt  11160
ttgtggggaa aggaggctta gaggctcaag ctataggctg tcctagagca actaggcgag  11220
aacctggccc caaactccct ccttacgccc tggcacaggt tccggcgac tggtgttccc   11280 aagggagccc cctgagccta ccgcccttgc aggggtcgt gctgcggctt ctgggtcata   11340
aacgccgagg tcggggtgg cggagctgta gaggctgccc cgcagaaag ctccaggatc    11400 ccaatatgtg cttgcgtgga gcagggagcg gaagaggcag ccggtcctca ccctcctctc  11460
ccgccacgca catatccttc ttgacttcga agtggtttgc aatccgaaag tgagaccttg   11520
agtcctcaga tggccggcaa cgcgccgagg tcacgctccc cagaaacacc cctctcccct  11580
cccctacccc agctcccccct ggggcgggtg gtaattgggg gaggagaggc cgcaggcagg 11640
gaaggggtgg gaaagccaga gagggaggca caaagtgatg gcagcccggc aaacactggg  11700
gcttcgggct gggccgcgct cgtttaatcc cacaaaaatc ccattttgga ggtgagaaat   11760
agaggttaga ggtcgggccc ttctggagat cagaccgagg agacgggccc agctggcgtc  11820
ttaaagcaag gaggggagt cgggaggagg tgagacccct gcacccaggt ggggctccca   11880
```

-continued

```
aaccgttctg gatttaccac actcccaggt ccgattttcc atggagggct ggggttaggg    11940
actggcacct tcttgttgtt aaccgcattt gatattcaca agaaccctgt gaggagactt    12000
tgtcaccgtt tttagatgcc tgaggttgcc ggaggggcag tgagagaatc gtctaacctg    12060
gtgttcctac cacagtccag gccctgtgtc ctgggctgga cccacagccc ctgccaccac    12120
ccagaggaag gcgcgaagct ggctgcctcc tttacgggtc tcccttaggt gccctcatga    12180
aggggggacgg ccacctcaca gtgcaggaac tatctcccg tttgctccca aatagtcttc    12240
ttggtgtggt gctgtctatg gtctgtgacc tgcatctgga gttaccccca ggaccagctt    12300
cggaagagga gggatcgctt ggaggccgtg cagtgtgagg aacggcaggc agggtgtggg    12360
accaacatgc acacactcgc aggtgctggg gccagggagg aatgaggcgc tggctcccct    12420
tccctccatt tctccctggg ggtcccagca acctggccat ccctgacttc caacagcaca    12480
gcgtccccac aggtcctgca gtgctctgca ggggtgcagg gagctcccct cccccagcc    12540
gcaacctcac cttcctcacc cccacccctc cggcaggaaa ccacaggctg ggttggggac    12600
ccctggtgct ccaagagagc agtgagtgct gggagccgct aaccccgagg cgcctagcac    12660
agactcttct cacccctat ttctgaaata aagcccttcc ttaggtccag atgaggacca    12720
cgtgctcagt gcctcacttt cgtgggagtg tatatcactt tacagtatca agacaatttt    12780
ctttcgttac aaatcttat ttagtctctg cgtttagacc aaagtagatt tttatgggct    12840
gagtgaaaaa acctcgcccg cattggtttc tgatggaaca gctggcagcg ccacggcccc    12900
gggtggggtg gcctagaggc aggggtgctt gggaggaaca tctagcaccc gaccacctcc    12960
accaggtggg aaagggacgt ttgcaccaaa tctccgccgg caaagcagag ctttgggga    13020
attacagaaa aactataatg atctaaaaga gaacaagtta tcttgaactg tgcgggtatt    13080
tgaatcatac agaaaattgt cctgtgtgcc caatgcactt ttgcatgtag agccagggcc    13140
ttcgaggaag ctttcaggag atcccgggca gcggagtctg gtctggagtt tcatttccgt    13200
aggtgcagat ttctccccaa gtcttcccgc catgggcttt gcaagaagcc agggcccaga    13260
ggccacgctc accgttaaca ctgcacaggg caaaggtggc tccaggacaa ctgcccaacc    13320
ccaggaacga cccagcagca gagaaaagga cagctgccag ggtgcctttg tcgctttttg    13380
gaaatcagaa ttcctgggtc cttagttaag tcttacttca ccaaatccca ggaccttcac    13440
attttggttc ttgccattgc taacagttgt aaatgctgcc gccacgaggc ctgggaggaa    13500
ggacccgctg gtgagagcac agggagtgct gctgtgatca cggtggtgat gcggggtgag    13560
cgcgatttcc cgggattaaa aagccaccgc tgccccccgtg gtggaggctg ggggcccccg    13620
aataatgagc tgtgattgta ttcccgggat cgtgtatgtg gaaattagcc acctcctcag    13680
ccaggataag cccctaattc cttgagccca ggaggagaaa ttaaaggtca tccctttttta    13740
aattgaggaa tagtggtttt ttttaacttt ttttttttta ggttttagt tgccgaatag    13800
ggaagggttt gcgaagccgc tgccctgggc cgaggtgcat tttacgcttc cagaggtcga    13860
ggcctccaga gaccgcgatg cccagggcgt tcccggggag gctgagagac ccagggtgct    13920
ctgggtgact gcacggcgac tcctcgggaa cccactcgtg gctgcccgct tggaagggct    13980
ttgcggcccc gggaacgatc tccaggatct ccacggctgg tcaggttccc cgtcccctcgt    14040
atcccgcgct gcccgggggc tcctgccttt ggttcagtgc tcgcggcacc accgcactca    14100
ggacggcagt ggggggctgg ggctgggggct gggcctggcc cagcgtgggt tggggcgggg    14160
gacgcgccag cagcgcccgc agctcgctcc gcagggggtcg cagccagggg tcggagcta    14220
ggctcgtggg ccgggagacg ccgggcgcgt tgtcctccgg ggaggttggg gtgcaggcgg    14280
```

```
tgcaccgacc ctcgccatct ggcgctgcag ccaccagcca cggcgcttag tggagggtct    14340
gcggccaggc tcccggcgga aagattccgg ggagggctcg ggggttgtcc cagcccgcgc    14400
taagcgccgc agcctcgccc ggctttcctg cttcctcgga ctgtgcaggg gaagcctggg    14460
gtctcgcggg gcgcagcagt caggtcgagg gtgcagcagg aggggagtcc tgacgggcag    14520
gtccctcttt ccoctggtgc gcaacactgg ttggtagctt ttgcggaggt ggtgaagaag    14580
ggcaggaggc ctgttgagcg gaggagtccg gggatcccta attatgtgac aggagaccct    14640
ttccagttcg gcctgtggcc catccctctc tcaccgccgg cagattggag tctgctctcg    14700
gggagccccc aggtaaaccc ctcacaggga aaggtttcg gattggaagg aggaccgcgc    14760
tcgtggggcg cctgtgagag ctgggaagcc caaggggtag cgtgtagggg gttttttatg    14820
cgggaggagc tgcctcctgg gcggcgggga ctttctgtct cagcctgtct gcctttggga    14880
aaacaaggag ttgccggaga agcagggaaa gaaaggaggg agggaaggag ggtccttggg    14940
ggaatatttg cgggtcaaat cgatatcccc gtttggccac gagaatggcg atttcaaagc    15000
agattagatt actttgtggc atttcaaata aaacggcaat tcagggcca tgagcacgtg    15060 ggcgacccgc gggagctgtg ggcctggcag gctcgcacag gcgcccgggc tgccggccgc    15120
tgcggggatt tctcccccag cctttcttt ttaacagagg gcaaaggggc gacggcgaga    15180
gcacagatgg cggctgcgga gccggggagg cggcggggag acgcgcggga ctcgtgggga    15240
gggctggcag ggtgcagggg ttccgcgtga cctgcccggc tcccaggcat cgggctgggc    15300
gctgcagttt accgatttgc tttcgtccct cgtccaggtt taggagacgc gtggggacag    15360
ccgagccgcg ccgggcccct ggacggcgtc gccaaggagc tgggatcgca cttgctgcag    15420
gtagagcggc ctcgcggggg gaggagcgca gccgccgcag gctcccttcc caccccgcca    15480
ccccagcctc caggcgtccc ttccccagga gcgcaggca gatccagagg ctgccggggg    15540
ctggggatgg ggtggtcccc actgcggagg gatggacgct tagcatgtcg gatgcggcct    15600
gcggccaacc ctaccctaac cctacgtctg cccccacacc ccgccaagg ccccaggact    15660 ccccaggcca cctgagacct acgccagggg cgcctcccga gcgtggtcaa gtgctttcca    15720
atctcacttc cctcagcagg ttccacccag cgcttgctct gtgccaggcg ccagggctgg    15780
agcagcagaa atgattgggc tgctctgagc tctgaagcat tcggccgctg tgtgtgtgca    15840
aggggcgcaa ggacggagag acagcatcaa taatacaata ttaacaggag cacttgtcca    15900
gagcttactg caagccacat tcagttccgg accttattga cttccccctc ccatctagag    15960
tggattctgt ttttcaatt tgtttttgttt tgtttttgt ttgtttgttt gttttgaga    16020 cggagtctca ctctgtggcc caggctagag tgcaatggcg cgatctcggc tcactccaac    16080
ctccgcctcc cgggttcaag cgattctccc gcttcagcct cccagtagc caggattgca    16140 ggcacccgcc atcatgcctg gctaattttt gtagagacag ggttcaccc aggctggtct    16200 cgatctcctg acctccgatg atccgcccac ctcagcctc caaagtgttg ggattacagg    16260
cgtgagccaa cgcgtcctgc cttgattctg ttttaactc cattttttag aggaggaaat    16320
tgaggcacag agaggttaaa taacatgtct aaggtcacac agcaagggt ggagcggagt    16380 tagcccactg gcctagctct agagcccacc cggataacca gaacttggtg aggcctccgg    16440
gctcttgctt ggtttggagc caggtgctta gcgccccgag cccggggcca ttcaccctgc    16500
aggagctgca cgcgccctg acctcggctt ttccctggca gcagagggc tttgcgggtc    16560 ggccgggtag ccctgagcac agctcgccac ttccaggtgg gctgttggcg ctggctgggg    16620
```

| | |
|---|---|
| acacatcccg atctttcaaa tgcccttac agagcctcat caacgacccg attcattccc | 16680 |
| ccctcctgtc atttgtctct gccatcgaaa aatgcctacc gagagctgct ctgcatttcc | 16740 |
| gccctctatt ttgtgtttta ctttaaaata ataataaaaa aaatgttggc tgcaggacgc | 16800 |
| catgacttag gtcagcgagt cagccgctag ctctgcattt ccaaaaagca gatcttttca | 16860 |
| caactctctt gccccaagtg ccctggtgtg gtttatttt taaaatgcat gcctgcggaa | 16920 |
| gagaagaccc ggggaatatt cgaaaccccg agcttttaca acataaagcg catggtgtgg | 16980 |
| ccgcggcgag taatggcgct | 17000 |

<210> SEQ ID NO 165
<211> LENGTH: 1500
<212> TYPE: DNA
<213> ORGANISM: Homo sapiens

<400> SEQUENCE: 165

| | |
|---|---|
| caaatcactt gaactcaagt tcaagaccag cctgggcaac atggtgaaac cacatctcta | 60 |
| caaaagtaaa gaaaattagc caggcatggt gctgtgtgcc tgtagttcca gctactcctg | 120 |
| gggaggtcga ggctgcagtg agccgcaatc acgccacttg tactccagcc tgggcgacag | 180 |
| agcaagtccc catctcaaaa aaaaaaaaaa aaaaaaaaaa aaaaggctgg gtgtggtggt | 240 |
| cccagatact cagaggctga aagggagga ttgcttgagc ccaggagttc aaggctgcag | 300 |
| tgagctgcga tcacatcaat gcactccatc agcctgagc aatggagtga ccctgact | 360 |
| atatttaaaa aaaaaaaaaa taggaagaaa caactcaacc acagggctag tatgttactc | 420 |
| ggttataaaa tgataaagcc ctaaacagag aattagcccg tttccagaag aggccaagaa | 480 |
| cagatgatac agctgaactg aactcctgcc tgtacagctc gttttctaca agattccaga | 540 |
| cctggaagat gatggcatcc agcccccatt gaagcacctc gaacaagaaa aacgccgagt | 600 |
| ccgaagagcc aggccttgaa cacacgattc ctgtctataa ataactcccc ctggggaata | 660 |
| aaaagcagga tccaaggcag gaaacccgag ccgtggaatc tggtaagttc ttaggaaacc | 720 |
| cactcacggg cctgagtccc ccgtggaagc ggcgacttcg gcacctggac acccgagtcc | 780 |
| ccagagcccc gggcggccgc gcgtccctac ctgcaggcct gataccggcc gcggagcgct | 840 |
| cctggccccg ctcccgccag gctccgggac cgctgaaacg cacccagggg ggtgaaggcg | 900 |
| tagtcgccaa ggacagcgca gatggcagcg gaggcatggg agccggaacc taccgtggca | 960 |
| aagggccagg tcgggacgcc cctcggcgca gccccaaatc ctgcccgcgc ccagccccg | 1020 |
| ctcaggccgc gccctgcca cctctggcca cacgggctga acgtctggc tcctgcacag | 1080 |
| cgcacttccc gctgcccttc tccactggct gctcaggccc tgcctcgcca gcacggcatc | 1140 |
| cgcgggggat ccctacctgt cctttagggc ttgcctcata ggtcaaacgt cacctcccag | 1200 |
| ggaggtatgg cctgccccct ggccaggtgg gcccttcca cgctcgcctg caacaccacc | 1260 |
| cacccacctt gataactgct tgtaaaggtt gtactgcttt ccccccttgag actgcaaacc | 1320 |
| ttcaagggca ggaaatgggt ctgttttcct ggcaaaataa tgaagttggc ttaaggtttt | 1380 |
| gctgaataaa atgagtgaca gacaaaagta gccaaatttg gcactcctga tgggttattt | 1440 |
| gatgaaggag gtgcaatgta tgggcttaac tagttattct ggatttcttt ccccatgtta | 1500 |

<210> SEQ ID NO 166
<211> LENGTH: 200
<212> TYPE: DNA
<213> ORGANISM: Homo sapiens

<400> SEQUENCE: 166

| | | |
|---|---|---|
| caaggccggt gcacgcggac ccgaggattc ggtagatgtc cccgaagacc cgctgccgct | 60 |
| ctaaggcggt ggaagcgaga ttctccggaa acccagggaa tccgatgctc gcacaggacc | 120 |
| aaagcccgag gccgcgggga ccacagaggg acggagaagc cgggactcct cacatcccac | 180 |
| atccggcagg ggaagcccag | 200 |

<210> SEQ ID NO 167
<211> LENGTH: 2000
<212> TYPE: DNA
<213> ORGANISM: Homo sapiens

<400> SEQUENCE: 167

| | |
|---|---|
| ctgataataa agttttacca ttttataatt taaaaatgta aatatggagt tgggcatggt | 60 |
| ggttgggagg ctgagaccag aagatcgctt gagcccaggg gtttgagacc agcctgggca | 120 |
| acatgcagaa accctgtctc tacaaataaa aaattagcca agcgtggtag cacgcacctg | 180 |
| taatcccagc tactcgggag gctgaggcag gagaatcgct tgagcctggg aggtggaggc | 240 |
| tgcagtgagc tgagactgta ccactgcact ccagcctggg tgacagagtg aggctctgtc | 300 |
| tcaaaaaaac aaaacacaaa aaaacaaaca aaaaaaagca aatatatgta aaaataggaa | 360 |
| gtgcggtttc ccaaaatgag gtctgtaaac aactgatcta gaaaatgttc tggaaaaagt | 420 |
| aaaaaaggat caggatctga ggtcaactga cctctccctg cgctctggac aggcaaacag | 480 |
| gcaaggttcc ctctgaggcc gtagcggctt ctcgtgggcg agtccctgtt cgcaggtgac | 540 |
| gtgtggacca cgctcttccg aagcgtctgg cctgtgtgct ctcggggagg ggacgcaggt | 600 |
| cagcccacct agccgatggc taacaagtca gtttgttttc tgaacggaag cttaaaccta | 660 |
| gaaaagtaac tgggttgggg tggggtgta gccacatgca gtaaaagcac tgcctgtctg | 720 |
| tataacaacg acctgatgaa aaaggaacg cgtgaaatgg ggagtgttag ggcgtcacaa | 780 |
| actccagtgt ggttgaaatg aaagcagaaa gcaaatggca agctggcttc cccttccagc | 840 |
| ttttcacaac cctgccttgc tcatggtcag ccccaagcac gggcggaaga aaggactgga | 900 |
| gggggagggaa aggggtgggg agcgagggta ccagaggcgt gggaggacgg ggacaaaggg | 960 |
| gcagcaaggg accggcggaa aggaaagtcg gcgttagctg gattggaaac agtccagaca | 1020 |
| gaacgatggg ctctgctgcc tccgggtggg gcaccaagcg gggagcgggg ccacgaggca | 1080 |
| ggggacagtg aagcaccatg cagcgcccac cagccggcag cgcccaccag cctgcgctgc | 1140 |
| gctgcacatg gtacccgcgg ccccagctgg ccagtgtgtg gcggagatga gaccctcgtg | 1200 |
| aagagactaa gcggccacag caggggaag ggttgctcac ataacccat actgctcaca | 1260 |
| ctacgaggtt aactgccgtg agatctgcct gcagccagca gaaacccgtt ctaggaaaac | 1320 |
| gttgcccagt gacttcagtg agtgccactg accggcgc ctccgccccg gcgtccggca | 1380 |
| gcagcaccga ttgcgcagga ggcaccttgc aaacaacctt tcctgatccg cgctgcagtt | 1440 |
| cccaggccgg ttgcagccgt ttcacagaga ctgcgcacac aaagcgtctc cgtgccctgc | 1500 |
| cattcacctt tcgacacagc cgcaacccct cttttcagtg ttaaaacctg cgccaaaag | 1560 |
| gaacatgcga tgtgacgtgt tacctctgcg catgcgccgg gcattcccag cgccccgaac | 1620 |
| ctgatgaacg cgcggtgggg accccaggct tccgtgcttt cgttttcctg gaagctacgt | 1680 |
| gtcctcagtc tacatattgt tacctggaaa ataaagtttt ctccttttt cttcctttgt | 1740 |
| taacaggcag aaggtgtagg ctgcaggttt cgggcctaag agagggcatg gctgcgaca | 1800 |
| cggagtagac tcctagatga cataacgag gcgagtctgc accgggggact cggcattagg | 1860 |

```
aggaggcaga ggaaaagccc accaccgtgg ccgagggaga tctagcaagc agcttgcagg   1920
gggtgaagtg tgtgcaaagc aggctgagac ctgtccagta tcgaaacacg ccgcggtggt   1980
caagcaggct ttaccatgct                                                2000

<210> SEQ ID NO 168
<211> LENGTH: 700
<212> TYPE: DNA
<213> ORGANISM: Homo sapiens

<400> SEQUENCE: 168
tgaggctcaa acaggtgtc tgtgagcttc acaggcggta aggccgtgtc tacatggccg     60
ggacatgcat cccggggctg cccctgccgt gctgcccgag tgcacggggg atgaggacct   120
gacaaggcca ttgatcttgc gggagcttcc tgaactactc cagcgtgaaa atcttccaga   180
aggattctcc acagggcaat gaggcaagaa atttacagct tagcctgatt aatgggccag   240
gcagttaaga gttctttgcc aagctatgag cataatttat agtcatcacg gcaggaggaa   300
aggccacata actcacatcc ttaaagggcc cttagaacaa gagacacgcc ggatcattga   360
aaacgtctcc actcctggcg ccaaaagaga tcggcacgtt tctgggtatt ctggtcaaag   420
aacagggagt ctggattaat atacacggca gaaaaaagcg aagaaaagac acacaggtca   480
tatatttctg actgatattc cgtttgttgt tttcggaggg acttggtatt tatttaacca   540
cattctcact tgcacacgcc cctccccaca ccttgtaaat gccttcctct ttagccgagt   600 cattttttcat cacatagaat tgaaatgttg ccaggaaggc ggtttatgag attgtagaaa   660
tggcactaga gaaagcagtg tgaaaagagg cctagaacgt                          700

<210> SEQ ID NO 169
<211> LENGTH: 600
<212> TYPE: DNA
<213> ORGANISM: Homo sapiens

<400> SEQUENCE: 169
tctctacatg ctatctacta aaaacttagg caaggaaatg catcagacca acacccccac    60
agcacagaga accgaccggc cattgctttc caatctccgc aaacctaacc attgctggaa   120
gaaatcttac tcacagtgca cagacagtag gtattttatt gaagataaac atatagtgga   180
acaaaccaaa ttcccccat ttgagttacg tgagcactca gttctcagcg tggatgtccc    240
acaaatcaag tcaacatttg cgtcccatta ccagcagcca cttgccgagt atctcttcgc   300
ttccactggg actgcctggc atccctgatg ctaaggagcc actgaagagc ctccaaatgt   360
ctgacattca caaacgcatc ttttgctttg acccgaccct tcaacctctc cgagtctgct   420
gccttttctc agacacacat ccaggcaccg ttagggatag ttagagaatc tgaaaattca   480
gaagcgctcc gaaaagcctt tccaaaagta atccacagca ctcaacagtg aatttagaaa   540
ccccaatttt tttctgagtt tgaagttttt aagccttgcg gatggttgga gtaggaaaaa   600

<210> SEQ ID NO 170
<211> LENGTH: 1100
<212> TYPE: DNA
<213> ORGANISM: Homo sapiens

<400> SEQUENCE: 170
tcagacaagc tctgtgcagt cggaattttt taaagatgca ctgtcacttg aggaagacag    60
gtgatcttcc tgcggcacaa atagaagcaa agagatttct cttcttctct gtagagcaac   120
acaattgata aatggccgat aatctccacc aaattggcag cagtaggctg cccgaaggca   180
```

```
gcaggcatat tcgtctttgt gaattgtttt actatgatgc tgtcacattt ccaggaataa      240
gacggttaaa atgatatatt gttgtggttt ggcatttgca gctttgctct gacttccctg      300
gtaactgcca acatctgcaa attattatgt gcttaaaaaa aaaatcaacc gccaccgcag      360
gctgccccca cggtccctgg ctgggccagg cctcctgcca ggccacaggg cagagttctt      420
ggaccaggag gcagcagggt caaaacccag gttgcctagg aagcccccaa agacagttat      480
ggatagagct gggagcccga acacatgcg gcagtctctc agtttccagg taccggttct       540
cacatcatcc atgcatgtgt ttgaggaaaa acaaaaaaaa attgatggtt gccaaaaaca      600
aaaatgcttc catatcaaag tttatcagtg tcaatgtcaa gagacttctg gttcgtagac       660 tcatttggc ttgaggccac cagaagtgaa ctctggtttc taaatgcaga agcagaggca        720
ctggccgatc atgaagatg cagggaactg ttcaagaggc ccaagcctgg tgctcagaaa        780
cttggcagga tcaagcatct cgcccaggaa ttcatcccct gcttgtctaa gccggctggc      840
tctcgtgact gactcggaac aacagagcag atgtttgcgt gggaggcaag cctcacccaa      900
catctgtcct gcggcgggaa ggcctgggtg ttcacagata gagctggagt tccccggtgg      960
gtggcacaga caattagctg gggctgcctc acatgtaatc taattacagg ggaaacaggc     1020
tcaaacaccg ggtgataagc agcgcaactg tttcgggtga ctctgtaatt tttcctccat     1080
taattttctc cataacgcac                                                  1100

<210> SEQ ID NO 171
<211> LENGTH: 250
<212> TYPE: DNA
<213> ORGANISM: Homo sapiens

<400> SEQUENCE: 171
gttgcctggg atatgcttat atcaaaaact tacgtgtcac ttacctagca tttgcatttc       60
actgggcctc ctaaattctg tgtggtaacc gactgccacc ggacatgctg tttacttctc      120
tatcctcacg cagccagttg ccacattcaa cataacactg caaatattgc cggtggatcc      180
tgacttcctc gtggacccta ctgtgtcggg aaaaacaaac aaacgaaccc tggaaggaaa      240
caccatgagt                                                             250

<210> SEQ ID NO 172
<211> LENGTH: 600
<212> TYPE: DNA
<213> ORGANISM: Homo sapiens

<400> SEQUENCE: 172
tcataaatat ttccaaatgt attcctattt gtctctacag agtctaacag acataaatag        60
cgaattgaag gttctgtctt aaacccagc agaaagaaaa acaatgacca gaaaaaaaaa       120
acaattgtct ttggcttccc aagaacagca tcggatttca actggaacca cagatggtcc      180
gttgatagaa gcgactactt tttagctctg gaggacgaca aaaggaacca gcttcttcct      240
gtgggtgtca cagcgaggtc gcctggccac atcaggtacc agagcgagcg ccctcacctg      300
ataggccctg tacaacctca gccacagcac tgtcaggagg aacacgcgga actagcaacc      360
taggagggta aaggcggagt tgggagggaa cacgaggcag gcaggtcggc tggctgctga      420
gctacaggct gcactcctag gacgtctacg tgtaattgag aaaaataaga caaaaataac      480
ttactgtgca ggcaattaat tctggttggc atagcgatcc tcttaagtta aagggaatga      540
gcatgagatg aagagaagta agaggcagaa agaattatgc aagagcaaca tcagagtgga      600
```

<210> SEQ ID NO 173
<211> LENGTH: 2000
<212> TYPE: DNA
<213> ORGANISM: Homo sapiens

<400> SEQUENCE: 173

| | | | | | | |
|---|---|---|---|---|---|---|
| acgccgagcc | gcctctgcag | gggaaaccga | agcagatgtg | gtgagataat | acatccaacc | 60 |
| ctgagtgcta | ctctaacctg | ccagaggcgg | agggttctca | gtgagatgaa | agcattacag | 120 |
| atgcgttaga | tctaagggag | gggcctgcag | atgcgcagct | ggcagagaaa | ccagggaggg | 180 |
| gctgaactgt | cagtcgcgac | caccagggat | ctgaatcagt | tcaccgacag | ccttggggac | 240 |
| attcaccttg | gctccacaa | cctgtcagaa | atgcccccaa | gcccaaaggc | gtcgagagaa | 300 |
| tggccaggtt | gtttcagatt | gacacatatc | ctaatgtaca | agtcagccca | cacacccccac | 360 |
| gtgcactgag | cgtctcttgt | tgttcacccc | aaataaactc | tgccggaact | ggggcgggac | 420 |
| tcgcagggggc | ggagaagggg | ggagacgggc | agagggcaga | agtggatggt | gagaagagcc | 480 |
| aatggagggg | ccccgtgaga | gtgagcaagg | ctgcacccct | aaccgacgtc | ctggggctac | 540 |
| tgtacaaaca | aagaaccaca | ggctgggagg | ctgaacaaca | gacctgcact | ctctcgcagc | 600 |
| tcggaggctg | caggtctgaa | atcgaggggc | tgacagcgct | ggtttcctct | ggaggctgcg | 660 |
| agggagaaac | cgtcccctgc | ctctcccagg | ctctggggtg | agcccttcct | ggcatcccgg | 720 |
| gctcattgta | gatggatcac | tccaatctcc | atggcttctc | agggcttccc | tccatgcacc | 780 |
| tcaaatctct | ctctccttcc | ttttgtaagg | atgccagtca | ttggatttag | gttcacctta | 840 |
| aatccaggat | gatctcatct | aaattacatc | tgcaaaaaga | cccttttttcc | aagtaagttg | 900 |
| acattcacag | gtacctgggg | ttaggattgg | acatatcttt | tgcaggggtg | caggggggctg | 960 |
| ccactgagcc | cgctgcacag | ggtgacctgg | gccaagggcc | cttcactttc | acttcctcat | 1020 |
| tggcaagctg | ccctgtgttt | ggactgggtc | gaggctgtca | accttgctgc | ccctcggagt | 1080 |
| ccccctggt | gtcccccaaa | cagattctaa | gctgctttcc | tggggctgga | ggccaggcat | 1140 |
| tgggatttttt | taaagagctt | cccagcaggt | gagcagcctt | tcatgggtat | caggagacct | 1200 |
| tcctggcaaa | tgtggtgaag | gtccttcctc | ctgagcgatg | ccttagaccc | aggagcccag | 1260 |
| ggaggctgct | cacctgatcg | ttaggacagg | agcagtggaa | acctctggcc | tcagaccccc | 1320 |
| tggaggaatc | cctccctcta | agactctggg | actggtgcac | gcaaggagct | atcgtgaaca | 1380 |
| ttgctcccaa | ctggccgctt | gcttgtcccc | cggctcccct | tggccccagt | ggcggctttg | 1440 |
| cctgaattag | agggcgtgag | agccaccgt | gtctcagcac | tgcaattaaa | gcaggaagcc | 1500 |
| ctttcggaag | cagccgtgtg | caccagcctc | ccatgggtgg | agcagagcaa | accacccact | 1560 |
| tctgccctct | gccttcttc | ccttttctcg | acccctgcg | gccccccagt | ttcagcagag | 1620 |
| tttatttggg | gtgaaaaaca | agagatgctc | agcgcctgtg | ggatgtgtgg | gctgactcgt | 1680 |
| acattaggat | gtgtgtcaat | ctgaaataac | ctggccgtta | tatggatgcc | ttggggcttg | 1740 |
| gggggttttct | ggcagtctgt | cgagcccgag | gtgaatgtcc | ccaaggctgc | tggtgaatca | 1800 |
| gatccctggc | gttctccgtt | ggcagttcag | cccaacagtt | tctctgccgg | ccgtgcctct | 1860 |
| gcaggtccct | cctctgatct | gattggatta | atatttgaat | caatagactg | agtcaagcag | 1920 |
| aatgtgggtg | ggcctcatgc | aatcagctga | agccctgaaa | agagcaaaag | ggctgcccct | 1980 |
| tcccccgagg | aggagagaac | | | | | 2000 |

<210> SEQ ID NO 174
<211> LENGTH: 200

-continued

```
<212> TYPE: DNA
<213> ORGANISM: Homo sapiens

<400> SEQUENCE: 174
gaatgttcaa agaaagagcc ctccttgcct tcctcttctt ccaccctgc cctctgcaga      60 ctggggttct gtagaccccc aaagtaagtc cgccacaccg gaaggaagtg agttacacag    120
gggcccacat gggaaccgct ttttgtcctg tcttggtggg aaaatggcca cgaccccagc   180
ccaggctctg ccacgccaca                                                200

<210> SEQ ID NO 175
<211> LENGTH: 400
<212> TYPE: DNA
<213> ORGANISM: Homo sapiens

<400> SEQUENCE: 175
aggcagcagg gttaggactt caacatacaa cttttggggg gagatgtact tcagcccata    60
acacaccacg tgggaggata acaccgattt cagagcttgc agaggaagcc gccaggaact   120
ccagtgagac atcagccccc aggtgcctgt caggcacgcc gggctgtggg gggcacctgg   180
gcccatctga gtaacggagg cgcatccgca cttcccccag gagtacattt ttagaaccca   240
cagcgccata aaccaaagac aaggagactt cctggtgccc cgtcagcttc tggaggcgac   300
gttctcggct gacagctctg gcagcctccc ctgtaggtga gagacaggta aatgggactc   360
ttgcttccaa aacggaacag ggtaaaaatt ctcaagcgtt                          400

<210> SEQ ID NO 176
<211> LENGTH: 300
<212> TYPE: DNA
<213> ORGANISM: Homo sapiens

<400> SEQUENCE: 176 ttaaaggga gtggttgtat gaagagttcc tcagtcaaag gtgtgcagct gggaagccca    60
ccccacctaa gagggaggtc tgacaaactg tccacactga accactcaga cctgcatcag   120
ggccccgttt cttccataag ccgccaagta cagccctgag tcaactgaac tcaggcctgg   180
gaggcttccc aaagctgact tgactcagct ttgaactgaa atgaccgtac catgacaacc   240
ctgatgaaaa gctaaactga gcccaattat tcaacagtaa aattcagttg gtctcactca   300

<210> SEQ ID NO 177
<211> LENGTH: 450
<212> TYPE: DNA
<213> ORGANISM: Homo sapiens

<400> SEQUENCE: 177
tgctaccagc tgcttgggct tgggcaagtc accctagctc tcagatgtca tctgtaaatg    60
atgacaatgc caatgtggca ctgttctgag agtcagacag aacgtatgtg tgcttcacat   120
atggtgctca tgaagtgcta tcattatcta aggaaaacaa aaaacgaagt tcagagtctc   180
tctaaacgca tgacaccaga ccaacaggga gtttcaaaaa ataggtctga agtaaatcaa   240
ttctcctggt ctcaatacac tgaaaacaaa ctattagggg actgaccgaa cccaccttag   300
gaaccacctt acgtcaccttt ctgtctctac tgcaaaaccc tccctaata ctgttcaaat    360 acgctgacaa tccagatcca tatccaatgg aaccagcaat catgcctgtg tgccagcaat   420
gtcagggagg gaagccgatc tctgatgaat                                     450

<210> SEQ ID NO 178
```

```
<211> LENGTH: 1300
<212> TYPE: DNA
<213> ORGANISM: Homo sapiens

<400> SEQUENCE: 178
caagcctgtg gtagggacca ggtcagagta aacaggaaga cagctttcgg ccaggcggtg     60
cacctcggtg ccggtgagtg tgagcgtgtg tgcgtgtgca cgtgtgcaga tgtgtgtgga    120
cgctcccttc tccgcagcag ctcctgaccc cctgcaggtg accctcagcc agccccaggg    180
ctgcccccac tctcccctgt ggacacctac ctcatttggg gtgaagtggg gggactgggg    240
tgtgaggggt gctttggggg gcacacttcg acccctctct ctgcaggcca agtcctgagg    300
ctcagttttcc tcctctgtgc cccggcgacg tggtgcaggc ctcgcgagtg acgtgagggt    360
tcatgaccca ggtgtgggca gccagcccctt cacgggaggc cacccacctg gccacagtgc    420
ctgggaattt aggtcgggca ctgccgatat gtcgccttcc acaaggcggg cccgggcctc    480
tgctgaccgt gcaccggtcc tggggctggg taattctgca gcagcagcgc agcccatgcc    540
ggggaatttg cgggcagagg agacagtgag gcccgcgttc tgtgcgggaa ctcccgagct    600
cacagagccc aagaccacac ggctgcatct gcttggctga ctgggccagg cccacgcgta    660
gtaacccgga cgtctctctc tcacagtccc cttgcgtctg gccagggagc tgccaggctg    720
cacccccgcgg tggggatcgg gagaggggca gtgtcgccca tccccggaag gctgagcctg    780
gtgcagccag ggagtgaggg ggcgggaagc cggggtgctg ccctgagggt gccccgacac    840
gctctcctgg ggccctgagc ggctgccacg tgcgtccagg gttctggcca cagggtgggc    900
aggggccctg tgctcctcac tggaggcccc tgaggctctg gaactgagac catccacccg    960
ccggccccct ctcgccggct ccggcacccc tgcctactgt gacttcctgc cccggactcg   1020
ctctgccagc ttggggcaaa ccacttccct ctggggtttt cacttccctc tttcccaagt   1080
ggggaaagac cacctgtccc cgacccagaa agggcccctg cccgagggca gcagcagtgc   1140
caggctggca tgtgaggctt ggggcaggcc cggcccccag aggcacaggg cgatgctctg   1200
tgggacgctg tgtcgtttct aagtacaagg tcaggagagg agcccctga ccccggaggg    1260
gaggagaggc agggcaggaa accgccacca tctcagccca                          1300

<210> SEQ ID NO 179
<211> LENGTH: 200
<212> TYPE: DNA
<213> ORGANISM: Homo sapiens

<400> SEQUENCE: 179
gcccactgtg ggtgtgcccg tgtgtgtggc tgtgaggcgt gagtgcaggc gtgaagtgtc     60
tgggagtggg agcgggcatg agtgtgtgcc acgggcctgc tgttgggtcc ttggaggcca    120
cggttgcccc tgaagggact gcaagctctt ttttgatttg tagttatttg agaagtctat    180
acaggaagaa aattaaaccg                                                200

<210> SEQ ID NO 180
<211> LENGTH: 1000
<212> TYPE: DNA
<213> ORGANISM: Homo sapiens

<400> SEQUENCE: 180
agcgcccagc gcagggccgg gacccagagt ggactctacc gtggggctgc ctcaaagaaa     60
tctcagcaaa cacaggaagc cagcccaccc gtgcagccat ggggccagga agcccgccct    120
ttaccaagtc atttgggcat ttttctctg tgctaacagc ccagatggag ccatagcctc    180
```

```
aacctctgtg ttctgataac accaagctgg gacgccggag ccatgcaggg gacagtgccc    240
ggcctgaggc tgcagcctgg gtctggatgc ctttctaatt cagggcctcc tcatggcctg    300
gttccataaa tggtcaaatg cagcctgaca gcgcagcctc ctatcagcgc tgggctccgt    360
accgccacac agcccacata ccccgttccc caggagacgc ccgcaggtgg gcagcgtcac    420
tcccacccgc cgagcacacg ctgtccccgt ctcgtgtccc gaggagccgg aagcagctgc    480
ttcctcccag cctgaaagct gcacctcggg ctgcactcgg ctccccgaac ccgcctccg     540 ctgccctgca attcgccaag ggagctaccc ttcccatata aaatttcac ctccatttcc     600 ttgtagagaa gaaacatttc tgacagcaag gaagattcta atttgaaaag caagtgattc    660
atctcccggt gccaaacagc agacgcaggc gttaccagtc tgggtggggc cccgagctg     720 gggacctggg gtcctctggg aggggcaaga aggcagcgat gctggccccc gcctccatct    780
gcccatccca tctgcttcca cacaccgccc tgccgtagct gcttgcagcc cttctctgtc    840
agtttctcca tcttttggtt tggtgataaa tgagagttcc catcgggtgt gccaccctct    900
gtgtgacggg gagcagagaa gaccctgcgt ccaagtcctc ctgggggaag agcgaagatg    960
ctgggaccag ccccagctgt caggggtct ccaatcccag                          1000

<210> SEQ ID NO 181
<211> LENGTH: 300
<212> TYPE: DNA
<213> ORGANISM: Homo sapiens

<400> SEQUENCE: 181
cgcacacaca gcacagacgc ctgcatcttc ccatgcgtgg tttctgctct tgcctctctg     60 ggttttttgtt tcacttcggt cgagttttg gtggtgttga gcggatagcc ggggaagttg    120
gagtcttgtt tgtggccgcc tcgtgctcgt gtctgtatct aagatcctca ggctgctcct    180
ttttgggtaa ggtctgttgc ttctctagga acagtgacgg tggcagagcc cgtggcccct    240
ctctcctgtc ccagagccaa gctgtttcct ctccccactc ccgggcaccc tgcgggcaag    300

<210> SEQ ID NO 182
<211> LENGTH: 5000
<212> TYPE: DNA
<213> ORGANISM: Homo sapiens

<400> SEQUENCE: 182
aagaggaaat tcccacctaa taaatttttgg tcagaccggt tgatctcaaa accctgtctc     60
ctgataagat gttatcaatg acaatggtgc ccgaaacttc attagcaatt ttaatttcgc    120
cttggagctg tggtcctgtg atctcgccct gcctccactg gccttgtgat attctattac    180
cctgttaagt acttgctgtc tgtcacccac acctattcgc acactccttc ccctttgaa     240 actccctaat aaaaacttgc tggttttttgc ggcttgtggg gcatcacaga tcctaccaac    300
gtgtgatgtc tccccggac gcccagcttt aaaatttctc tcttttgtac tctgtccctt    360
tatttctcaa gccagtcgat gcttaggaaa atagaaaaga acctacgtga ttatcggggc    420 aggtccccg ataaccccca gctgcagatc gaggcctagt gcgagcacag gtccccccag    480 accccttccca gtgcccacca accggcggcc taggccaggt agaactggca gcgcctcccc    540
tgctgcaaca ccaggctctg gtagaaactt cagaaaacat gcaccggcaa aaccaaggaa    600
gggtggctgc gtcccgggtt cttccgcgca gctgtgtgta cacgcatgca cacccaca    660 cgcacacacc cacgtgcaca cccccatgca cacgcaccca cttgcacgcc catgcacgca    720
```

```
cacacgcgcg tgcacccatg cgcacgcacc catgcacaca cacgcgcgca cacacccacg    780
tgcgcaccca catgtacaca cccacgtgca cacacccacg cgtacacacc cacgcgcaca    840
caccgctgtc cccagccgtg cagaacgatc ctccctgagt ccccggctcc gacccacacg    900
cagcactcgc taaacgcttc ccacgcagtc gttttgctgg gttgcgcttc acccacttct    960
cagagggggc ggccgaggca gaggtgtcgg ggatcgagca gctccgggcc tcaggggtcg   1020
ccccgccacc gttttccttt cccagatgct gggacggggg cagggagggg ctccccaggc   1080
tgaacccgac taggtcaccc tagaagcgag gcgagcttct cttctgtttt tcttcggcgc   1140
ccctgagccc ctgacagtgc caagctgcc catgggattg gattcgccag agcctcctac    1200
gcagacccca cccagggcca aagccaaccc caagcccac caccttggtg gtgtgggatg    1260
aaaagtgagc catcgagaga tggggtcccc ccaccccaa ccctccaag gacaaaggcg    1320
ggctgggaag cacccgcttt cacgtccgcc cctgcccggc tttcctagcg gaattggcgc   1380
cggcatcagt tggggttgt gggatcagtg aggaatcccg tggggtcgcc tccatttatc    1440
agttgtgtgg ggttgggcga gcaccccctag ccccagccca ggcgatcagg gcgcgaagcc   1500
cactggacgc ggatttggga ttaggacggg ggtgacagcc aggaggaccg cacctgccct   1560
ccccactcct gccgctccac ccctgccccc accgcaaac caaggtctcc accaggaaga   1620
tgggggtggg gaaaggacgc ggggtggggg ggggtgcggg gagagaggac acagggtcgg   1680
aagggtgagg ggtagtggca gaggcggagg ccgaggccac gcagctgcgg ggcgcaggga   1740
ggggcagagg aggggcgttc agatgggaac ctagtccaga cccgtcgggg ccctcgtgtg   1800
cggctcgtta tcctggaacc agagaggctg gagacccttg gcttgtctgg agcggaaccg   1860
tagtgtccaa tagagtgtgt ggggctcagc cctaaagcta acattctttt atttcctgat   1920
gaccatgggg gcggagcggg ggaaaagccc tggcccttata gtttagaatt ttataaaagg   1980
aaaggcgtgg ccactgacaa tttgcgcttc aggagtccca gagtgaccgc ctggctcgga   2040
gcagggaatg agggggtcct taactctgag atttgttttc tgagagacaa aggtgatggg   2100
tgaggcggct aagcctctga ttctctatag gtggcggtca ttcatttcag aacatgaatg   2160
gattcagtaa ataaacatga tagaaaaatg ccacaagccc taggcccatt ggagtggact   2220
ggacagtctg ttcccagtgt gtccctcagc ctcggtcccc cacccttccc ggagccctgg   2280
gggtcacaca catccctcct ggctgcctag cctgtgcccc ccgattcccc cctccccgc    2340
cccgcgcgtg cacacacaca cacacacaca cacacacaca cacacacacc acacagcacg   2400
aggcgacaga gatatgagag agagcgagcg agagaggacg ggagagagag ggagtgcaag   2460
tgtgcgctgg gggtaacccg tgcatgcatg cattgggggt aacaggctgg agctcagatc   2520
cctcccccag cccccagcag gggggactgc aggctcctgg tctgagtggg gagctgggcc   2580
ccctggacag aggactgggc tgcggggtca ggaatgggca cacttcctaa ctgcaggaca   2640
ctctaagggc tttggtcatg cacacgcagc caagagaagg tgtcgctggc acacagcctt   2700
ccaggagcgg acttggagac ctcgccaagg accaggactc cccagcactc acactcccttt  2760
aggcgctgaa gtccagagga cagaggttga gggcagagct cctgggagca ccagtggaag   2820
taggagggct gggctggaaa acctccccca acctcctatt gcaaagaggc tccagccagc   2880
agcctccaca ccccagtgat cttttaagat gcaaatctgc gccatcattt atttcctcag   2940
tgccttctcc agctcctggg atgcacactg cccgtcccca ggcccagaga cctgaccacc   3000
ctcattcctc cctcagccca ccctgggtc tctccaccag ctgacagcct tcctgcagtc   3060
ccctccccga atgctgctcc ctgaggccct cctggacacc tgcagggcag gcacagcccg   3120
```

```
cgggacctca cagcacttgc tccgggcaga gctgcagttt ggccaagttg ccagctccgt    3180
gtgggcaggg gccctggcct gtggctgcca catcccgggt gggggcacgg cctttcctgg    3240
cgtggatgct gagcaaacgt aggggggaagg ggagtgaatg aggagagcca ggtagctcag    3300
gggctgaggc ctcactgagc agggtcccgc gtgaccggtc cccaccgctg acggttcctg    3360
gggtaacact caggacaggg agaggcaatg gaaagagacg tggccgccct cgcatcctgc    3420
agctcccgca ctcccagcct cccagcctcc cacccagccc ccagagccc accagtgacc    3480 ccgcccactg ggtcctcaga tggctcccac gggatctcct gccttgatct cctgtccaca    3540
tggaggtgaa gtgggttgct ctgaatgagg ggtgccgagc ctagggcgca gcccactctc    3600
ctgggtccgc agcatcacgc agcccggacc acaggctcct tacaagaatc ggaagggtcc    3660
ctgcaatcgc ccttcgcact gaggcttcct actgtgtggt gtaaaaacac aggcttgtcc    3720
tcccttgctg cccacggggc tggagccgcc tgaaaatccc agcccacaac ttccccaaag    3780
cctggcagtc acttgaatag ccaaatgagt cctagaaagc gagagacgag aggggaatga    3840
gcgccgaaaa tcaaagcagg ttcccctcct gacaactcca gagaaggcgc atgggccccg    3900
tggcagaccc gaaccccag cctcgcgacc gcctgtgacc tgcgggtcaa ccacccgccg    3960
cggctccacg ccgtgggcac agactcaggg agcaggatga gaaagctgag acggcgcagc    4020 cacgcccgg tgccttcacg cgcacagcga cacagcccca gccagcgggg cccacgctaa    4080
ggcggaatcc cacagaagcc tacagagcga gcgcgcgcct gtgcttccca aaacggaatg    4140
gaaccaaggt gacttctaca gaacgatctg aagcccctggc tggccttat gctagtctct    4200 tgggagcgtt ccaaatgcag ctcaatatta cttacttgac ttttatcttt cctccctggt    4260
tcgtggtatt tataactggg tcatctttta actatttgca acgtagcttc aggggagagg    4320
gggagggctt tataaataac ctgtattatt attatgcagg ttgattctgt tccctgagct    4380
aaagggaaca tgaaaataca tgtctgtgac tcatgccccc ccaccccac tccagggtgt    4440 gctgaggagt ctctcagctg ccccggggtc ctcgagcagg ggagggagaa aggctggcgc    4500
tgcgccctcc atcgcgtgaa gccagggggat tttgctctgc gacaagctga cttggctctc    4560
gtattgtttg cagaatcacc cagttccaag gcagtccctg cgggcaggtg cagctgtgcg    4620
ggagcttcag tcctgtcccc aacacccagg cagtaatggt tccagcacgg aaggtctacc    4680
tacctcccac tgcacagccc gagggctgtc ctggaggcac agccatccgt ccctgggtgg    4740
gcaggcacgt ttatgacccc caccccacc cccacccccc acgcgagtca gcacgttcca    4800
tactcgggtg atcgtgctca tccctggtc atgtcatcgg gatctgagtg ccatccgagc    4860
agagagctgt ggcccggtgc cggggtgga cttcatctat tccagggaac caaggatgca    4920
tgatttgcaa acaaaaccag aagcgcaagc catctcctcg cctcccctga tagccgtgct    4980
gcggagcctg agtgctggag                                               5000

<210> SEQ ID NO 183
<211> LENGTH: 400
<212> TYPE: DNA
<213> ORGANISM: Homo sapiens

<400> SEQUENCE: 183
tgcgtttagt gtaaaaatat caggtgtggc tgcacggagt gaaaaatcac aggctccacg      60
gagccgggag gcctgctgcc ctgccctctt gctttgatga ggaaatggcg accgcagaag     120
gaaatgtagc agcaccggca accggcatcc gtggggccac gccgggctgc ttcccagggc     180
```

```
cctccagcca agcagccaca ggaaagagta gatgttgatc ccaagctagg actgaggagt    240
ccgtccctaa gagccgaggg agtcaggtgg gcgaaactgg ccgcatgtct gggtacaact    300
gctcagggtt tctcatctgc tgaatcacca agctaggttc tgaagccagg cgtgagtgag    360
caggactgga gcaggattct gggaacaatc ttttccctcc                          400
```

<210> SEQ ID NO 184
<211> LENGTH: 293
<212> TYPE: DNA
<213> ORGANISM: Homo sapiens

<400> SEQUENCE: 184

```
aggtggaggt tgcagtgagc cctcctcccc tcctccccct tcccttccca cctcccatgc     60 cccccttct tcctcccact ccctcccga ggccccgctt attctcccgg cctgtggcgg      120
ttcgtgcact cgctgagctc aggttctggt gaaggtgccc ggagccgggt cccgccttcg    180
gcctgagcta gagccgcgcg ggcggccggc ttccccaaa ccctgtggga ggggcatccc    240
gaggaggcga cccagagag tggggcgcgg acaccttccc tggggagggc cag           293
```

<210> SEQ ID NO 185
<211> LENGTH: 474
<212> TYPE: DNA
<213> ORGANISM: Homo sapiens

<400> SEQUENCE: 185

```
ccttccagat gttccagaag gagaaggcgg tgctggacga gctgggccga cgcacgggga     60
cccggctgca gccctgacc cggggcctct tcggagggag ctgagggccg cgttccttct    120
gaaagcggga cgcgggaggg gtggaggctg cggggagccg gggtcgcaca cgaataaata    180
acgaatgaac gtacgagggg aacctcctct tatttccttc acgttgcatc gggtattttt    240
cgttattgta aataaaacgg ttccgagccg tggcatcgag agggcgtctg gagttcaggg    300
aacgcgtggc ccccgcccgg gagcaccgcg cagcgctcgc ctctcgccct tcaaggggt    360 ccctgcccgg agcctgcgcc cccggagagg aaggggctcg aggggcttgg gtgccgcagc    420
gcgtccttcc gtagaaaagg cttgcgtcag tatttcctgc ttttacctcc tgag         474
```

<210> SEQ ID NO 186
<211> LENGTH: 346
<212> TYPE: DNA
<213> ORGANISM: Homo sapiens

<400> SEQUENCE: 186

```
cagtatttcc tgcttttacc tcctgagtat tggaatattc gagtaaaccc tggagtttca     60
gcgccagcgc acgcctcttc atcagggcag cgcgtcgcga gcgcgctggt tccccggggc    120 ctccccggcca cggacaccgc tctagccagg gccacggcga ggccgccgag cagcacctca    180
gagacctgcg tgagttctaa agcctgggc tactacaatt ctgctcatct gtttgtcctg    240
tgaaatgatt cagggacatg aaaatgcctt cccactgact tgcgtcctgt cttagcctgg    300
acttgtcccc ttgggaacac gggccaggcc cctctgttcc tgaagt                  346
```

<210> SEQ ID NO 187
<211> LENGTH: 2000
<212> TYPE: DNA
<213> ORGANISM: Homo sapiens

<400> SEQUENCE: 187

```
catacatggt tattagaaaa ggcatctcat ccaaatgtgg tggctcgtgc ttgtaatccc     60
```

```
agtgcttcag gaggccaagg gaggaggatt acttgagcct aagagtttga gaccagcctg        120
ggcaacacaa caagaccttg cctctacaaa aaacttaaaa actagctggg tatgatggtg        180
cacacctgta gtcccagcta cttgggaggc ggaggcgggc agatcgcctg aggtcaggag        240
ttcgagacca gcctggccaa catgatgaaa ccccgtctct actaaaaata caaaaattag        300
ccgagtgtgg tggtgcatgc ctgtaatccc agctactcag gaggctgagg caggagaatc        360
acttgaaccc gggaggcgga ggttgccatg agccgagatc acgtcactgc actccagcct        420
gggtgacaga gcacaaaaga caggcatgac tttgtactta actgctcagc tttgtaatca        480
ctgggggccc agatgctcac ttggattcta actttgttgg catctgggcc taaaagccgt        540
gatgcaggtg agcaatgatg cagagggctc tgtgcgcctg gcgggctctg tttgcctgct        600
gggctctgtg cgcctgctgg gctctgtgcg cccgggaagg tgcggccacc ctcacgcgga        660
aggcggccag cggatcccgg tgcgcgcagc tcccagcgct ggggttccag cgccccgcct        720
cttcctatag caaccagcgg gacctgccgt ccccgggc accccgaggg gtctgcgccc         780
gcttctttcc gaaacgggaa ggcgctgggg gctcggcagc cagagggacg ggttcaggga        840
gcgtccggtg agcctaagac gcgccttttgc cggggttgcc gggtgtctgc ctctcactta       900
ggtattagga accgtggcac aaatctgtag gttttcctct gggggtgggc ggaggctcca        960
aaccggacgt ttttctcctg gaggactgtg ttcagacaga tactggtttc cttatccgca       1020
ggtgtgcgcg cgctcgcaa gtggtcagca taacgccggg cgaattcgga aagcccgtgc        1080
gtccgtggac gacccacttg gaaggagttg ggagaagtcc ttgttcccac gcgcggacgc       1140
ttccctccgt gtgtccttcg agccacaaaa agcccagacc ctaacccgct cctttctccc       1200
gccgcgtcca tgcagaactc cgccgttcct gggagggaa gcccgcgagg cgtcgggaga        1260
ggcacgtcct ccgtgagcaa agagctcctc cgagcgcgcg gcggggacgc tgggccgaca       1320
ggggaccgcg ggggcagggc ggagaggacc cgccctcgag tcggcccagc cctaacactc       1380
aggaccgcct ccagccggag gtctgcgccc ttctgaggac cctgcctggg ggagcttatt       1440
gcggttcttt tgcaaatacc cgctgcgctt ggacggagga agcgcccacg cgtcgacccc       1500
ggaaacgaag gcctccctga tgggaacgca tgcgtccagg agcctttatt tactcttaat       1560
tctgcccgat gcttgtacgt gtgtgaaatg cttcagatgc ttttgggagc gaggtgttac       1620
ataaatcatg gaaatgcctc ctggtctcac cacacccagg gtgacagctg agatgcggct       1680
tctccagggt ggagcctcct cgttttccag agctgcttgt tgaagtcttc ccagggcccc       1740
tgacttgcac tggaaactgc tcaccttggc atcgggatgt ggagcaagaa atgcttttgt       1800
tttcattcat cctagtgttc ataaaatgga aaacaaataa ggacatacaa aaacattaat       1860
aaaataaatt aatggaacta gattttcag aaagcacaac aaaacacaaaa tccaagtatt       1920 gccatgtcag caacacattc ctactttaag ttttatgaag ttaattggag tagtggagaa       1980
caaaagtgga tgtggggcag                                                   2000

<210> SEQ ID NO 188
<211> LENGTH: 149
<212> TYPE: DNA
<213> ORGANISM: Homo sapiens

<400> SEQUENCE: 188
gctggaccag aaagtgttga gtacctgctc atgcgtgcaa gaggaggagg gaggagcaca         60
tcactgaact tcacatgaaa ttggataccc gggattagag acagtagagg gttttggtga        120
```
aatcagatac acattgcaaa gcagcacac          149

<210> SEQ ID NO 189
<211> LENGTH: 146
<212> TYPE: DNA
<213> ORGANISM: Homo sapiens

<400> SEQUENCE: 189
ggtcgagttt ttggtggtgt tgagcggata gccggggaag ttggagtctt gtttgtggcc    60
gcctcgtgct cgtgtctgta tctaagatcc tcaggctgct ccttttttggg taaggtctgt   120 tgcttctcta ggaacagtga cggtgg                                         146

<210> SEQ ID NO 190
<211> LENGTH: 133
<212> TYPE: DNA
<213> ORGANISM: Homo sapiens

<400> SEQUENCE: 190
cctcgtgctc gtgtctgtat ctaagatcct caggctgctc cttttgggt aaggtctgtt     60 gcttctctag gaacagtgac ggtggcagag cccgtggccc ctctctcctg tcccagagcc   120
aagctgtttc ctc                                                       133

<210> SEQ ID NO 191
<211> LENGTH: 95
<212> TYPE: DNA
<213> ORGANISM: Homo sapiens

<400> SEQUENCE: 191
ctgttgcatg agagcagagg ggagatagag agagcttaat tataggtacc cgcgtgcagc    60
taaaaggagg gccagagata gtagcgaggg ggacg                                95

<210> SEQ ID NO 192
<211> LENGTH: 127
<212> TYPE: DNA
<213> ORGANISM: Homo sapiens

<400> SEQUENCE: 192
tgcaggatat ttggcaaggt ttcttactgt tccaagtttt ttttccgaaa acctcccttg    60
aaacttttgt gcttacttgt ggtaacatac ccataatata ccctcttaac catttctacc   120
ggcacag                                                              127

<210> SEQ ID NO 193
<211> LENGTH: 104
<212> TYPE: DNA
<213> ORGANISM: Homo sapiens

<400> SEQUENCE: 193
tgaatcagtt caccgacagc cttggggaca ttcaccttgg gctccacaac ctgtcagaaa    60
tgcccccaag cccaaaggcg tcgagagaat ggccaggttg tttc                     104

<210> SEQ ID NO 194
<211> LENGTH: 127
<212> TYPE: DNA
<213> ORGANISM: Homo sapiens

<400> SEQUENCE: 194
ccgttatatg gatgccttgg ggcttggggg gtttctggca gtctgtcgag cccgaggtga    60
atgtccccaa ggctgctggt gaatcagatc cctggcgttc tccgttggca gttcagccca   120

```
<210> SEQ ID NO 195
<211> LENGTH: 144
<212> TYPE: DNA
<213> ORGANISM: Homo sapiens

<400> SEQUENCE: 195
ccaggcaaga tggcttatgt ctttaatctc agctgtttgg gaagccaagt ggaaagattg      60
cttgaggcca ggagttcaag accaacctgg ataatgtaag aagacctcgt ctctataaaa     120
aattaaaaat tggctgagca tggt                                            144

<210> SEQ ID NO 196
<211> LENGTH: 110
<212> TYPE: DNA
<213> ORGANISM: Homo sapiens

<400> SEQUENCE: 196
gacccagacg atacctggaa attatttgct catgtggcag tcactgttga ttgcctaccc      60
aaagccatta ctccttctcc ccacctaaca gaagccgagt tttgttcagc                110

<210> SEQ ID NO 197
<211> LENGTH: 101
<212> TYPE: DNA
<213> ORGANISM: Homo sapiens

<400> SEQUENCE: 197
ccacatcctg gccatctact tcctcttaaa caagaaactg gagcgctatt tgtcaggggt      60
aagtgcgacc ctagaggcga tcgtctctgc tgtctgtgga a                         101

<210> SEQ ID NO 198
<211> LENGTH: 88
<212> TYPE: DNA
<213> ORGANISM: Homo sapiens

<400> SEQUENCE: 198
tgagctcaca ggtctggaaa tggtctgaat agaaaggatt ggtctccgga ggaaagcata      60
ctcttcctat taccagaacc ctgtgggg                                         88

<210> SEQ ID NO 199
<211> LENGTH: 128
<212> TYPE: DNA
<213> ORGANISM: Homo sapiens

<400> SEQUENCE: 199
attctccaca gggcaatgag gcaagaaatt tacagcttag cctgattaat gggccaggca      60
gttaagagtt ctttgccaag ctatgagcat aatttatagt catcacggca ggaggaaagg     120
ccacataa                                                              128
```

MULTIPLEX DETECTION OF DNA THAT ORIGINATES FROM A SPECIFIC CELL-TYPE

CROSS-REFERENCE TO RELATED APPLICATIONS

This application is a divisional of U.S. application Ser. No. 14/707,363 filed 8 May 2015 now U.S. Pat. No. 10/017,818, which issued on 10 Jul. 2018, which claims priority to European patent application 14167769.0 filed 9 May 2014, the entire disclosures of which is hereby incorporated herein by reference in their entireties.

SEQUENCE LISTING

The instant application contains a Sequence Listing which has been submitted electronically in ASCII format and is hereby incorporated by reference in its entirety. Said ASCII copy, created on 29 Sep. 2017, is named DFMP-112-01_ST25.txt and is 296 kilobytes in size.

The present invention relates to methods to detect an amount of DNA that originates from cells of a given type, where the sample comprising such DNA in admixture with DNA that does not originate from such cells. Such methods are based on differential methylation, at certain regions, of the DNA that originates from the given type of cells compared to the admixed DNA. Such methods have particular application in the detection, from a biological fluid from a pregnant female, of cell free DNA that originates from a foetus or the placenta of a foetus, or the detection, from a biological fluid from an individual, of cell free DNA that originates from cells of a tumour. Accordingly, such methods have diagnostic, prognostic and/or predictive utility for detecting an increased risk of an individual suffering from or developing a medical condition such as preeclampsia or cancer, and/or to aid subsequent diagnostic, prognostic and/or predictive methods such as the detection of chromosomal trisomy in a foetus, including for twin-pregnancies. The present invention also relates to compositions, kits, computer program products and other aspects that are used in, useful for or related to the practice of such methods.

Cell-free DNA (cfDNA), especially that found in plasma or serum, has been the subject of considerable research over the past decade. Despite the original finding of circulating cell-free nucleic acids in the bloodstream being described by Mandel and Metais as early as 1948 (Mandel and Metais 1948, CR Acad Sci Paris 142:241), it took until the mid 1990s for proof that tumours shed DNA into the circulatory system (Sorenson et al 1994, Cancer Epidemiol Biomarkers Prev 3:67; Vassioukhin et al 1994, Br J Haematol 86:774), and until 1997 for the discovery of cfDNA originating from a foetus in the circulatory system of the mother (Lo et al 1997, Lancet 350:485).

Among other forms of characteristics shown by circulating cfDNA, numerous studies have described the presence of methylated circulating cfDNA in the plasma/serum and other body fluids of patients with various types of malignancy and the absence of methylated DNA in normal control patients (for review see Muller and Widschwendter 2003, Expert Rev Mol Diagn 3:443). Although other characteristics of circulating cfDNA exist and are important for diagnostic, prognostic or predictive studies (for example, sequence mutations and micro duplications/deletions), such methylation-based epigenetic characteristics have become an increasingly important source of serologic markers for diagnosis, risk assessment and even for therapy monitoring during follow-up of cancer patients.

Likewise, the use of differences in foetal cfDNA present in the maternal circulation has been the main goal for the development of non-invasive prenatal tests (NIPT). Foetal cfDNA is derived from embryonic cell degradation in maternal peripheral blood (Lo et al 2000, Clin Chem 46:1301) or from apoptotic placental cells (Smid et al 2006, Prenat Diagn 26:785). It has been demonstrated that foetal cfDNA from maternal plasma is cleared immediately (within a few hours) after pregnancy (Lo et al 1999, Am J Hum Genet 64:218). This finding is of great importance, since the presence of foetal cfDNA from previous pregnancies would otherwise interfere with the correct interpretation of subsequent pregnancies.

It is believed that 60% of tissue-specific differentially methylated regions are methylated in embryonic cells, while during the differentiation of embryonic tissues to adult tissues, they undergo de-methylation (Kawai et al 1993, Nucleic Acids Res 21:5604). Based on the evidence that foetal cfDNA in maternal plasma is of placental origin, epigenetic differences between maternal peripheral (whole) blood and placental DNA have been used to detect a hypomethylated gene sequence (maspin/SERPINB5) in maternal plasma derived from the foetus (Masuzaki et al 2004, J Med Genet 41:289; Fiori et al 2004, Hum Reprod 19:723; Chim et al 2005, Proc Natl Acad Sci USA 102:14753). Subsequently, a number of additional differential foetal methylation-based epigenetic molecular markers have been described, including the RASSF1A gene on chromosome 3, as well as a marker on chromosome 21 (Chiu et al 2007, Am J Pathol 170:941; Old et al 2007, Reprod Biomed Online 15:22; Chim et al 2008, Clin Chem 54:500) and others including T-box 3 (TBX3) (Nygren et al 2010, Clin Chem 65:10; WO 2010/033639; WO 2011/034631).

Various methodologies exist for NIPT based on the analysis of foetal cfDNA. For example, foetal sex determination using eg DYS14 (Lo et al 1997; Lancet 350:485), as well as foetal Rhesus D found in maternal circulation in pregnancies in which the mother was Rhesus D negative (Lo 1998, N Eng J Med 339:1734). Also, and of particular relevance, are those using next generation sequencing (NGS) technologies on cfDNA isolated from maternal plasma with the primary aim of detecting the most common chromosomal aneuploidies as commercially available tests (for example, those using random massively parallel sequencing: www.sequenom.com; www.lifecodexx.com; www.verinata.com). Other technologies include targeted approaches, the aim of which is to enrich specific genomic regions of interest before sequencing to reduce the number of sequence tags needed to perform a reliable statistical analysis (eg www.ariosadx.com or www.natera.com), polymorphism analysis or digital PCR (for review, see Go et al 2011, Human Reprod Update 17:372). However, regardless of the specific technology used, current applications of NIPT rely on the qualitative detection of foetal cfDNA to determine the genetic makeup of the foetus. Such an approach leads to an analytic dilemma, because test results from samples that do not contain any or sufficient foetal DNA or are contaminated with maternal cellular DNA can be misleading. The analogous issue arises in diagnostic, prognostic or predicative tests of tumour derived cfDNA from the circulatory system: the quality of the test result often is dependent on the presence of sufficient, or sufficiently pure, tumour-derived cfDNA in the total DNA from the sample.

The quantitative determination of an amount of DNA originating from such a cell type may, in itself, form a critical part of a diagnostic, prognostic or predicative test. For example, even though studies have demonstrated that the amount of foetal DNA released in maternal circulation increases with pregnancy progression (Lo et al 1998, Am J Hum Genet 62:768), preeclampsia, which results from abnormal trophoblast invasion, is also associated with further elevated foetal cfDNA levels in the maternal circulation. Lo et al (1999, Clin Chem 45:184) demonstrated a fivefold increase in circulating foetal cfDNA concentrations in the plasma of symptomatic preeclamptic women compared with control pregnant subjects, and further studies have investigated if elevated serum foetal cfDNA developed into early-onset preeclampsia (Yu et al 2013, Int J Mol Sci 14:7571), and the potential of cfDNA as a marker for preeclampsia is being increasingly studied (for review, see Hahn et al 2011, Placenta 32(SupI):517). An increased level of circulating cfDNA and/or the level of methylation of such DNA at certain regions is also associated with other medical conditions. For example, hypermethylation of serum cfDNA was found to be common in patients suffering from oesophageal squamous cell carcinoma, and diagnostic accuracy was increased when methylation of multiple genes (RAR-beta, DAPK, CDH1, p16 and RASSF1A) were analysed in combination (Li et al 2011, Epigenetics 6:307). Elevated levels of circulating cfDNA have been reported in patients with acute dengue virus infection (Ha et al 2011, PLoS One 6(10):e25969), in acute Puumala hantavirus infection Outinen et al 2012, PLoS One 7(2):e31455) and high cfDNA has been reported to predict fatal outcome among Staphylococcus aureus bacteraemia patients with intensive care unit treatment (Forsblom et al 2014, PLoS One 10; 9(2):e87741.

It is known that foetal cfDNA present in the maternal circulatory system and tumour derived circulating cfDNA is degraded. For example, studies characterising cfDNA in maternal plasma have found that the size of foetal DNA fragments were estimated to be <0.3 kb, whereas that of maternal DNA was >1 kb (Chan et al 2004, Clin Chem 50:88). Follow-up studies have demonstrated that the release of foetal DNA is due to the apoptosis of no more than three nucleosomal complexes, it has also been shown that the average foetal fragment size is 286+/−28 bp with a maximum foetal cfDNA fragment size ranging from 219 to 313 bp (Kimura et al 2011, Nagoya J Med Sci 73:129), and another study has reported that the most significant difference in the size distribution between foetal and total DNA is that foetal DNA exhibits a reduction in a 166-bp peak size and a relative prominence of the 143-bp peak; the latter likely corresponding to the trimming of a ~20-bp linker fragment from a nucleosome to its core particle of ~146 bp (Lo et al 2010, Sci Transl Med 2:61).

In cancer patients, circulating cfDNA in plasma is protein-bound (nucleosomal) DNA and has a short half-life (10 to 15 min) which is removed mainly by the liver (Elshimali et al 2013, Int J Mol Sci 14:18925). Accumulation of cfDNA in the circulation of cancer patients can result from an excessive release of DNA caused by massive cell death, inefficient removal of the dead cells, or a combination of both (Zeerleder 2006, Crit Care 10:142). It should be noted that although cancer patients requiring renal support have higher values of circulating cfDNA, the renal elimination is not the main mechanism of its clearance. The plasma levels of circulating cfDNA do not seem to be dramatically altered in chronic kidney disease, peritoneal dialysis or hemodialysis (Kirsch et al 2008, Ann NY Acad Sci 1137:135).

Although the nucleosome is a very stable protein-DNA complex, it is not static and has been shown to undergo a number of different structural re-arrangements including nucleosome sliding and DNA site exposure. Depending on the context, nucleosomes can inhibit or facilitate transcription factor binding. Also, packaging of DNA into nucleosomes varies depending on the cell cycle stage and by local DNA region (Russell 2010, 'iGenetics". 3rd ed. San Francisco: Pearson Benjamin Cummings, pp 24-27). The degree to which chromatin is condensed is associated with a certain transcriptional state. Unpackaged or loose chromatin is more transcriptionally active than tightly packaged chromatin because it is more accessible to transcriptional machinery. By remodeling chromatin structure and changing the density of DNA packaging, gene expression can thus be modulated. Accordingly, and without being bound by theory, the qualitative and/or quantitative level of chromatin packing of a given region of cfDNA may affect its stability, and hence the amount detected in the circulatory system at any given time, Correspondingly, differences between the level of chromatin packing between different DNA regions (for example, due to differences in each regions state of transcription) may influence the relative quantities of DNA from each of these regions when detected as cfDNA, particularly as two studies have investigated in more detail the kinetics of, and reported the rapid, clearance of cfDNA from the circulatory system (Gauthier et al 1996, J Immunol 156:1151; Lo et al 1999, Am J Hum Genet 64:218).

Various prior art methods have been described to detect, and quantify, cfDNA from a specific cell type. Quantitative analysis of aberrant p16 methylation was described using probe-based real-time quantitative PCR (Lo et al 1999, Cancer res 59:3899). Analogously, differences in the methylation of the placental mapsin gene found in material plasma has been described, and the methylation signature further analysed using MALDI-TOF mass-spectrometry (Chim et al 2005). Total cfDNA and that from male foetuses (only) were accurately and robustly quantified in materal plasma from 5 to 41 weeks of gestation using a Y-chromosome specific marker (SRY) (Birch et al 2005, Clin Chem 51:2). Hypermethylation of RASSF1A has been proposed as a universal foetal DNA marker to improve the reliability of NIPT, and was studied in a duplex probe-based real-time PCR reaction compared to the non-differentially methylated region on the beta-actin gene (Chan et al 2006, Clin Chem 52:12). A complex method of quantification has been described (Nygren et al 2010; Clin Chem 56:10; WO 2010/033639; WO 2011/034631): starting from a 13-plex competition-PCR reaction (5 differentially methylated regions (DMRs) including TBX3, 3 regions on different genes for total DNA quantification, 3 for quantification of chromosome Y and 2 for restriction enzyme controls), such a complex reaction is subsequently processed for singe-base extension reactions and finally mass-spectrometry is subsequently conducted to both quantify and identify each of the single alleles my mass differences. Also using a complex process starting from methylated DNA immunoprecipitation, and based on SYBR green based quantitative PCR of a plurality of DMRs, has been claimed to be able to accurately quantitate foetal cfDNA and use such quantitation from eg chromosome 21 DMRs, to prenatally diagnose trisomies (Papageorgiou et al 2011, Nat Med 4:510; WO 2012/092592); although technical concerns about such an approach to diagnose trisomies have been raised (Tong et al 2012; Nat Med 18:1327). High-throughout droplet digital PCR (ddPCR) has been described for absolute quantification of DNA copy number from normal and tumorous breast tissues, and also total and foetal cfDNA in maternal plasma using duplex probe-based quantitative PCR of RASSF1/RNaseP and RASSF1/beta-actin (Hindson et al 2011, Anal Chem 83:8604). Separate SYBR green quantitative PCR reactions of RASSF1A, SRY and DYS14 have been evaluated as an assay to detect RASSf1A to facilitate improved diagnostic reliability of NIPT (White et al 2012; PLOS ONE 7(9):e45073). However, generally considered as the "gold standard" for the quantitative measurement of foetal cfDNA against which other assays are often compared, remains the quantification of Y chromosome-specific genes (eg SFY) of male foetuses eg, as used by Yu and co-workers to determine whether the increased foetal cfDNA in maternal serum level of gravitas developed into early-onset preeclampsia (Yu et al 2013, Int J Mol Sci 14:7571).

Accordingly there is a need, from one or more of the above or perspectives, for improved methods to detect, preferably quantitatively, an amount of a species of DNA that originates from a particular cell type, such as a tumour-, foetal- or a placental cell, in particular to so detect cfDNA eg from the circulatory system of an individual.

Accordingly, it is an object of the present invention to provide alternative, improved, simpler, cheaper and/or integrated means or methods that address one or more of these or other problems. Such an object underlying the present invention is solved by the subject matter as disclosed or defined anywhere herein, for example by the subject matter of the attached claims.

Generally, and by way of brief description, the main aspects of the present invention can be described as follows:

In a first aspect, and as may be further described, defined, claimed or otherwise disclosed herein, the invention relates to a method for detecting in a sample from an individual an amount of a species of DNA originating from cells of a given type, which sample comprises said species of DNA in admixture with differently methylated DNA not originating from cells of said type; said method comprising the steps:
(a) treating the DNA present in said sample with a reagent that differentially modifies methylated and non-methylated DNA;
(b) detecting in said sample the presence of methylation in said species of DNA at two or more differentially methylated regions (DMRs) that are differently methylated between said species of DNA and the DNA not originating from cells of said type, the modification of DNA of such DMRs by said reagent is sensitive to methylation of DNA, wherein the presence of methylated DNA at one or more of said DMRs indicates the presence of said amount of species of DNA in said sample and the absence of methylated DNA at said DMRs indicates the absence of said species of DNA in said sample; and
(c) detecting an amount of total DNA present in said sample using at least one other region that is not differently methylated between said species of DNA and the DNA not originating from cells of said type, the modification of which region(s) by said reagent is insensitive to methylation of DNA, wherein, said detection in step (b) and said detection in step (c) are made using the same aliquot of DNA of said sample, and in the same vessel, and effectively simultaneously for such DMRs and other region(s), and using: (x) the same detectable labels(s) for each of said DMRs; and (y) a different detectable label(s) for said other region(s).

In another aspect, the invention also relates to a method for detecting an increased risk of an individual suffering from or developing a medical condition, said method comprising the steps:
(i) conducting a method of the first aspect of the invention, wherein each of the detection steps comprises quantitative detection; and
(ii) comparing the amount of said species of DNA detected with a threshold amount and/or a reference distribution of amounts, wherein an increase in, or outlying of, the amount of said species of DNA indicates an increased risk of the individual suffering from or developing said medical condition.

In other aspects, the invention also relates to a composition, a kit and a computer program product, in each case as may be described, defined, claimed or otherwise disclosed herein, for use within or in connection with a method of the invention.

The figures show:

FIG. 5 depicts a schematic representation of the operations conducted by a computer program product of the invention.

Figure 1:
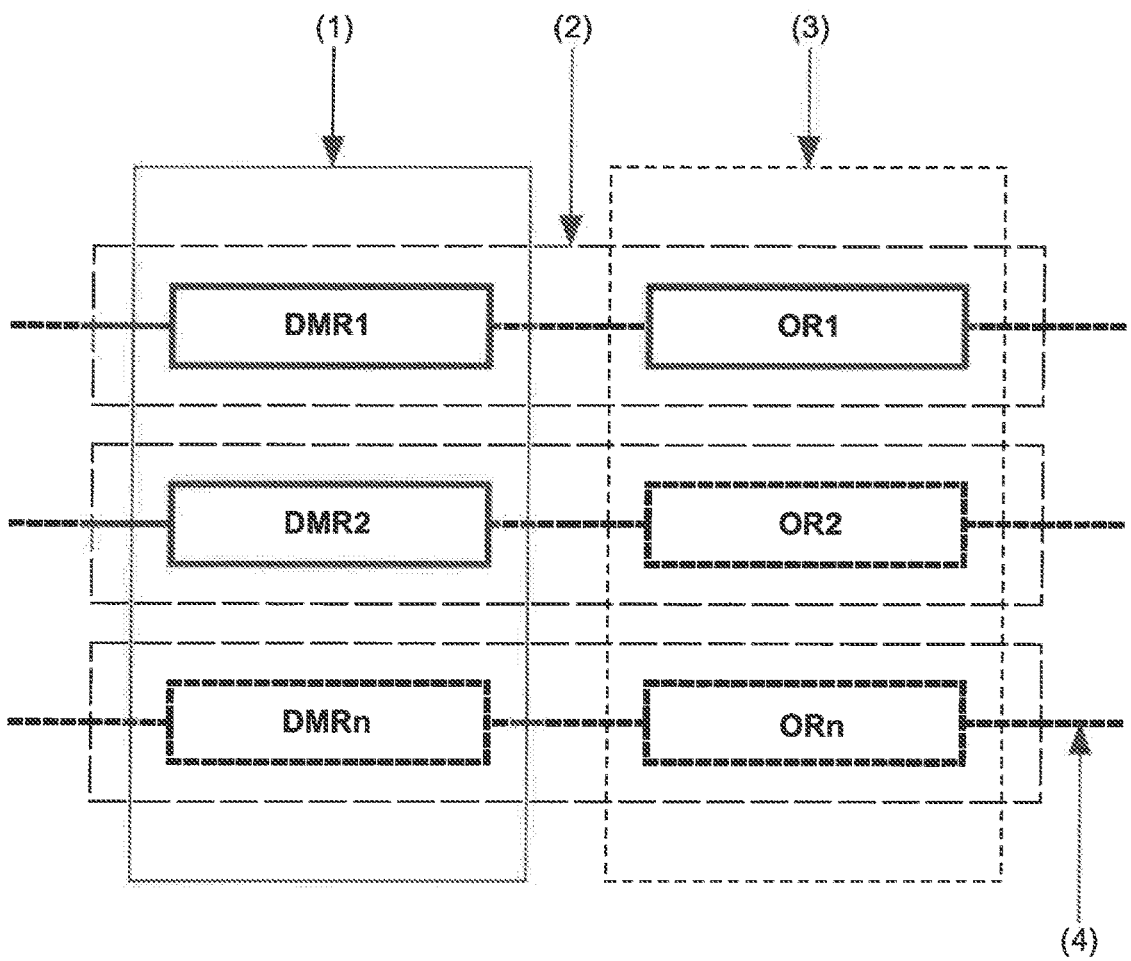
FIG. 1 depicts a schematic representation of the differentially methylated regions ("DMR") and other regions(s) ("OR") used in the method of the invention.

The present invention, and particular non-limiting aspects and/or embodiments thereof, can be described in more detail as follows:

In a first aspect, the invention relates to a method for detecting in a sample from an individual an amount of a species of DNA originating from cells of a given type, which sample comprises said species of DNA in admixture with differently methylated DNA not originating from cells of said type; said method comprising the steps:
(a) treating the DNA present in said sample with a reagent that differentially modifies methylated and non-methylated DNA;
(b) detecting in said sample the presence of methylation in said species of DNA at two or more differentially methylated regions (DMRs) that are differently methylated between said species of DNA and the DNA not originating from cells of said type, the modification of DNA of such DMRs by said reagent is sensitive to methylation of DNA, wherein the presence of methylated DNA at one or more of said DMRs indicates the presence of said amount of species of DNA in said sample and the absence of methylated DNA at said DMRs indicates the absence of said species of DNA in said sample; and
(c) detecting an amount of total DNA present in said sample using at least one other region that is not differently methylated between said species of DNA and the DNA not originating from cells of said type, the modification of which region(s) by said reagent is insensitive to methylation of DNA, wherein, said detection in step (b) and said detection in step (c) are made using the same aliquot of DNA of said sample, and in the same vessel, and effectively simultaneously for such DMRs and other region(s), and using: (x) the same detectable labels(s) for each of said DMRs; and (y) a different detectable label(s) for said other region(s).

Terms as set forth herein are generally to be understood by their common meaning unless indicated otherwise. Where the term "comprising" or "comprising of" is used herein, it does not exclude other elements. For the purposes of the present invention, the term "consisting of" is considered to be a particular embodiment of the term "comprising of". If hereinafter a group is defined to comprise at least a certain number of embodiments, this is also to be understood to disclose a group that consists of all and/or only of these embodiments. Where used herein, "and/or" is to be taken as specific disclosure of each of the two specified features or components with or without the other. For example "A and/or B" is to be taken as specific disclosure of each of (i) A, (ii) B and (iii) A and B, just as if each is set out individually herein. In the context of the present invention, the terms "about" and "approximately" denote an interval of accuracy that the person skilled in the art will understand to still ensure the technical effect of the feature in question. The term typically indicates deviation from the indicated numerical value by ±20%, ±15%, ±10%, and for example ±5%. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. Where an indefinite or definite article is used when referring to a singular noun, e.g. "a", "an" or the, this includes a plural of that noun unless something else is specifically stated.

In certain embodiments of the present invention, the individual is a human or a non-human animal, where such non-human animal may, in particular embodiments, be selected from the group consisting of: horse, sheep, cow, pig, chicken, mouse and rat. In a more specific embodiment, the individual is a pregnant female human or a human individual suspected of being at increased risk of developing or suffering (or suffering from) a medical condition, such as one or more of the medical conditions disclosed herein. Such a method of the present invention is not intended to be practiced on the human or animal body; for example it is intended to be practiced in an in-vitro manner.

In all aspects of the invention, the cell(s) of a given type may be a cell of a particular organ or tissues of the same individual. For example, the cell may be a tumour cell of the individual. Alternatively, such cell(s) may originate from a different individual or organism. For example, in the case of an individual being a pregnant female, the cell of a given type may be a cell of the foetus, including of the placenta of such foetus, and in other embodiments, the cell type may be an infectious agents such as a bacteria or a protozoa.

In certain embodiments of the present invention, said species of DNA and/or said differently methylated DNA is cell-free DNA, and in particular of such embodiments is circulating cell-free DNA. In one particular embodiment, said species of DNA and the differently methylated DNA that is admixed therewith are both circulating cell-free DNA. The term "cell-free DNA" (or "cfDNA") is art recognised, and includes the meaning of DNA that is found outside of a cell, such as in a biological fluid (eg blood, or a blood fraction) of an individual. "Circulating" is also an art-recognised term, and includes the meaning that an entity or substance (eg cfDNA) is present in, detected or identified in, or isolated from, a circulatory system of the individual, such as the blood system or the lymphatic system. In particular, when cfDNA is "circulating" it is not located in a cell, and hence may be present in the plasma or serum of blood, or it may be present in the lymph of lymphatic fluid.

The term "differentially methylated region" or "DMR" will be recognised by the person of ordinary skill in the art, and is also intended to refer to a region in chromosomal DNA that is differentially methylated (eg at a CpG motif) between said species of DNA and the other DNA with which it is admixed in the sample. For example in one embodiment, the DMRs used in the present invention are differentially methylated between foetal and maternal DNA, or are differentially methylated between tumour-derived and non-tumour-derived DNA from the same individual. In particular embodiments of the present invention, the DMRs are hypermethylated in foetal DNA and hypo methylated in maternal DNA, or are hypermethylated in tumour-derived DNA and hypomethylated in DNA that is derived from non-tumour tissue of the individual. That is, in such regions exhibit a greater degree (ie more) methylation in said species of DNA (eg the foetal or tumour cfDNA) as compared to the other DNA (eg maternal or non-tumour DNA), such as about 10%, 20%, 30%, 40%, 50%, 60%, 70%, 80%, 90% or 100% or, or more of, the sites available for methylation at a given DMR are methylated in said species of DNA as compared to the same sites in the other DNA.

A reagent is used in the present invention that differentially (eg selectively) modifies methylated as compared to non-methylated DNA. For example, treatment of DNA with a reagent comprising bisulphite (bisulfite) converts cytosine residues to uracil, but leaves 5-methylcytosine residues unaffected. Thus, bisulphite treatment introduces specific changes in the DNA sequence that depend on the methylation status of individual cytosine residues, yielding single-nucleotide resolution information about the methylation status of a segment of DNA. Various analyses can be performed on the altered sequence to retrieve this information, including the use of PCR primers and/or probes that can distinguish between such singe-nucleotide changes.

Such a reagent may alternatively (or in addition) comprise a restriction enzyme that is sensitive to the DNA methylation states. Cleavage of such a restriction enzyme's recognition sequence may be blocked, or impaired, when a particular base in the enzyme's recognition site is modified, eg methylated. In particular embodiments of all aspects of the invention, the reagent comprises a methylation-sensitive restriction enzyme, such as a methylation-sensitive restriction enzyme disclosed herein; including such embodiments that comprise two, three, four, five or more of such methylation-sensitive restriction enzymes.

Prior to step (a), the sample may be processed to isolate, enrich and/or purify, the DNA present therein. For example, a plasma sample may be processed using a cfDNA isolation process or kit to provide a (non-natural) subsequent solution that comprises an admixture of said species of DNA together with the differentially methylated DNA that does not originate from the cell-type. The step of treating in (a) may comprise the step of adding a separate solution that comprises said reagent (eg a methylation sensitive restriction enzyme) to the admixed DNA of the sample (eg, to a non-natural solution comprising such admixed DNA); and/or may comprise maintaining (or changing to) certain conditions. In particular, when said reagent comprises one or more methylation sensitive restriction enzyme, the step of treating in (a) may comprise incubating the DNA and the enzyme(s) together at about 37° C. for between about 5 min and 300 min, such as between about 30 min and 90 min or about 60 min, and optionally may comprise a step of incubating such mixture at a higher temperature (for example, between about 50° C. and 90°C.m such as about 80° C.) so as to deactivate the enzyme(s). In certain embodiments, the composition formed for a treating step of (a) may be non-naturally occurring. For example, particular salts of components of the solution (or buffer); and/or the mixture of (eg human) cfDNA together with one or more bacterial-derived restriction enzymes (or a non-natural mutant thereof) may be a non-natural composition or mixture.

In contrast, an "other region" ("OR") used in the present invention is not (significantly) differentially methylated between said species of DNA and other DNA with which it is admixed in the sample. For example, under the conditions and nature of the reagent used, there is not detectable difference between modification by such reagent at the other region of said species of DNA (eg foetal DNA) as compared to the other region of the admixed DNA (eg the maternal DNA). Such a non-difference may be achieved if the other region comprises no sites for methylation, if there is no difference in the degree of methylation if such sites are present or by the use of a reagent that does not recognise any sites of methylation present in the other region. In particular embodiments, the other region used in the present invention (that is not so differentially methylated) may be non-overlapping with the DMRs used in the present invention. For example, the other region can be located further than about 10 bp, 20 bp, 50 bp, or more than 100 bp, 500 bp, 1 kb or 10 kp, away from either of the DMRs.

One feature of the present invention is that the detection of the various DNA regions, ie the DMRs and the other region(s), occurs in a simplified process. For example, using a single aliquot of DNA from the sample, such DNA regions are detected in a single vessel. This feature simplifies the method, and can provide for more efficient and accurate detection (especially in those embodiments when detection is quantitative). The term "vessel" will be art recognised, and includes embodiments of a vessel (such as a tube, well of a microtitre plate, nano-well, capillary reaction vessel etc) in which a process or procedure comprised in the method occurs, such as a reaction and/or detection process or a step of a method of the present invention. Other such vessels may include droplets in oil/water emulsions, nanoparticles or a hybridisation chamber; as appropriate to the detection technology used. The detectable labels used, in such methods is the same for each DMR and, in certain embodiments, is the same for each other region, provided that the label(s) used for the other region(s) is different (ie, can be separately detected) to the label(s) used for the DMRs. Detectable labels that are "the same", can also include labels while structurally different, are functionally (essentially) similar as they cannot be significantly differentiated by the detection technology employed. For example, structurally different fluorescent dyes may be considered "the same" if their excitation and emission spectra are (substantially or essentially) similar, or overlap to such a degree that they are able to be excited and detected simultaneously with the same wavelength(s). Suitable labels (and detection modalities) are further described elsewhere herein. In addition, the detection of the DMRs and other region(s) is made effectively simultaneously. For example, within the same (reaction/detection) vessel, all such regions (and hence said species of DNA and total DNA) can be detected within less than about 5 s, 1 s, 0.5 s, 100 ms, 10 ms, 1 ms, 100 us, 10 us or 1 us of each other, and for example without transferring the vessel, or the reaction/mixture, to any subsequent vessel, assay or equipment, or for example, without adapting or recalibrating the detection process for either of the DMRs or the other region(s) separately. The use of two different detectable label(s)—one for said DMRs and one for the other region(s)—utilises components, process and/or steps that are non-natural. For example, a composition of two specific labels together with the specific DNA regions would (generally) not be found in nature. In particular, short probes used in quantitative probe-based PCR, while may comprise a DNA sequence that is a fragment of that found in a natural genome, when linked to a one or more labels (such as a fluorescent dye) form a specific labelled fragment that is non-natural.

Collectively, the features of the present invention provide for certain advantages over prior art methods. These can include sensitive detection of methylation (and hence the species of DNA to be detected) and/or accurate quantification of the amount of said species of DNA by reference to the amount of total DNA detected within the same assay, from the same aliquot of admixed DNA and effectively simultaneously with the detection of the two or more DMRs, and optionally using a co-located other region.

By way of graphical description, a schematic representation of the general arrangement of the DMRs, the other region(s) and the detectable label(s), as used for the present invention, is presented in FIG. 1. (1) The presence of methylation in DNA at two or more DMRs, DMR1 and DMR2 (and, optionally, up to DMRn), is in each case detected using the same detectable label(s). (2) Optionally, an other region ("OR") is located within the same portion of the genome (eg, between about 20 bp and about 20 kb upstream or downstream of) one of the DMRs. (3) The amount of total DNA detected using at least one OR (OR1, and optionally, OR2 or up to ORn) is detected using different detectable label(s) to those used to detect methylation at the DMRs (optionally, the detectable label(s) used is the same for all the ORs). (4) Optionally, methylation at more than two DMRs is so detected, and/or the amount of total DNA is detected at more than one OR.

In certain embodiments, prior to or as part of the detection that occurs as part of a step (b) and/or a step (c) of any method of present invention, each DNA region comprising said DMRs and/or said other region(s), respectively, is(are) amplified. Amplification of DNA may be conducted using any suitable replication process, and in particular of such embodiments, each of the DMRs and/or an other region, is amplified by a polymerase chain reaction (PCR) using primers suitably designed for each DMR and/or other region. The person of ordinary skill will readily be able to design such PCR primers for use in the method of the invention, for example by use of primer design algorithms and programs such as Clone Manager Professional 9 (Sci-Ed Software), Vector NTI (Life Technologies), or web-based tools such as those found from www.ncbi.nlm.nih.gov/tools/primer-blast/ or molbiol-tools.ca/PCR.htm. Those embodiments of the present invention that comprise PCR amplification can further comprises specific steps that are related to the practice of PCR, such as any of those described herein, or in particular the steps of: (A) providing a reaction mixture comprising a double-stranded target DNA, a pair of primers (for example, a pair of primers disclosed herein) designed to amplify a region of such DNA (such as a DMR or an other region as described herein) wherein the first primer is complementary to a sequence on the first strand of the target DNA and the second primer is complementary to a sequence on the second strand of the target DNA, Taq polymerase, and a plurality of free nucleotides comprising adenine, thymine, cytosine and guanine; (B) heating the reaction mixture to a first predetermined temperature for a first predetermined time to separate the strands of the target DNA from each other; (C) cooling the reaction mixture to a second predetermined temperature for a second predetermined time under conditions to allow the first and second primers to hybridise with their complementary sequences on the first and second strands of the target DNA, and to allow the Taq polymerase to extend the primers; and (D) repeating steps (B) and (C) at least 20 times.

In other embodiments, a detectable label used in step (b) and/or step (c) of a method of the invention is independently selected from the group consisting of: fluorescent, protein, small molecule or radioactive label. For example, fluorescent labels that are the same (including, by having similar or overlapping excitation and/or emission spectra) may be used for the DMRs, and a fluorescent label that has an excitation and/or emission spectra (in particular, a different emission spectrum) may be used for detection of the other region(s). The person of ordinary skill will be able to select appropriate such fluorescent label(s) for use in the present invention from, for example, the group consisting of: FAM, TET, JOE, VIC, HEX, NED, PET, ROX, TAMRA, Quasar and Texas Red. In other embodiments, a detectable label may be a protein or small molecule tag that, for example, can be detected using a specific antibody and ELISA-type detection approaches. The use of the same protein or small molecule for each of the DMRs, and a detectably different protein or small molecule for the other region(s), may also be utilised for the detectable label(s) used in the present invention. Different radioactive labels may be distinguished by their emission energy, penetration/excitation characteristics and particle-type (for example, by distinguishing between alpha and beta particles). Other detectable labels (such as nucleic-acid coded tag) may also be employed in the present invention.

In particular embodiments, the detection in step (b) of a method of the example comprises real-time quantitative probe-based PCR, eg by using at least two labelled probes, each of which is specific for one of said DMRs. PCR amplification of said two or more DMRs in the same reaction can be considered as "multiplex" (or "duplex" if only two DMRs are so amplified). Likewise, the detection in step (c) in the methods of the invention may, in addition or alternatively, comprise real-time quantitative probe-based PCR, such as by using at least one labelled probe specific for one of said other region(s).

The term "probe-based" quantitative PCR is art recognised, and encompasses various embodiments described and marketed under different brand names (such as "TaqMan" PCR of Roche), and uses a (eg fluorescent) reporter probe that is specific for the detection of a given amplicon (eg a DMR or an other region). Probe-based quantitative PCR is distinct from quantitative PCR using double-stranded DNA-binding dyes (eg SYBR Green) as reporters, as such double-stranded DNA-binding dyes bind non-specially to any double-stranded amplicon and eg cannot be used to distinguish between detection of the DMRs (ie said species of DNA) from detection of the other region(s) (ie detection of total DNA). As the person of ordinary skill will appreciate, a specific amplicon of PCR may be detected using a single probe or by using multiple probes (such as two or three probes) for an amplicon.

Such probe-based quantitative PCR may be conducted in an analogue-approach, using a machine such as a LightCycler in which the intensity of signal (eg over time) is measured and used to quantitatively determine detection. Alternatively, digital PCR (dPCR), ie, PCR conducted in multiple events so as to determine the number of amplification events as method to quantitate an amount of detected DNA. For example, dPCR that is conducted in nano-wells or droplets (ddPCR).

The person of ordinary skill will be able to design suitable primers and probes (and with suitable labels, eg dyes) for probe-based quantitative PCR detection of the DMRs and/or other regions(s); for example by using primer/probe design software as described elsewhere herein. As will be known, the PCR primers may overlap methylation site(s) specific for the methylation-specific modifying reagent used in the methods, in particular when the reagent comprises one or more methylation sensitive restriction enzyme, such as one (or a combination thereof) as disclosed herein. In particular such embodiments, one or other (or when considered together, both) of the PCR primers for a given DMR may overlap two or three such methylation sites (such as two or three restriction sites for methylation-sensitive restriction enzymes, each of which may comprise, or comprises, a methylation site). Alternatively or in addition, the primers for a DMR may be designed to flank one, two, three or more such methylation sites, such as up to 10, 15, 20, 25 or 50 such methylation sites, in particular flanking restriction sites for one, two, three or more such methylation sites, such as up to 10, 15, 20, 25 or 50 methylation-sensitive restriction enzymes, each of which may comprise, or comprises, a methylation site.

In a particular embodiment, the genomic location of the other region used in the present invention is generally located in the same portion of the genome, such as between about 20 bp and about 20 kb upstream or downstream of (including embodiments within the same gene as) the genomic location of at least one of the DMRs used herein. In certain embodiments, the other region does not overlap with the DMR. The inventors find that detection (and particularly quantification) of the species of DNA is enhanced (eg, in terms of sensitivity, accuracy and/or precision) if the other region is so located in the same portion of the genome as one of the DMRs. Without being bound by theory, it is believed that with such similarly-located DMR(s) and other region, the effect of variation in chromatin/nucleosome packing across the genome—and hence stability/degradation of different regions of genomic DNA—is mitigated, such that any difference in stability/degradation of a DMR (ie detecting the species of DNA) as compared to the other region (is detecting total DNA) is less, and hence a relative (and absolute) quantification may be made without it being (significantly) confounded by quantitative differences brought about by (significantly) differential chromatin/nucleosome packing across the genome between a DMR and an other region. The combination of this feature (similarly-located DMR(s) and other region) with another feature of the present invention (the use of at least two DMRs, and the detection in step (b) and the detection in step (c) are made using the same aliquot of DNA of the sample, and in the same reaction/detection vessel, and effectively simultaneously for such DMRs and other region, and using: (x) the same detectable labels(s) for each of said DMRs; and (y) a different detectable label for said other region(s)), is a preferred embodiment of the present invention. The use of such a combination of features in the present invention provides opportunity for efficiency improvements and/or synergistic enchantment of outcome. For example, an improved sensitivity and/or accuracy and/or precision of detection (eg, detection of a quantitative amount) or said species of DNA can be obtained by the use of such a combination; the degree of improvement of which can be synergistic, as compared to the use of each feature alone; eg the enhancement obtained by use of the combined features being greater than the sum of each enhancement obtained by the use of each feature individually.

The present invention includes the use of one other region to provide for the detection of an amount of total DNA in the admixture. However, the present invention also encompasses embodiments that use more than one other region. For example, the invention includes such embodiments wherein said detection in step (c) comprises using at least two of said other regions, such as two, three or four of said other regions. In particular embodiments of all aspects of the present invention, the number of said other regions is the same as the number of DMRs used in step (b). For example, if two DMRs are used then two other regions are used in such an embodiment, and if three DMRs are used then three other regions are used (such as depicted in FIG. 1).

As described elsewhere herein, certain embodiments of the present invention include where the other region is generally located in the same portion of the genome, such as between about 20 bp and about 20 kb upstream or downstream of (including embodiments within the same gene as) the genomic location of at least one of the DMRs used herein. In certain embodiments, the other region does not overlap with the DMR Accordingly, if multiple other regions are used in the present invention, then embodiments are included where two or more of such other regions are similarly located in the genome to the two or more DMRs. For example, one of said other regions may be located between about 20 bp and about 20 kb upstream or downstream of (including embodiments within the same gene as) a DMR used in step (b) and each other of the said other regions (eg, a second other region) is located between about 20 bp and about 20 kb upstream or downstream of (including embodiments within the same gene as) another of said (eg, non-overlapping) DMRs (eg, the second DMR). In certain embodiments an additional other region, may overlap with a DMR.

An other region used in the present invention, when generally located in the same portion of the genome as a DMR, may be located upstream or downstream of one of said DMRs within a distance selected from the group consisting of: between about 16 kb to 20 bp, 14 kb to 20 bp, 12 kb to 20 bp, 10 kb to 20 bp, 8 kb to 20 bp, 6 kb to 20 bp, 5 kb to 20 bp, 4 kb to 20 bp, 3 kb to 2 bp, 16 kb to 20 bp, 1 kb to 20 bp, 500 bp to 20 bp, 200 bp to 20 bp, 20 kb to 15 kb, 15 kb to 10 kb, 12 kb to 8 kb, 10 kb to 8 kb, 11 kb to 7 kb, 11 kb to 10 kb, 9 kb to 8 kb, 8 kb to 6 kb, 6 kb to 4 kb, 4 kb to 2 kb, 2 kb to 500 bp, 1 kb to 100 bp, 500 bp to 50 bp, 400 bp to 200 bp and 500 bp to 100 bp. In particular embodiments, each other region used in the present invention is so generally located to a different of the DMRs used.

If multiple other regions are used, then the present invention includes embodiments where the detection in step (c) is made using the same detectable label for each of said other regions and/or comprises multiplex real-time quantitative PCR using at least two labelled probes each of which is specific for one of said other regions.

In particular embodiments, all detection steps (ie, those required for all DMRs and all other regions) are conducted in an efficient and effective manner using multiplex quantitative probe-based (eg TaqMan) PCR, in one process step or reaction. For example, the detection in step (c) and said detection in step (b) are made using the same aliquot of DNA of said sample, and in the same reaction/detection vessel, and effectively simultaneously with each other, and by multiplex real-time quantitative PCR using at least one labelled probe specific for each of the said DMRs and other region(s). In particular of such embodiments, the reagent comprises one or more methylation sensitive restriction enzyme, such as one (or a combination thereof) as disclosed herein.

The present invention may also include further procedures, such as one or more control procedures. For example, the present invention can include one or more steps directed to the detection of a third class of DNA region that acts as a control for the modification step (eg, as a control for restriction enzyme digestion). Such embodiments may, for example, also be conducted using multiplex real-time quantitative probe-based PCR wherein such control region is amplified and detected by a third set of primer/probe(s) with a third detectable label used for such class of region.

In one embodiment of the present invention of particular relevance, said species of DNA originates from cells of a foetus and/or the placenta of a foetus and said sample is from a pregnant female. In such embodiments, the sample may be obtained in a non-invasive manner. For example, said species of DNA is circulating cell-free DNA that has been detected from the sample being blood or a blood fraction (such as plasma or serum) that has been obtained from the pregnant female by conventional means such as a blood collection tube.

The present invention includes embodiments where the DMRs are hypermethlyated in foetal DNA and hypo methylated in maternal DNA. In certain embodiments, such a DMR may be located in a promoter, enhancer region or an exon of a gene, such as a gene disclosed herein. Alternatively, a DMR may be located in an intron of such a gene, or in a non-coding region of the genome. In particular embodiments of all aspects of the present invention, such genome and/or gene is a human genome or gene. Specifically included in the present invention are embodiments wherein said DMRs comprises at least one, preferably at least two, methylation site(s) specific for said reagent, and at least one of said DMRs is located in a portion of the genome and/or gene (eg a human genome or gene) that is RASSF1A and/or TBX3, or selected from the group consisting of: RASSF1A, TBX3, HLCS, ZFY, CDC42EP1, MGC15523, SOX14 and SPN. Also, embodiments are included wherein said DMRs comprises at least one, preferably at least two, methylation site(s) specific for said reagent, and at least one of said DMRs is located in a region and/or gene selected from the group consisting of: AIRE, SIM2, ERG, VAPA-APCDDI, one disclosed in WO 2011/034631 as being hypermethylated in foetal DNA relative to maternal DNA (eg, SEQ ID NOs: 1-59, 90-163, 176, 179, 180, 184, 188, 189, 190, 191, 193, 195, 198, 199, 200, 201, 202, 203, 205, 206, 207, 208, 209, 210, 211, 212, 213, 214, 221, 223, 225, 226, 231, 232, 233, 235, 239, 241, 257, 258, 259, and/or 261 of WO 2011/034631 and one disclosed in WO 2011/092592 (eg, EP1, EP2, EP3, EP4, EP5, EP6, EP7, EPB, EP9, EP10, EP11 and/or EP12 of WO 2011/092592, as further investigated in Lim et al 2014, BMC Medical Genomics 7:1).

In particular embodiments of all aspects of the present invention, the two DMRs used are not located in the same portion of the genomic and/or gene. For example, such DMRs may be located on separate chromosomes, or separated by more than about 20 kb, or more than about 15 kb, 10 kb, 8 kb, 6 kb, 4 kb, 2 kb, 1 kb, 500 bp or 200 bp. Alternatively, it is envisioned, that the two (or more) DMRs used in the present invention may, in certain embodiments, be located in the same region or gene (such as one described herein) and, further, may overlap with each other.

In particular embodiments of the present invention, both of said DMRs are (or each, in the case of more than two DMRs are being used, is) located in a portion of the genome and/or gene (preferably that is human) that is RASSF1A and/or TBX3, or is selected from the group consisting of: RASSF1A, TBX3, HLCS, ZFY, CDC42EP1, MGC15523, SOX14 and SPN; and/or at least one of said DMRs is located between about positions 4,700 bp and 5,600 bp of RASSF1A (NCBI Reference Sequence: NG_023270.1: Homo sapiens Ras association (RaIGDS/AF-6) domain family member 1 (RASSF1), RefSeqGene on chromosome 3; SEQ ID NO.: 13) or about positions 1,660 bp and 2,400 bp of TBX3 (NCBI Reference Sequence: NG_008315.1: Homo sapiens T-box 3 (TBX3), RefSeqGene on chromosome 12; SEQ ID NO.: 14). In a more particular embodiment, two (or more) DMRs are used, and a first DMR comprises one located between about positions 4,700 bp and 5,600 bp of RASSF1A and a second DMR comprises one located between about positions 1,660 bp and 2,400 bp of TBX3.

In particular embodiments, a DMR is located in RASSF1A between about positions 4,900 bp and 5,500 bp, 5,000 bp and 5,400 bp, or 5,100 bp and 5,300 bp of RASSF1A; and/or is located in TBX3 between about positions 1,800 bp and 2,260 bp, 1,920 bp and 2,160 bp or 1,920 bp and 2,080 bp of TBX3.

Figure 2:
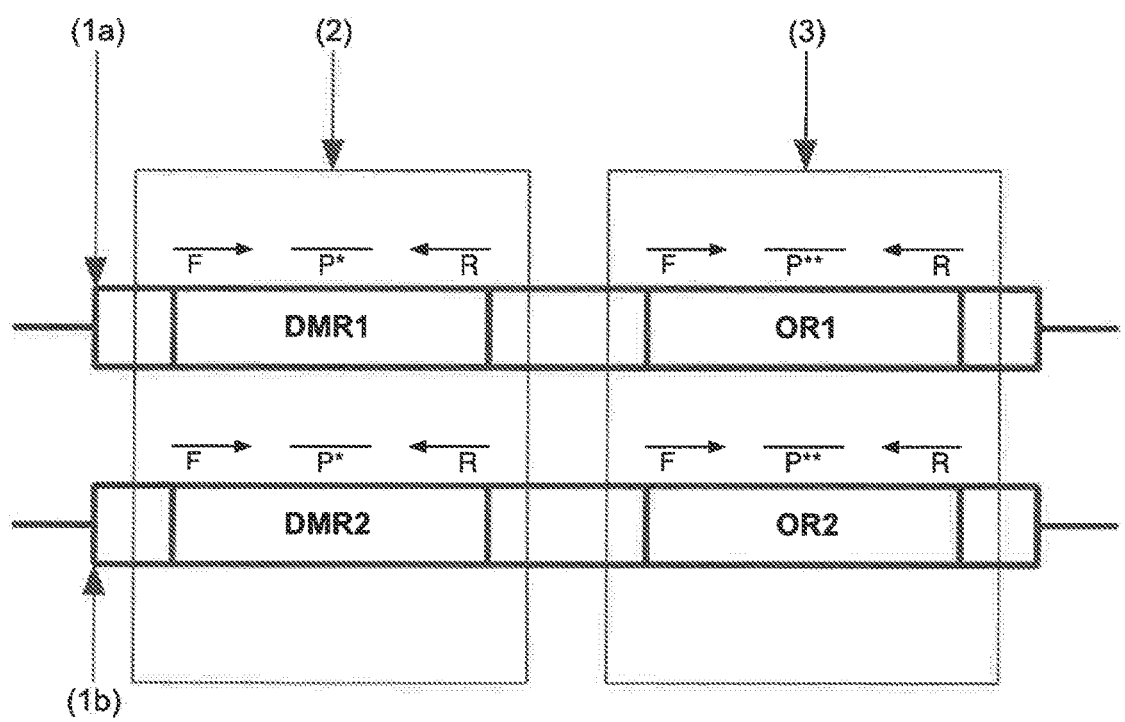
FIG. 2 depicts a schematic representation of the differentially methylated regions ("DMR") and other regions ("OR") used in Example 1.

The general arrangement of the DMRs and other regions ("OR") used in one embodiment of the present invention, is graphically represented by FIG. 2: (1a) DMR1 is found in exon 2 of RASSF1A and OR1 is located within exon 4 of RASSF1A, with DMR1 located between positions 50,340,672 bp and 50,340,784 bp and OR1 located between positions 50,331,604 bp and 50,331,702 bp of the RASS1A genomic sequence (NCBI Reference Sequence: NC_000003.12 Homo sapiens chromosome 3, GRCh38 Primary Assembly), separating DMR1 and OR1 by a distance of 8,969 bp. (1b) DMR2 is found in the promoter region of TBX3, with DMR2 located between positions 114,687,095 bp and 114,687,189 bp and OR2 is located between positions 114,676,384 bp and 114,676,454 bp of the TBX3 genomic sequence (NCBI Reference Sequence: NC_000012.12 Homo sapiens chromosome 12, GRCh38 Primary Assembly), separating DMR2 and OR2 by a distance of 10,640 bp. (2) Methylation in DNA at the two DMRs is detected using probe-based quantitative PCR using the respective forward (F) and reverse (R) PCR primers and region-specific probes, each probe labelled with the same labels (P*). (3) Total DNA is detected at two ORs using probe-based quantitative PCR using the respective forward (F) and reverse (R) PCR primers and region-specific probes, each probe labelled with the same labels for the ORs that is different to the labels used for the two DMRs (P**). Details of primer and probe sequences and probe labels are set out in TABLE 1.

The term "methylation site(s)" will be art-recognised, and has a meaning that encompasses, for example, a CpG motif within a short nucleotide sequence (eg one that is 4, 6, 8, 10 or 12 bp in length) that is, preferably, recognised by a methylation-sensitive restriction enzyme, such as one disclosed elsewhere herein.

Analogously, the other region may be located in particular portions and/or genes of the genome, and may be located in a promoter, enhancer region or an exon of a gene, or alternatively, located in an intron of such a gene, or in a non-coding region of the genome. In particular embodiments of all aspects of the present invention, such genome and/or gene is a human genome or gene. In particular embodiments, an other region used in the present invention is located in a (eg human) housekeeping gene (such as GAPDH, beta-actin, ALB, APOE or RNASEP). Alternatively (and in particular when said species of DNA is foetal cfDNA), said other region may be located in the same portion of the genome and/or gene that feature one or more DMRs (such as those RASSF1A, TBX3, HLCS, ZFY, CDC42EP1, MGC15523, SOX14 or SPN), and preferably does not overlap with a DMR used in the invention. In particular embodiments, said other region comprises a portion of the genome without a methylation site specific for said reagent, and said other region is located in the (eg human) genes RASSF1A or TBX3 (eg SEQ ID NOs,: 13 and 14 respectively), and includes more particular embodiments wherein two or more of said other regions are used in detection step (c) and the first other region is located between about positions 14,220 bp and 13,350 bp of such RASSF1A and the second other region is located between about positions 12,400 bp and 13,000 bp of such TBX3. In particular embodiments, an other region is located in RASSF1A between about positions 14,230 bp and 14,340 bp, 14,230 bp and 14,330 bp, 14,230 bp and 14,320 bp, or 14,230 bp and 14,310 bp of such RASSF1A; and/or is located in TBX3 between about positions 12,400 bp and 12,940 bp, 12,700 bp and 12,850 bp or 12,710 bp and 12,790 bp of such TBX3. Alternatively, an other region may be located in an exon such as between about positions 13,790 bp and 13,880 bp, or 14,490 bp and 14,600 bp of such RASSF1A, or between about positions 8,040 bp and 8,180 bp or 6,230 bp and 6,350 bpof such TBX3; or an other region may be located in an intron such as between about positions 10,500 bp and 11,90 bp of such RASSF1A, or between about positions 10,000 bp and 11,000 bp of such TBX3

There is now strong evidence that the level of foetal cfDNA (and/or total cfDNA) present in the circulatory system (eg in plasma) of a pregnant female is a marker of one or more forms of preeclampsia, such as early-onset preeclampsia, mild and/or severe preeclampsia (see Hahn et al 2011, Placenta 32(Supl):S17). The present invention shows particular utility in the efficient, effective, sensitive and/or low-variability detection/quantification of foetal cfDNA present in plasma of pregnant females, and the present invention has particular utility therein. Accordingly, in particular embodiments of the present invention, the individual is a pregnant female and is susceptible to suffering or developing a pregnancy-associated medical condition; particularly where said pregnancy-associated medical condition is preeclampsia. As used herein, an individual "susceptible to" a medical condition may alternatively be described as "is suspected to" or to "be considered at risk of being susceptible to" suffering or developing a medical condition; and in certain embodiments, the present invention is used to screen and/or diagnose the individual for susceptibility to, risk of suffering or developing, or suffering from or developing, a medical condition.

In alternative embodiments, the individual is a pregnant female and is susceptible to (or considered at risk of being susceptible to) suffering or developing a pregnancy-associated medical condition selected from the group consisting of: preterm labour, intrauterine growth retardation and vanishing twin. In particular, the inventors were surprised that the sensitivity of the present invention was such that discrepancies between cfDNA levels determined by the method of the invention and that determined by counts of Y-chromosome sequences as determined by massively parallel sequencing approaches, was useful in identifying one or more cases of a vanishing twin in (mixed-sex) twin pregnancies that previously were believed to be singleton pregnancies, and/or to follow the relative development and health of one or other of such (mixed-sex) twin pregnancies.

The present invention may also be utilised in gender determination of twin pregnancies, by consideration of the relative values for foetal cfDNA compared to counts of Y-chromosome sequences determined from cfDNA (eg by using parallel sequencing approaches). In these regards, it should be noted that approaches that use massively-parallel sequencing of random cfDNA in maternal blood typically always count a very low frequency of "Y-chomomosone" sequences (such as between about 0.003% and 0.004% of all sequences, or between about 0.0015% and 0.01% or 0.002% and 0.005% of all sequences) in all female pregnancies due to homology of certain Y-chromosome short sequences to other chromosomes. A cut off of "Y-chromosome" sequence counts of about 0.005%, or between about 0.003%, 0.004%, 0.006% or 0.007%, may therefore be employed for female samples.

As described elsewhere herein, there is also increasing evidence that the presence and amount of methylated DNA at certain DMRs is indicative or prognostic of certain medical conditions that are not associated with pregnancy. Accordingly, in another particular embodiment of the present invention, said species of DNA originates from a cell type associated with such a medical condition, particularly in those embodiments where said species of DNA is circulating cell-free DNA and said sample is a blood fraction such as plasma or serum. For example, the medical condition may be a cell proliferative disorder, such as a tumour or cancer. In particular embodiments, the medical condition is a tumour or a cancer of an organ selected from the list consisting of: liver, lung, breast, colon, oesophagus, prostate, ovary, cervix, uterus, testis, brain, bone marrow and blood; and/or said species of DNA may originate from cells of a tumour; particularly where such tumour is a carcinoma or cancer of an organ selected from the group consisting of: liver, lung, breast, colon, oesophagus, prostate, ovary, cervix, uterus, testis, brain, bone marrow and blood.

When used in the context of a medical condition being a tumour or cancer, the present invention includes embodiment wherein said DMRs comprises at least one, preferably at least two, methylation site(s) specific for said reagent, and at least one of said DMR is located in a portion of the genome and/or a gene (in particular, when such genome and/or gene is a human genome or gene) selected from the group consisting of: a tumour suppressor gene, p16, SEPT9, RASSF1A, GSTP1. DAPK, ESR1, APC, HSD17B4 and H1C1. In particular, one of said two or more DMRs may be located in RASSF1A (eg SEQ ID NO. 13) such as located between about positions 4,700 bp and 5,600 bp of such RASSF1A; and/or said other region is located between about positions 14,220 bp and 13,350 bp of such RASSF1A. Other particular locations of the DMRs and/or other region(s) within RASSF1A for use in this embodiment are disclosed elsewhere herein. Furthermore, the person of ordinary skill will now recognise that other DMRs and/or other regions located in other portions of the genome of in other genes may be identified from the relevant scientific literature (eg, for review, see Elshimali 2013). In particular when used in the context of a medical condition being a tumour or cancer, the present invention includes embodiments where at least one other region (preferably two or more) are located in a (eg human) housekeeping gene (such as GAPDH, beta-actin, ALB, APOE or RNASEP). Alternatively for such context, said other region(s) may be located in the same portion of the genome and/or gene that feature one or more DMRs (such as those p16, SEPT9, RASSF1A, GSTP1. DAPK, ESR1, APC, HSD17B4 and H1C1).

In yet another particular embodiment of the present invention, said species of DNA originates from a cell type associated with a medical condition selected from the group consisting of: an infection/infectious disease, a wasting disorder, a degenerative disorder, an (auto)immune disorder, kidney disease, liver disease, inflammatory disease, acute toxicity, chronic toxicity, myocardial infarction, and a combination of any of the forgoing (such as sepsis) and/or with a cell proliferative disorder, particularly in those embodiments where said species of DNA is circulating cell-free DNA and said sample is a blood fraction such as plasma or serum. For example, the medical condition may be an infection/infectious disease, such as one caused by a bacterial, viral or protozoan pathogen, including a pathogen selected from the group consisting of: a retrovirus (such as HIV), a herpes virus (such as HSV, EBV, CMV, HHV or VSV), dengue virus, mycobacteria (eg Mycobacterium tuberculosis), and hantavirus. In certain embodiments, the medical condition is sepsis and/or excludes kidney disease.

In all aspects of the present invention, there exist embodiments wherein the sample is a tissue sample or a sample of biological fluid. In particular, the sample is whole blood or a blood fraction (eg, such as plasma or serum). In alterative embodiments, the sample is biological fluid selected from the group consisting of: urine, saliva, sweat, ejaculate, tears, phlegm, vaginal secretion, vaginal wash and colonic wash. In more particular embodiments, the sample is a plasma or serum sample from the individual., or is urine from the individual In other embodiments, the sample is largely (or essentially) free from cells, and/or is not a whole blood and/or ejaculate sample. In certain embodiments, the sample is not ejaculate if the individual is female and the sample is not a vaginal wash if the individual is male.

In all aspects of the present invention, the reagent that differentially modifies methylated and non-methylated DNA may comprise bisulphite and/or an agent that selectively digests unmethylated over methylated DNA (for example, such agent may digest unmethylated DNA but not methylated DNA). In particular embodiments, the reagent agent comprises: at least one methylation sensitive enzyme; at least one methylation sensitive restriction enzyme; and/or an agent selected from the group consisting of: AatII, AciI, AcII, AfeI, AgeI, AgeI-HF, AscI, AsiSI, AvaI, BceAI, BmgBI, BsaAI, BsaHI, BsiEI, BsiWI, BsmBI, BspDI, BsrFI, BssHII, BstBI, BstUI, ClaI, EagI, FauI, FseI, FspI, HaeII, HgaI, HhaI, HinP1I, HpaII, Hpy99I, HpyCH4IV, KasI, MluI, NaeI, NarI, NgoMIV, NotI, NotI-HF, NruI, Nt.BsmAI, Nt.CviPII, PaeR7I, PluTI, PmlI, PvuI, PvuI-HF, RsrII, SacII, SalI, SalI-HF, SfoI, SgrAI, SmaI, SnaBI, TspMI and ZraI. In particular embodiments, said reagent is one selected from the group consisting of: BstUI, HhaI and HpaII.

In related embodiments, the reagent may comprise two or more of any of the reagents disclosed herein. For example, it may comprise two, three, four, five or more (eg up to seven, eight or ten) methylation sensitive restriction enzymes, including a reagent comprising or essentially consisting of two or three of the methylation sensitive restriction enzymes selected from the group consisting of: BstUI, HhaI and HpaII The use of bisulphite or methylation-sensitive restriction enzymes to study differential methylation will be well known to the person of ordinary skill, who may apply teachings of standard texts or adaptation of published methods such as Poon et al (2002), Nygren et al (2010) or Yegnasubramanian; et al (2006, Nuc Acid Res 34:e19). By way of illustration, the inventors provide examples herein that employ the use of methylation-sensitive restriction enzymes as the reagent that differentially modifies methylated and non-methylated DNA. For further illustration using bisulphite as reagent, it will be apparent to the person of ordinary skill that bisulphite-modified DNA methylation sites may be detected using eg methylation-specific PCR (such as using primers and/or probes that selectively bind to the bisulphite-modified sequences) and/or by the subsequent use of restriction enzymes the recognition site of which is created upon such bisulphite-modification.

In particular embodiments of all aspects of the invention, a quantitative amount of said species of DNA (and/or or said total DNA) is to be detected and/or determined. Accordingly in such embodiments, one or more (eg each) of said detection steps comprises quantitative detection and said detected amount of said species of DNA is expressed as a relative concentration of said species of DNA to the total DNA present in said sample.

If an absolute amount of total DNA is known, then correspondingly an absolute amount (for example, as represented by a concentration such as ug/mL or genome-equivalents such as Eg/mL) of the species of DNA can be determined from such relative concentration. An absolute amount of total DNA for a sample may be determined, for certain embodiments, by including the further steps of: detecting an amount of total DNA in a standard sample of DNA of known amount using the same other regions(s) as used in step (c); and comparing the signal detected from said standard sample of DNA to the signal detected in step (c). Such a standard sample of DNA (of known amount/concentration) is readily available from commercial sources, and especially if prepared and analysed using a dilution series, can readily and efficiently be used to determine (by interpolation/estimation from the standard curve) an absolute amount of total DNA present in the sample. Practically, such standard curve may be prepared and analysed essentially as described for the other regions (but in a separate set of standard vessels/reactions), preferably in the same run as the detection of the DMRs/other region(s); and may even use the same reaction master-mix. Accordingly, while the "DMRs" of the DNA control may be detected for such standard DNA, such a signal is not required to generate a standard curve. Accordingly, if the signal from a such a standard DNA sample is used to compare, the in certain embodiments where each of said detection steps comprises quantitative detection, said detected amount of said species of DNA can be expressed as an absolute amount of said species of DNA in said sample.

A determined quantitative amount of said species of DNA has utility in assessing the risk of the individual to certain medial conditions and/or if there is sufficient of such species of DNA in the sample to enable further analysis of such species of DNA to be conducted efficiently, accurately and/or in a cost effective manner.

Accordingly, certain embodiments of the present invention further include the step of: comparing the amount of said species of DNA detected with a threshold amount and/or reference distribution of amounts, wherein an increase in the (or outlying) amount of said species of DNA indicates an increased risk of the individual suffering from or developing a medical condition. Threshold amounts and/ or a set of amounts to form a reference distribution may be obtained from published literature and or empirical studies. For example, using published threshold values (Papantoniou et al 2013, Prenat Diag 33:682) if the total cfDNA exceeds an amount of about 7,500 Eg/mL plasma or if the foetal cfDNA fraction exceeds an amount of about 500 Eg/mL plasma, then the woman may be determined to have such an increased risk. Such a risk may instead or additional be assessed by considering: (i) the fold-increase (eg 1.5, 3, 3.5 or 4-fold increase) of foetal cfDNA (determined for such woman compared to a threshold amount), factoring into the determination that for later-term pregnancies a higher fold-increase in foetal cfDNA may be utilised (Zeybek et al 2013, J Obstet Gynaecol Res 39:632); and/or (ii) into which percentile the amount of cfDNA determined from the woman falls, from consideration of a reference distribution of amounts such as those determined from low-risk women or those which did not suffer from or develop preeclampsia, for example if the foetal cfDNA fraction falls within the $90^{th}$ percentile of such a distribution, then the woman may be considered to have an increased risk of suffering mild or severe preeclampsia (Jakobsen et al 2013, Transfusion 53:1956). Other relevant factors may be considered in determining a suitable threshold amount. For example, a pregnant women who is also suffering from breast cancer, may have a higher bias of methylation at RASSF1A present in her plasma due to both factors.

Analogously, certain embodiments of the present invention further include the step of: comparing the amount of said species of DNA detected with a threshold amount and/or reference distribution of amounts, wherein an amount of said species of DNA in excess to said threshold (or is not an outlier compared to said population) indicates that a diagnosis for an abnormality in the said species of DNA present in said sample may be performed on, preferably a separate aliquot of DNA of, said sample. For example, if foetal cfDNA fraction is greater than about 10%, 9%, 8%, 7%, 6%, 5%, 4%, 3%, 2%, 1% or 0.5% of total cfDNA present in maternal plasma, then there would be sufficient fraction or foetal cfDNA to effectively conduct a subsequent test to investigate one or more characteristics of the foetal cfDNA, for example to investigate the chance or existence of a chromosomal anomaly of mutation comprised within such foetal cfDNA (such as using NIPT based on massively parallel sequencing). In the case of twin pregnancies, the inventors determine that a minimum foetal fraction of cfDNA for NIPT of a twin pregnancy could be considered to be 8%, or about 5%, 6%, 7%, 9% or 10%, and for monochorionic twin pregnancies with concordant genotypes (apart from rare exceptions, Chen et al, 2013, Am J Med Genet A, 161A:1817), a foetal cfDNA fraction of 4%, or about 2%, 3% or 5%, would be sufficient.

Therefore, the present invention also includes embodiments where comprising a further step of: performing on, preferably with a separate aliquot of DNA of, said sample an in-vitro diagnosis for an abnormality in said species of DNA present in said sample; preferably wherein, said species of DNA originates from cells of a foetus and/or the placenta of a foetus, said sample is from a pregnant female and said diagnosis is a prenatal diagnosis. Such diagnosis directed at said species of DNA present may comprise a step that uses a detection technology selected from the group consisting of: DNA sequencing, SNP analysis, digital PCR and hybridization, and in particular embodiments said detection technology is massively parallel sequencing of DNA, such as massively parallel sequencing of random and/or (exon) enriched DNA.

Such a diagnosis or test may be directed at the foetal DNA to identify a genetic mutation or chromosomal abnormality of the foetal DNA. Accordingly in certain embodiments, said species of DNA originates from cells of a foetus and/or the placenta of a foetus, said sample is from a pregnant female and said abnormality is a genetic mutation or a chromosomal abnormality, such as a chromosomal trisomy, associated with a foetal abnormality and/or a congenital disorder, In particular such embodiments, the genetic mutation is selected from the group consisting of: colour blindness, cystic fibrosis, hemochromatosis, haemophilia, phenylketonuria, polycystic kidney disease, sickle-cell anemia, Tay-Sachs disease; and/or the chromosomal abnormality is selected from the group consisting of: a trisomy (such as trisomy 21, trisomy 18, or trisomy 13), a sex-chromosome abnormality (such as Turners syndrome, Klinefelter syndrome, Noonan syndrome, Triple X syndrome, XXY syndrome, or Fragile X syndrome), a chromosomal deletion (such as Prader-Willi syndrome, Cris-du-chat syndrome, Wolf-Hirschhorn syndrome, or 22q11 deletion syndrome, Duchene muscular dystrophy), Beckwith-Wiedemann syndrome, Canvan syndrome, and neurofibromatosis. In other embodiments, the genetic mutation or chromosomal abnormality may be one or more selected from those having a clinical utility gene cards (CUGCs) of the EuroGentest2 initiative (www.eurogentest.org). In particular embodiments, the chromosomal abnormality is a trisomy (such as trisomy 21, trisomy 18, or trisomy 13), a sex-chromosome abnormality or a chromosomal deletion.

Such diagnosis or test may be directed at a species DNA to identify a genetic mutation or chromosomal abnormality of such DNA that is derived from a cell or cell-type associated with a medical condition. Accordingly in one of such embodiments, said species of DNA originates from cells of a tumour and said abnormality is a genetic mutation or a chromosomal abnormality associated with the diagnosis, prognosis or predictive treatment of a carcinoma or cancer. In particular such embodiments, the genetic mutation is selected from the group consisting of: a mutation in a tumour suppressor gene (such as TP53 (p53), BRCA1, BRCA2, APC or RB1), a mutation in a proto-oncogene (such as RAS, WNT, MYC, ERK, or TRK) and a DNA repair gene (such as HMGA1, HMGA2, MGMT or PMS2); and/or the chromosomal abnormality is a translocation (such as t(9;22)(q34;q11) [ie, Philadelphia chromosome or BCL-ABL], t(8;14)(q24;q32), t(11;14)(q13;q32), t(14;18)(q32;q21), t(10;(various))(q11;(various)), t(2;3)(q13;p25), t(8;21)(q22;q22), t(15;17)(q22;q21), t(12;15)(p13;q25), t(9;12)(p24;p13), t(12;21)(p12;q22), t(11;18)(q21;q21), t(2;5)(p23;q35), t(11;22)(q24;q11.2-12), t(17;22), t(1;12)(q21;p13), t(X;18)(p11.2;q11.2), t(1;19)(q10;p10), t(7,16)(q32-34;p11), t(11,16)(p11;p11), t(8,22)(q24;q11) or t(2;8)(p11;q24)).

A related aspect of the present invention relates to an alternative method for detecting in a sample from an individual an amount of a species of DNA originating from cells of a given type, which sample comprises said species of DNA in admixture with differentially methylated DNA not originating from cells of said type; said method comprising the steps:
(a) treating the DNA present in said sample with a reagent that differentially modifies methylated and non-methylated DNA; and
(b) detecting in said sample the presence of methylation in said species of DNA at two or more DMRs that are differently methylated between said species of DNA and the DNA not originating from cells of said type the modification of DNA of such DMRs by said reagent is sensitive to methylation of DNA, wherein the presence of methylated DNA at one or more of said DMRs indicates the presence of said amount of species of DNA in said sample and the absence of methylated DNA at said DMRs indicates the absence of said species of DNA in said sample,
wherein, said detection in step (b) is made using the same aliquot of DNA of said sample, and in the same reaction/detection vessel, and effectively simultaneously for such DMRs, and using (x) multiplex real-time quantitative PCR; and (y) at least two labelled probes each of which specific for one of said DMRs and that are labelled with the same detectable label(s) for each of said DMRs. Such an alternative method of the present invention is not intended to be practiced on the human or animal body; for example it is intended to be practiced in an in-vitro manner. Further characterisation of any of the features of this alternative method of the present invention (or any combination of such features) can include the characterisations (and their combinations) as described elsewhere herein in respect of the first aspect of the invention. In particular embodiments of this alternative method of the present invention, the reagent comprises one or more methylation sensitive restriction enzyme, such as one (or a combination thereof) as disclosed herein.

In a second aspect, the invention relates to a method for detecting an increased risk of an individual suffering from or developing a medical condition, said method comprising the steps:
(i) conducting a method of the present invention that determines a quantitative amount said species of DNA (and/or total DNA) in the sample; and
(ii) comparing the amount of said species of DNA detected with a threshold amount and/or a reference distribution of amounts,
wherein an increase in the (or outlying of) amount of said species of DNA (and/or total DNA) indicates an increased risk of the individual suffering from or developing said medical condition.

A third aspect of the invention relates to a composition (eg, one that is useful for, or used in, a method of the present invention), said inventive composition comprising:
two pairs of PCR primers, each pair for amplifying one of said two of more DMRs as set forth anywhere herein;
one pair of PCR primers for amplifying said other region as set forth anywhere herein;
two labelled probes for quantitative probe-based PCR, each of which specific for one of said DMRs, and labelled with the same detectable labels(s) for each of said probe; and
one labelled probe for quantitative probe-based PCR specific for said other region and labelled with different detectable label(s) to the probes used for said DMRs.

Such a composition of the present invention may further comprising:
a further pair of PCR primers for amplifying a second other region as set forth anywhere herein; and
a further labelled probe for quantitative probe-based PCR specific for said other region and labelled with detectable label(s) that is different to those used probes for said DMRs; and optionally that is the same as that used for the probe(s) specific the first other region.

A fourth aspect of the invention relates to a kit (for example a kit of separate components; such as a kit of holders or vessels, each holding a different component of the kit), such kit comprising a set of primers and probes as comprised in a composition of the present invention. A kit of the present invention may comprise additional components. For example, the kit may additionally comprise: (i) a printed manual or computer readable memory comprising instructions to use said primers and probes, including to use them to practice a method of the present invention and/or to produce or use a composition of the present invention; and/or (ii) one or more other item, component or reagent useful for the practice of a method of the present invention; and/or the production or use of the composition of the present invention, including any such item, component or reagent disclosed herein, such as a reagent that differently modifies methylated and non-methylated DNA as set forth anywhere herein.

A further aspect of the invention relates to a computer program product comprising a computer readable medium encoded with a plurality of instructions for controlling a computing system to perform and/or manage an operation for determining: (x) an increased risk of an individual suffering from or developing a medical condition and/or (y) if a diagnosis for an anomaly in a species of DNA originating from cells of a given type may be performed, in each case from a sample from an individual comprising a species of DNA originating from cells of a given type in admixture with differently methylated DNA not originating from cells of said type, the DNA in present in said sample being treated with a reagent that differentially modifies methylated and non-methylated DNA as set forth herein; said operation comprising the steps of:

receiving: (i) one signal representing the essentially simultaneous quantitative detection of methylation at two or more DMRs as set forth in step (b) as described anywhere herein; and (ii) one signal representing the essentially simultaneous quantitative detection of total DNA using at least one other region as set forth in step (c) as described anywhere herein;

determining a parameter from the signals (i) and (ii), wherein the parameter represents a quantitative amount of said species of DNA (and/or said total DNA);

comparing the parameter to with a threshold amount and/or reference distribution of amounts; and based on such comparison, determining a classification of whether, respectively, (x) an increased risk of an individual suffering from or developing a medical condition exists; and/or (y) a diagnosis for an anomaly in a species of DNA originating from cells of a given type may be performed.

In certain embodiments, a computer program product of the present invention the operation further comprises steps of: receiving a further signal representing the quantitative detection of total DNA in a standard sample of DNA as set forth anywhere else herein; and comparing said signal with the signal representing the essentially simultaneous quantitative detection of total DNA using at least one other region, so as to determine said parameter that represents an absolute quantitative amount of said species of DNA.

In particular embodiments, the computer program product of the present invention is for an operation for determining if a diagnosis for an anomaly in said species of DNA may be performed, and said operation further comprises the step of determining from said parameter a number of random and/or enriched DNA molecules to be sequenced from, preferably from a separate aliquot of DNA of, said sample as part of said diagnosis.

One embodiment of operations performed and/or controlled by the computer program product of the invention is depicted in FIG. 5. Operation (A) receives signals (1) and (2) that represent, respectively, the methylation at the DMRs and the total DNA, and optionally signal (3) then represents an amount of total DNA from a standard sample. Operation (A) determines a parameter (4) from signals (1), (2) and optional (3) that represents a relative or absolute amount of DNA (eg from foetal vs total DNA). This parameter (4) is compared by operation (B) against a threshold amount (5) and/or a reference population of amounts (6) so as to classify (7) the risk of an individual suffering from a medial condition and/or if a diagnosis for an anomaly in either of the DNA in the sample may be performed.

It is to be understood that application of the teachings of the present invention to a specific problem or environment, and the inclusion of variations of the present invention or additional features thereto (such as further aspects and embodiments), will be within the capabilities of one having ordinary skill in the art in light of the teachings contained herein.

Unless context dictates otherwise, the descriptions and definitions of the features set out above are not limited to any particular aspect or embodiment of the invention and apply equally to all aspects and embodiments which are described.

All references, patents, and publications cited herein are hereby incorporated by reference in their entirety.

Certain aspects and embodiments of the invention will now be illustrated by way of example and with reference to the description, figures and tables set out herein. Such examples of the methods, uses and other aspects of the present invention are representative only, and should not be taken to limit the scope of the present invention to only such representative examples.

EXAMPLE 1

Use of the Method of the Invention in NIPT in Multiple Pregnancies, Including in Cases of Vanishing Twins Sample Collection, Processing and DNA Extraction:

36 blood samples from women pregnant with multiple gestations (mono-, di- and trichorionic twin and triplet pregnancies) were collected between Nov. $6^{th}$2012 and Nov. $16^{th}$ 2013, for research & development (R&D) purposes and as part of routine non-invasive prenatal testing (NIPT) laboratory procedure. One blood sample came from a woman pregnant with triplets, the remaining 35 samples came from twin pregnancies. From each pregnant woman carrying a multiple pregnancy two samples each with 7-10 ml venous blood were collected using Streck cell-free DNA blood collection tubes (Streck). The blood samples were shipped to the diagnostic laboratory with a maximum delivery time of 4 days. Other blood samples from pregnant females analysed herein were similarly collected.

Plasma preparation was performed by centrifugation (1600 g for 10 min at 4° C.) and plasma separation followed by a second centrifugation step (16000 g for 10 min at 4° C.). Extraction of total cell-free DNA (cfDNA) was performed with QIAamp Circulating Nucleic Acid Kit (Qiagen) according to the manufacturer protocol using 3.0-4.0 ml plasma with a final elution volume of 60 ul AVE-buffer (Qiagen).

DNA Quantification:

Foetal cell-free DNA (foetal cfDNA) was detected and quantified in relation to total cell-free DNA (total cfDNA) in order to determine the foetal cfDNA fraction as both a relative concentration and absolute amount using a method of the present invention. From the eluted cell-free DNA, 11 ul were digested with the CpG-methylation sensitive enzymes HhaI (0.4 U/ul), HpaII (0.3 U/ul) and BstUI (0.3 U/ul) in a 22 ul reaction using CutSmart™ Buffer (New England Biolabs). The reaction was incubated for 60 min at 37° C. and 60 min at 60° C. 10 ul from the digestion reaction was used as template DNA for quantitative probe-based PCR (reactions were conducted in duplicate), described briefly as follows.

A 25 ul PCR reaction using a 2-fold concentrated PCR master mix (QuantiFast Multiplex PCR Kit, Qiagen) was conducted. Primers that span CpG methylation sensitive restriction enzyme sites of the respective region that is differentially methylated between foetal and maternal DNA (as a DMR) were used in combination with FAM-labelled probes for such DMRs, and primers that do not span any restriction enzyme sites, an other region that is not differentially methylated between foetal and maternal DNA (as an OR) are used in combination with VIC-labelled probes for such ORs. The sequences of the primers and labelled probes used in this example are described in TABLE 1, and the thermocycler profiles used for the quantitative probe-based (TaqMan) PCR (LightCycler 480 II Instrument; Roche) are described in TABLE 2. In this example, the probes used to detect the presence of the two DMRs, are each labelled with the same detectable fluorescein amidite (FAM) fluorescent moiety, and each with the same minor binding grove (MGB) non-fluorescent quencher (NFQ) moiety, and the probes used to detect the presence of the two ORs, are each labelled with the same detectable VIC (life Technologies) fluorescent moiety, and each with the same MGBNFQ moiety.

maternal DNA and hypermethylated in foetal DNA (Nygren, et al, 2010: Clin Chem 56, 1627; Chan et al, 2006: Clin Chem 42, 2211; Chiu et al, 2007: Am J Pathol 170, 941), and two other regions (ORs) not differentially methylated between maternal and foetal DNA which are each located between about 20 bp and 20 kb of their DMR. In particular, the methylation insensitive locus located in RASSF1A is located between 8 kb and 9 kb (8.97 kb) downstream of the methylation sensitive locus located in RASSF1A, and the methylation insensitive locus located in TBX3 is located between 10 kb and 11 kp (10.64 kb) downstream of the methylation sensitive locus located in TBX3. FIG. 2 depicts the respective arrangements and detection modalities of the two DMRs and the two other regions used in this example.

Parallel probe-based quantitative PCR reactions were performed (in separate reactions within the same PCR run) using for template a serial dilution of male genomic DNA (Promega) having known concentrations as a standard. The foetal cfDNA fraction was calculated by relative quantification of signals in the FAM channel (DMR; ie detecting foetal cfDNA) versus the VIC channel (ORs; ie detecting total cfDNA), and the absolute total cfDNA amount was calculated by absolute quantification of signals in the VIC channel obtained from the sample compared to the VIC channel obtained from the dilution series of standard DNA

TABLE 1

Quantitative (probe-based) PCR components

| Region | Component | Sequence (5'-3')* | SEQ ID No. | Stock Conc | ul for 1x | Final uM Conc |
|---|---|---|---|---|---|---|
| RASSF1A DMR | Master-mix | N/A | | 2x | 12.5 | 1x |
| | DMR1-For | ATT GAG CTG CGG GAG CTG GC | 1 | 100 uM | 0.35 | 1.4 |
| | DMR1-Rev | TGC CGT GTG GGG TTG CAC | 2 | 100 uM | 0.35 | 1.4 |
| | DMR1-Probe | [FAM]-ACC CGG CTG GAG CGT-[MGBNFQ] | 3 | 100 uM | 0.035 | 0.14 |
| RASSF1A Other region | OR1-For | GGT CAT CCA CCA CCA AGA AC | 4 | 100 uM | 0.35 | 1.4 |
| | OR1-Rev | TGC CCA AGG ATG CTG TCA AG | 5 | 100 uM | 0.35 | 1.4 |
| | OR1-Probe | [VIC]-GGG CCT CAA TGA CTT CAC GT-[MGBNFQ] | 6 | 100 uM | 0.035 | 0.14 |
| TBX3 DMR | DMR2-For | GGT GCG AAC TCC TCT TTG TC | 7 | 100 uM | 0.35 | 1.4 |
| | DMR2-Rev | TTA ATC ACC CAG CGC ATG GC | 8 | 100 uM | 0.35 | 1.4 |
| | DMR2-Probe | [FAM]-CCC TCC CGG TGG GTG ATA AA-[MGBNFQ] | 9 | 100 uM | 0.035 | 0.14 |
| TBX3 Other region | OR2-For | TGT TCA CTG GAG GAC TCA TC | 10 | 100 uM | 0.35 | 1.4 |
| | OR2-Rev | CAG TCC ATG AGG GTG TTT G | 11 | 100 uM | 0.35 | 1.4 |
| | OR2-Probe | [VIC]-GAG GTC CCA TTC TCC TTT-[MGBNFQ] | 12 | 100 uM | 0.035 | 0.14 |
| General reagents | DMSO | N/A | | 100% | 0.025 | 0.625 |
| | MgCl2 | N/A | | 50 mM | 2 | 1 |
| | DNA sample | N/A | | | | 10 |
| | Water | | | | | — |
| | Total | | | | | 25 |

*The dyes used for each probe are shown in "[]" parentheses

TABLE 2

Thermocycler profiles

| Step | Temperature | Time | Cycles | Analysis mode |
|---|---|---|---|---|
| Pre-incubation | 95° C. | 5 min | 1 | None |
| Denaturation | 95° C. | 10 sec | 45 | Quantification |
| Annealing | 60° C. | 10 sec | | None |
| Elongation | 72° C. | 8 sec | | Single |
| Cooling | 40° C. | | | None |

The assay design used in this example is based on two marker DMRs which are described to be hypomethylated in of known concentration. Such relative and absolute quantifications were conducted using LightCycler 480 Software release 1.5.0 (Roche).

Maternal Plasma DNA Sequencing and Data Analysis to Identify foetal aneuploidy.

DNA sequencing libraries were prepared using NEBNext Ultra™ DNA Library Prep Kit from Illumina. Libraries were prepared according to the manufacturer protocol automated on a Hamilton STARplus robot. Library quality and quantity was measured using a Bioanalyzer instrument (Agilent) and a Qbit Fluorometer (Invitrogen). Based on the library quantification dilutions and equimolar pools of 12 samples per pool were prepared. The pooled samples were sequenced on one lane of an Illumina v3 flow cell on an Illumina HiSeq2000 sequencer. Clonal clusters were generated using TruSeq SR Cluster Kit v3-cBot-HS on a cBot Cluster generation System according to the manufacturer protocol. Bioinformatic analysis to identify foetal chromosomal aneuploidy was carried out as described previously, with z-scores ≥3 indicating the presence of a foetal trisomy 21 (Stumm et al 2014, Europ Prenat Diag34:185). In cases of a positive test result for foetal aneuploidy from this method, the result was confirmed by invasive diagnostic methods.

Results:

Characteristics, % foetal fraction of cfDNA and aneuploidy test results for the blood samples are given in TABLE 3. There were two positive test results indicating foetal trisomy 21. Both were confirmed by karyotyping after amniocentesis; thus, the false positive rate in this study was 0%. One blood sample represented monochorionic twins with concordant karyotypes [47,XY,+21]and the other one represented dichorionic twins with discordant karyotypes [47,XY,+21 and 46,XX]. In both samples the foetal fraction was as high as 18.0 and 24.8%, respectively. All other NIPT results were negative for trisomies 21, 18 and 13. There is no evidence for false-negative NIPT results so far in the pregnancies included in this study. Nevertheless, a number of pregnancies are still on-going (with the last birth of the patients expected in mid May 2014) and therefore, the final detection rate is still uncertain.

The reliable detection of foetal aneuploidy in twin pregnancies by NIPT is dependent on a sufficiently high amount of foetal cfDNA from each foetus in the maternal blood. Different data and considerations have been published on how the lower limit of foetal cfDNA fraction should be defined to ensure that each twin's contribution is above the detection threshold (Leung et al 2013, Prenat Diag 33:675; Qu et al 2007, Am J Pathol 170:941; Struble et al 2013, Fetal Diagn Ther Dec 7 Epub ahead of print). This is especially important for dichorionic twin pregnancies with discordant karyotypes. In the study described above, supporting information was used for the definition of the minimum foetal cfDNA fraction for twin pregnancies derived from the Y-chromosomal representation, if only one of the two foetuses is male. Using the method of the present invention, the total foetal cfDNA fraction can be determined, which reflects the summary of foetal cfDNA derived from both foetuses. Using the Y-chromosomal representation from the next generation sequencing, the foetal cfDNA amount can be determined for male foetuses (as described in Stumm et al 2014). Thus, in the case of mixed foetal gender the contributing amount of each foetus can be determined by subtraction of the amount of foetal cfDNA determined by the Y-chromosomal representation from the foetal cfDNA fraction measured by method of the present invention. The foetal cfDNA fractions determined by the method of the present invention were compared with the values obtained from Y-chromosomal reads from next generation sequencing for cases with known gender (see FIG. 3). There is a

TABLE 3

Characteristics and NIPT results for the collected blood samples

Figure 3:
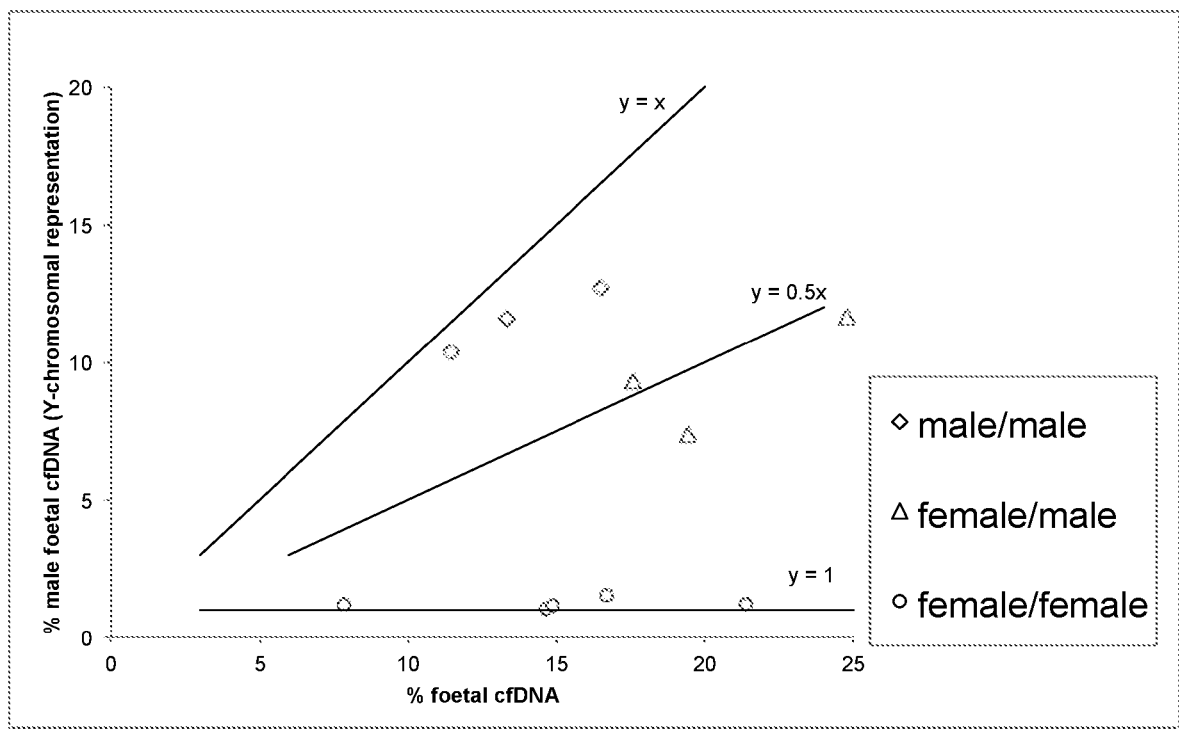
FIG. 3 depicts the correlation of the amount of male specific DNA (Y chromosomal-representation) to the foetal cfDNA fraction measured by a method of the present invention (Example 1) for study twin cases with known foetal genders.

| Sample | Chr13 z-score | Chr18 z-score | Chr21 z-score | Foetal DNA fraction (%) | Gestational age (p.m.) | No. of foetuses, chorionicity amnionicity | NIPT result |
|---|---|---|---|---|---|---|---|
| LCMPC05 | 1.3 | −1.0 | −0.8 | 16.7 | 11 + 5 | 3, trichorionic, triamniotic | negative |
| LCMPC06 | −0.4 | 1.1 | 8.5 | 18.0 | 13 + 2 | 2, monochorionic, n.a. | T21 positive |
| LCMPC07 | −1.0 | 0.3 | 0.9 | 7.9 | 19 + 0 | 2, dichorionic, diamniotic | negative |
| LCMPC08 | 0.7 | 1.2 | 0.0 | 16.5 | 18 + 1 | 2, dichorionic, diamniotic | negative |
| LCMPC09 | 0.6 | −0.8 | 0.7 | 8.9 | 11 + 5 | 2, monochorionic, diamniotic | negative |
| LCMPC10 | 0.3 | 0.7 | −0.7 | 17.6 | 20 + 4 | 2, dichorionic, diamniotic | negative |
| LCMPC11 | −0.9 | −0.8 | 0.7 | 11.5 | 23 + 0 | 2, dichorionic, diamniotic | negative |
| LCMPC12 | −0.9 | −0.7 | −2.0 | 13.3 | 11 + 1 | 2, monochorionic, diamniotic | negative |
| LCMPC13 | 1.3 | 0.1 | 0.3 | 21.4 | 16 + 0 | 2, dichorionic, diamniotic | negative |
| LCMPC14 | 0.2 | −0.3 | 0.0 | 6.8 | 12 + 5 | 2, n.a., n.a. | negative |
| LCMPC15 | 2.2 | 0.1 | 14.7 | 24.8 | 16 + 0 | 2, dichorionic, diamniotic | T21 positive |
| LCMPC16 | 1.1 | 1.7 | 0.5 | 5.4 | 12 + 5 | 2, n.a., n.a. | negative |
| LCMPC17 | 0.7 | 1.4 | 0.5 | 16.5 | 14 + 2 | 2, n.a., n.a. | negative |
| LCMPC18 | 0.3 | 2.6 | 0.0 | 18.5 | 18 + 3 | 2, n.a., n.a. | negative |
| LCMPC19 | −0.2 | 0.8 | 0.3 | 16.6 | 14 + 0 | 2, dichorionic, diamniotic | negative |
| LCMPC20 | −0.7 | −0.9 | 0.1 | 13.1 | 15 + 4 | 2, dichorionic, diamniotic | negative |
| LCMPC21 | 1.0 | −0.7 | 1.2 | 8.4 | 9 + 3 | 2, dichorionic, diamniotic | negative |
| LCMPC22 | −1.1 | −0.2 | 0.3 | 5.6 | 16 + 2 | 2, monochorionic, n.a. | negative |
| LCMPC23 | −2.2 | 2.2 | −0.8 | 20.6 | 19 + 5 | 2, monochorionic, n.a. | negative |
| LCMPC24 | −1.6 | −0.4 | −0.5 | 14.7 | 22 + 2 | 2, monochorionic, diamniotic | negative |
| LCMPC25 | −0.8 | −0.2 | −1.5 | 12.1 | 11 + 5 | 2, n.a., n.a. | negative |
| LCMPC26 | −0.4 | −0.6 | −1.3 | 7.5 | 13 + 0 | 2, dichorionic, diamniotic | negative |
| LCMPC27 | 0.5 | −0.8 | −0.4 | 16.3 | 12 + 6 | 2, n.a., n.a. | negative |
| LCMPC28 | −1.2 | −0.3 | −0.7 | 19.4 | 10 + 1 | 2, dichorionic, diamniotic | negative |
| LCMPC29 | −0.8 | 0.7 | −0.4 | 14.2 | 13 + 2 | 2, monochorionic, n.a. | negative |
| LCMPC30 | 0.7 | 0.3 | 0.9 | 14.9 | 12 + 2 | 2, monochorionic, monoamniotic | negative |
| LCMPC31 | −0.2 | 0.3 | −0.9 | 19.3 | 19 + 1 | 2, dichorionic, diamniotic | negative |
| LCMPC32 | −1.1 | 2.5 | −2.2 | 11.6 | 20 + 0 | 2, dichorionic, diamniotic | negative |
| LCMPC33 | 0.2 | 2.2 | −1.6 | 8.6 | 11 + 0 | 2, dichorionic, diamniotic | negative |
| LCMPC34 | −1.0 | 1.2 | 0.0 | 15.1 | 15 + 4 | 2, dichorionic, diamniotic | negative |
| LCMPC35 | −0.3 | −0.8 | −0.3 | 19.2 | 12 + 0 | 2, dichorionic, diamniotic | negative |
| LCMPC36 | −1.4 | −0.5 | −0.8 | 13.9 | 12 + 0 | 2, dichorionic, diamniotic | negative |
| LCMPC37 | 1.8 | −0.7 | 0.1 | 13.8 | 17 + 6 | 2, dichorionic, diamniotic | negative |
| LCMPC38 | −0.1 | 1.1 | −0.7 | 13.4 | 13 + 1 | 2, dichorionic, diamniotic | negative |
| LCMPC39 | −1.9 | 0.2 | −2.2 | 15.0 | 17 + 0 | 2, dichorionic, diamniotic | negative |
| LCMPC40 | 0.6 | −0.4 | 0.8 | 16.2 | 18 + 3 | 2, dichorionic, diamniotic | negative | correlation of the amount of male specific cfDNA (y axis) to the foetal cfDNA fraction measured by method of the present invention (x axis). Thus, for twin pregnancies with male/male gender approximately true is: [y=x], for female/male genders it is: [y=0.5x] and for female/female: [y=1]. The genders of cases with similar values are male/male and in case of differing values with low Y-chromosomal representation the genders are female/female. The intermediate cases, which show about half the percentage of foetal fraction as Y-chromosomal representation, are of mixed gender. The data presented in FIG. 3 show that it is not only possible to determine the foetal genders using NIPT results for twin pregnancies, but also that the measurement of the amount of foetal fraction of cfDNA determined by the method of the present invention is surprisingly accurate as compared to frequency counting of Y chromosome sequences. On the other hand, these data support the hypothesis that each foetus of a twin pregnancy contributes roughly about half of the total foetal cfDNA fraction. This leads to the conclusion that for twin pregnancies, twice the amount of foetal cfDNA would be required, and thus a recommended minimum foetal fraction of cfDNA for NIPT of a twin pregnancy could be considered to be 8%.

For monochorionic twin pregnancies with concordant genotypes (apart from rare exceptions, Chen et al 2013, Am J Med Genet A 161A:1817), a foetal cfDNA fraction of 4% would be enough to detect a foetal aneuploidy, just as for single pregnancies. However, for routine laboratory NIPT service one major issue speaks against the implication of such different quality criteria for mono- and dichorionic pregnancies: the determination of chorionicity is dependent on the gestational age and the practical experience of the physician performing the ultrasound examination. The chorionicity is clearly detectable in the first trimester of a multiple pregnancy, but in later stages detection becomes more difficult (Sperling et al 2001, Acta Obstet Gynecol Scand 80:287). Therefore, it is a safer strategy to generally define a minimum foetal cfDNA fraction for twin pregnancies, which is applicable for monochorionic as well as for dichorionic multiple pregnancies.

Identification of Vanishing Twins

In two cases of NIPT aneuploidy testing in which the foetal cfDNA fraction was measured using the method of the present invention, identified a trisomy 21 (z-scores 13.5 and 3.4 respectively), but also a striking discrepancy between the total foetal cfDNA fraction measured by the method of the invention and the cf-Foetal-DNA amount measured by Y-chromosome representation were observed.

For case A, two analyses of blood samples (first and back-up samples) estimated the total foetal cfDNA fraction measured the method of the present invention was 20.7% and 24.8%, respectively, whereas the foetal cfDNA according to the Y-chromosomal representation from next generation sequencing was 9.2% and 9.3%, respectively. It was speculated, and reported to the physician, that the pregnancy may be a mixed-sex twin pregnancy, who confirmed that a deceased twin had been observed during ultrasound scan at week 10. A further blood sample taken in the third trimester of the pregnancy (38+2) turned out to be negative for trisomy 21 and the foetal cfDNA amount measured by Y-chromosomal representation correlated with the foetal amount measured by QuantYfeX (21.7% and 21.4), which matched the male gender determined by karyotyping of the living foetus. At birth a foetus papyraceus was found in the placental tissue from which a sufficient amount of cells could be isolated for cell culture and following GTG banding, a trisomy 21 positive, female karyotype was confirmed (47,XX,+21).

For case B, a slightly increased Y-chromosomal representation was monitored indicating male specific cf-Foetal-DNA of 3.0% and 2.7% respectively. As the foetal cfDNA fraction estimates measured by the method of the invention were far above that (13.4% and 10.0%) we hypothesized from this discrepancy in the foetal fraction measured, that two foetuses with discordant gender contribute to the foetal fraction and the male foetus being the one affected by trisomy 21. This suggestion was derived from the correlation of Y-chromosome specific foetal cfDNA amount of roughly 3 with the elevated z-score around the cut-off value of 3.0. Since the examination was clearly requested for a singleton pregnancy, the male specific foetal cfDNA was suspected to stem from a vanishing twin—maybe the carrier of a trisomy 21—that was either not recognized or not indicated on the consent form for NIPT. Thus, the result was reported to be indecisive for chromosome 21 and the conflicting data was reported to the responsible physician, including a notice regarding the potential vanishing twin, for further clarification via ultrasound. The responsible physician subsequently confirmed that the pregnancy had started as twin and later continued as a singleton pregnancy. The gender of the living and apparently healthy foetus was confirmed to be female and thus, the foetal cfDNA that caused the increased z-score for trisomy 21 can clearly be assigned to a deceased male foetus. The pregnancy is still on-going and further analysis of placental tissue and blood of the living foetus is not yet possible.

EXAMPLE 2

Figure 4:
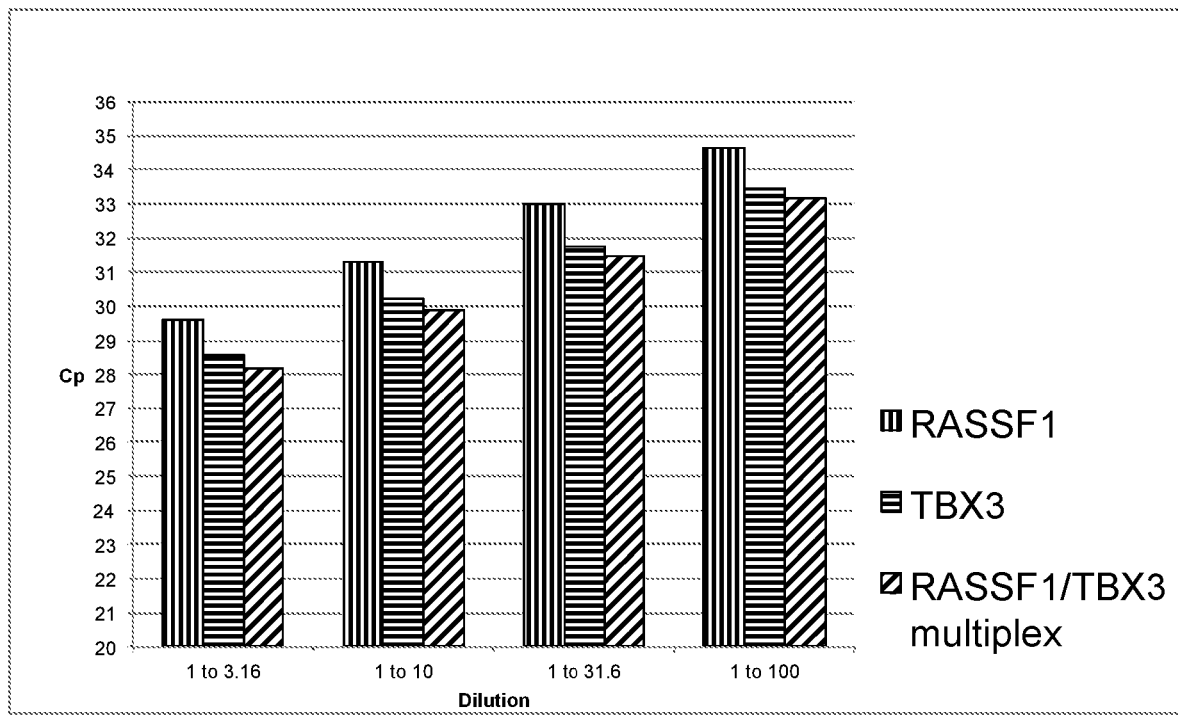
FIG. 4 depicts the improved sensitivity of a method of the invention compared to foetal cfDNA fraction detected using separate reactions of a single DMR. The number of PCR cycles (Cp) required for detection of foetal cfDNA (Example 2) in a sample using either RASSF1A or TBX3 alone as a single DMR, or as a multiplex (using the same labels) of RASSF1A and TBX3.

Improved Detection Sensitivity Using Two Differentially Methylated Regions Using the Same Detectable Moiety/Moieties for Each Differentially Methylated Region The inventors were surprised to observe that a complex and multiplex reaction detecting two DMRs using the same detectable moiety/moieties for each of said DMR (as well as two other regions (OR) not differentially methylated) was more sensitive to detect foetal cfDNA fraction than previous detection reactions that each detected—in separate PCR reactions—a single DMR (as well as a single OR) (FIG. 4).

In a method of the present invention, two DMRs (those found in RASSF1A and TBX3, as described in Example 1) were detected (over 4 dilutions) with the same aliquot of DNA and reaction—effectively simultaneously (using quantitative probe-based (TaqMan) PCR) with two ORs (those found in RASSF1A and TBX3, as described in Example 1), using: (x) the same detectable moiety/moieties for each of said DMR; and (y) a detectable moiety/moieties for said at least one OR that is/are different to the detectable moiety/moieties used for said DMRs. In comparison, detection of foetal cfDNA fraction was less sensitive, as shown by detection at higher cycle numbers (Cp), if each DMR (and corresponding OR) was detected independently in separate reactions. The regions/markers, primers/probes and detection methodology was substantially as described in Example 1, except that for the single locus reactions, only the DMR and OR from a given gene (RASSF1A or TBX3) were detected simultaneously in a single reaction.

In contrast, detection of foetal cf DNA fraction using a multiplex reaction of the two DMRs using different detectable moieties (eg FAM for the RASSF1A locus and VIC for the TBX3 locus) is determined to be even less sensitive, and further is difficult to detect simultaneously with any OR; without being bound by theory, believed due to the higher complexity of colour compensation, the limited number of separately detectable fluorescent markers and/or the "bleaching" effects from so many fluorescent markers being present in the same reaction.

Given the exponential nature of quantitative PCR detection, a higher sensitivity of detection (ie lower cycle numbers) would also equate to higher accuracy of quantification, as the correction to standard curves, and interpolation between data points, would be subject to less error than that arising with the amounts of DNA correlating to detection at higher cycle numbers.

EXAMPLE 3

Detection of an Increased Risk of a Pregnant Woman Suffering from or Developing Preeclampsia (Prophetic Example)

Using a method of the present example, pregnant women are assessed for their risk of suffering from or developing preeclampsia as follows. Firstly, a blood sample is collected from the woman for whom such risk to be assessed and total cfDNA extracted from the plasma of such sample substantially in accordance with the procedures described in Example 1. Secondly, using a method substantially as described in Example 1, a relative and/or absolute amount of foetal cfDNA and total cfDNA present in the plasma is determined, where the absolute amount of foetal and/or total cfDNA can be expressed as the amount of genome equivalents ("Eq"). Thirdly, such determined amount of cfDNA and/or total cfDNA is compared to a threshold amount or a reference distribution of amounts, and the women is determined to be at increased risk of suffering from or developing preeclampsia if the amount of foetal cfDNA or total cfDNA exceeds such threshold value and/or is an outlier in such distribution.

For example, using published threshold values (Papantoniou et al 2013, Prenat Diag 33:682) if the total cfDNA exceeds an amount of about 7,500 Eg/mL plasma or if the foetal cfDNA fraction exceeds an amount of about 500 Eg/mL plasma, then the woman is determined to have such an increased risk. Such a risk may instead or additional be assessed by considering: (i) the fold-increase (eg 1.5, 3, 3.5 or 4-fold increase) of foetal cfDNA (determined for such woman compared to a threshold amount), factoring into the determination that for later-term pregnancies a higher fold-increase in foetal cfDNA may be utilised (Zeybek et al 2013, J Obstet Gynaecol Res 39:632); and/or (ii) into which percentile the amount of cfDNA determined from the woman falls, from consideration of a reference distribution of amounts determined from low-risk women or women who did not suffer from or develop preeclampsia, for example if the foetal cfDNA fraction falls within the $90^{th}$ percentile of such a distribution, then the woman is considered to have an increased risk of suffering mild or severe preeclampsia (Jakobsen et al 2013, Transfusion 53:1956).

In this example, t detection of a risk is conducted using a computer program product that performs the operations represented by FIG. 5. Operation (A) receives signals (1) and (2) representing, respectively, foetal and total cfDNA are used by the computer program product to determine a parameter (4) that represents the relative and/or absolute amount of foetal (or total) cfDNA present in the plasma of the woman. This operation may optional receive a signal (3) representing an absolute amount of standard DNA. A second operation (B) compares such determined parameter (4) against a threshold amount (5) and/or a reference population of amounts (6) so as to determine and report (7) whether or not—and based on such comparison—the woman is determined to be at increase risk of suffering or developing preeclampsia.

EXAMPLE 4

Detection of Tumour-Associated DNA in Samples from Cancer Patients (Prophetic Example)

Methylation of RASSF1A and at least one other DMR such as ER-beta (oestrogen receptor beta), RAR-beta2 (retinoic acid receptor beta 2) and/or Cyclin D2 is used to detect cfDNA derived from a tumour and to assess the risk of women suffering from breast cancer. Specific methylation at such DMRs is a characteristic of tumour-derived cfDNA, and a method of the present invention is used to detect and to quantify the amount tumour derived cfDNA in the plasma of women, and those determined to have elevated (or outlying) amounts of tumour-derived cfDNA are determined to be at increased risk from suffering from or developing breast cancer. Essentially, the process described in Example 3 is followed except that DMR2 and OR2 are located in one of ER-beta, RAR-beta2 or Cyclin D2, rather than TBX3. Primers and probes to detect such DMR2 and OR2 for use in this embodiment of the present invention are designable by the person of ordinary skill.

In this example, a similar computer program product as described in Example 3 can be used to asses—the risk for a given woman is based on the amount of tumour-derived cfDNA present in her blood, but in this example this parameter is compared against a threshold amount or distribution of amounts that is derived from a study of the amount of tumour-derived cfDNA present in control and breast-cancer patients; and those women having an elevated (or outlying) amount of tumour-derived cfDNA are considered to have an increased risk of suffering from or developing breast cancer.

In view of the above, it will be appreciated that the present invention also relates to the following items:

1. A method for detecting in a sample from an individual an amount of a species of DNA originating from cells of a given type, which sample comprises said species of DNA in admixture with differently methylated DNA not originating from cells of said type; said method comprising the steps:
   (a) treating the DNA present in said sample with a reagent that differentially modifies methylated and non-methylated DNA;
   (b) detecting in said sample the presence of methylation in said species of DNA at two or more differentially methylated regions (DMRs) that are differently methylated between said species of DNA and the DNA not originating from cells of said type, the modification of DNA of such DMRs by said reagent is sensitive to methylation of DNA, wherein the presence of methylated DNA at one or more of said DMRs indicates the presence of said amount of species of DNA in said sample and the absence of methylated DNA at said DMRs indicates the absence of said species of DNA in said sample; and
   (c) detecting an amount of total DNA present in said sample using at least one other region that is not differently methylated between said species of DNA and the DNA not originating from cells of said type, the modification of which region(s) by said reagent is insensitive to methylation of DNA, wherein, said detection in step (b) and said detection in step (c) are made using the same aliquot of DNA of said sample, and in the same vessel, and effectively simultaneously for such DMRs and other region(s), and using: (x) the same detectable labels(s) for each of said DMRs; and (y) a different detectable label(s) for said other region(s).

2. The method of item 1, wherein prior to or as part of said detection in step (b) and/or step (c), each DNA region comprising said DMRs and/or said other region(s), respectively, is(are) amplified.
3. The method of item 1 or 2, wherein each detectable label used in step (b) and/or step (c) is independently selected from the group consisting of: fluorescent, protein, small molecule or radioactive label.
4. The method of any one of items 1 to 3, wherein said detection in step (b) comprises multiplex real-time probe-based quantitative probe-based PCR using at least two labelled probes each of which specific for one of said DMRs.
5. The method of any one of items 1 to 4, wherein said detection in step (c) comprises real-time quantitative PCR using at least one labelled probe specific for one of said other region(s).
6. The method of any one of items 1 to 5, wherein said other region is located between about 20 bp and about 20 kb upstream or downstream of, and/or within the same gene as, at least one of said DMRs.
7. The method of any one of items 1 to 6, wherein said detection in step (c) comprises using at least two of said other regions; preferably wherein, the number of said other regions is the same as the number of DMRs used in step (b); more preferably wherein, one of said other regions is located between about 20 bp and about 20 kb upstream or downstream of a DMR used in step (b) and each other of the said other regions is located between about 20 bp and about 20 kb upstream or downstream of another of said DMRs.
8. The method of item 7, wherein said detection in step (c) is made using the same detectable label(s) for each of said other regions.
9. The method of item 7 or 8, wherein said detection in step (c) comprises multiplex real-time quantitative probe-based PCR using at least two labelled probes each of which is specific for one of said other regions.
10. The method of any one of items 1 to 9, wherein said detection in step (c) and said detection in step (b) are made using the same aliquot of DNA of said sample, and in the same reaction/detection vessel, and effectively simultaneously with each other, and by multiplex real-time quantitative probe-based PCR using at least one labelled probe specific for each of the said DMRs and other region(s).
11. The method any one of items 1 to 10, wherein said species of DNA originates from cells of a foetus and/or the placenta of a foetus and said sample is from a pregnant female; preferably wherein, said species of DNA is circulating cell-free DNA and said sample is a blood fraction such as plasma or serum.
12. The method of item 11, wherein said DMRs comprises at least one, preferably at least two, methylation site(s) specific for said reagent, and at least one of said DMRs is located in a portion of the genome and/or gene selected from the group consisting of: RASSF1A, TBX3, HLCS, ZFY, CDC42EP1, MGC15523, SOX14 and SPN; preferably wherein,
   each of said DMRs is located in a portion of the genome and/or gene selected from the group consisting of: RASSF1A, TBX3, HLCS, ZFY, CDC42EP1, MGC15523, SOX14 and SPN; and/or
   at least one of said DMRs is located between about positions 4,700 bp and 5,600 bp of RASSF1A or about positions 1,660 bp and 2,400 bp of TBX3; more preferably wherein,
   said two or more DMRs comprise those located between about positions 4,700 bp and 5,600 bp of RASSF1A and about positions 1,660 bp and 2,400 bp of TBX3.
13. The method of item 11 or 12, wherein said other region is located in a portion of the genome and/or gene selected from the group consisting of: GAPDH, beta-actin, ALB, APOE, RNASEP, RASSF1A, TBX3, HLCS, ZFY, CDC42EP1, MGC15523, SOX14 and SPN; preferably wherein,
   said other region comprises a region without a methylation site specific for said reagent and said locus is located in the genes RASSF1A or TBX3, more preferably wherein,
   two or more of said other regions are used in detection step (c) and comprise those located between about positions 14,220 bp and 13,350 bp of RASSF1A and about positions 12,400 bp and 13,000 bp of TBX3.
14. The method any one of items 11 to 13, wherein said pregnant female is susceptible to a pregnancy-associated medical condition; preferably wherein, said pregnancy-associated medical condition is selected from the group consisting of: preeclampsia, preterm labour, intrauterine growth retardation and vanishing twin.
15. The method of any one of items 1 to 10, wherein said species of DNA originates from a cell type associated with a medical condition; preferably wherein, said medical condition is one selected from the group consisting of: a cell proliferative disorder, an infection/infectious disease, a wasting disorder, a degenerative disorder, an (auto)immune disorder, kidney disease, liver disease, inflammatory disease acute toxicity, chronic toxicity, myocardial infarction, and a combination of any of the forgoing; more preferably wherein, said species of DNA is circulating cell-free DNA and said sample is a blood fraction such as plasma or serum.
16. The method of item 15, wherein said species of DNA originates from cells of a tumour; preferably wherein, said tumour is a carcinoma or cancer of an organ selected from the group consisting of: liver, lung, breast, colon, oesophagus, prostate, ovary, cervix, uterus, testis, brain, bone marrow and blood.
17. The method of item 16, wherein said DMRs comprises at least one, preferably at least two, methylation site(s) specific for said reagent, and at least one of said DMR is located in a portion of the genome and/or a gene selected from the group consisting of: a tumour suppressor gene, p16, SEPT9, RASSF1A, GSTP1. DAPK, ESR1, APC, HSD17B4 and H1C1; preferably wherein, one of said two or more DMRs is located in RASSF1A; more preferably wherein, one of said two or more DMRs is located between about positions 4,700 bp and 5,600 bp of RASSF1A; and/or more preferably wherein, said other region is located between about positions 14,220 bp and 13,350 bp of RASSF1A.

18. The method of any one of items 1 to 17, wherein said sample is a tissue sample or a sample of biological fluid; preferably wherein, said sample is a sample of biological fluid selected from the group consisting of: whole blood, a blood fraction, urine, saliva, sweat, ejaculate, tears, phlegm, vaginal secretion, vaginal wash and colonic wash; more preferably wherein, said sample is a plasma or serum sample.

19. The method of any one of items 1 to 18, wherein said reagent that differentially modifies methylated and non-methylated DNA comprises bisulphite.

20. The method of any one of items 1 to 18, wherein said reagent that differentially modifies methylated and non-methylated DNA comprises an agent that selectively digests unmethylated over methylated DNA, preferably wherein, said agent comprises:
   at least one methylation sensitive enzyme;
   at least one methylation sensitive restriction enzyme; and/or
   an agent selected from the group consisting of: AatII, AciI, AcII, AfeI, AgeI, AgeI-HF, AscI, AsiSI, AvaI, BceAI, BmgBI, BsaAI, BsaHI, BsiEI. BsiWI, BsmBI, BspDI, BsrFI, BssHII, BstBI, BstUI, ClaI, EagI, FauI, FseI, FspI, HaeII, HgaI, HhaI, HinP1I, HpaII, Hpy99I, HpyCH4IV, KasI, MluI, NaeI, NarI, NgoMIV, NotI, NotI-HF, NruI, Nt.BsmAI, Nt.CviPII, PaeR7I, PluTI, PmlI, PvuI, PvuI-HF, RsrII, SacII, SalI, SalI-HF, SfoI, SgrAI, SmaI, SnaBI, TspMI and ZraI.

21. The method of any one of items 1 to 20, wherein each of said detection steps comprises quantitative detection and said detected amount of said species of DNA is expressed as a relative concentration of said species of DNA to the total DNA in said sample.

22. The method of any one of items 1 to 20, further comprising the steps:
   detecting an amount of total DNA in a standard sample of DNA of known amount using the same other regions(s) as used in step (c); and
   comparing the signal detected from said standard sample of DNA to the signal detected in step (c).

23. The method of item 22, wherein each of said detection steps comprises quantitative detection and said detected amount of said species of DNA is expressed as an absolute amount of said species of DNA in said sample.

24. The method of item 21 or 23, further comprising the step:
   comparing the amount of said species of DNA detected with a threshold amount and/or reference distribution of amounts, wherein: (x) an increase in, or outlying of, the amount of said species of DNA indicates an increased risk of the individual suffering from or developing a medical condition; and/or (y) an amount of said species of DNA in excess to said threshold, or outlying from said distribution, indicates that a diagnosis for an abnormality in the said species of DNA present in said sample may be performed on, preferably a separate aliquot of DNA of, said sample.

25. The method of any one of items 21 to 24, further comprising the step:
   performing on, preferably with a separate aliquot of DNA of, said sample, a diagnosis for an abnormality in said species of DNA present in said sample; preferably wherein, said species of DNA originates from cells of a foetus and/or the placenta of a foetus, said sample is from a pregnant female and said diagnosis is a prenatal diagnosis.

26. The method of item 25, wherein said diagnosis comprises a step that uses a detection technology selected from the group consisting of: DNA sequencing, SNP analysis, digital PCR and hybridisation; preferably wherein, said detection technology is massively parallel sequencing of DNA; more preferably wherein said detection technology is massively parallel sequencing of random and/or enriched DNA.

27. The method of item 25 or 26, wherein:
   (x) said species of DNA originates from cells of a foetus and/or the placenta of a foetus, said sample is from a pregnant female and said abnormality is a genetic mutation or a chromosomal abnormality, such as a chromosomal trisomy, associated with a foetal abnormality and/or a congenital disorder; preferably wherein,:
   said genetic mutation is selected from the group consisting of: colour blindness, cystic fibrosis, hemochromatosis, haemophilia, phenylketonuria, polycystic kidney disease, sickle-cell and disease, Tay-Sachs disease; and/or
   said chromosomal abnormality is selected from the group consisting of: a trisomy (such as trisomy 21, trisomy 18, or trisomy 13), a sex-chromosome abnormality (such as Turners syndrome, Klinefelter syndrome, Noonan syndrome, Triple X syndrome, XXY syndrome, or Fragile X syndrome), a chromosomal deletion (such as Prader-Willi syndrome, Cris-du-chat syndrome, Wolf-Hirschhorn syndrome, or 22q11 deletion syndrome, Duchene muscular dystrophy), Beckwith-Wiedemann syndrome, Canvan syndrome, and neurofibromatosis; or
   (y) said species of DNA originates from cells of a tumour and said abnormality is a genetic mutation or a chromosomal abnormality associated with the diagnosis, prognosis or predictive treatment of a carcinoma or cancer; preferably wherein,:
   said genetic mutation is selected from the group consisting of: a mutation in a tumour suppressor gene (such as TP53 (p53), BRCA1, BRCA2, APC or RB1), a mutation in a proto-oncogene (such as RAS, WNT, MYC, ERK, or TRK) and a DNA repair gene (such as HMGA1, HMGA2, MGMT or PMS2); and/or
   said chromosomal abnormality is a translocation (such as t(9;22)(q34;q11) [ie, Philadelphia chromosome or BCL-ABL] , t(8;14)(q24;q32), t(11;14)(q13;q32), t(14;18)(q32;q21), t(10;(various))(q11;(various)), t(2;3)(q13;p25), t(8;21)(q22;q22), t(15;17)(q22;q21), t(12;15)(p13;q25), t(9;12)(p24;p13), t(12;21)(p12;q22), t(11;18)(q21;q21), t(2;5)(p23;q35), t(11;22)(q24;q11.2-12), t(17;22), t(1;12)(q21;p13), t(X;18)(p11.2;q11.2), t(1;19)(q10;p10), t(7;16)(q32-34;p11), t(11,16)(p11;p11), t(8,22)(q24;q11) or t(2;8)(p11;g24)).

28. A method for detecting an increased risk of an individual suffering from or developing a medical condition; said method comprising the steps:
   (i) conducting the method of item 21 or 23; and
   (ii) comparing the amount of said species of DNA detected with a threshold amount and/or a reference distribution of amounts,
   wherein an increase in, or outlying of, the amount of said species of DNA indicates an increased risk of the individual suffering from or developing said medical condition.

29. A composition comprising:
    two pairs of PCR primers, each pair for amplifying one of said two of more DMRs as set forth in any of items 1 to 28;
    one pair of PCR primers for amplifying said other region as set forth in any of items 1 to 28;
    two labelled probes as set forth in item 4; and
    one labelled probe as set forth in item 5.
30. The composition of item 29, further comprising:
    a further pair of PCR primers for amplifying a second other region as set forth in any of items 9 to 28; and
    a further labelled probe as set forth in item 9.
31. A kit comprising:
    the primers and probes as set forth in item 29 or 30; and
    optionally, further comprising: (i) a printed manual or computer readable memory comprising instructions to use said primers and probes to practice a method of any one of items 1 to 28 and/or to produce or use the composition of item 29 or 30; and/or (ii) one or more other item, component or reagent useful for the practice of a method of any one of items 1 to 28 and/or the production or use of the composition of item 29 or 30, including any such item, component or reagent disclosed herein, such as the reagent that differently modifies methylated and non-methylated DNA as set forth in any one of items 1 to 28.
32. A computer program product comprising a computer readable medium encoded with a plurality of instructions for controlling a computing system to perform and/or manage an operation for determining: (x) an increased risk of an individual suffering from or developing a medical condition and/or (y) if a diagnosis for an anomaly in a species of DNA originating from cells of a given type may be performed, in each case from a sample from an individual comprising a species of DNA originating from cells of a given type in admixture with differently methylated DNA not originating from cells of said type, the DNA in present in said sample being treated with a reagent that differentially modifies methylated and non-methylated DNA as set forth in any one of items 1 to 28; said operation comprising the steps of:
    receiving: (i) one signal representing the essentially simultaneous quantitative detection of methylation at two or more DMRs as set forth in step (b) of any one of items 1 to 28; and (ii) one signal representing the essentially simultaneous quantitative detection of total DNA using at least one other region as set forth in step (c) any of items 1 to 28;
    determining a parameter from the signals (i) and (ii), wherein the parameter represents a quantitative amount of said species of DNA;
    comparing the parameter to with a threshold amount and/or reference distribution of amounts; and
    based on such comparison, determining a classification of whether, respectively, (x) an increased risk of an individual suffering from or developing a medical condition exists; and/or (y) a diagnosis for an anomaly in a species of DNA originating from cells of a given type may be performed.
33. The computer program product of item 32, wherein said operation further comprises the steps:
    receiving a further signal representing the quantitative detection of total DNA in a standard sample of DNA as set forth in item 22; and
    comparing said signal with the signal set forth in (ii) of item 32, so as to determine said parameter that represents an absolute quantitative amount of said species of DNA.
34. The computer program product of item 32 or 33, wherein said operation is for determining if a diagnosis for an anomaly in said species of DNA may be performed, and further comprises the step of determining from said parameter a number of random and/or enriched DNA molecules to be sequenced from, preferably from a separate aliquot of DNA of, said sample as part of said diagnosis.
35. A method for detecting in a sample from an individual an amount of a species of DNA originating from cells of a given type, which sample comprises said species of DNA in admixture with differentially methylated DNA not originating from cells of said type; said method comprising the steps:
    (a) treating the DNA present in said sample with a reagent that differentially modifies methylated and non-methylated DNA; and
    (b) detecting in said sample the presence of methylation in said species of DNA at two or more DMRs that are differently methylated between said species of DNA and the DNA not originating from cells of said type the modification of DNA of such DMRs by said reagent is sensitive to methylation of DNA, wherein the presence of methylated DNA at one or more of said DMRs indicates the presence of said amount of species of DNA in said sample and the absence of methylated DNA at said DMRs indicates the absence of said species of DNA in said sample,
    wherein, said detection in step (b) is made using the same aliquot of DNA of said sample, and in the same reaction/detection vessel, and effectively simultaneously for such DMRs, and using (x) multiplex real-time quantitative PCR; and (y) at least two labelled probes each of which specific for one of said DMRs and that are labelled with the same detectable label(s) for each of said DMRs; preferably wherein, said reagent comprises agent as set forth in item 20.

The invention claimed is:

1. A composition comprising:
a first pair of PCR primers for amplifying one first region located in a region and/or a gene selected from the group consisting of SEQ ID NOs: 15-199;
a second pair of PCR primers for amplifying another first region located in a region and/or a gene selected from the group consisting of SEQ ID NOs: 15-199; and
a first and a second fluorescently labelled real-time quantitative PCR probe, each of which is specific for one of said first regions, wherein a same detectable fluorescent label is used for each of said first and second fluorescently labelled real-time quantitative PCR probes,
a DNA sample comprising circulating cell-free DNA originating from cells of a fetus and/or the placenta of a fetus in a sample from a pregnant female, wherein said cell-free DNA is in admixture with differentially methylated DNA not originating from the fetal cells or placenta of the fetus, and wherein the DNA sample comprises the first regions, wherein said composition is contained in a single reaction/detection vessel,
and wherein said first and second pair of PCR primers and said first and second fluorescently labelled real-time quantitative PCR probes in the single reaction/detection vessel are capable of generating detectable and quantifiable amplified first regions corresponding to a number of one or more fetal chromosomes in the DNA sample and wherein said first region and said another first region are located on separate chromosomes.

2. The composition of claim 1, wherein said composition further comprises:
   a third pair of PCR primers for amplifying one other region in the human genome; and
   a third fluorescently labelled real-time quantitative PCR probe specific for said other region, wherein the fluorescent label of the third fluorescently labelled real-time quantitative PCR probe is a detectable fluorescent label that is different from the detectable fluorescent label of the first and second fluorescently labelled probes which are specific for each of said first regions.

3. The composition of claim 1, wherein said composition further comprises amplified DNA regions comprising said first regions, wherein each of said amplified DNA regions hybridize to the first or the second fluorescently labelled real-time quantitative PCR probes, and optionally an amplified DNA region comprising one other region in the human genome that hybridizes to a third fluorescently labelled real-time quantitative PCR probe specific for said other region, wherein the fluorescent label of the third fluorescently labelled real-time quantitative PCR probe is a detectable fluorescent label different from the detectable fluorescent label of said first and second fluorescently labelled real-time quantitative PCR probes hybridized to the amplified DNA regions comprising the first regions.

4. A method for quantitatively detecting in a sample from an individual an amount of a species of DNA originating from cells of a given type, which sample comprises said species of DNA in admixture with differentially methylated DNA not originating from cells of said type,
   wherein said species of DNA originates from cells of a fetus and/or the placenta of a fetus and said sample is from a pregnant female, and wherein said species is circulating cell-free DNA and said sample is a plasma or serum sample of maternal origin;
   said method comprising the steps of:
   (a) treating the DNA present in said sample with a reagent that differentially modifies methylated and non-methylated DNA; and
   (b) quantitatively detecting in said sample the presence of methylation in said species of DNA at two or more first regions that are differently methylated between said species of DNA and the DNA not originating from cells of said type, the modification of DNA of such first regions by said reagent being sensitive to methylation of DNA, and wherein the presence of methylated DNA at one or more of said first regions indicates the presence of said amount of species of DNA in said sample and the absence of methylated DNA at said first regions indicates the absence of said species of DNA in said sample,
   wherein, said quantitative detection in step (b) is made using the same aliquot of DNA of said sample, and in the same reaction/detection vessel, and effectively simultaneously for such first regions, and using a first and a second fluorescently labelled real-time quantitative PCR probe, each of which is specific for one of said first regions, wherein the same detectable label is used for each of said first and second probes;
   wherein said quantitative detection in step (b) comprises amplifying with a first pair of PCR primers one of said first regions located in a region and/or a gene selected from the group consisting of SEQ ID NOS: 15-199 and amplifying with a second pair of PCR primers another of said first regions located in a region and/or a gene selected from the group consisting of SEQ ID NOS: 15-199, in the same reaction/detection vessel, wherein said first region and said another first region are located on separate chromosomes, and wherein quantitation of the amplified first regions corresponds to a number of one or more fetal chromosomes in said sample from said pregnant female.

5. The method of claim 4 further comprising the step:
   (c) quantitatively detecting an amount of total DNA present in said sample using at least one other region that is not differently methylated between said species of DNA and the DNA not originating from cells of said type, the modification of which other region(s) by said reagent is insensitive to methylation of DNA,
   wherein, said detection in step (b) and said detection in step (c) are made using the same aliquot of DNA of said sample, and in the same reaction/detection vessel, and effectively simultaneously for such first regions, and other region(s), and using: (x) a first and a second fluorescently labelled real-time quantitative PCR probe, each of which is specific for one of said first regions, wherein the same detectable label is used for each of said first and second probes; and (y) a third fluorescently labelled real-time quantitative PCR probe specific for one of said other regions, and that has a different detectable label than that of the first and second fluorescently labelled probes which are specific for each of said first regions; and
   wherein said detection in step (c) comprises amplifying the one of said other regions with a third pair of PCR primers.

6. The method of claim 5, wherein said other regions(s) is/are located upstream or downstream of one of said first regions within a distance selected from the group consisting of: between about 15 kb to 10 kb, 12 kb to 8 kb, 10 kb to 8 kb, 11 kb to 7 kb, 11 kb to 10 kb, 9 kb to 8 kb, 8 kb to 6 kb, 6 kb to 4 kb, 4 kb to 2 kb, and 2 kb to 500 bp; and/or another of said other region is located upstream or downstream of another of said first regions within a distance selected from the group consisting of: between about 15 kb to 10 kb, 12 kb to 8 kb, 10 kb to 8 kb, 11 kb to 7 kb, 11 kb to 10 kb, 9 kb to 8 kb, 8 kb to 6 kb, 6 kb to 4 kb, 4 kb to 2 kb, and 2 kb to 500 bp.

7. The method of claim 4, wherein said first region and/or said another first region is located in a region and/or a gene selected from the group consisting of SEQ ID NOS 15-147.

8. The method of claim 4, wherein said first region and/or said another first region is located in a region and/or a gene selected from the group consisting of SEQ ID NOS 74-147.

9. The method of claim 4, wherein said detection in step (b) comprises multiplex real-time probe-based quantitative PCR.

10. The method of claim 4, wherein said detection in step (b) does not comprise digital PCR.

11. The method of claim 4, wherein a fetal DNA fraction of the circulating cell-free DNA ranges from 5% to 19%.

* * * * *